United States Patent [19]

Selby et al.

[11] 4,421,550
[45] Dec. 20, 1983

[54] HERBICIDAL TRIAZOLE UREAS

[75] Inventors: Thomas P. Selby, Hockessin, Del.; Anthony D. Wolf, Elkton, Md.

[73] Assignee: E. I. Du Pont de Nemours & Co., Wilmington, Del.

[21] Appl. No.: 382,711

[22] Filed: May 28, 1982

Related U.S. Application Data

[63] Continuation-in-part of Ser. No. 282,174, Jul. 10, 1981, abandoned.

[51] Int. Cl.³ .............. A01N 47/36; C07D 249/12; C07D 249/14; C07D 401/12

[52] U.S. Cl. .................................. 71/92; 71/76; 71/90; 546/276; 548/265; 548/267; 548/268; 549/65; 260/453 AR; 260/454; 260/545 R; 260/239 A; 260/453.2

[58] Field of Search ............ 548/265, 267, 268; 546/276; 71/76, 90, 92

[56] References Cited

U.S. PATENT DOCUMENTS

| | | | |
|---|---|---|---|
| 4,127,405 | 11/1978 | Levitt | 71/92 |
| 4,238,621 | 12/1980 | Levitt | 71/92 |
| 4,302,241 | 11/1981 | Levitt | 71/92 |
| 4,348,219 | 9/1982 | Levitt | 71/92 |

*Primary Examiner*—Alton D. Rollins

[57] ABSTRACT

Triazole ureas demonstrate utility as agricultural chemicals and in particular as herbicides.

42 Claims, No Drawings

HERBICIDAL TRIAZOLE UREAS

RELATED APPLICATION

This application is a continuation-in-part of my copending application U.S. Ser. No. 282,174, filed July 10, 1981, now abandoned.

BACKGROUND OF THE INVENTION

This invention relates to triazole ureas and in particular their use as agricultural chemicals and particularly as herbicides.

U.S. Pat. No. 4,127,405 teaches compounds which are useful for controlling weeds in wheat having the formula:

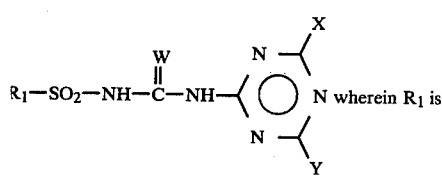

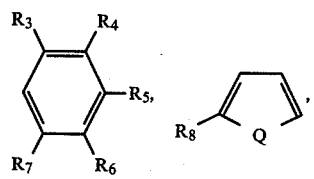

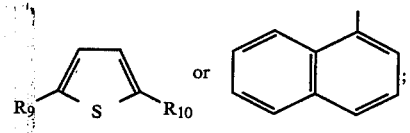

$R_3$ and $R_6$ are independently hydrogen, fluorine, chlorine, bromine, iodine, alkyl of 1–4 carbon atoms, alkoxy of 1–4 carbon atoms, nitro, trifluoromethyl, cyano, $CH_3S(O)_n$— or $CH_3CH_2S(O)_n$—;

$R_4$ is hydrogen, fluorine, chlorine, bromine or methyl;

$R_5$ is hydrogen, fluorine, chlorine, bromine, methyl or methoxy;

$R_7$ is hydrogen, fluorine, chlorine, bromine, alkyl of 1–2 carbon atoms or alkoxy of 1–2 carbon atom;

$R_8$ is hydrogen, methyl, chlorine or bromine;

$R_9$ and $R_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1–3 carbon atoms, trifluoromethyl, $CH_3S$- or $CH_3OCH_2$-; and Y is methyl or methoxy; or their agriculturally suitable salts; provided that:

(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;

(b) when $R_5$ is hydrogen an all of $R_3$, $R_4$, $R_6$ and $R_7$ are other than hydrogen, then all of $R_3$, $R_4$, $R_6$ and $R_7$ must be either chlorine or methyl; and (c) when $R_3$ and $R_7$ are both hydrogen, at least one of $R_4$, $R_5$ or $R_6$ must be hydrogen.

French Pat. No. 1,468,747 discloses the following para-substituted phenylsulfonamides, useful as antidiabetic agents:

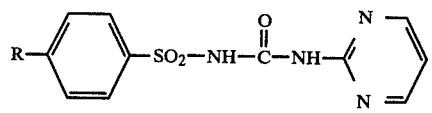

wherein R=H, halogen, $CF_3$ or alkyl.

Logemann et al., Chem. Ab., 53, 18052g (1959), disclose a number of sulfonamides, including uracil derivatives and those having the formula:

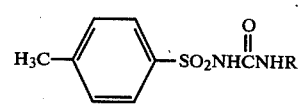

wherein R is butyl, phenyl or

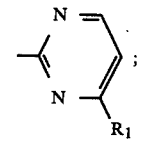

and $R_1$ is hydrogen or methyl. When tested for hypoglycemic effect in rats (oral doses of 25 mg/100 g), the compounds in which R is butyl and phenyl were most potent. The others were of low potency or inactive.

Wojciechowski, J. Acta. Polon. Pharm. 19, p. 121–5 (1962) [Chem. Ab., 59, 1633 e] describes the synthesis of N-[(2,6-dimethoxypyrimidin-4-yl)aminocarbonyl]-4-methylbenzenesulfonamide:

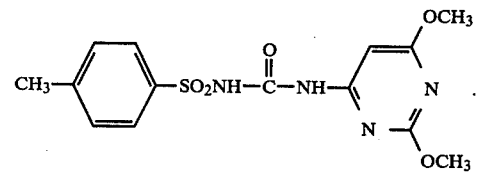

Based upon similarity to a known compound, the author predicted hypoglycemic activity for the foregoing compound.

Netherlands Pat. No. 121,788, published Sept. 15, 1966, teaches the preparation of compounds of Formula (i), and their use as general or selective herbicides,

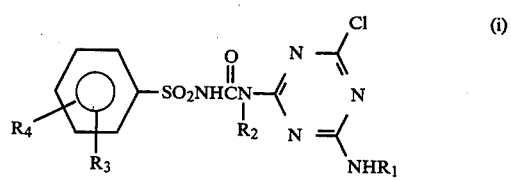

wherein $R_1$ and $R_2$ may independently be alkyl of 1–4 carbon atoms; and $R_3$ and $R_4$ may independently be hydrogen, chlorine or alkyl of 1–4 carbon atoms.

Compounds of Formula (ii), and their use as antidiabetic agents, are reported in *J. Drug. Res.* 6, 123 (1974),

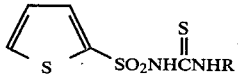
(ii)

wherein R is pyridyl.

The presence of undesired vegetation causes substantial damage to useful crops, especially agricultural products that satisfy man's basic food needs, such as soybeans, barley, wheat, and the like. The current population explosion and concomitant world food shortage demand improvements in the efficiency of producing these crops. Prevention or minimizing the loss of a portion of valuable crops by killing, or inhibiting the growth of undesired vegetation is one way of improving this efficiency.

A wide variety of materials useful for killing, or inhibiting (controlling) the growth of undesired vegetation is available; such materials are commonly referred to as herbicides. The need exists, however, for still more effective herbicides that destroy or retard weeds without causing significant damage to useful crops.

SUMMARY OF THE INVENTION

This invention relates to novel compounds of Formula I, suitable agricultural compositions containing them, and their method of use as pre-emergence and post-emergence herbicides.

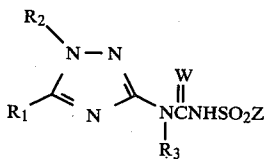
I wherein
$R_1$ is H, $C_1$–$C_4$ alkyl, $C_3$–$C_4$ alkenyl, $C_3$–$C_4$ alkynyl, $SR_4$, $OR_5$, $CH_2OR_6$, $CH_2CH_2OR_6$, $CF_3$, $CF_2CF_3$, Cl, $NHCH_3$, $N(CH_3)_2$, $CH(OCH_3)_2$ or

$R_2$ is $C_1$–$C_4$ alkyl, $C_3$–$C_4$ alkenyl, $C_3$–$C_4$ alkynyl, $CH_2OCH_3$, $CH_2CH_2OCH_3$, $CH_2SCH_3$, $CH_2CH_2SCH_3$ or $C_1$–$C_4$ alkyl substituted with 1–3 F atoms;
$R_3$ is H or $CH_3$;
$R_4$ is $C_1$–$C_4$ alkyl, $C_3$–$C_4$ alkenyl, $C_3$–$C_4$ alkynyl, $CH_2CO_2R_6$ or $CH(CH_3)CO_2R_6$;
$R_5$ is $C_1$–$C_4$ alkyl, $C_3$–$C_4$ alkenyl, $C_3$–$C_4$ alkynyl, $CH_2CO_2R_6$, $CH(CH_3)CO_2R_6$ or $CH_2CF_3$;
$R_6$ is $C_1$–$C_4$ alkyl;
W is O or S;
Z is $R_7$ is H, $C_1$–$C_4$ alkyl, $C_1$–$C_4$ alkoxy, F, $C(O)NR_{21}R_{22}$, Cl, Br, $NO_2$, $CF_3$, $CO_2R_9$, $SO_2NR_{10}R_{11}$, $C(O)SR_{10}$, $SO_2N(OCH_3)CH_3$, $QSO_2R_{12}$, $S(O)_nR_{13}$, $CH_2CO_2R_{20}$, $CH(CH_3)CO_2R_{20}$, $CH_2S(O)_nR_{13}$, $CH(CH_3)S(O)_nR_{13}$, $C_3$–$C_4$ alkenyloxy, $C_3$–$C_4$ alkynyloxy, $C_1$–$C_2$ alkyl substituted with either $OCH_3$ or $OC_2H_5$, or $C_1$–$C_3$ alkoxy substituted with either (a) 1–5 atoms of Cl, Br or F or (b) $OCH_3$ or $OC_2H_5$;
$R_8$ is H, F, Cl, Br, $CF_3$, $NO_2$, $C_1$–$C_3$ alkyl or $C_1$–$C_3$ alkoxy;
$R_9$ is $C_1$–$C_6$ alkyl, $CH_2CH_2OCH_3$, $CH_2CH_2OCH_2CH_3$, $CH_2CH_2CH_2OCH_2CH_3$, $C_3$–$C_6$ alkenyl, $C_3$–$C_6$ alkynyl or $C_1$–$C_3$ alkyl substituted with 1–3 atoms of Cl or F;
$R_{10}$ and $R_{11}$ are independently $C_1$–$C_3$ alkyl;
$R_{12}$ is $C_1$–$C_4$ alkyl, $CH_2CH_2OCH_3$, $CH_2CH_2CH_2OCH_3$ or $C_1$–$C_4$ alkyl substituted with 1–3 atoms of F, Cl or Br;
$R_{13}$ is $C_1$–$C_4$ alkyl, allyl, $C_1$–$C_3$ alkyl substituted with 1–5 atoms of F, Cl or Br;
n is 0, 1 or 2;
Q is O or $NCH_3$;
$R_{14}$ is H, $CH_3$, $OCH_3$, F, Cl, Br, $NO_2$, $SO_2NR_{10}R_{11}$, $SO_2N(OCH_3)CH_3$, $OSO_2R_{12}$ or $S(O)_nR_{13}$;
$R_{15}$ is H, Cl, Br, $CH_3$, $OCH_3$ or $NO_2$;
$R_{16}$ is H, $C_1$–$C_4$ alkyl, $C_1$–$C_4$ alkoxy, F, Cl, Br, $CF_3$, $CO_2R_{20}$, $SO_2NR_{10}R_{11}$, $SO_2N(OCH_3)CH_3$ or $S(O)_nR_{13}$;
$R_{17}$ is H, F, Cl, Br, $CH_3$ or $OCH_3$;
W' is O or S;
$R_{18}$ is H, $C_1$–$C_4$ alkyl, $C_1$–$C_4$ alkoxy, F, Cl, Br, $NO_2$, $CO_2R_{20}$, $SO_2NR_{10}R_{11}$, $SO_2N(OCH_3)CH_3$ or $S(O)_nR_{13}$;
$R_{19}$ is Cl, $NO_2$, $CF_3$, $CO_2R_9$, $SO_2N(OCH_3)CH_3$, $SO_2NR_{10}R_{11}$, $QSO_2R_{12}$, $S(O)_nR_{13}$ or $C_1$–$C_3$ alkoxy substituted with 1–5 atoms of Cl or F;
$R_{20}$ is $C_1$–$C_4$ alkyl, $CH_2CH_2OCH_3$, $CH_2CH_2Cl$ or $CH_2CH=CH_2$;
$R_{21}$ is $C_1$–$C_3$ alkyl or $C_6H_5$;
$R_{22}$ is $C_1$–$C_3$ alkyl; and
$R_{21}$ and $R_{22}$ may be taken together to be

provided that
(1) the total number of carbon atoms of $R_{10}$ and $R_{11}$ is less than or equal to 4;
(2) the total number of carbon atoms of $R_1$ and $R_2$ is less than or equal to 6;
(3) when W' is O, then $R_{18}$ is H, Cl, Br, $CH_3$ or $CO_2R_{20}$;
(4) when W' is O and $R_{18}$ is H, Cl, Br or $CH_3$, then Z is

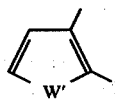

(5) when W is S, then $R_3$ is H;
(6) when $R_7$ is H, then $R_8$ is H; and
(7) $R_{14}$ and $R_{15}$ may not both be $NO_2$.

Preferred for reasons of higher herbicidal activity or more favorable ease of synthesis are:
(1) Compounds of Formula I wherein W is O and $R_3$ is H.
(2) Compounds of Preferred 1 where Z is

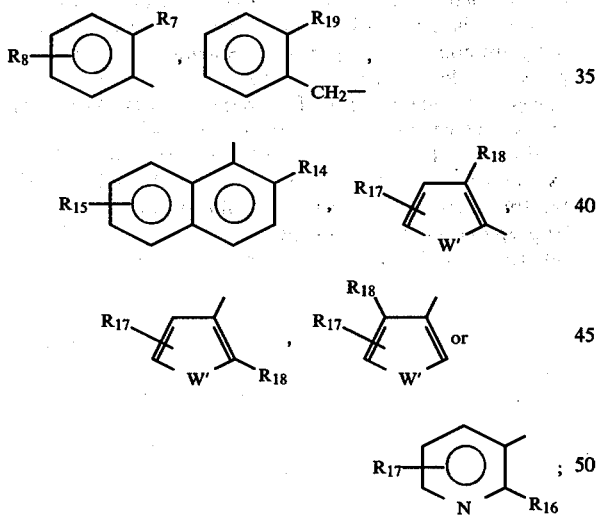

W' is S;
$R_{19}$ is $CO_2CH_3$, $SO_2N(CH_3)_2$ or $SO_2CH_3$; and
$R_{15}$ and $R_{17}$ are H.
(3) Compounds of Preferred 2 where Z is

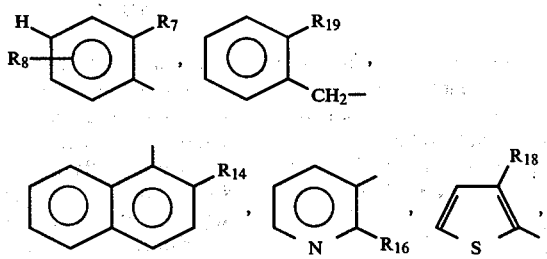

-continued

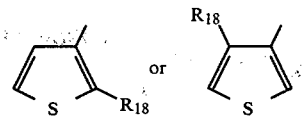

(4) Compounds of Preferred 3 where
$R_1$ is $C_1-C_2$ alkyl, $SR_4$, $OR_5$, $CH_2OCH_3$, $N(CH_3)_2$ or Cl;
$R_2$ is $C_1-C_2$ alkyl, $CH_2CF_3$, $CH_2CH=CH_2$ or $CH_2C\equiv CH$; and
$R_4$ and $R_5$ are independently $CH_3$ or $C_2H_5$.
(5) Compounds of Preferred 4 where Z is

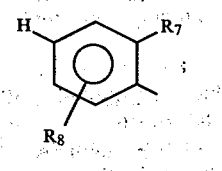

$R_7$ is other than H; and
$R_8$ is H, F, Cl, Br, $CF_3$, $CH_3$ or $OCH_3$.
(6) Compounds of Preferred 5 where
$R_7$ is Cl, $NO_2$, $CO_2R_9$, $SO_2NR_{10}R_{11}$ or $OSO_2R_{12}$;
$R_8$ is H;
$R_9$ is $C_1-C_3$ alkyl, $CH_2CH=CH_2$, $CH_2CH_2OCH_3$ or $CH_2CH_2Cl$;
$R_{10}$ and $R_{11}$ are independently $C_1-C_2$ alkyl; and
$R_{12}$ and $R_{13}$ are independently $C_1-C_3$ alkyl.
(7) Compounds of Preferred 6 where $R_9$, $R_{10}$, $R_{11}$, $R_{12}$ and $R_{13}$ are $CH_3$.

Specifically preferred for reasons of their highest herbicidal activity and/or most favorable ease of synthesis are:
2-[[(5-methylthio-1-methyl-1H-1,2,4-triazol-3-yl)aminocarbonyl]aminosulfonyl]benzoic acid, methyl ester;
2-[[(5-ethylthio-1-methyl-1H-1,2,4-triazol-3-yl)aminocarbonyl]aminosulfonyl]benzoic acid, methyl ester;
2-[[(5-ethyl-1-methyl-1H-1,2,4-triazol-3-yl)aminocarbonyl]aminosulfonyl]benzoic acid, methyl ester;
2-[[(5-methoxy-1-methyl-1H-1,2,4-triazol-3-yl)aminocarbonyl]aminosulfonyl]benzoic acid, methyl ester;
N-[(5-methoxy-1-methyl-1H-1,2,4-triazol-3-yl)aminocarbonyl]-2-chlorobenzenesulfonamide; and
N-[(5-methoxy-1-methyl-1H-1,2,4-triazol-3-yl)aminocarbonyl]-N',N'-dimethyl-1,2-benzenedisulfonamide.

Synthesis

Many of the compounds of Formula I can be prepared by reacting an appropriate 3-amino-1,2,4-triazole of Formula II with an appropriately substituted sulfonylisocyanate or isothiocyanate of Formula III, as shown in Equation 1.

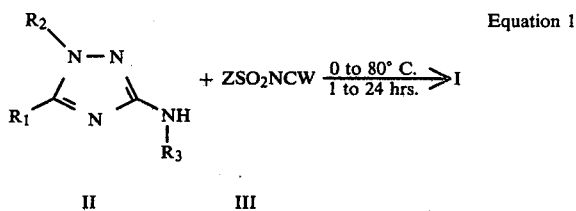

Equation 1 wherein Z, $R_1$, $R_2$, $R_3$ and W are as previously defined. The reaction of Equation 1 is best carried out in inert organic solvents such as methylene chloride, tetrahydrofuran, or acetonitrile at ambient pressure and temperature. The mode of addition is not critical; however, it is often convenient to add the sulfonylisocyanate or isothiocyanate to a stirred suspension or solution of the aminotriazole. Since such isocyanates and isothiocyanates usually are liquids, their additions can be easily controlled.

The reaction is generally exothermic. In some cases, the desired product is insoluble in the warm reaction medium and crystallizes from it in pure form. Products soluble in the reaction medium are isolated by evaporation of the solvent, trituration of the solid residue with solvents such as 1-chlorobutane or ethyl ether, and filtration.

An alternate method for synthesizing compounds of Formula I in which W=O is illustrated in Equation 2. An appropriate sulfonylisocyanate of Formula III is allowed to react with an appropriate 3-amino-1H-1,2,4-triazole of Formula IV to give an intermediate urea of Formula V which is then alkylated with a reagent of Formula $R_2X$ to yield compounds of Formula I:

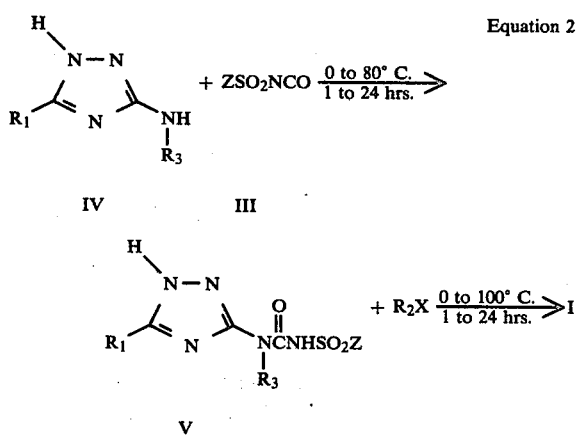

Equation 2 wherein X is a good leaving group such as bromine, iodine, chlorine, alkylsulfonate, $R_2OSO_3^\ominus$, or p-toluenesulfonate, and Z, $R_1$, $R_2$ and $R_3$ are as previously defined.

The conditions for reacting the 3-amino-1H-triazole of Formula IV and sulfonylisocyanate or sulfonylisothiocyanate in Equation 2 are similar to that described for the condensation involving triazole II in Equation 1, however it is desirable to have an equimolar amount of sulfonylisocyanate react with triazole IV.

The alkylation reaction illustrated in Equation 2 between the sulfonylurea intermediate V and $R_2X$ (wherein X is a good leaving group such as bromine, iodine, chlorine, alkylsulfonate, $R_2OSO_3^\ominus$, or p-toluenesulfonate) is preferably carried out in the presence of an alkaline material and preferably in the presence of a solvent. Suitable alkaline materials, include, for example, the alkali and alkaline earth metal carbonates, bicarbonates, acetates, and hydroxides such as potassium carbonate, sodium carbonate, potassium carbonate, potassium acetate, sodium and potassium hydroxide. Other organic bases such as pyridine and triethylamine may also be used. Suitable solvents include inert aprotic solvents such as acetone, methyl ethyl ketone, acetonitrile, methylene chloride, dimethylformamide, dimethylacetamide, and dimethylsulfoxide. The alkylation reaction conditions of Equation 2 vary according to the nature of the reactants, the base and solvent present. Usually, the reaction is facilitated by the application of heat (between 45° and 128°) however, lower reaction temperatures may be desirable in some instances as will be readily apparent to one skilled in the art.

The intermediate aryl sulfonylisocyanates of Formula III (W=O) can be prepared by reacting the corresponding aryl sulfonamides with phosgene in the presence of n-butyl isocyanate at reflux in a solvent such as chlorobenzene or xylenes, according to the procedure of H. Ulrich and A. A. Y. Sayigh, *Newer Methods of Preparative Organic Chemistry*, Vol. VI, p. 223-241, Academic Press, New York and London, W. Forest Ed., or by the methods taught in U.S. Pat. No. 4,127,405 (1978), U.S. Pat. No. 4,238,671 (1980) and European Pat. No. 23,141.

The intermediate pyridyl sulfonylisocyanates of Formula III (W=O) can be prepared by reacting an N-(alkylaminocarbonyl)pyridinesulfonamide with phosgene as described in European Pat. No. 13,480, the disclosure of which is hereby incorporated by reference. The N-(alkylaminocarbonyl)pyridinesulfonamide can be prepared, as described in U.S. Ser. No. 966,258, by the reaction of a pyridinesulfonamide, an alkyl isocyanate and an anhydrous base in an anhydrous solvent.

Similarly, the preparation of the furan sulfonyl isocyanates is described in U.S. Pat. No. 4,127,405 (1978); the thiophene and naphthalene sulfonylisocyanates can be prepared as shown in Equations 3 and 4 respectively, wherein $R_{14}$, $R_{15}$, $R_{17}$ and $R_{18}$ are as previously defined.

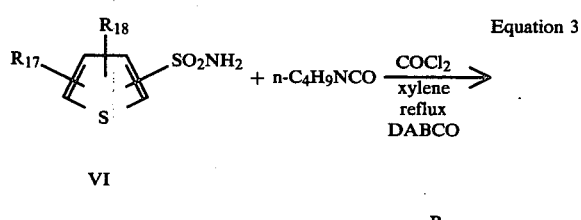

Equation 3

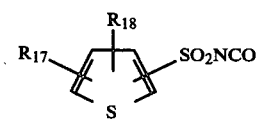

VII

A mixture of the appropriate sulfonamide, e.g., an 2-alkoxycarbonyl-3-thiophene sulfonamide VI such as the methyl ester, which is known in the art, an alkyl isocyanate such as butyl isocyanate and a catalytic amount of 1,4-diaza[2.2.2]bicyclooctane (DABCO) in xylene or other inert solvent of sufficiently high boiling point (e.g. >135° C.) is heated to approximately 130°-150° C. Phosgene is added to the mixture until an excess of phosgene is present as indicated by a drop in the boiling point. After the mixture is cooled and filtered to remove a small amount of insoluble by-products, the solvent and alkyl isocyanate are distilled off in-vacuo leaving a residue which is the crude sulfonyl isocyanate VII.

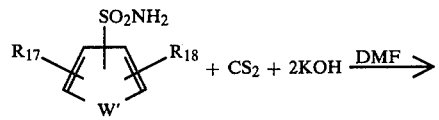

Equation 6

XII

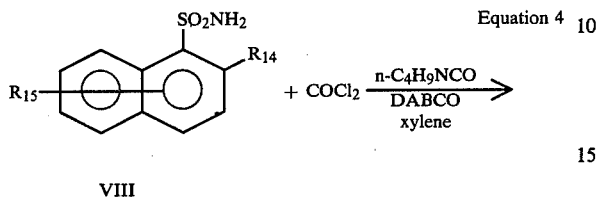

Equation 4

VIII

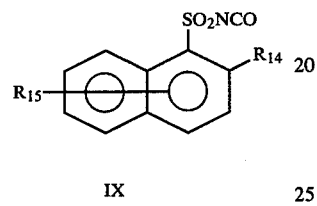

IX

The preparations of naphthalene sulfonylisocyanates IX can be obtained from the corresponding sulfonamides VIII. Reaction conditions for the phosgenation would be the same as that for the thiophene sulfonamides in Equation 3.

The phenyloxysulfonylisocyanates of Formula XI are readily prepared from the corresponding phenols of Formula X as taught in U.S. Pat. No. 4,191,553 and as shown in Equation 5. Reaction of X with chlorosulfonylisocyanate in a high boiling solvent, for example, dichlorobenzene, toluene or xylene, will produce the sulfonylisocyanate of Formula XI.

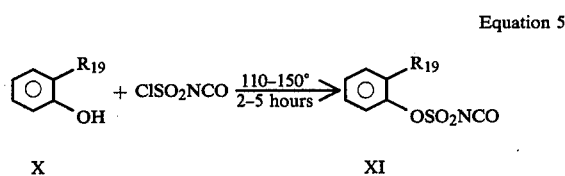

Equation 5

X    XI

Arylsulfonylisothiocyanates of Formula III (W=S) can be prepared by treatment of sulfonamides with carbon disulfide and potassium hydroxide followed by reaction of the dipotassium salt with phosgene according to the teaching of K. Hartke, *Arch. Pharm.* 229, 174 (1966).

Pyridine sulfonylisothiocyanates can be prepared according to the procedure taught by K. Dickere and E. Kuhle in U.S. Pat. No. 3,346,590. A suitable pyridinesulfonyliminodithiocarbonate is reacted with phosgene in the presence of a solvent such as toluene or xylene.

The thiophene and furan sulfonylisothiocyanate intermediates of Formula XIII prepared according to Equations 6 and 7 are useful for the preparation of compounds of Formula I where W=S.

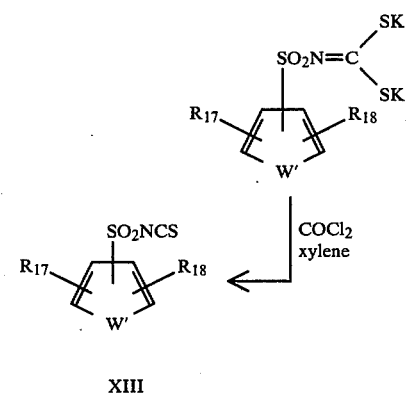

XIII

The substituted sulfonamide is dissolved in dimethylformamide (DMF) with an equivalent amount of carbon disulfide and two equivalents of potassium hydroxide are added portionwise at room temperature. The mixture is stirred for 1-8 hours and diluted with ethyl acetate, ethyl ether or similar aprotic solvent to cause the dipotassium salt or the dithiocarbamic acid to precipitate. The salt is isolated, dried and suspended in an inert solvent such as xylene, benzene, carbon tetrachloride or methylene chloride. Phosgene is added to the stirred suspension at or below room temperature and the mixture stirred for 1-3 hours. In place of phosgene, a chloroformic ester (e.g. methyl chloroformate), phosphorous pentachloride, sulfuryl chloride or thionyl chloride can be used.

The sulfonyisolthiocyanate which is formed is usually soluble in the solvent and is isolated by filtering off the insoluble potassium chloride and concentrating the filtrate. These isothiocyanates tend to be unstable and dimerize readily, (Equation 7), however, the dimers can be used in the same manner as the parent isothiocyanates for the purposes of this invention.

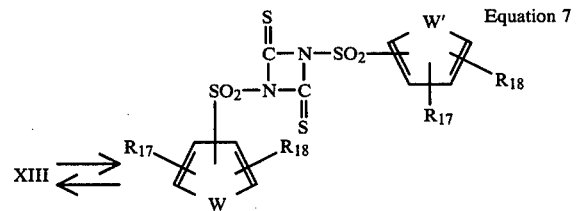

Equation 7

The naphthalene sulfonylisothiocyanate intermediate XIV may also be prepared from the sulfonamide VIII according to Equation 8 and following similar reaction conditions as that in Equation 6. These isothiocyanates may also be unstable and dimerize, however, these dimers can be used in the same way as the parent isothiocyanates for the purpose of the invention.

$$\text{VIII} + \text{CS}_2 + \text{KOH} \xrightarrow{\text{DMF}}$$

Equation 8

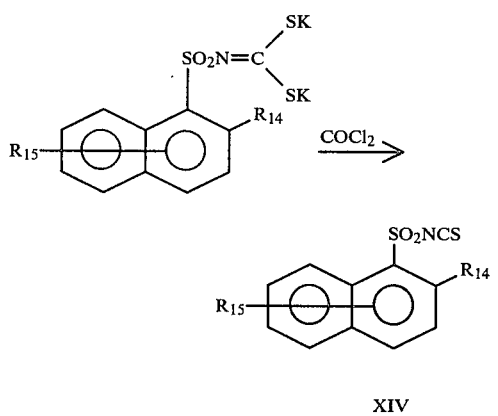

XIV

The preparation of sulfonamides from ammonium hydroxide and sulfonyl chloride is widely reported in the literature, e.g., Crossley et al., *J. Am. Chem. Soc.* 60, 2223 (1938). Certain sulfonyl chlorides are best prepared by chlorosulfonation of a substituted aromatic in carbon tetrachloride according to the teaching of H. T. Clarke et al., *Org. Synth.*, coll. Vol. 1, 2nd Ed., 1941, p. 85. Other benzenesulfonyl chlorides are best made by diazotization of the appropriate aniline with sodium nitrite in HCl, followed by reaction of the diazonium salt with sulfur dioxide and cuprous chloride in acetic acid according to the teaching of H. L. Yale and F. Sowinski, *J. Org. Chem.* 25, 1824 (1960). The preparation of pyridyl sulfonyl chlorides is described in *Chem. Abs.* 88, 190603 m (1978).

Preparations of the aryl sulfonamides are given in U.S. Pat. No. 4,127,405 (1978) wherein $R_7$=H, $C_1$–$C_4$ alkoxy, F, Cl, Br, $NO_2$, $CF_3$; EPO Publication #7687 wherein $R_7$=$CO_2R_9$, $CO_2NR_{21}R_{22}$, $C(O)SR_{10}$; European Patent 23,141 ($R_7$=$SO_2NR_{10}R_{11}$, $SO_2N(OCH_3)CH_3$); European Patent 23,422 ($R_7$=$OCF_3$, $OCHF_2$, $OCF_2CF_2H$, $S(O)_nR_{13}$ where $R_{13}$ is fluorinated alkyl); European Pat. No. 44,209 ($R_7$=$CH_2CO_2R_{20}$, $CH(CH_3)CO_2R_{20}$, $CH_2S(O)_nR_{13}$, $CH(CH_3)S(O)_nR_{13}$); European Patent 44,212 ($R_7$=$QSO_2R_{12}$ where Q=O or $NCH_3$); European Patent Application 44,807 ($R_7$=$C_3$–$C_4$ alkenyloxy, $C_1$–$C_3$ alkoxy substituted with $OCH_3$ or $OC_2H_5$, $S(O)_nR_{13}$ where $R_{13}$=allyl); and European Patent Application 44,808 ($R_7$=$C_1$–$C_3$ alkoxy substituted with 1–5 atoms of Cl, Br or F). The arylsulfonamides wherein $R_7$=$C_3$–$C_4$ alkynyloxy may be prepared by methods taught in European Patent Application No. 44,807. The synthesis of pyridylsulfonamides is described in G. Machek, *Monatsch* 2, 84 (1939); L. Thunus and C. L. Lapiere, *Ann. Farn.* 33, 663 (1975), and European Pat. No. 13,480.

Equation 9 describes the procedure for making aryl and naphthalene intermediates of Formula III when $R_7$ and $R_{14}$ are $S(O)_nR_{13}$. The thioether of Formula XVb may be prepared from the appropriate 2-aminothiophenol or aminothionaphthalene and an alkyl halide as described in the literature, e.g., R. N. Prasad et al., *Can. J. Chem.* 44, 1247 (1966). The formation of the sulfonamide XVd is accomplished in the following manner.

Equation 9

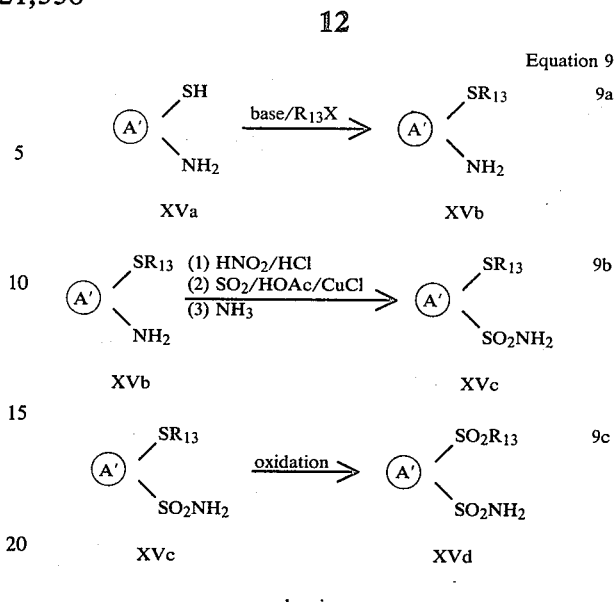

wherein

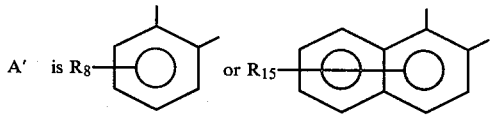

A solution of the thioether of Formula XVb in a mixture of concentrated hydrochloric acid and glacial acetic acid is treated with a solution of sodium nitrite in water at −5° to 0°. After stirring for 10–15 minutes at 0° to insure complete diazotization, this solution is added to a mixture of an excess of sulfur dioxide and a catalytic amount of cuprous chloride in glacial acetic acid at 0°–5°. The temperature is kept at 0°–5° for ¼ to 1 hour and is then raised to 20°–25° and held at that temperature for 2–4 hours. This solution is then poured into a large excess of ice water. The sulfonyl chloride products can be isolated by filtration or by extraction into solvent such as ethyl ether or methylene chloride followed by evaporation of the solvent.

The amination described in step (9b) is conveniently carried out by treating a solution of the sulfonyl chloride with an excess of anhydrous ammonia in a solvent such as ethyl ether or methylene chloride at 0°–25°. If the product sulfonamide is insoluble, it may be isolated by filtration followed by washing out the salts with water. If the product sulfonamide is soluble in the reaction solution, it may be isolated by filtering off the precipitated ammonium chloride and evaporating the solvent.

Sulfonamides of Formula XVc wherein A'=aryl may also be prepared from the appropriate chlorobenzenesulfonamides (synthesis taught in U.S. Pat. No. 4,127,405) as shown in Equation 10. Heating an equimolar mixture of the appropriate sulfonamide and mercaptan in the presence of two equivalents of base will yield XVc following acidic work-up. As in Equation 9, the sulfonamides XVd can be prepared by oxidation of XVc.

Equation 10

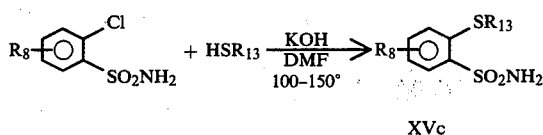

Synthesis of thiophene sulfonamides of Formula XVIe and XVIf may be accomplished by the method outlined in Equation 11. The sulfonyl chlorides of Formula XVIa are described by H. D. Hartough in "The Chemistry of Heterocyclic Compounds," v. 3, Interscience Publishers, Inc., N.Y. 1952. These may be converted to the corresponding N-t-butyl sulfonamides XVIb by admixture with at least twice the equivalent amount of t-butylamine in an inert solvent, such as ether, filtration of the amine hydrochloride, and evaporation of the solvent. The lithiation of thiophenes and of aromatic N-t-butylsulfonamides with n-butyllithium, t-butyllithium, lithium diisopropylamide and lithium 2,2,6,6-tetramethyl piperidide is reviewed by H. W. Gschwend and H. R. Rodriguez in *Org. React.*, 26, 1 (1979), and is generally carried out by cooling to $-78°$ a solution of twice the equimolar amount of base kept under an inert atmosphere, in an ethereal solvent such as diethyl ether or THF, and adding a solution of the compound of Formula XVIb. The compounds of Formula XVIc may be prepared as shown in Equation (11b) by adding an equimolar quantity of the appropriate disulfide $(R_{13}S)_2$, allowing the mixture to warm to room temperature, washing the mixture with acidic brine, and evaporation of the solvent.

Equation 11

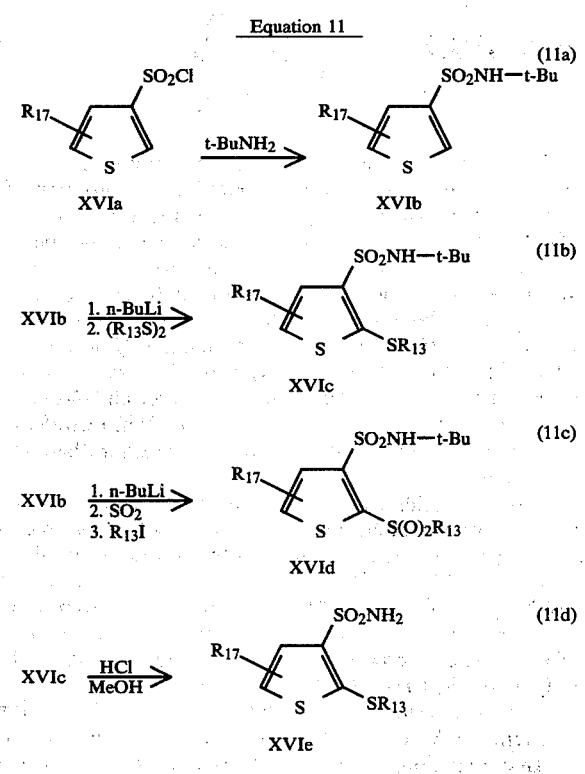

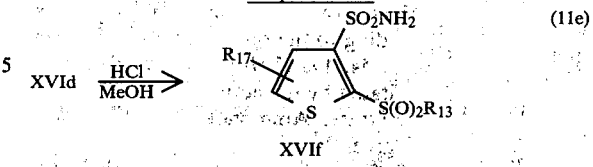

Alternatively, as shown in Equation (11c), in order to prepare the compounds of Formula XVId, the lithiation mixture may be treated with an equimolar quantity of sulfur dioxide, allowing the mixture to warm to room temperature, filtration of the solid precipitate, dissolution of this salt in ethanol and adding an equimolar amount of the appropriate alkyl iodide. This alkylation step may be carried out at temperatures of 25° to 78°. The cooled reaction mixture may be diluted with dilute aqueous hydrochloric acid to precipitate the product XVId. The t-butyl sulfonamides of Formula XVIc and XVId may be converted to the compounds of Formulae XVIe and XVIf, respectively, by heating in methanol containing at least an equimolar quantity of hydrochloric acid, followed by concentration of the reaction mixture and precipitation of the product with ether.

An alternate preparation of the thiophene sulfonamides of Formula XVIf is described in Equation 12.

Equation 12

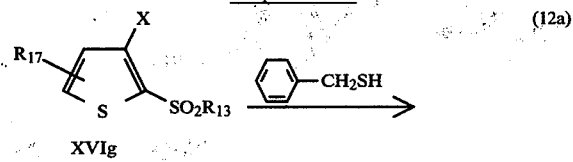

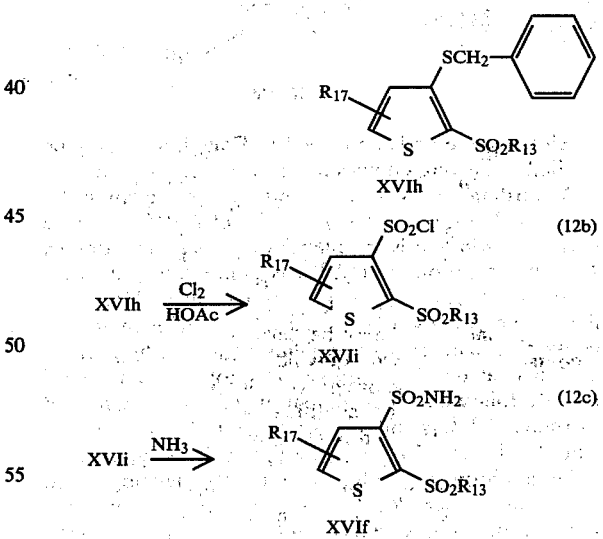

wherein $X = Cl$ or $Br$ and $R_{13}$ and $R_{17}$ are as previously defined.

The reaction of Equation (12a) is accomplished by mixing equimolar quantities of the appropriate halide XVIg with an equimolar quantity of benzyl mercaptan in a polar solvent, such as dimethylformamide, containing an equimolar amount of a strong base, such as sodium methoxide or sodium hydride, heating at a temperature between 50° and 120°, and isolating the product by precipitation with ice-water and washing with hexane. The sulfides of Formula XVIh are converted to the sulfonyl chlorides XVIi as shown in Equation (12b) by contacting with at least three equivalents of chlorine in acetic acid according to the procedure of R. F. Langler, *Can. J. Chem.*, 54, 498 (1976). The sulfonyl chlorides can be precipitated by the addition of ice-water to the chlorination mixture. Ammonolysis of thiophene sulfonyl chlorides gives XVIf.

Compounds of Formulae XVIIb (Equation 13) wherein $R_{13}$ and $R_{17}$ are as previously defined may be prepared by adding twice the equimolar amount of chlorosulfonic acid, diluted in an inert solvent, such as dichloromethane, to the appropriate 3-thienyl sulfide XVIIa at temperatures between $-30°$ and $25°$, washing the mixture with ice-water and evaporating the solvent. These may be converted to the appropriate compounds of Formula XVIIc by treatment with ammonia. The sulfides of Formula XVIIc may be oxidized to compounds of Formula XVIId.

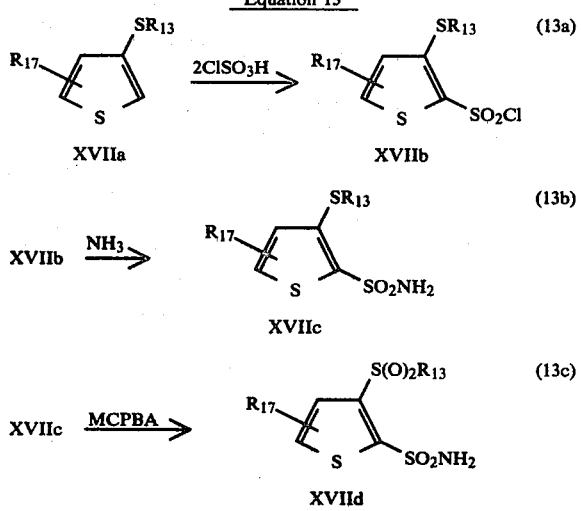

Also, the methods described in Equation 11 may be applied in making compounds of Formula XVIId.

According to the method outlined in Equation 14, compounds of Formulae XVIIIf and XVIIIh can be prepared, wherein $R'_{17}$ equals H, chlorine, or bromine, X=chlorine, bromine and $R_{13}$ is as previously defined. Starting with sulfonyl chlorides of Formula XVIIIa, the dihalo-compounds may be partially dehalogenated by contacting with two equivalents of 5% sodium amalgam in an alcoholic or aqueous alcoholic solution at 25° to 78°, followed by acidification of the products of Formulae XVIIIe and XVIIIg wherein $R'_{17}$=Cl or Br. The 2-halo and 5-halo isomers may be separated by column chromatography. The totally dehalogenated compounds where $R'_{17}$=H, may be prepared by using three or more equivalents of the sodium amalgam in the reaction. These compounds may be converted to XVIIIf and XVIIIh as previously described.

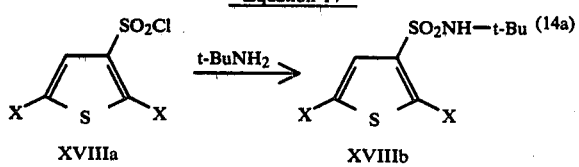

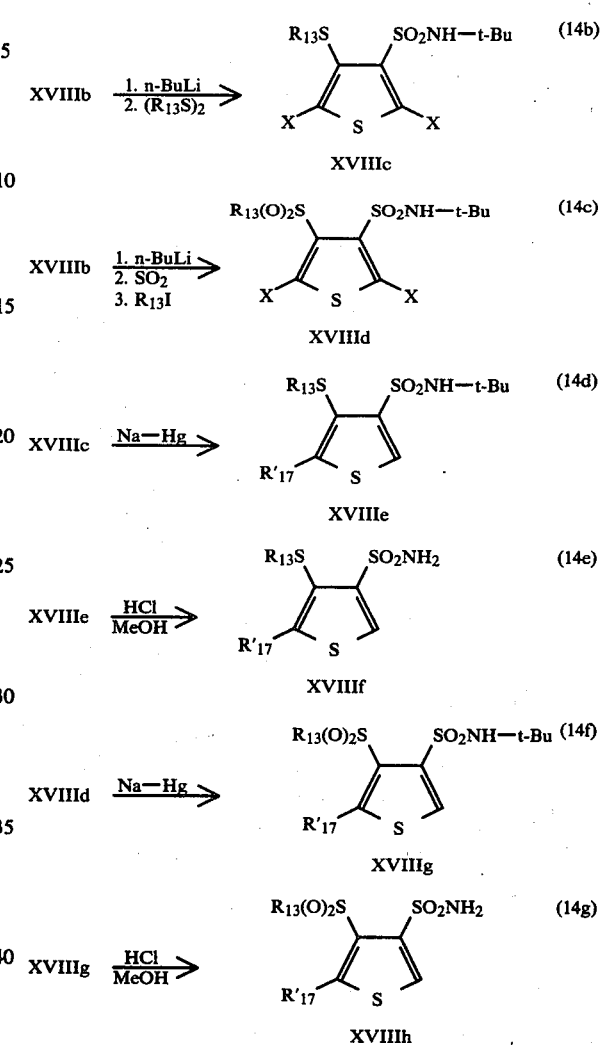

Precursors to the required thiophene sulfonyl chlorides and sulfonamides are prepared by a variety of synthetic routes depending on the chemical properties of the substituent and its position on the thiophene ring.

Direct sulfonation or chlorosulfonation to sulfonic acid or sulfonyl chloride derivatives can be carried out according to the references cited in "Thiophene and its Derivatives," H. D. Hartough, Interscience, New York, 1952. The structure of sulfonation products of 3-alkyl thiophenes has been reported as uncertain. Nuclear magnetic resonance studies indicate the chlorosulfonation occurs predominantly at the 2- rather than the 5-position.

Sulfonic acids are readily converted to sulfonyl chlorides, using methods well known in the art, by chlorinating agents such as phosphorus pentachloride, phosphorus oxychloride or thionyl chloride. A mixture of sulfuryl chloride in dimethylformamide can also be used to prepare thiophenesulfonyl chlorides of active thiophene intermediates according to the method of E. Testa et al., *Helv. Chim. Acta.*, 47, 766 (1963).

Other intermediates can be prepared via lithiation reactions. A review of this chemistry appears in Organic Reactions, Vol. 26., Gschwind, H. W. and Rodriquez, H. R., John Wiley and Sons, Inc., New York, 1979. Examples of the application of this chemistry to the preparation of intermediates used here is shown in the following equations.

Equation 15 shows the preparation of sulfamyl thiophene sulfonamides via lithiated intermediates.

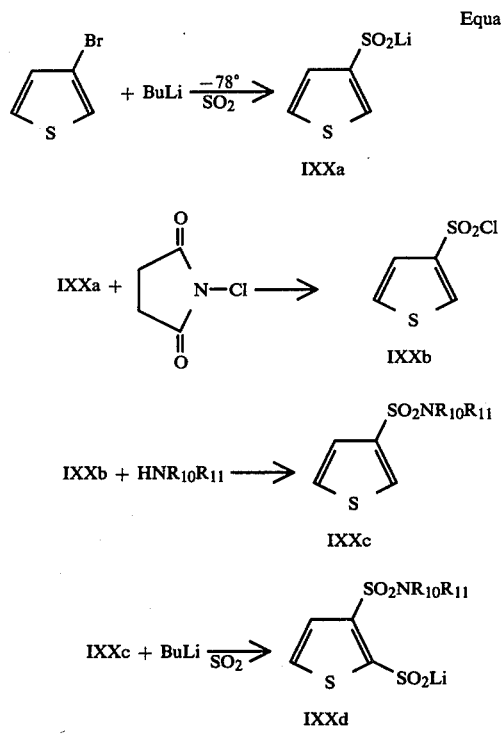

As shown in Equation 15, 3-bromothiophene is converted to 3-lithiothiophene at $-78°$ in an inert solvent such as tetrahydrofuran and the mixture is then contacted with sulfur dioxide. The resultant lithio sulfinate is stirred at room temperature in acetic acid or aqueous 2-propanol with N-chlorosuccinimide to yield the 3-thiophenesulfonyl chloride IXXb. This product is then contacted with an amine, $HNR_{10}R_{11}$ wherein $R_{10}$ and $R_{11}$ are as previously defined. The 3-thiophenesulfonamide IXXc, thus formed is reacted with butyl lithium at $-40°$ to $0°$ C. followed by sulfur dioxide to form the lithio 3-sulfamyl-2-thiophenesulfinate IXXd which is converted to the sulfonyl chloride as described above. Conversion of this sulfonyl chloride to the sulfonamide and sulfonylisocyanate is carried out as previously described.

The synthesis of other intermediates via lithiation is shown in Equation 16, wherein $R_{18}$ is optionally Cl, Br, $C_1$-$C_4$ alkyl, $C_3$ alkenyl or $OCH_3$.

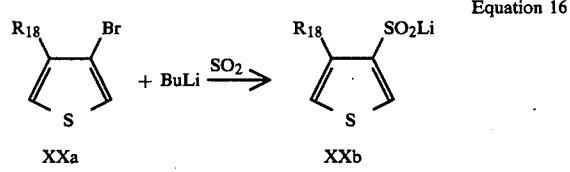

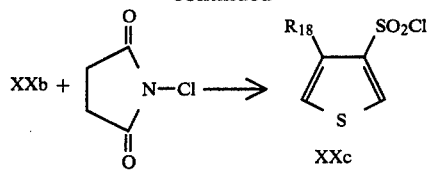

The reactions described in Equation 16 are carried out in the same manner as those described in Equation 15 as would be expected by one skilled in the art. Displacement of activated halogen atoms from the thiophene nucleus by benzyl mercaptan and chlorination of the resulting product is also a useful route to intermediates for compounds of this invention as illustrated by Equation 17.

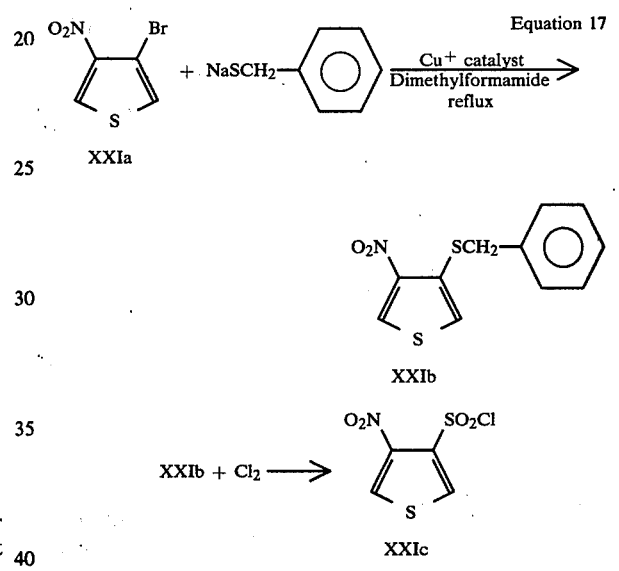

The reaction of benzyl mercaptan with a halothiophene, wherein the halo atom is susceptible to replacement by a nucleophile, is best carried out in an inert polar, high boiling solvent such as dimethylformamide or N-methylpyrrolidone at reflux in the presence of a copper catalyst over six to forty-eight hours. The thioether intermediate XXIb is converted to the sulfonyl chloride XXIc by passing chlorine gas into aqueous hydrochloric acid or acetic acid solution or suspension of XXIb.

Disulfides such as structure XXII, reported by Henriksen and Autruys, Acta. Chem. Scands., 24, 2629 (1970), are also useful intermediates for conversion to sulfonyl chlorides as shown in Equation 18.

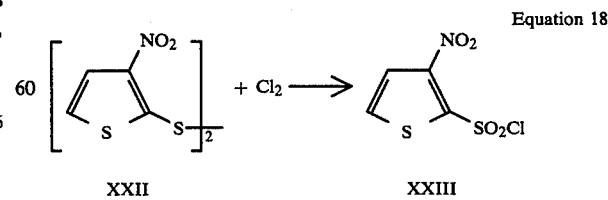

The chlorination shown in Equation 18 is carried out in the same manner as described for the chlorination of structure XXIb.

Alternatively, the diazotization reaction of thiophene amines to sulfonyl chlorides such as structure XXIV shown in Equation 19 are carried out according to the general procedure of H. L. Yale and F. Sowinski, *J. Org. Chem.*, 25, 1824 (1960).

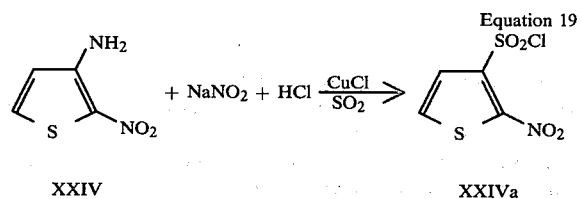

The o-alkoxymethyl nitrobenzenes XXVb are in turn prepared via "Williamson Synthesis", according to Equations 20a or 20b.

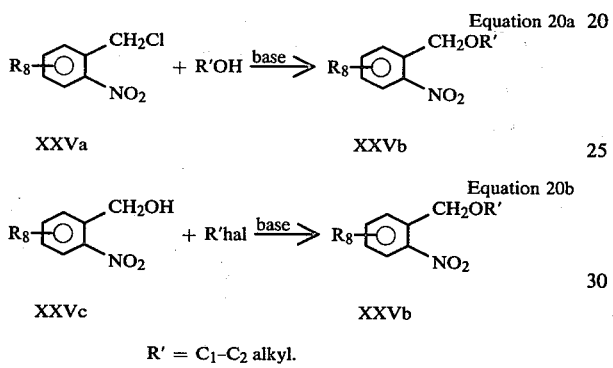

R' = $C_1$–$C_2$ alkyl.

"Williamson Synthesis" has been widely used for the preparation of ethers as reviewed by W. Theilheimer, *Syn. Methods of Org. Chem.*, Vol. VII, p. 112.

Alternatively, o-alkoxymethyl methylbenzenesulfonyl chlorides, XXVf, can be obtained from an appropriately substituted α-hydroxy-o-toluenesulfonic acid-α-sultone, XXVd, via ring-opening reaction with an alkoxide anion as depicted in Equations 20c and 20d.

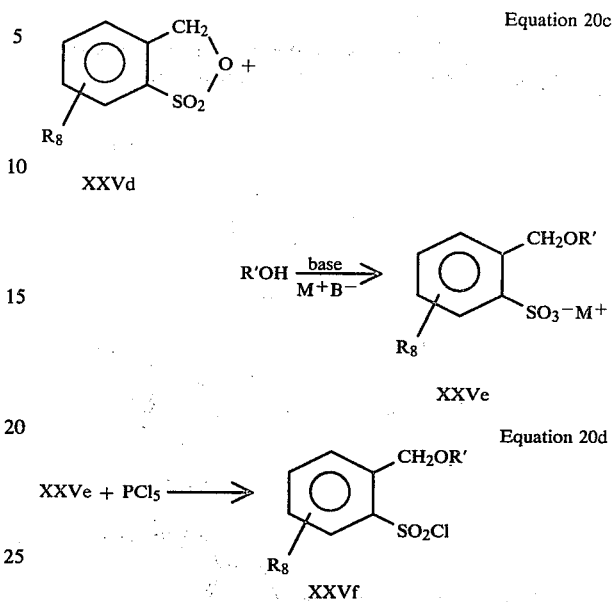

Reaction 20c is closely related to the alkylation of acyloxides and acetamide with sultones as disclosed by J. H. Helberger et al., *Ann.*, 565 22 (1949). Conversion of the sulfonic acid salt to the sulfonyl chloride is then carried out according to the teaching of *Org. Synthesis*, Coll. Vol. IV, 846, 693.

Benzenesulfonamides of Formula XXVIb can also be derived from compound XXVIa as illustrated in Equation 21.

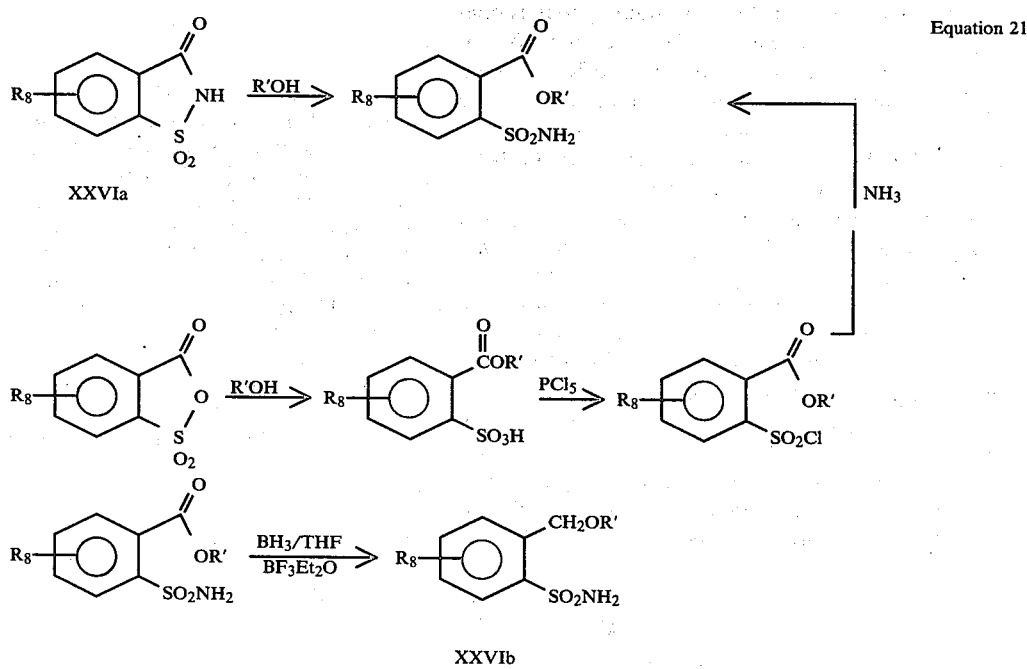

The o-alkoxyethylbenzenesulfonamides of Formula XXVIIb can be prepared from the appropriate benzenesulfonyl chlorides of Formula XXVIIa via lithiation chemistry as shown in Equation 22. Reactions of this type are well known in the literature and have been reviewed in Organic Reactions, Vol. 26, Gschwend, H. W. and Rodriguez, H. R., John Wiley and Sons, Inc., New York, 1979.

Equation 22

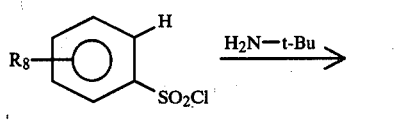

XXVIIa

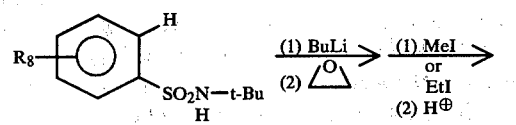

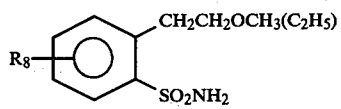

XXVIIb

Preparation of o-sulfamylbenzoic acid esters, from saccharin or sulfobenzoic acid anhydride is well known in the art, e.g., B. Loev and M. Kormendy, *J. Org. Chem.* 27, 1703 (1962). The esters can be readily reduced to the ethers with diborane in a suitable organic solvent, e.g., tetrahydrofuran, in the presence of fifteen fold excess of boron trifluoride etherate under reflux for 18 hours, as described by R. P. Graber and M. B. Meyers, *J. Org. Chem.*, 26, 4773 (1961).

Most generally, the naphthalene sulfonamides may be prepared from the sulfonyl chlorides XXVIIIb (Equation 23) as described in "Preparative Organic Chemistry", ed. G. Hilgetag and A. Martini, J. Wiley and Sons, New York (1972). The sulfonyl chlorides may be prepared by chlorination of the sulfonic acids XXVIIIa by methods described by Hilgetag and Martini, op. cit. The preparation of these acids is described in the art. These compounds may be further transferred by methods known in the art to yield other disclosed sulfonic acids.

Equation 23

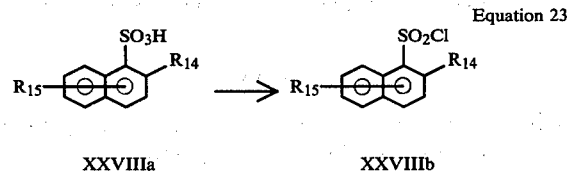

XXVIIIa    XXVIIIb

The desired sulfamyl naphthalene sulfonamides can be prepared by methods analogous to those taught in European Pat. No. 23,141.

The benzylsulfonamides of Formula XXIXd are most easily prepared as shown in Equation 24. The appropriately substituted toluene derivatives of Formula XXIXa are brominated and then reacted with thiourea to give the thiouronium salts of Formula XXIXb. Preparation of the sulfonyl chlorides of Formula XXIXc is readily accomplished by oxidation/chlorination of XXIXb [for the preparation and oxidative chlorination of thiouronium salts see: T. B. Johnson and J. M. Sprague, *J. Am. Chem. Soc.*, 58, 1348 (1936); ibid., 59, 1837, 2439 (1937); ibid., 61, 176 (1939)]. Amination of XXIXc will give the sulfonamides of Formula XXIXd.

Equation 24

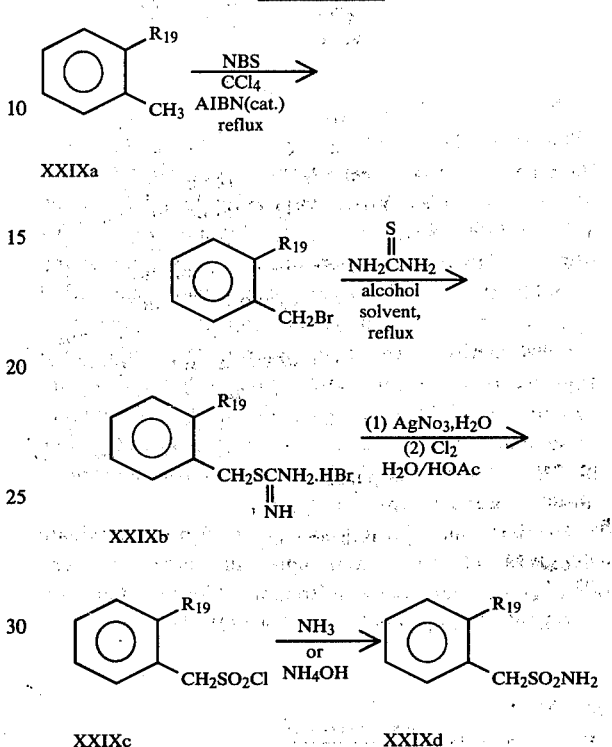

XXIXc    XXIXd

Alternatively, the benzyl chlorides of Formula XXIXe can be converted to the benzylsulfonamides of Formula XXIXd as shown in Equation 25.

Equation 25

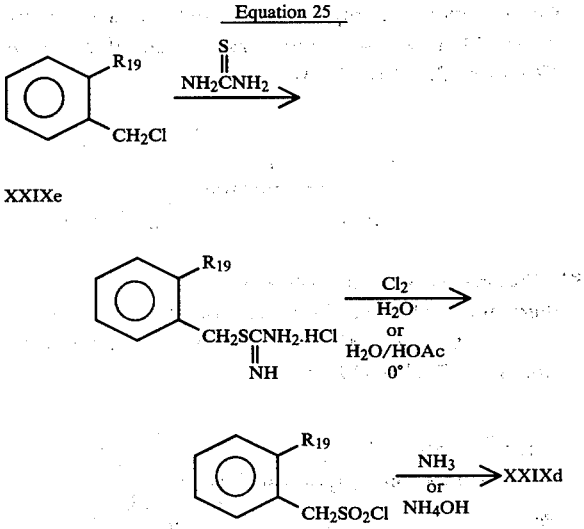

Phosgenation of XXIXd to the corresponding benzylsulfonylisocyanates of Formula XXIXf proceeds readily as shown in Equation 26. (See Equation 3 for complete details.)

Equation 26

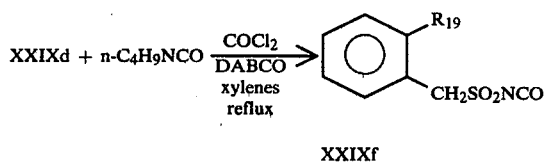

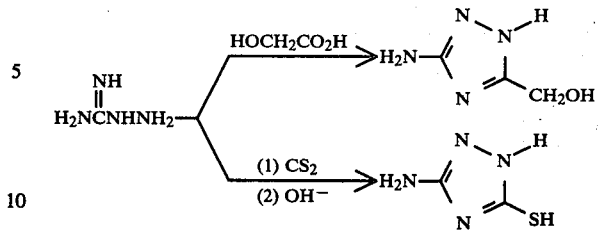

Preparation of 3-amino-1,2,4-triazoles are known in the art and 1,2,4-triazoles are reviewed in *The Chemistry of Heterocyclic Compounds* "Triazoles 1,2,4"(John Wiley & Sons, New York, 1981). Commonly used starting materials containing nitrogen are N-aminoguanidine, hydrazine, alkylhydrazines, cyanamide, ethyl cyanoacetimidate, dimethyl cyanodithioimidocarbonate, dimethyl cyanoimidocarbonate, ethoxymethylenecyanamide, and acylhydrazines. Some literature syntheses are illustrated below. Using these techniques or suitable modifications that would be apparent to one skilled in the art, the 3-amino-1,2,4-triazole intermediates can be readily prepared.

Heating equimolar amounts of ethyl propionimidate hydrochloride and N-aminoguanidine nitrate in pyridine gives 3-amino-5-ethyltriazole; German Pat. No. 1,073,499 (1960); *Berichte*, 96, 1064 (1963).

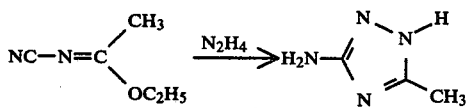

Condensation of hydrazine with ethyl N-cyanoacetimidate yields 3-amino-5-methyltriazole; *Journal of Organic Chemistry*, 28, 1816 (1963).

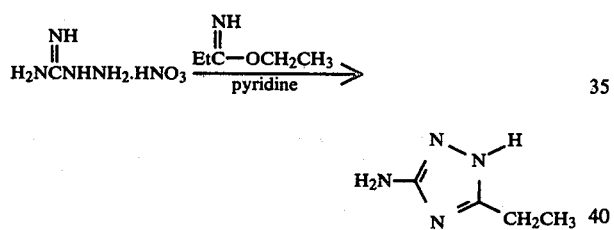

Trifluoromethyl 3-aminotriazole can be obtained by thermal dehydration of the hydrazide of trifluoroacetic acid. *Zh. Obshch. Khim.*, 39, 2525 (1969); *Chemical Abstracts*, 72: 78954v (1970).

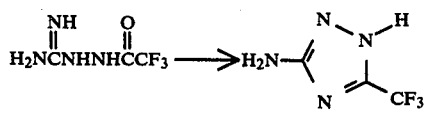

U.S. Pat. No. 2,835,581 (1958) teaches the preparation of 3-amino-5-(hydroxymethyl)triazole from N-aminoguanidine and glycolic acid and British Pat. No. 736,568 (1955) describes the synthesis of 3-amino-5mercaptotriazole.

Condensing hydrazine with dimethyl cyanodithioimidocarbonate in acetonitrile gives 3-amino-5-methylthio-1,2,4-triazole while reaction of hydrazine with dimethyl N-cyanoimidocarbonate produces 3-amino-5-methoxy-1,2,4-triazole; *Journal of Organic Chemistry*, 39, 1522 (1974).

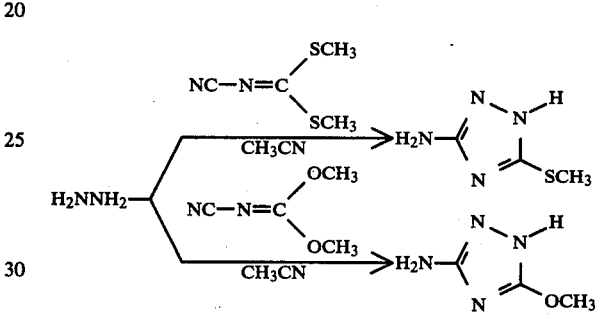

Reaction of substituted hydrazines with N-cyanothioimidocarbonates (prepared according to the procedure given in D. M. Wieland, Ph.D. Thesis, 1971, pp. 123–124) yields disubstituted aminotriazoles as shown below.

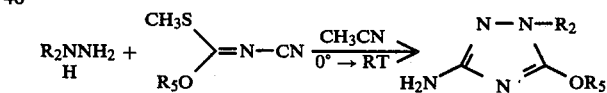

The following examples teach the preparation of compounds of this invention in more detail. Unless otherwise indicated, all parts are by weight and temperatures in °C.

EXAMPLE I

2-[[(5-Methylthio-1H-1,2,4-triazol-3-yl)aminocarbonyl]aminosulfonyl]benzoic acid, methyl ester To a mixture of 5.0 grams (0.0385 mole) 3-amino-5-methylthio-1H-1,2,4-triazole (Aldrich Chemicals) and 75 ml of dry methylene chloride stirring in a 200 ml RB single neck flask, 10.5 grams of 2-(methoxycarbonyl)-benzenesulfonylisocyanate was added at ambient temperature; a clear solution gradually formed. After stirring overnight at room temperature, the white solid which precipitated was filtered and washed with methylene chloride, yield 11.7 grams, m.p.147°–153°.

NMR (tfa-D): δ2.85 (s, 3H, SCH$_3$), 4.10 (s, 3H, CO$_2$CH$_3$), 7.60–8.55 (m, ArH). IR (Nujol): 3.0–3.20 (NH), 5.75 (C=O), 6.20 (C=N) microns.

EXAMPLE II

2-[[(1-Methyl-5-methylthio-1H-1,2,4-triazol-3-yl)aminocarbonyl]aminosulfonyl]benzoic acid, methyl ester Method A: Methyl iodide (0.6 ml) was added by syringe at ambient temperature to a stirred mixture of 0.8 grams (0.0022 mole) of methyl 2-[(5-methylthio-1H-1,2,4-triazol-3-yl)aminocarbonyl]aminosulfonylbenzoate and 0.6 grams of potassium carbonate in 30 ml of acetone in a 100 ml RB single neck flask. The mixture was stirred at room temperature overnight. The reaction mixture was then poured into 250 ml of ice water and acidified to pH 3–4 with glacial acetic acid. After extracting the aqueous mixture with 1:1 mixture of ethyl acetate and ethyl ether, the organic layer was washed with brine, dried ($MgSO_4$), filtered, and the solvent evaporated to dryness to yield a white solid residue which was suspended in acetonitrile, filtered, and recrystallized from the acetonitrile; yield 0.3 g, m.p. 198°–200°.

NMR (tfa-D): δ2.95 (s, 3H, $SCH_3$), 4.0 (s, 3H, $CH_3$), 4.15 (s, 3H, $CO_2CH_3$), 7.80–8.60 (m, ArH). IR (Nujol): 5.75–5.85 (C=O), 6.30 (C=N) 13.10, 13.55 microns.

Method B: To 1.0 gram (0.0069 mole) of 3-amino-1-methyl-5-methylthio-1H-1,2,4-triazole stirring in 15 ml of dry methylene chloride, 3.0 grams of 2-(methoxycarbonyl)benzenesulfonylisocyanate was added at ambient temperature and a cloudy solution immediately formed followed by precipitation of a white solid. The white suspension was stirred at room temperature overnight. Chlorobutane (4 ml) was added to the mixture and the white solid filtered, washed with methylene chloride followed by a chlorobutane wash, yield 2.0 g, m.p. 198°–200° (recrystallized from acetonitrile). The spectral characteristics and melting points were identical to the solid obtained in Method A. A mixed melting point was not depressed.

EXAMPLE III

3-Amino-1-methyl-5-methylthio-1H-1,2,4-triazole

At 0°, 6.5 grams of methyl hydrazine was added dropwise to a stirred suspension of 20.0 grams (0.137 mole) dimethyl cyanodithioimidocarbonate in 35 ml of acetonitrile. A yellow solution immediately formed after the addition followed by precipitation of a white solid. The ice bath was removed, and upon warming to room temperature a yellow solution formed which was stirred at room temperature overnight. After stirring overnight, a solid precipitated which was filtered, washed with cold acetonitrile, followed by 1-chlorobutane, yield 8.5 grams, m.p. 104°–109°. The literature [*Journal of Organic Chemistry*, 39, 1522 (1974)] reported a similar melting point of 103°–106° for the title compound, however, a different isomeric structure was assigned to the compound (5-amino-1-methyl-3-methylthio-1H-1,2,4-triazole). The assignment of 3-amino-1-methyl-5-methylthio-1H-1,2,4-triazole as the correct structure was verified by X-ray crystal structure analysis.

EXAMPLE IV

2-[[(1,5-Dimethyl-1H-1,2,4-triazol-3-yl)aminocarbonyl]amiosulfonyl]benzoic acid, methyl ester In 20 ml of acetonitrile at room temperature, 0.63 grams of 3-amino-1,5-dimethyl-1H-1,2,4-triazole [*Journal of Organic Chemistry*, 39, 1522 (1974)] and 1.49 grams of 2-(methoxycarbonyl)benzenesulfonylisocyanate were stirred for 12 hours. The white solid which precipitated was filtered and washed with ether to yield 1.3 grams of the title product melting at 175°–178°.

EXAMPLE V

2-[[(1-Methyl-5-methylthio-1H-1,2,4-triazol-3-yl)aminocarbonyl]aminosulfonyl]benzoic acid, 2-propyl ester A mixture of 0.7 grams (0.00486 mole) of 3-amino-1-methyl-5-methylthio-1H-1,2,4-triazole and 4.0 grams of 2-(isopropoxycarbonyl)benzenesulfonylisocyanate was stirred in 12 ml of dry methylene chloride at ambient temperature overnight. After addition of 4 ml of 1-chlorobutane, a white solid precipitated which was filtered, washed with 1-chlorobutane and dried, yield 1.3 grams, m.p. 192°–194°.

NMR (tfa-D): δ1.55 (d, 6H, $2CH_3$), 2.90 (s, 3H, $SCH_3$), 3.95 (s, 3H, $N-CH_3$), 4.90–5.40 (m, 1H, $CO_2CH$), 7.60–8.50 (m's, ArH). IR (Nujol): 2.95 (NH), 5.75 (C=O), 6.30 (C=N), 13.10, 13.50 microns.

EXAMPLE VI

2-[(1-Methyl-5-methylthio-1H-1,2,4-triazol-3-yl)aminocarbonyl]-2-nitrobenzenesulfonamide After the addition of 3.0 grams 2-nitrobenzenesulfonylisocyanate to 0.7 grams (0.00486 mole) 3-amino-1-methyl-5-methylthio-1H-1,2,4-triazole stirring in 15 ml of dry methylene chloride, a solid precipitated and the suspension was stirred at room temperature overnight. The solid was filtered and washed with 1-chlorobutane to yield 1.6 grams of product, m.p. 210°–213°.

NMR (tfa-D): δ2.90 (s, 3H, $SCH_3$), 4.00 (s, 3H, $N-CH_3$), 7.85–8.60 (m, ArH), IR (Nujol): 3.0–3.20 (NH), 5.80 (C=O), 6.25 (C=N), 12.70, 13.45, 13.60 microns.

EXAMPLE VII

2-[[(1-Ethyl-5-methylthio-1H-1,2,4-triazol-3-yl)aminocarbonyl]aminosulfonyl]benzoic acid, methyl ester To a stirred mixture of 1.0 gram (0.0027 mole) of methyl 2-[(5-methylthio-1H-1,2,4-triazol-3-yl)aminocarbonyl]aminosulfonylbenzoate and 0.7 grams of potassium carbonate in 30 ml of acetone at room temperature, 0.8 ml of ethyl iodine was added by way of syringe and the resulting white suspension stirred 3 days. The mixture was poured into 250 ml of ice water and acidified to pH 3–4 with glacial acetic acid. The aqueous acidic mixture was extracted with 1:1 mixture of ethyl ether/ethyl acetate and the extract washed with brine, dried ($MgSO_4$), and evaporated to yield a white solid residue which was suspended in acetonitrile and filtered, yield 0.3 grams, m.p. 188°–191°.

NMR (tfa-D): δ1.45 (t, 3H, $CH_3$), 2.80 (s, 3H, $SCH_3$), 4.05 (s, 3H, $CO_2CH_3$), 4.25 (q, 2H, $CH_2$), 7.60–8.45 (m, ArH).

EXAMPLE VIII

3-Amino-5-methoxy-1-methyl-1H-1,2,4-triazole

Methylhydrazine (98%, 6.30 g, 0.136 mol) was added dropwise to a solution of dimethyl-N-cyanothioimidocarbonate (17.3 g, 0.133 mol, prepared according to procedure given in D. M. Wieland, Ph.D. Thesis, 1971, pp. 123–124.) in acetonitrile (35 ml) at −5°–0° with stirring under nitrogen. The reaction mixture was allowed to warm to room temperature and stirred for 2 days. Isolation of the product by filtration and washing with acetonitrile gave 12.7 g of a white powder, m.p. 177°–180°.

NMR (DMSO/CDCl$_3$): δ3.35 (s, N-CH$_3$), 3.95 (s, O-CH$_3$); and 5.0 (broad, NH$_2$).

EXAMPLE IX

2-[[(5-Methoxy-1-methyl-1H-1,2,4-triazol-3-yl)aminocarbonyl]aminosulfonyl]benzoic acid, methyl ester To a solution of 2-(methoxycarbonyl)benzenesulfonylisocyanate (80%, 1.41 g, 4.7 mmol) in methylene chloride (10 ml) at room temperature under nitrogen was added 3-amino-5-methoxy-1-methyl-1H-1,2,4-triazole (0.50 g, 3.9 mmol). DABCO (catalytic amount) was added, and the reaction mixture was stirred for 3 days. Isolation of the product by filtration and washing with methylene chloride gave 1.05 g of a white powder, m.p. 177°–180°.

NMR (CDCl$_3$/DMSO): δ3.5 (s, N-CH$_3$); 3.9 (s, CO$_2$CH$_3$); 4.1 (s, O-CH$_3$); 7.5–7.8 (m, Ar-H); 8.1–8.4 (m, Ar-H); 9.7 (broad, NH); and 11.0 (broad, NH).

IR(KBr) 3150 (NH), 1740 (c=o), 1700 (c=o), 1600, 1530, 1475, 1420, 1360 (SO$_2$), 1340, 1295, 1260, 1180 (SO$_2$), 1115 and 1050 cm$^{-1}$.

By application of one or more of the procedures of Examples I-IX and/or the methods described above and using the appropriate reactants, the compounds of Tables 1 to 12 can be prepared.

TABLE 1

| R$_1$ | R$_2$ | R$_3$ | W | R$_7$ | R$_8$ | m.p. (°C.) |
|---|---|---|---|---|---|---|
| H | n-C$_3$H$_7$ | H | O | CO$_2$CH$_3$ | H | |
| H | C$_2$H$_5$ | H | O | CO$_2$C$_2$H$_5$ | H | |
| H | CH(CH$_3$)$_2$ | H | O | SO$_2$CH$_3$ | H | |
| CH$_3$ | C$_2$H$_5$ | H | O | CO$_2$CH$_3$ | H | |
| CH$_3$ | C$_2$H$_5$ | H | S | Cl | H | |
| CH$_3$ | C$_2$H$_5$ | CH$_3$ | O | CO$_2$CH$_3$ | H | |
| CH$_3$ | C$_2$H$_5$ | CH$_3$ | O | SO$_2$CH$_3$ | H | |
| CH$_3$ | C$_2$H$_5$ | H | O | CF$_3$ | H | |
| CH$_3$ | C$_2$H$_5$ | H | O | Br | H | |
| CH$_3$ | C$_2$H$_5$ | H | O | Cl | H | |
| CH$_3$ | C$_2$H$_5$ | H | S | CH$_3$ | H | |
| CH$_3$ | C$_2$H$_5$ | H | O | C$_2$H$_5$ | H | |
| CH$_3$ | C$_2$H$_5$ | H | O | NO$_2$ | H | |
| CH$_3$ | C$_2$H$_5$ | H | O | SO$_2$(CH$_2$)$_2$CH$_3$ | H | |
| CH$_3$ | C$_2$H$_5$ | H | O | SO$_2$N(CH$_3$)$_2$ | H | |
| CH$_3$ | C$_2$H$_5$ | CH$_3$ | O | NO$_2$ | H | |
| CH$_3$ | C$_2$H$_5$ | H | O | OCH$_3$ | H | |
| OCH$_3$ | C$_2$H$_5$ | H | O | CO$_2$CH(CH$_3$)$_2$ | H | |
| CH$_3$ | C$_2$H$_5$ | H | O | CO$_2$CH$_2$CH=CH$_2$ | H | |
| OCH$_3$ | C$_2$H$_5$ | H | O | OCF$_2$CF$_2$H | H | |
| CH$_3$ | C$_2$H$_5$ | H | O | CH$_2$OCH$_3$ | H | |
| OCH$_3$ | C$_2$H$_5$ | H | O | OSO$_2$CHCl$_2$ | H | |
| CH$_3$ | C$_2$H$_5$ | H | O | CF$_3$ | H | |
| CH$_3$ | C$_2$H$_5$ | H | O | SC$_2$H$_5$ | H | |
| OCH$_3$ | C$_2$H$_5$ | H | O | OSO$_2$C$_2$H$_5$ | H | |
| OCH$_3$ | C$_2$H$_5$ | H | O | OSO$_2$CH$_2$CF$_3$ | H | |
| CH$_3$ | C$_2$H$_5$ | H | O | CO$_2$CH$_2$CH$_2$Cl | H | |
| OCH$_3$ | C$_2$H$_5$ | H | O | OSO$_2$CH$_2$CH$_2$OCH$_3$ | H | |
| OCH$_3$ | C$_2$H$_5$ | H | O | SO$_2$N(OCH$_3$)CH$_3$ | H | |
| OC$_2$H$_5$ | CH$_3$ | H | O | CO$_2$CH$_3$ | H | 165–166° |
| C$_2$H$_5$ | CH$_3$ | H | O | Br | H | |
| C$_2$H$_5$ | CH$_3$ | H | O | NO$_2$ | H | |
| C$_2$H$_5$ | CH$_3$ | CH$_3$ | O | CO$_2$CH$_3$ | H | |
| C$_2$H$_5$ | CH$_3$ | CH$_3$ | O | SO$_2$CH$_3$ | H | |
| OC$_2$H$_5$ | CH$_3$ | CH$_3$ | O | CO$_2$CH$_2$CH$_2$OCH$_3$ | H | |
| OC$_2$H$_5$ | CH$_3$ | CH$_3$ | O | OSO$_2$CH$_2$(CH$_2$)$_2$OCH$_3$ | H | |
| C$_2$H$_5$ | CH$_3$ | H | S | CH$_3$ | H | |
| C$_2$H$_5$ | CH$_3$ | H | S | Cl | H | |
| C$_2$H$_5$ | CH$_3$ | CH$_3$ | O | CH$_3$ | H | |
| C$_2$H$_5$ | CH$_3$ | H | O | CO$_2$CH(CH$_3$)$_2$ | H | |
| C$_2$H$_5$ | CH$_3$ | H | O | Cl | H | |
| C$_2$H$_5$ | CH$_3$ | H | O | CO$_2$CH$_2$CH=CH$_2$ | H | |
| OC$_2$H$_5$ | CH$_3$ | H | O | OSO$_2$CH$_2$CF$_2$H | H | |
| OC$_2$H$_5$ | CH$_3$ | H | O | OSO$_2$CCl$_3$ | H | |
| OC$_2$H$_5$ | CH$_3$ | H | O | OSO$_2$CHCl$_2$ | H | |
| C$_2$H$_5$ | CH$_3$ | H | O | OSO$_2$CH$_3$ | H | |
| C$_2$H$_5$ | CH$_3$ | H | O | CH$_2$OC$_2$H$_5$ | H | |
| C$_2$H$_5$ | CH$_3$ | H | O | SO$_2$C$_2$H$_5$ | H | |
| OC$_2$H$_5$ | CH$_3$ | H | O | OSO$_2$CF$_3$ | H | |
| C$_2$H$_5$ | CH$_3$ | H | O | OCF$_3$ | H | |
| OC$_2$H$_5$ | CH$_3$ | H | O | OCH$_3$ | H | |
| C$_2$H$_5$ | CH$_3$ | H | O | NO$_2$ | 5-CF$_3$ | |
| C$_2$H$_5$ | CH$_3$ | H | O | NO$_2$ | 3-Cl | |

TABLE 1-continued $$\begin{array}{c} R_2 \\ \diagdown N^1 - N^2 \\ R_1 - \overset{5}{\underset{N_4}{\diagdown}} \overset{3}{\underset{}{\diagdown}} \overset{W}{\underset{R_3}{\overset{\|}{N}CNHSO_2}} - \text{phenyl}(R_7, R_8) \end{array}$$

| $R_1$ | $R_2$ | $R_3$ | W | $R_7$ | $R_8$ | m.p. (°C) |
|---|---|---|---|---|---|---|
| $C_2H_5$ | $CH_3$ | H | O | Cl | 6-$NO_2$ | |
| $C_2H_5$ | $CH_3$ | H | O | $CF_3$ | 5-$NO_2$ | |
| $CH_3$ | $C_2H_5$ | H | O | Cl | 5-Cl | |
| $OCH_3$ | $C_2H_5$ | H | O | $NO_2$ | 5-Cl | |
| $CH_3$ | $C_2H_5$ | H | O | $SO_2N(CH_3)_2$ | 3-Cl | |
| $OC_2H_5$ | $CH_3$ | H | O | $CO_2CH_3$ | 5-$C_2H_5$ | |
| $C_2H_5$ | $CH_3$ | H | O | Cl | 3-Br | |
| $OC_2H_5$ | $CH_3$ | H | O | Cl | 5-Br | |
| $C_2H_5$ | $CH_3$ | H | O | $NO_2$ | 6-F | |
| $OC_2H_5$ | $CH_3$ | H | O | Cl | 5-F | |
| $C_2H_5$ | $CH_3$ | H | O | Cl | 4-F | |
| $OC_2H_5$ | $CH_3$ | H | O | Br | 3-F | |
| $C_2H_5$ | $CH_3$ | H | O | $NO_2$ | 5-$NO_2$ | |
| $C_2H_5$ | $CH_3$ | H | O | $CO_2CH_3$ | 3-$CF_3$ | |
| $OC_2H_5$ | $CH_3$ | H | O | $CH_3$ | 3-$NO_2$ | |
| $C_2H_5$ | $C_2H_5$ | H | O | $CO_2CH_3$ | H | |
| $C_2H_5$ | $CH_3$ | H | O | $CO_2C_2H_5$ | H | |
| $C_2H_5$ | $C_2H_5$ | H | S | Cl | H | |
| $C_2H_5$ | $C_2H_5$ | H | O | $NO_2$ | H | |
| $C_2H_5$ | $C_2H_5$ | H | S | $CH_3$ | H | |
| $C_2H_5$ | $C_2H_5$ | H | O | $CO_2CH_2CH=CH_2$ | H | |
| $C_2H_5$ | $C_2H_5$ | H | O | $CO_2CH(CH_3)_2$ | H | |
| $C_2H_5$ | $C_2H_5$ | H | O | $SO_2CH_3$ | H | |
| $C_2H_5$ | $C_2H_5$ | H | O | $SO_2(CH_2)_2CH_3$ | H | |
| $OC_2H_5$ | $C_2H_5$ | H | O | $SO_2CHF_2$ | H | |
| $C_2H_5$ | $C_2H_5$ | H | O | $SO_2N(CH_3)_2$ | H | |
| $C_2H_5$ | $C_2H_5$ | H | O | $SO_2N(OCH_3)CH_3$ | H | |
| $OC_2H_5$ | $C_2H_5$ | H | O | $OSO_2CH_3$ | H | |
| $C_2H_5$ | $C_2H_5$ | H | O | $(CH_2)_2CH_3$ | H | |
| $C_2H_5$ | $C_2H_5$ | H | O | $OC_2H_5$ | H | |
| $C_2H_5$ | $C_2H_5$ | H | O | $SCH_3$ | H | |
| $CH(CH_3)_2$ | $CH_3$ | H | O | $NO_2$ | H | |
| n-$C_3H_7$ | $CH_3$ | H | O | Cl | H | |
| $CH_2CH(CH_3)_2$ | $CH_3$ | H | O | $CO_2CH_3$ | H | |
| $CH_2CH=CH_2$ | $CH_3$ | H | O | $CF_3$ | H | |
| $CH_2C(CH_3)=CH_2$ | $CH_3$ | H | O | $CO_2CH_3$ | H | |
| $CH_2C\equiv CH$ | $CH_3$ | H | O | $CO_2CH_3$ | H | |
| $CH_2C\equiv CCH_3$ | $CH_3$ | H | O | $CO_2CH_3$ | H | |
| $OCH_3$ | $CH_2CH=CH_2$ | H | O | $CO_2C_2H_5$ | H | |
| $CH_3$ | $CH_2C(CH_3)=CH_2$ | H | O | $SO_2CH_3$ | H | |
| $CH_3$ | $CH_2CH=CHCH_3$ | H | O | $CO_2CH_3$ | H | |
| $CH_3$ | $CH_2C\equiv CCH_3$ | H | O | $CO_2CH_3$ | H | |
| $OCH_3$ | $CH_2C\equiv CH$ | H | O | $NO_2$ | H | |
| $SCH_3$ | $CH_3$ | $CH_3$ | O | $CO_2CH_3$ | H | |
| $SCH_3$ | $CH_3$ | H | O | $SO_2CH_3$ | H | 208–213° |
| $SCH_3$ | $CH_3$ | $CH_3$ | O | $NO_2$ | H | |
| $SCH_3$ | $CH_3$ | $CH_3$ | O | $SO_2N(CH_3)_2$ | H | |
| $SCH_3$ | $CH_3$ | $CH_3$ | O | $SO_2N(CH_3)C_2H_5$ | H | |
| $SCH_3$ | $CH_3$ | H | S | $CH_3$ | H | |
| $SCH_3$ | $CH_3$ | H | S | $NO_2$ | H | |
| $SCH_3$ | $CH_3$ | H | O | Cl | H | 230–237° |
| $SCH_3$ | $CH_3$ | H | O | $OSO_2CH_3$ | H | |
| $SCH_3$ | $CH_3$ | H | O | $CO_2CH_2CH_2CH_3$ | H | |
| $SCH_3$ | $CH_3$ | H | O | $CO_2CH_2CH=CH_2$ | H | 160–163° |
| $SCH_3$ | $CH_3$ | H | O | $CO_2CH_2CH_2Cl$ | H | |
| $SCH_3$ | $CH_3$ | H | O | $CO_2CH_2CH_2OCH_3$ | H | |
| $SCH_3$ | $CH_3$ | H | O | $CO_2CH(CH_3)C_2H_5$ | H | |
| $SCH_3$ | $CH_3$ | H | O | $CO_2(CH_2)_3CH_3$ | H | |
| $SCH_3$ | $CH_3$ | H | O | $OSO_2(CH_2)_3CH_3$ | H | |
| $SCH_3$ | $CH_3$ | H | O | $OSO_2(CH_2)_3OCH_3$ | H | |
| $SCH_3$ | $CH_3$ | H | O | $CH_2OCH_3$ | H | |
| $SCH_3$ | $CH_3$ | H | O | $OSO_2CH_2CF_2H$ | H | |
| $SCH_3$ | $CH_3$ | H | O | H | H | |
| $SCH_3$ | $CH_3$ | H | O | F | H | |
| $SCH_3$ | $CH_3$ | H | O | H | 4-F | |
| $SCH_3$ | $CH_3$ | H | O | H | 5-F | |
| $SCH_3$ | $CH_3$ | H | O | $OSO_2CH_2CCl_3$ | H | |
| $SCH_3$ | $CH_3$ | H | O | $OSO_2CH_2CHCl_2$ | H | |
| $SCH_3$ | $CH_3$ | $CH_3$ | O | $SO_2CH_3$ | H | |
| $SCH_3$ | $CH_3$ | H | O | $OSO_2CF_3$ | H | |
| $SCH_3$ | $CH_3$ | H | O | $OSO_2CHCl_2$ | H | |
| $SCH_3$ | $CH_3$ | H | O | $SO_2(CH_2)_2CH_3$ | H | |

TABLE 1-continued

| R1 | R2 | R3 | W | R7 | R8 | m.p. (°C.) |
|---|---|---|---|---|---|---|
| SCH3 | CH3 | H | O | SO2N(CH3)2 | H | |
| SCH3 | CH3 | H | O | SO2N(C2H5)2 | H | |
| SCH3 | CH3 | H | O | SO2N(CH3)[CH(CH3)2] | H | |
| SCH3 | CH3 | H | O | SO2CH(CH3)2 | H | |
| SCH3 | CH3 | H | O | CH2OC2H5 | H | |
| SCH3 | CH3 | H | O | C2H5 | H | |
| SCH3 | CH3 | H | O | CF3 | H | |
| SCH3 | CH3 | H | O | Cl | 5-Br | |
| SCH3 | CH3 | H | O | Cl | 6-Cl | |
| SCH3 | CH3 | H | O | NO2 | 5-Cl | |
| SCH3 | CH3 | H | O | CO2CH3 | 3-Br | |
| SCH3 | CH3 | H | O | SO2CH3 | 4-OCH3 | |
| SCH3 | CH3 | H | O | CO2CH3 | 4-OCH3 | |
| SCH3 | CH3 | H | O | Cl | 5-NO2 | |
| SCH3 | CH3 | H | O | SO2N(CH3)2 | 5-NO2 | |
| SCH3 | CH3 | H | O | Cl | 5-CH(CH3)2 | |
| SCH3 | CH3 | H | O | NO2 | 5-C2H5 | |
| SCH3 | CH3 | H | O | NO2 | 5-CF3 | |
| SCH3 | CH3 | H | O | NO2 | 3-CF3 | |
| SCH3 | CH3 | H | O | SCF3 | H | |
| SCH3 | CH3 | H | O | OCF3 | H | |
| SCH3 | CH3 | H | O | NO2 | 6-F | |
| SCH3 | CH3 | H | O | Cl | 5-OC2H5 | |
| SCH3 | CH3 | H | O | Br | 5-NO2 | |
| SCH3 | CH3 | H | O | NO2 | 3-F | |
| SCH3 | CH3 | H | O | Cl | 5-F | |
| SCH3 | CH3 | H | O | NO2 | 6-F | |
| SCH3 | CH3 | H | O | Cl | 4-F | |
| SCH3 | CH3 | H | O | OSO2CHF2 | H | |
| SCH3 | CH3 | H | O | OSO2(CH2)3Br | H | |
| SC2H5 | CH3 | H | O | CO2CH3 | H | 205–208° |
| SC2H5 | CH3 | H | O | SO2CH3 | H | |
| SC2H5 | CH3 | CH3 | O | SO2CH3 | H | |
| SC2H5 | CH3 | H | O | NO2 | H | 186–190° |
| SC2H5 | CH3 | H | S | Cl | H | |
| SC2H5 | CH3 | H | S | CH3 | H | |
| SC2H5 | CH3 | H | O | CF3 | H | |
| SC2H5 | CH3 | H | O | CO2CH(CH3)2 | H | 152–156° |
| SC2H5 | CH3 | H | O | CO2CH2CH=CH2 | H | 172–174° |
| SC2H5 | CH3 | CH3 | O | NO2 | H | |
| SC2H5 | CH3 | H | O | CH2OCH3 | H | |
| SC2H5 | CH3 | H | O | SO2C2H5 | H | |
| SC2H5 | CH3 | H | O | SO2N(CH3)C2H5 | H | |
| SC2H5 | CH3 | H | O | Br | H | |
| SC2H5 | CH3 | H | O | OCF3 | H | |
| SCH3 | C2H5 | H | O | CO2CH3 | H | |
| SCH3 | C2H5 | H | O | Cl | H | |
| SCH3 | C2H5 | H | O | NO2 | H | |
| SCH3 | C2H5 | H | S | Br | H | |
| SCH3 | C2H5 | H | S | CH3 | H | |
| SCH3 | C2H5 | H | O | CF3 | H | |
| SCH3 | C2H5 | H | O | OCH3 | H | |
| SCH3 | C2H5 | H | O | CO2(CH2)2CH3 | H | |
| SCH3 | C2H5 | H | O | OSO2(CH2)2CH3 | H | |
| SCH3 | C2H5 | H | O | SO2N(CH3)C2H5 | H | |
| SCH3 | C2H5 | H | O | SO2N(OCH3)CH3 | H | |
| SCH3 | C2H5 | H | O | SO2(CH2)2CH3 | H | |
| SCH3 | C2H5 | H | O | OCHF2 | H | |
| SCH3 | C2H5 | H | O | CH(CH3)2 | H | |
| SCH3 | C2H5 | H | O | SCF3 | H | |
| SCH3 | C2H5 | H | O | OSO2(CH2)2OCH3 | H | |
| SCH3 | C2H5 | H | O | SC2H5 | H | |
| S(CH2)2CH3 | CH3 | H | O | Cl | H | |
| S(CH2)2CH3 | CH3 | H | O | CO2CH3 | H | |
| SCH(CH3)2 | CH3 | H | O | CO2C2H5 | H | |
| S(CH2)3CH3 | CH3 | H | O | SO2CH3 | H | |
| SCH(CH3)C2H5 | CH3 | H | O | CO2C2H5 | H | |
| SCH2CH=CH2 | CH3 | H | O | NO2 | H | |
| SCH2C(CH3)=CH2 | CH3 | H | O | CO2CH3 | H | |
| SCH2CH=CHCH3 | CH3 | H | O | SO2CH3 | H | |
| SCH2CO2CH3 | CH3 | H | O | Cl | H | |
| SCH2CO2(CH2)3CH3 | CH3 | H | O | Br | H | |

TABLE 1-continued

| R₁ | R₂ | R₃ | W | R₇ | R₈ | m.p. (°C.) |
|---|---|---|---|---|---|---|
| SCH(CH₃)CO₂CH₃ | CH₃ | H | O | NO₂ | H | |
| SCH₂C≡CH | CH₃ | H | O | CO₂CH₃ | H | |
| SCH₂C≡CCH₃ | CH₃ | H | O | CO₂CH₃ | H | |
| CH₃ | CH₂OCH₃ | H | O | CO₂C₂H₅ | H | |
| CH₃ | CH₂OCH₃ | H | O | SO₂C₂H₅ | H | |
| CH₃ | CH₂SCH₃ | H | O | CH₂OCH₃ | H | |
| CH₃ | CH₂CH₂OCH₃ | H | O | Cl | H | |
| CH₃ | CH₂CH₂SCH₃ | H | O | SO₂CH₃ | H | |
| CH₂OC₂H₅ | CH₃ | H | O | CH₃ | H | |
| CH₂OC₂H₅ | CH₃ | H | O | CO₂CH(CH₃)₂ | H | |
| CH₂OC₂H₅ | CH₃ | CH₃ | O | CO₂CH₃ | H | |
| CH₂OCH(CH₃)₂ | CH₃ | H | O | Br | H | |
| CH₂O(CH₂)₃CH₃ | CH₃ | H | O | SO₂C₂H₅ | H | |
| CH₂CH₂OCH₃ | CH₃ | H | O | NO₂ | H | |
| CH₂CH₂OC₂H₅ | CH₃ | H | O | CO₂CH₃ | H | |
| CH₂CH₂O(CH₂)₂CH₃ | CH₃ | H | O | CO₂CH₃ | H | |
| OCH₃ | CH₃ | H | S | Cl | H | |
| OCH₃ | C₂H₅ | H | S | NO₂ | H | |
| OCH₃ | C₂H₅ | H | S | CH₃ | H | |
| OCH₃ | CH₃ | H | S | CF₃ | H | |
| OCH₃ | CH₃ | H | S | Br | H | |
| OCH₃ | CH₃ | CH₃ | O | CO₂CH₃ | H | |
| OCH₃ | CH₃ | CH₃ | O | SO₂CH₃ | H | |
| OCH₃ | CH₃ | CH₃ | O | SCH₃ | H | |
| OCH₃ | CH₃ | H | O | OSO₂(CH₂)₃OCH₃ | H | |
| OCH₃ | C₂H₅ | H | O | OSO₂CH₂CHCl₂ | H | |
| OCH₃ | C₂H₅ | H | O | OSO₂CH₂CF₂H | H | |
| OCH₃ | C₂H₅ | H | O | OCF₃ | H | |
| OCH₃ | C₂H₅ | H | O | SCHF₂ | H | |
| OCH₃ | C₂H₅ | H | O | OSO₂CH(CH₃)₂ | H | |
| OC₂H₅ | CH₃ | H | O | H | H | |
| OC₂H₅ | CH₃ | H | O | F | H | |
| OC₂H₅ | CH₃ | H | O | CO₂CH₃ | 3-Br | |
| OC₂H₅ | CH₃ | H | O | SO₂CH₃ | H | 190–208° |
| OC₂H₅ | CH₃ | H | O | S(CH₂)₃CH₃ | H | |
| OC₂H₅ | CH₃ | H | O | OSO₂(CH₂)₃CH₃ | H | |
| OC₂H₅ | CH₃ | H | O | OCF₃ | H | |
| OC₂H₅ | CH₃ | H | O | SCF₃ | H | |
| OC₂H₅ | CH₃ | H | O | OCHF₂ | H | |
| OC₂H₅ | CH₃ | H | O | SCHF₂ | H | |
| OC₂H₅ | CH₃ | H | O | OCF₂CF₂H | H | |
| OC₂H₅ | CH₃ | H | O | SCF₂CF₂H | H | |
| OC₂H₅ | CH₃ | H | O | CH₂OC₂H₅ | H | |
| OC₂H₅ | CH₃ | H | O | SCH₃ | H | |
| OC₂H₅ | CH₃ | H | O | CO₂CH₂CH₂Cl | H | |
| OC₂H₅ | CH₃ | H | O | CO₂CH₂CH=CH₂ | H | 119–122° |
| OC₂H₅ | CH₃ | H | O | CO₂CH(CH₃)₂ | H | |
| OC₂H₅ | CH₃ | H | O | OSO₂CHFCF₂H | H | |
| OC₂H₅ | CH₃ | H | O | OSO₂CHFCCl₃ | H | |
| OC₂H₅ | CH₃ | H | O | OSO₂CHFCH₂F | H | |
| OC₂H₅ | CH₃ | H | O | CO₂C₂H₅ | H | 148–151° |
| OC₂H₅ | CH₃ | H | O | OSO₂CH₂CH₂Cl | H | |
| OC₂H₅ | CH₃ | H | O | SO₂N(CH₃)₂ | H | 169–175° |
| OC₂H₅ | CH₃ | H | O | SO₂N(CH₃)[(CH₂)₂CH₃] | H | |
| OC₂H₅ | CH₃ | H | O | CO₂CH₂CH(CH₃)₂ | H | |
| OC₂H₅ | CH₃ | H | O | OCH₂CH(CH₃)₂ | H | |
| OC₂H₅ | CH₃ | H | O | CO₂CH₃ | H | 187–189° |
| OC₂H₅ | CH₃ | CH₃ | O | SO₂CH₃ | H | |
| OC₂H₅ | CH₃ | CH₃ | O | CO₂CH₃ | H | |
| OC₂H₅ | CH₃ | CH₃ | O | OSO₂CH(CH₃)₂ | H | |
| OC₂H₅ | CH₃ | CH₃ | O | CF₃ | H | |
| OC₂H₅ | CH₃ | CH₃ | O | OCF₂CF₂H | H | |
| OC₂H₅ | C₂H₅ | CH₃ | O | Cl | H | |
| OC₂H₅ | C₂H₅ | H | O | SCHF₂ | H | |
| OC₂H₅ | C₂H₅ | H | O | SO₂(CH₂)₂CH₃ | H | |
| OC₂H₅ | C₂H₅ | H | O | CO₂C₂H₅ | H | |
| OC₂H₅ | CH₃ | H | O | OSO₂(CH₂)₃Cl | H | |
| O(CH)CH₃ | CH₃ | H | O | Cl | H | |
| O(CH₂)₂CH₃ | CH₃ | H | O | C₂H₅ | H | |
| OCH(CH₃)₂ | CH₃ | H | O | CO₂CH(CH₃)₂ | H | |
| O(CH₂)₃CH₃ | CH₃ | H | O | CO₂CH₃ | H | |
| OCH₂CH=CH₂ | CH₃ | H | O | SO₂CH₃ | H | |

TABLE 1-continued

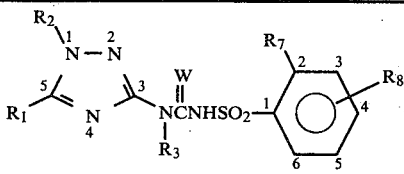

| R1 | R2 | R3 | W | R7 | R8 | m.p. (°C.) |
|---|---|---|---|---|---|---|
| OCH2C(CH3)=CH2 | CH3 | H | O | CO2CH3 | H | |
| OCH2C≡CCH3 | CH3 | H | O | CO2CH3 | H | |
| OCH2C≡CH | CH3 | H | O | CO2C2H5 | H | |
| CF3 | CH3 | H | O | CO2CH3 | H | |
| CF3 | CH3 | H | O | Cl | H | |
| CF3 | C2H5 | H | O | NO2 | H | |
| CF3 | C2H5 | H | O | CH3 | H | |
| CF2CF3 | CH3 | H | O | CO2CH(CH3)2 | H | |
| CF2CF3 | CH3 | H | O | CO2CH3 | H | |
| N(CH3)2 | CH3 | H | O | CO2CH3 | H | |
| CF3 | C2H5 | H | O | CO2CH3 | H | |
| CF3 | C2H5 | H | O | CF3 | H | |
| CF3 | C2H5 | H | O | CH2OCH3 | H | |
| SCH3 | CH2CH=CH2 | H | O | CO2CH3 | H | 146–149° |
| SC2H5 | CH3 | H | O | CH3 | 5-CH3 | 193–195° |
| SC2H5 | C2H5 | H | O | CO2CH3 | H | 150–152° |
| CH(CH3)2 | CH3 | H | O | CO2CH3 | H | 190–197° |
| OCH3 | CH3 | H | H | H | H | |
| OCH3 | CH3 | H | H | CH3 | H | 210–213° |
| OCH3 | CH3 | H | H | C2H5 | H | |
| OCH3 | CH3 | H | H | CH2CH2CH3 | H | |
| OCH3 | CH3 | H | H | CH(CH3)2 | H | |
| OCH3 | CH3 | H | H | (CH2)3CH3 | H | |
| OCH3 | CH3 | H | H | OCH3 | H | |
| OCH3 | CH3 | H | H | OCH2CH3 | H | |
| OCH3 | CH3 | H | H | OCH2CH2CH3 | H | 154–157° |
| OCH3 | CH3 | H | H | OCH(CH3)C2H5 | H | |
| OCH3 | CH3 | H | H | F | H | |
| OCH3 | CH3 | H | H | Cl | H | 200–205° |
| OCH3 | CH3 | H | H | Br | H | |
| OCH3 | CH3 | H | H | NO2 | H | 185–189° |
| OCH3 | CH3 | H | H | CF3 | H | |
| OCH3 | CH3 | H | H | CO2C2H5 | H | 144–148° |
| OCH3 | CH3 | H | H | CO2(CH2)2CH3 | H | 117–120° |
| OCH3 | CH3 | H | H | CO2CH(CH3)2 | H | 165–169° |
| OCH3 | CH3 | H | H | CO2CH(CH3)C2H5 | H | |
| OCH3 | CH3 | H | H | CO2(CH2)5CH3 | H | |
| OCH3 | CH3 | H | H | CO2CH2CH=CH2 | H | 139–144° |
| OCH3 | CH3 | H | H | CO2CH2CH=CHCH3 | H | |
| OCH3 | CH3 | H | O | CO2CH2C≡CH | H | |
| OCH3 | CH3 | H | O | CO2CH2CH2OCH3 | H | |
| OCH3 | CH3 | H | O | CO2CH2CH2Cl | H | |
| OCH3 | CH3 | H | O | CO2CH2CH2OC2H5 | H | |
| OCH3 | CH3 | H | O | CO2(CH2)3OC2H5 | H | |
| OCH3 | CH3 | H | O | CO2CH2C≡CC2H5 | H | |
| OCH3 | CH3 | H | O | CO2CF2CFH2 | H | |
| OCH3 | CH3 | H | O | CO2CH2CH2—F | H | |
| OCH3 | CH3 | H | O | CO2CH2CHFCF2H | H | |
| OCH3 | CH3 | H | O | SO2N(CH3)2 | H | 183–186° |
| OCH3 | CH3 | H | O | SO2N(C2H5)2 | H | |
| OCH3 | CH3 | H | O | SO2N(CH3)C2H5 | H | |
| OCH3 | CH3 | H | O | SO2N(CH3)CH2CH2CH3 | H | |
| OCH3 | CH3 | H | O | SO2N(OCH3)CH3 | H | |
| OCH3 | CH3 | H | O | OSO2CH3 | H | 174–176° |
| OCH3 | CH3 | H | O | OSO2C2H5 | H | |
| OCH3 | CH3 | H | O | OSO2CH2CH2CH3 | H | |
| OCH3 | CH3 | H | O | OSO2CH2CH2OCH3 | H | |
| OCH3 | CH3 | H | O | OSO2CF3 | H | |
| OCH3 | CH3 | H | O | OSO2CH2CH2Cl | H | |
| OCH3 | CH3 | H | O | SOCH3 | H | |
| OCH3 | CH3 | H | O | SCH3 | H | |
| OCH3 | CH3 | H | O | SO2CH3 | H | 183–190° |
| OCH3 | CH3 | H | O | SC2H5 | H | |
| OCH3 | CH3 | H | O | SO2C2H5 | H | 174–177° |
| OCH3 | CH3 | H | O | SO2CH2CH2CH3 | H | |
| OCH3 | CH3 | H | O | SO2CH(CH3)2 | H | |
| OCH3 | CH3 | H | O | SO2(CH2)3CH3 | H | |
| OCH3 | CH3 | H | O | SO2CH2CH=CH2 | H | |
| OCH3 | CH3 | H | O | SO2CF3 | H | |
| OCH3 | CH3 | H | O | SO2CH2CH2Cl | H | |
| OCH3 | CH3 | H | O | SO2CF2CF3 | H | |
| OCH3 | CH3 | H | O | SO2CCl2CF3 | H | |

TABLE 1-continued

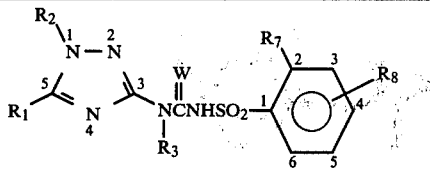

| R₁ | R₂ | R₃ | W | R₇ | R₈ | m.p. (°C.) |
|---|---|---|---|---|---|---|
| OCH₃ | CH₃ | H | O | N(CH₃)SO₂CH₃ | H | |
| OCH₃ | CH₃ | H | O | N(CH₃)SO₂C₂H₅ | H | |
| OCH₃ | CH₃ | H | O | N(CH₃)SO₂(CH₂)₃CH₃ | H | |
| OCH₃ | CH₃ | H | O | N(CH₃)SO₂CH₂CH₂OCH₃ | H | |
| OCH₃ | CH₃ | H | O | N(CH₃)SO₂CF₃ | H | |
| OCH₃ | CH₃ | H | O | N(CH₃)SO₂CH₂CH₂Cl | H | |
| OCH₃ | CH₃ | H | O | CH₂CO₂CH₃ | H | |
| OCH₃ | CH₃ | H | O | CH₂CO₂C₂H₅ | H | |
| OCH₃ | CH₃ | H | O | CH₂CO₂CH(CH₃)₂ | H | |
| OCH₃ | CH₃ | H | O | CH₂CO₂CH₂CH₂OCH₃ | H | |
| OCH₃ | CH₃ | H | O | CH₂CO₂CH₂CH₂Cl | H | |
| OCH₃ | CH₃ | H | O | CH₂CO₂CH₂CH=CH₂ | H | |
| OCH₃ | CH₃ | H | O | CH(CH₃)CO₂CH₃ | H | |
| OCH₃ | CH₃ | H | O | CH₂SCH₃ | H | |
| OCH₃ | CH₃ | H | O | CH₂SOC₂H₅ | H | |
| OCH₃ | CH₃ | H | O | CH₂SO₂CH₃ | H | |
| OCH₃ | CH₃ | H | O | CH₂SO₂CH₂CH=CH₂ | H | |
| OCH₃ | CH₃ | H | O | CH₂SO₂CF₃ | H | |
| OCH₃ | CH₃ | H | O | CH₂SO₂CF₂CF₃ | H | |
| OCH₃ | CH₃ | H | O | CH₂SO₂CH₂CH₂CH₃ | H | |
| OCH₃ | CH₃ | H | O | CH(CH₃)SO₂CH₃ | H | |
| OCH₃ | CH₃ | H | O | OCH₂CH=CH₂ | H | |
| OCH₃ | CH₃ | H | O | OCH₂CH=CHCH₃ | H | |
| OCH₃ | CH₃ | H | O | OCH₂C≡CH | H | |
| OCH₃ | CH₃ | H | O | CH₂CH₂OCH₃ | H | |
| OCH₃ | CH₃ | H | O | CH₂CH₂OC₂H₅ | H | |
| OCH₃ | CH₃ | H | O | OCF₃ | H | |
| OCH₃ | CH₃ | H | O | OCF₂CF₃ | H | |
| OCH₃ | CH₃ | H | O | OCH₂CH₂Cl | H | |
| OCH₃ | CH₃ | H | O | OCH₂CF₂CF₃ | H | |
| OCH₃ | CH₃ | H | O | OCH₂OCH₃ | H | |
| OCH₃ | CH₃ | H | O | OCH₂CH₂OCH₃ | H | |
| OCH₃ | CH₃ | H | O | OCH₂OC₂H₅ | H | |
| OCH₃ | CH₃ | H | O | OCH₂CH₂OC₂H₅ | H | |
| OCH₃ | CH₃ | H | O | CH₂OCH₃ | H | |
| OCH₃ | CH₃ | H | O | CH₂OC₂H₅ | H | |
| OCH₃ | CH₂CF₃ | H | O | CO₂CH₃ | H | 154–157° |
| OCH₃ | CH₂CF₃ | H | O | SO₂N(CH₃)₂ | H | 150–157° |
| OCH₃ | CH₂CF₃ | H | O | Cl | H | 90–100° |
| OCH₃ | CH₂CF₃ | H | O | SO₂CH₃ | H | 195–225° |
| OCH₃ | CH₂CF₃ | H | O | NO₂ | H | 158–160° |
| OC₂H₅ | CH₃ | H | O | CH₃ | H | 199–202° |
| OC₂H₅ | CH₃ | H | O | CH₂CH₃ | H | |
| OC₂H₅ | CH₃ | H | O | CH₂(CH₃)₂ | H | |
| OC₂H₅ | CH₃ | H | O | OCH₂CH₂CH₃ | H | 155–163° |
| OC₂H₅ | CH₃ | H | O | Cl | H | 180–183° |
| OC₂H₅ | CH₃ | H | O | Br | H | |
| OC₂H₅ | CH₃ | H | O | NO₂ | H | 160–163° |
| OC₂H₅ | CH₃ | H | O | CF₃ | H | |
| OC₂H₅ | CH₃ | H | O | CO₂(CH₂)₅CH₃ | H | |
| OC₂H₅ | CH₃ | H | O | CO₂CH₂CH₂OCH₃ | H | |
| OC₂H₅ | CH₃ | H | O | CO₂CH₂C≡CH | H | |
| OC₂H₅ | CH₃ | H | O | N(CH₃)SO₂CH₃ | H | |
| OC₂H₅ | CH₃ | H | O | N(CH₃)SO₂C₂H₅ | H | |
| OC₂H₅ | CH₃ | H | O | OSO₂CH₃ | H | 145–150° |
| OC₂H₅ | CH₃ | H | O | SO₂CH₂CH₂CH₃ | H | 170–173° |
| OC₂H₅ | CH₃ | H | O | SO₂CH₂CH=CH₂ | H | |
| OC₂H₅ | CH₃ | H | O | SO₂CF₃ | H | |
| OC₂H₅ | CH₃ | H | O | CH₂CO₂CH₃ | H | |
| OC₂H₅ | CH₃ | H | O | CH(CH₃)CO₂CH₃ | H | |
| OC₂H₅ | CH₃ | H | O | CH₂CO₂CH₂CH₂Cl | H | |
| OC₂H₅ | CH₃ | H | O | CH₂SO₂CH₃ | H | |
| OC₂H₅ | CH₃ | H | O | CH₂SCH₃ | H | |
| OC₂H₅ | CH₃ | H | O | CH(CH₃)SO₂CH₃ | H | |
| OC₂H₅ | CH₃ | H | O | OCH₂CH=CH₂ | H | |
| OC₂H₅ | CH₃ | H | O | OCH₂C=CCH₃ | H | |
| OC₂H₅ | CH₃ | H | O | CH₂OCH₃ | H | |
| OC₂H₅ | CH₃ | H | O | CH₂CH₂OC₂H₅ | H | |
| OC₂H₅ | CH₃ | H | O | OCF₂CF₂CH₃ | H | |
| OC₂H₅ | CH₃ | H | O | OCH₂OCH₃ | H | |
| OC₂H₅ | CH₃ | H | O | OCH₂CH₂OCH₃ | H | |
| OC₂H₅ | CH₃ | H | O | OCH₂CH₂OCH₂CH₃ | H | |

TABLE 1-continued

| R₁ | R₂ | R₃ | W | R₇ | R₈ | m.p. (°C.) |
|---|---|---|---|---|---|---|
| OC₂H₅ | CH₃ | H | O | O(CH₂)₃OCH₃ | H | |
| Cl | CH₃ | H | O | CH₃ | H | |
| Cl | CH₃ | H | O | CH(CH₃)₂ | H | |
| Cl | CH₃ | H | O | OCH₃ | H | |
| Cl | CH₃ | H | O | OCH₂CH₂CH₃ | H | |
| Cl | CH₃ | H | O | Cl | H | |
| Cl | CH₃ | H | O | NO₂ | H | |
| Cl | CH₃ | H | O | CF₃ | H | |
| Cl | CH₃ | H | O | CO₂CH₃ | H | |
| Cl | CH₃ | H | O | CO₂C₂H₅ | H | |
| Cl | CH₃ | H | O | CO₂CH₂CH=CH₂ | H | |
| Cl | CH₃ | H | O | SO₂N(CH₃)₂ | H | |
| Cl | CH₃ | H | O | OSO₂CH₃ | H | |
| Cl | CH₃ | H | O | N(CH₃)SO₂CH₃ | H | |
| Cl | CH₃ | H | O | SO₂CH₃ | H | |
| Cl | CH₃ | H | O | SO₂CH₂CH₂CH₃ | H | |
| Cl | CH₃ | H | O | CH₂CO₂CH₃ | H | |
| Cl | CH₃ | H | O | CH₂SCH₃ | H | |
| Cl | CH₃ | H | O | CH₂SO₂CH₃ | H | |
| Cl | CH₃ | H | O | OCH₂CH=CH₂ | H | |
| Cl | CH₃ | H | O | OCH₂C≡CCH₃ | H | |
| Cl | CH₃ | H | O | CH₂OCH₃ | H | |
| Cl | CH₃ | H | O | CH₂CH₂OCH₃ | H | |
| Cl | CH₃ | H | O | CH₂CH₂Cl | H | |
| NHCH₃ | CH₃ | H | O | CH₃ | H | |
| NHCH₃ | CH₃ | H | O | CH₂CH₃ | H | |
| NHCH₃ | CH₃ | H | O | OCH₃ | H | |
| NHCH₃ | CH₃ | H | O | Br | H | |
| NHCH₃ | CH₃ | H | O | Cl | H | |
| NHCH₃ | CH₃ | H | O | NO₂ | H | |
| NHCH₃ | CH₃ | H | O | CF₃ | H | |
| NHCH₃ | CH₃ | H | O | CO₂CH₃ | H | |
| NHCH₃ | CH₃ | H | O | CO₂CH(CH₃)₂ | H | |
| NHCH₃ | CH₃ | H | O | CO₂CH₂CH₂Cl | H | |
| NHCH₃ | CH₃ | H | O | SO₂N(CH₃)₂ | H | |
| NHCH₃ | CH₃ | H | O | SO₂N(OCH₃)CH₃ | H | |
| NHCH₃ | CH₃ | H | O | OSO₂CF₃ | H | |
| NHCH₃ | CH₃ | H | O | SO₂CH₃ | H | |
| NHCH₃ | CH₃ | H | O | SO₂CH₂CH₂CH₃ | H | |
| NHCH₃ | CH₃ | H | O | SO₂CH₂CH=CH₂ | H | |
| NHCH₃ | CH₃ | H | O | CH₂CO₂CH₃ | H | |
| NHCH₃ | CH₃ | H | O | CH₂CO₂CH₂CH₂Cl | H | |
| NHCH₃ | CH₃ | H | O | CH₂SOCH₃ | H | |
| NHCH₃ | CH₃ | H | O | CH₂SO₂CH₃ | H | |
| NHCH₃ | CH₃ | H | O | OCH₂CH=CH₂ | H | |
| NHCH₃ | CH₃ | H | O | OCH₂C≡CH | H | |
| NHCH₃ | CH₃ | H | O | CH₂CH₂OC₂H₅ | H | |
| NHCH₃ | CH₃ | H | O | OCH₂CF₂CF₃ | H | |
| NHCH₃ | CH₃ | H | O | OCH₂OCH₃ | H | |
| NHCH₃ | CH₃ | H | O | OCH₂CH₂OCH₃ | H | |
| NHCH₃ | CH₃ | H | O | OCH₂CH₂OC₂H₅ | H | |
| CH(OCH₃)₂ | CH₃ | H | O | CH₃ | H | |
| CH(OCH₃)₂ | CH₃ | H | O | CH(CH₃)₂ | H | |
| CH(OCH₃)₂ | CH₃ | H | O | OCH₃ | H | |
| CH(OCH₃)₂ | CH₃ | H | O | OCH₂CH₂CH₃ | H | |
| CH(OCH₃)₂ | CH₃ | H | O | F | H | |
| CH(OCH₃)₂ | CH₃ | H | O | Cl | H | |
| CH(OCH₃)₂ | CH₃ | H | O | Br | H | |
| CH(OCH₃)₂ | CH₃ | H | O | NO₂ | H | |
| CH(OCH₃)₂ | CH₃ | H | O | CF₃ | H | |
| CH(OCH₃)₂ | CH₃ | H | O | CO₂CH₃ | H | |
| CH(OCH₃)₂ | CH₃ | H | O | CO₂C₂H₅ | H | |
| CH(OCH₃)₂ | CH₃ | H | O | CO₂CH₂CH=CH₂ | H | |
| CH(OCH₃)₂ | CH₃ | H | O | SO₂N(CH₃)₂ | H | |
| CH(OCH₃)₂ | CH₃ | H | O | SO₂N(CH₃)C₂H₅ | H | |
| CH(OCH₃)₂ | CH₃ | H | O | OSO₂CF₃ | H | |
| CH(OCH₃)₂ | CH₃ | H | O | SO₂CH₃ | H | |
| CH(OCH₃)₂ | CH₃ | H | O | SO₂CH₂CH₂CH₃ | H | |
| CH(OCH₃)₂ | CH₃ | H | O | SO₂CH₂CH=CH₂ | H | |
| CH(OCH₃)₂ | CH₃ | H | O | CH₂CO₂CH₃ | H | |
| CH(OCH₃)₂ | CH₃ | H | O | CH₂CO₂CH₂CH₂OCH₃ | H | |
| CH(OCH₃)₂ | CH₃ | H | O | CH₂SO₂CH₃ | H | |

TABLE 1-continued

[structure diagram]

| R₁ | R₂ | R₃ | W | R₇ | R₈ | m.p. (°C.) |
|---|---|---|---|---|---|---|
| CH(OCH₃)₂ | CH₃ | H | O | OCH₂CH=CH₂ | H | |
| CH(OCH₃)₂ | CH₃ | H | O | CH₂CH₂OCH₃ | H | |
| CH(OCH₃)₂ | CH₃ | H | O | CH₂OCH₃ | H | |
| CH(OCH₃)₂ | CH₃ | H | O | OCH₂CH₂OCH₃ | H | |
| CH(OCH₃)₂ | CH₃ | H | O | OCF₂CF₃ | H | |
| CH(OCH₃)₂ | CH₃ | H | O | OCH₂CF₂CF₃ | H | |
| 1,3-dioxolan-2-yl | CH₃ | H | O | CH₃ | H | |
| 1,3-dioxolan-2-yl | CH₃ | H | O | CH(CH₃)₂ | H | |
| 1,3-dioxolan-2-yl | CH₃ | H | O | OCH₂CH₃ | H | |
| 1,3-dioxolan-2-yl | CH₃ | H | O | Cl | H | |
| 1,3-dioxolan-2-yl | CH₃ | H | O | NO₂ | H | |
| 1,3-dioxolan-2-yl | CH₃ | H | O | CF₃ | H | |
| 1,3-dioxolan-2-yl | CH₃ | H | O | CO₂CH₃ | H | |
| 1,3-dioxolan-2-yl | CH₃ | H | O | CO₂CH₂CH₂Cl | H | |
| 1,3-dioxolan-2-yl | CH₃ | H | O | CO₂CH(CH₃) | H | |
| 1,3-dioxolan-2-yl | CH₃ | H | O | SO₂N(CH₃)₂ | H | |
| 1,3-dioxolan-2-yl | CH₃ | H | O | SO₂N(OCH₃)CH₃ | H | |

TABLE 1-continued

[Structure diagram showing compound with R1, R2, R3, R7, R8, W substituents on a pyrazole-sulfonylurea-phenyl framework]

| R₁ | R₂ | R₃ | W | R₇ | R₈ | m.p. (°C.) |
|---|---|---|---|---|---|---|
| (1,3-dioxolan-2-yl) | CH₃ | H | O | N(CH₃)SO₂CH₃ | H | |
| (1,3-dioxolan-2-yl) | CH₃ | H | O | OSO₂CH₃ | H | |
| (1,3-dioxolan-2-yl) | CH₃ | H | O | SO₂CH₃ | H | |
| (1,3-dioxolan-2-yl) | CH₃ | H | O | SO₂CH₂CH₂CH₃ | H | |
| (1,3-dioxolan-2-yl) | CH₃ | H | O | CH₂CO₂CH₃ | H | |
| (1,3-dioxolan-2-yl) | CH₃ | H | O | CH(CH₃)CO₂CH₃ | H | |
| (1,3-dioxolan-2-yl) | CH₃ | H | O | CH₂SO₂CH₃ | H | |
| (1,3-dioxolan-2-yl) | CH₃ | H | O | CH₂SC₂H₅ | H | |
| (1,3-dioxolan-2-yl) | CH₃ | H | O | OCH₂CH=CH₂ | H | |
| (1,3-dioxolan-2-yl) | CH₃ | H | O | CH₂OCH₃ | H | |
| (1,3-dioxolan-2-yl) | CH₃ | H | O | CH₂CH₂OCH₃ | H | |
| (1,3-dioxolan-2-yl) | CH₃ | H | O | OCH₂CH₂OCH₃ | H | |
| (1,3-dioxolan-2-yl) | CH₃ | H | O | OCF₂CF₃ | H | |

TABLE 1-continued

Structure: R₂-N1-N2, R1-C5=N4, C3 with W=NCNHSO2-phenyl(R7 at 2, R8 at 4), N-R3

| R₁ | R₂ | R₃ | W | R₇ | R₈ | m.p. (°C.) |
|---|---|---|---|---|---|---|
| (1,3-dioxolan-2-yl, CH with two O) | CH₃ | H | O | OCH₂CF₂CF₃ | H | |
| (1,3-dioxolan-2-yl) | CH₃ | H | O | OCH₂CH₂CH₂OCH₃ | H | |
| (1,3-dioxolan-2-yl) | CH₃ | H | O | OCCl₂CF₃ | H | |
| OCH₃ | CH₃ | H | O | CO₂N(CH₃)₂ | H | |
| OCH₃ | CH₃ | H | O | CO₂N(C₂H₅)₂ | H | |
| OCH₃ | CH₃ | H | O | CO₂N(CH₃)C₂H₅ | H | |
| OCH₃ | CH₃ | H | O | CO₂N(CH₃)CH₂CH₂CH₃ | H | |
| OCH₃ | CH₃ | H | O | CO₂(CH₃)C₆H₅ | H | |
| OCH₃ | CH₃ | H | O | CO₂N(CH₂)₄ | H | |
| OCH₃ | CH₃ | H | O | C(O)SCH₃ | H | |
| OCH₃ | CH₃ | H | O | C(O)SC₂H₅ | H | |
| OCH₃ | CH₃ | H | O | C(O)SCH₂CH₂CH₃ | H | |
| OCH₃ | CH₃ | H | O | C(O)SCH(CH₃)₂ | H | |
| OC₂H₅ | CH₃ | H | O | CO₂N(CH₃)₂ | H | |
| OC₂H₅ | CH₃ | H | O | CO₂N(C₂H₅)₂ | H | |
| OC₂H₅ | CH₃ | H | O | CO₂N(CH₃)C₂H₅ | H | |
| OC₂H₅ | CH₃ | H | O | CO₂N(CH₃)CH₂CH₂CH₃ | H | |
| OC₂H₅ | CH₃ | H | O | CO₂(CH₃)C₆H₅ | H | |
| OC₂H₅ | CH₃ | H | O | CO₂N(CH₂)₄ | H | |
| OC₂H₅ | CH₃ | H | O | C(O)SCH₃ | H | |
| OC₂H₅ | CH₃ | H | O | C(O)SC₂H₅ | H | |
| OC₂H₅ | CH₃ | H | O | C(O)SCH₂CH₂CH₃ | H | |
| OC₂H₅ | CH₃ | H | O | C(O)SCH(CH₃)₂ | H | |
| SCH₃ | CH₃ | H | O | CO₂N(CH₃)₂ | H | |
| SCH₃ | CH₃ | H | O | CO₂N(C₂H₅)₂ | H | |
| SCH₃ | CH₃ | H | O | CO₂N(CH₃)C₂H₅ | H | |
| SCH₃ | CH₃ | H | O | CO₂N(CH₃)CH₂CH₂CH₃ | H | |
| SCH₃ | CH₃ | H | O | CO₂(CH₃)C₆H₅ | H | |
| SCH₃ | CH₃ | H | O | CO₂N(CH₂)₄ | H | |
| SCH₃ | CH₃ | H | O | C(O)SCH₃ | H | |
| SCH₃ | CH₃ | H | O | C(O)SC₂H₅ | H | |
| SCH₃ | CH₃ | H | O | C(O)SCH₂CH₂CH₃ | H | |
| SCH₃ | CH₃ | H | O | C(O)SCH(CH₃)₂ | H | |

TABLE 2

Structure: R₂-N1-N2, R1-C5=N4, C3 with W=NCNHSO2-pyridinyl (R16 at 3, R17 at 5, N at 1), N-R3

| R₁ | R₂ | R₃ | W | R₁₆ | R₁₇ | m.p. (°C.) |
|---|---|---|---|---|---|---|
| H | C₂H₅ | H | O | CO₂CH₃ | H | |
| H | n-C₃H₇ | H | O | Cl | H | |
| CH₃ | CH₂CH(CH₃)₂ | H | O | CO₂CH₃ | H | |
| CH₃ | C₂H₅ | H | O | Cl | H | |
| CH₃ | C₂H₅ | H | O | H | H | |
| CH₃ | C₂H₅ | H | S | Cl | H | |
| CH₃ | C₂H₅ | H | O | CO₂CH(CH₃)C₂H₅ | H | |
| CH₃ | C₂H₅ | CH₃ | O | CO₂CH₃ | H | |
| C₂H₅ | CH₃ | H | O | CO₂(CH₂)₃CH₃ | H | |
| C₂H₅ | CH₃ | CH₃ | O | Cl | H | |
| C₂H₅ | CH₃ | H | S | Cl | H | |

TABLE 2-continued

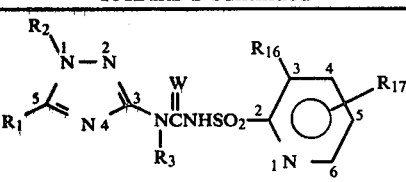

| $R_1$ | $R_2$ | $R_3$ | W | $R_{16}$ | $R_{17}$ | m.p. (°C.) |
|---|---|---|---|---|---|---|
| $C_2H_5$ | $CH_3$ | H | O | $CO_2CH_2CH_2OCH_3$ | H | |
| $C_2H_5$ | $C_2H_5$ | H | O | $CO_2CH_2CH(CH_3)_2$ | H | |
| $n\text{-}C_4H_9$ | $CH_3$ | H | O | $CO_2CH_3$ | H | |
| $CH(CH_3)_2$ | $CH_3$ | H | O | $NO_2$ | H | |
| $n\text{-}C_3H_7$ | $CH_3$ | H | O | $CF_3$ | H | |
| $CH_3$ | $n\text{-}C_3H_7$ | H | O | $CO_2CH_3$ | H | |
| $CH_3$ | $CH_2CH=CH_2$ | H | O | Cl | H | |
| $CH_3$ | $CH_2C(CH_3)=CH_2$ | H | O | $OCH_3$ | H | |
| $CH_2CH=CH_2$ | $CH_3$ | H | O | $C_2H_5$ | H | |
| $CH_2C(CH_3)=CH_2$ | $CH_3$ | H | O | $SO_2CH_3$ | H | |
| $CH_3$ | $CH_2C\equiv CCH_3$ | H | O | $SO_2CH_3$ | H | |
| $CH_2C\equiv C\text{-}CH_3$ | $CH_3$ | H | O | $SO_2C_2H_5$ | H | |
| $C_2H_5$ | $CH_3$ | H | O | $SO_2N(CH_3)_2$ | H | |
| $C_2H_5$ | $CH_3$ | H | O | $SO_2N(CH_3)OCH_3$ | H | |
| $CH_3$ | $C_2H_5$ | H | O | $SCH_3$ | H | |
| $C_2H_5$ | $CH_3$ | H | O | $S(CH_2)_3CH_3$ | H | |
| $C_2H_5$ | $CH_3$ | H | O | F | H | |
| $C_2H_5$ | $CH_3$ | H | S | $CH_3$ | H | |
| $C_2H_5$ | $CH_3$ | $CH_3$ | O | $SO_2CH_3$ | H | |
| $C_2H_5$ | $C_2H_5$ | H | O | $n\text{-}C_4H_9$ | H | |
| $CH_3$ | $CH_2C\equiv CH$ | H | O | Cl | H | |
| $SCH_3$ | $CH_3$ | H | O | $CH_3$ | H | |
| $SCH_3$ | $CH_3$ | H | O | H | H | |
| $SCH_3$ | $CH_3$ | H | O | Cl | H | |
| $SCH_3$ | $CH_3$ | H | O | $NO_2$ | H | |
| $SCH_3$ | $CH_3$ | H | S | Cl | H | |
| $SCH_3$ | $CH_3$ | $CH_3$ | O | Cl | H | |
| $SCH_3$ | $CH_3$ | H | O | Cl | 5-F | |
| $SCH_3$ | $CH_3$ | H | O | $SO_2CH_3$ | 4-Br | |
| $SCH_3$ | $C_2H_5$ | H | O | $SO_2CH_3$ | 6-Br | |
| $SCH_3$ | $CH_3$ | H | O | $SO_2N(CH_3)_2$ | 6-Cl | |
| $CH_3$ | $C_2H_5$ | H | O | $NO_2$ | 5-F | |
| $C_2H_5$ | $CH_3$ | H | O | $CH_3$ | 4-Cl | |
| $SCH_3$ | $CH_3$ | $CH_3$ | O | Cl | 6-Cl | |
| $SCH_3$ | $C_2H_5$ | H | S | $OCH_3$ | H | |
| $SCH_3$ | $CH_3$ | H | O | $CO_2CH_2CH=CH_2$ | H | |
| $SCH_3$ | $CH_3$ | H | O | $CO_2CH(CH_3)_2$ | H | |
| $SCH_3$ | $C_2H_5$ | H | O | $CO_2CH_2CH_2Cl$ | H | |
| $SCH_3$ | $CH_3$ | H | O | $CO_2CH_2CH(CH_3)_2$ | H | |
| $SCH_3$ | $C_2H_2H_5$ | H | O | $n\text{-}C_4H_9$ | H | |
| $SCH_3$ | $CH_3$ | H | O | $SCH_3$ | H | |
| $SCH_3$ | $CH_3$ | H | O | $S(CH_2)_2CH_3$ | H | |
| $SCH_3$ | $CH_3$ | H | O | F | H | |
| $SC_2H_5$ | $CH_3$ | H | S | $CH_3$ | H | |
| $SC_2H_5$ | $CH_3$ | H | O | $SO_2CH_3$ | H | |
| $S(CH_2)_2CH_3$ | $CH_3$ | H | O | $SO_2CH_3$ | H | |
| $SCH(CH_3)C_2H_5$ | $CH_3$ | H | O | Cl | H | |
| $SCH(CH_3)_2$ | $CH_3$ | H | O | $SO_2C_2H_5$ | H | |
| $SCH_2CH=CH_2$ | $CH_3$ | H | O | $CO_2C_2H_5$ | H | |
| $SCH_2C(CH_3)=CH_2$ | $CH_3$ | H | O | $SO_2CH_3$ | H | |
| $SCH_2C\equiv C\text{-}CH_3$ | $CH_3$ | H | O | $CO_2CH_3$ | H | |
| $SCH_3C\equiv CH$ | $CH_3$ | H | O | Cl | H | |
| $SCH_2CO_2CH_3$ | $CH_3$ | H | O | $CF_3$ | H | |
| $SCH_2CO_2CH(CH_3)_2$ | $CH_3$ | H | O | $NO_2$ | H | |
| $SCH(CH_3)CO_2CH_3$ | $CH_3$ | H | O | $CO_2CH_3$ | H | |
| $OCH_3$ | $C_2H_5$ | H | S | Cl | H | |
| $OCH_3$ | $C_2H_5$ | $CH_3$ | O | Cl | H | |
| $OCH_3$ | $C_2H_5$ | H | O | H | H | |
| $OCH_3$ | $C_2H_5$ | H | O | F | H | |
| $OCH_3$ | $C_2H_5$ | H | O | H | 4-F | |
| $OCH_3$ | $C_2H_5$ | H | O | H | 5-F | |
| $OCH_3$ | $C_2H_5$ | H | O | Cl | H | |
| $OCH_3$ | $C_2H_5$ | H | O | $SO_2CH_3$ | H | |
| $OCH_3$ | $C_2H_5$ | H | O | $CF_3$ | H | |
| $OCH_3$ | $C_2H_5$ | H | O | $NO_2$ | H | |
| $OC_2H_5$ | $CH_3$ | H | S | $CH_3$ | H | |
| $OC_2H_5$ | $CH_3$ | H | O | $OC_2H_5$ | H | |
| $OC_2H_5$ | $CH_3$ | $CH_3$ | O | Cl | H | |
| $OC_2H_5$ | $CH_3$ | $CH_3$ | O | $SO_2CH_3$ | H | |
| $OC_2H_5$ | $CH_3$ | H | S | $SO_2CH_3$ | H | |
| $OC_2H_5$ | $CH_3$ | H | O | $SO_2N(CH_3)[(CH_2)_2CH_3]$ | H | |
| $OCH_3$ | $C_2H_5$ | H | O | $SO_2N(CH_3)_2$ | H | |

TABLE 2-continued

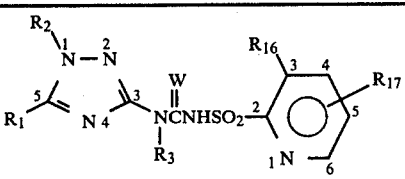

| $R_1$ | $R_2$ | $R_3$ | W | $R_{16}$ | $R_{17}$ | m.p. (°C.) |
|---|---|---|---|---|---|---|
| OCH$_3$ | C$_2$H$_5$ | H | O | SO$_2$N(CH$_3$)OCH$_3$ | H | |
| OCH$_3$ | C$_2$H$_5$ | H | O | SO$_2$C$_2$H$_5$ | H | |
| OC$_2$H$_5$ | CH$_3$ | H | O | SO$_2$(CH$_2$)$_3$CH$_3$ | H | |
| OC$_2$H$_5$ | CH$_3$ | H | O | Cl | 6-CH$_3$ | |
| OCH$_3$ | C$_2$H$_5$ | H | O | NO$_2$ | 5-Cl | |
| OCH$_3$ | C$_2$H$_5$ | H | O | Cl | 5-CH$_3$ | |
| OCH$_3$ | C$_2$H$_5$ | H | O | Br | 4-Cl | |
| OCH$_3$ | C$_2$H$_5$ | H | O | OCH$_3$ | 5-F | |
| OCH$_3$ | C$_2$H$_5$ | H | O | SO$_2$CH$_3$ | 4-Br | |
| OCH$_3$ | C$_2$H$_5$ | H | O | SO$_2$CH$_3$ | 6-Cl | |
| OC$_2$H$_5$ | CH$_3$ | H | O | SO$_2$CH$_3$ | 5-OCH$_3$ | |
| OCH$_3$ | C$_2$H$_5$ | H | O | SO$_2$CH$_3$ | 4-OCH$_3$ | |
| OCH$_3$ | C$_2$H$_5$ | H | O | SCH$_3$ | H | |
| OC$_2$H$_5$ | CH$_3$ | H | O | S(CH$_2$)$_3$CH$_3$ | H | |
| OC$_2$H$_5$ | CH$_3$ | H | O | SO$_2$N(CH$_3$)C$_2$H$_5$ | H | |
| OC$_2$H$_5$ | CH$_3$ | H | O | CF$_3$ | H | |
| OCH$_3$ | C$_2$H$_5$ | H | O | Br | H | |
| OCH$_3$ | C$_2$H$_5$ | H | O | NO$_2$ | H | |
| OCH$_3$ | C$_2$H$_5$ | H | O | n-C$_3$H$_7$ | H | |
| OC$_2$H$_5$ | CH$_3$ | H | O | OCH$_2$(CH$_2$)$_2$CH$_3$ | H | |
| OC$_2$H$_5$ | CH$_3$ | H | O | OCH$_2$CH(CH$_3$)$_2$ | H | |
| OC$_2$H$_5$ | CH$_3$ | H | O | OC$_2$H$_5$ | H | |
| OCH$_3$ | CH$_3$ | H | O | CO$_2$CH$_2$CH$_2$OCH$_3$ | H | |
| OCH$_3$ | C$_2$H$_5$ | H | O | CO$_2$(CH$_2$)$_3$OCH$_3$ | H | |
| OCH$_3$ | C$_2$H$_5$ | H | O | CO$_2$(CH$_2$)$_2$OCH$_3$ | H | |
| OC$_2$H$_5$ | C$_2$H$_5$ | H | O | CO$_2$CH$_2$CH$_2$Cl | H | |
| OCH$_3$ | C$_2$H$_5$ | CH$_3$ | O | CO$_2$C$_2$H$_5$ | H | |
| OCH$_3$ | C$_2$H$_5$ | CH$_3$ | O | CO$_2$CH$_3$ | H | |
| OC$_2$H$_5$ | C$_2$H$_5$ | CH$_3$ | O | SO$_2$N(C$_2$H$_5$)$_2$ | H | |
| OCH$_2$CH=CH$_2$ | CH$_3$ | H | O | SO$_2$CH$_3$ | H | |
| OCH$_2$C(CH$_3$)=CH$_2$ | CH$_3$ | H | O | Cl | H | |
| OCH(CH$_3$)C$_2$H$_5$ | CH$_3$ | H | O | SO$_2$CH$_3$ | H | |
| O(CH$_2$)$_2$CH$_3$ | CH$_3$ | H | O | SO$_2$CH$_3$ | H | |
| OCH(CH$_3$)$_2$ | CH$_3$ | H | O | CO$_2$C$_2$H$_5$ | H | |
| O(CH$_2$)$_2$CH$_3$ | CH$_3$ | H | O | CO$_2$CH(CH$_3$)$_2$ | H | |
| OCH$_2$CH=CHCH$_3$ | CH$_3$ | H | O | Cl | H | |
| OCH$_2$C≡CCH$_3$ | CH$_3$ | H | O | SO$_2$CH$_3$ | H | |
| CH$_2$OCH$_3$ | CH$_3$ | H | O | NO$_2$ | H | |
| CH$_2$OCH$_3$ | CH$_3$ | H | O | SO$_2$N(CH$_3$)[CH(CH$_3$)$_2$] | H | |
| CH$_2$OCH$_3$ | CH$_3$ | H | O | SO$_2$N(CH$_3$)$_2$ | H | |
| CH$_2$OCH$_3$ | CH$_3$ | H | O | SO$_2$CH$_3$ | H | |
| CH$_2$OCH$_3$ | CH$_3$ | H | O | Cl | H | |
| CH$_2$OCH$_3$ | CH$_3$ | H | O | F | H | |
| CH$_2$OCH$_3$ | CH$_3$ | H | O | H | H | |
| CH$_2$OCH$_3$ | CH$_3$ | H | S | Cl | H | |
| CH$_2$OCH$_3$ | CH$_3$ | CH$_3$ | O | CH$_3$ | H | |
| CH$_2$OCH$_3$ | CH$_3$ | CH$_3$ | O | Cl | H | |
| CH$_2$OCH$_3$ | CH$_3$ | H | O | SC$_2$H$_5$ | H | |
| CH$_2$OCH$_3$ | CH$_3$ | H | O | OCH$_3$ | H | |
| CH$_2$OCH$_3$ | CH$_3$ | H | O | CO$_2$CH$_2$CH$_2$Cl | H | |
| CH$_2$OC$_2$H$_5$ | CH$_3$ | CH$_3$ | O | CO$_2$CH(CH$_3$)$_2$ | H | |
| CH$_2$OC$_2$H$_5$ | CH$_3$ | H | O | CO$_2$CH$_2$CH=CH$_2$ | H | |
| CH$_2$O(CH$_2$)$_3$CH$_3$ | CH$_3$ | H | O | CO$_2$CH$_3$ | H | |
| CH$_2$CH(CH$_3$)$_2$ | CH$_3$ | H | O | Cl | H | |
| CH$_2$CH$_2$OCH$_3$ | CH$_3$ | H | O | CO$_2$C$_2$H$_5$ | H | |
| CH$_2$CH$_2$OCH(CH$_3$)$_2$ | CH$_3$ | H | O | CO$_2$CH(CH$_3$)$_2$ | H | |
| CH$_2$CH$_2$O(CH$_2$)$_2$CH$_3$ | CH$_3$ | H | O | SO$_2$CH$_3$ | H | |
| N(CH$_3$)$_2$ | CH$_3$ | H | O | Cl | H | |
| CF$_2$CF$_3$ | CH$_3$ | H | O | SO$_2$CH$_3$ | H | |
| CF$_3$ | CH$_3$ | H | O | Cl | H | |
| CF$_2$CF$_3$ | CH$_3$ | H | O | CO$_2$CH$_3$ | H | |
| CF$_2$CF$_3$ | CH$_3$ | H | O | NO$_2$ | H | |
| CF$_2$CF$_3$ | CH$_3$ | H | O | SO$_2$CH(CH$_3$)$_2$ | H | |
| CH$_3$ | CH$_2$OCH$_3$ | H | S | Cl | H | |
| CH$_3$ | CH$_2$OCH$_3$ | H | O | SO$_2$C$_2$H$_5$ | H | |
| CH$_3$ | CH$_2$OCH$_3$ | H | O | CO$_2$CH$_3$ | H | |
| CH$_3$ | CH$_2$CH$_2$OCH$_3$ | H | O | Cl | H | |
| CH$_3$ | CH$_2$SCH$_3$ | H | O | CO$_2$CH$_3$ | H | |
| CH$_3$ | CH$_2$CH$_2$SCH$_3$ | H | O | SO$_2$C$_2$H$_5$ | H | |
| SCH$_3$ | CH$_3$ | CH$_3$ | O | SO$_2$N(CH$_3$)$_2$ | H | |
| SCH$_3$ | CH$_3$ | H | O | SO$_2$(CH$_2$)$_3$CH$_3$ | H | |
| SCH$_3$ | CH$_3$ | H | O | S(CH$_2$)$_3$CH$_3$ | H | |

TABLE 2-continued

| $R_1$ | $R_2$ | $R_3$ | W | $R_{16}$ | $R_{17}$ | m.p. (°C.) |
|---|---|---|---|---|---|---|
| SCH$_3$ | CH$_3$ | H | O | SO$_2$CH$_2$CH(CH$_3$)$_2$ | H | |
| SCH$_3$ | CH$_3$ | H | O | SCH(CH$_3$)$_2$ | H | |
| OC$_2$H$_5$ | CH$_3$ | H | O | NO$_2$ | 4-F | |
| SCH$_3$ | CH$_3$ | H | O | NO$_2$ | 4-OCH$_3$ | |
| SCH$_3$ | CH$_3$ | CH$_3$ | O | CO$_2$CH$_2$CH$_2$OCH$_3$ | H | |
| SCH$_3$ | CH$_3$ | H | O | O—CH(CH$_3$)C$_2$H$_5$ | H | |
| SCH$_3$ | CH$_3$ | CH$_3$ | O | SO$_2$(CH$_2$)CH$_3$ | H | |
| OC$_2$H$_5$ | C$_2$H$_5$ | H | O | F | H | |
| CF$_3$ | C$_2$H$_5$ | CH$_3$ | O | SO$_2$CH$_3$ | H | |
| SCH$_3$ | CH$_3$ | CH$_3$ | O | SO$_2$N(OCH$_3$)CH$_3$ | H | |
| OCH$_3$ | CH$_3$ | H | O | CH$_3$ | H | |
| OCH$_3$ | CH$_3$ | H | O | CH(CH$_3$)$_2$ | H | |
| OCH$_3$ | CH$_3$ | H | O | OCH$_3$ | H | |
| OCH$_3$ | CH$_3$ | H | O | O(CH$_2$)$_3$CH$_3$ | H | |
| OCH$_3$ | CH$_3$ | H | O | F | H | |
| OCH$_3$ | CH$_3$ | H | O | Cl | H | |
| OCH$_3$ | CH$_3$ | H | O | Br | H | |
| OCH$_3$ | CH$_3$ | H | O | CF$_3$ | H | |
| OCH$_3$ | CH$_3$ | H | O | CO$_2$CH$_3$ | H | |
| OCH$_3$ | CH$_3$ | H | O | CO$_2$C$_2$H$_5$ | H | |
| OCH$_3$ | CH$_3$ | H | O | CO$_2$CH(CH$_3$)$_2$ | H | |
| OCH$_3$ | CH$_3$ | H | O | CO$_2$CH$_2$CH$_2$CH$_2$CH$_3$ | H | |
| OCH$_3$ | CH$_3$ | H | O | CO$_2$CH$_2$CH$_2$Cl | H | |
| OCH$_3$ | CH$_3$ | H | O | CO$_2$CH$_2$CH=CH$_2$ | H | |
| OCH$_3$ | CH$_3$ | H | O | SO$_2$N(CH$_3$)$_2$ | H | |
| OCH$_3$ | CH$_3$ | H | O | SO$_2$N(CH$_3$)C$_2$H$_5$ | H | |
| OCH$_3$ | CH$_3$ | H | O | SO$_2$N(C$_2$H$_5$)$_2$ | H | |
| OCH$_3$ | CH$_3$ | H | O | SO$_2$N(OCH$_3$)CH$_3$ | H | |
| OCH$_3$ | CH$_3$ | H | O | SO$_2$CH$_3$ | H | |
| OCH$_3$ | CH$_3$ | H | O | SOCH$_3$ | H | |
| OCH$_3$ | CH$_3$ | H | O | SCH$_3$ | H | |
| OCH$_3$ | CH$_3$ | H | O | SC$_2$H$_5$ | H | |
| OCH$_3$ | CH$_3$ | H | O | SO$_2$C$_2$H$_5$ | H | |
| OCH$_3$ | CH$_3$ | H | O | SO$_2$CH$_2$CH$_2$CH$_3$ | H | |
| OCH$_3$ | CH$_3$ | H | O | SO$_2$CH(CH$_3$)$_2$ | H | |
| OCH$_3$ | CH$_3$ | H | O | SO$_2$CH$_2$CH=CH$_2$ | H | |
| OCH$_3$ | CH$_3$ | H | O | SCH$_2$CH=CH$_2$ | H | |
| OCH$_3$ | CH$_3$ | H | O | SO$_2$CF$_3$ | H | |
| OCH$_3$ | CH$_3$ | H | O | SO$_2$CF$_2$CF$_3$ | H | |
| OC$_2$H$_5$ | CH$_3$ | H | O | Cl | H | |
| OC$_2$H$_5$ | CH$_3$ | H | O | Br | H | |
| OC$_2$H$_5$ | CH$_3$ | H | O | SO$_2$CH$_3$ | H | |
| OC$_2$H$_5$ | CH$_3$ | H | O | CO$_2$CH$_3$ | H | |
| OC$_2$H$_5$ | CH$_3$ | H | O | CO$_2$C$_2$H$_5$ | H | |
| OC$_2$H$_5$ | CH$_3$ | H | O | CO$_2$CH$_2$CH=CH$_2$ | H | |
| OC$_2$H$_5$ | CH$_3$ | H | O | SO$_2$N(CH$_3$)$_2$ | H | |
| OC$_2$H$_5$ | CH$_3$ | H | O | CH$_3$ | H | |
| OC$_2$H$_5$ | CH$_3$ | H | O | CH(CH$_3$)$_2$ | H | |
| OC$_2$H$_5$ | CH$_3$ | H | O | CO$_2$CH(CH$_3$)$_2$ | H | |
| OCH$_3$ | CH$_2$CF$_3$ | H | O | Cl | H | |
| OCH$_3$ | CH$_2$CF$_3$ | H | O | SO$_2$CH$_3$ | H | |
| OCH$_3$ | CH$_2$CF$_3$ | H | O | SO$_2$N(CH$_3$)$_2$ | H | |
| OCH$_3$ | CH$_2$CF$_3$ | H | O | CO$_2$CH$_3$ | H | |
| OCH$_3$ | CH$_2$CF$_3$ | H | O | Br | H | |
| Cl | CH$_3$ | H | O | Cl | H | |
| Cl | CH$_3$ | H | O | Br | H | |
| Cl | CH$_3$ | H | O | CH$_3$ | H | |
| Cl | CH$_3$ | H | O | OCH$_3$ | H | |
| Cl | CH$_3$ | H | O | CF$_3$ | H | |
| Cl | CH$_3$ | H | O | CO$_2$CH$_3$ | H | |
| Cl | CH$_3$ | H | O | CO$_2$CH$_2$CH=CH$_2$ | H | |
| Cl | CH$_3$ | H | O | SO$_2$N(CH$_3$)$_2$ | H | |
| Cl | CH$_3$ | H | O | SO$_2$CH$_3$ | H | |
| NHCH$_3$ | CH$_3$ | H | O | Cl | H | |
| NHCH$_3$ | CH$_3$ | H | O | CO$_2$CH$_3$ | H | |
| NHCH$_3$ | CH$_3$ | H | O | SO$_2$CH$_3$ | H | |
| CH(OCH$_3$)$_2$ | CH$_3$ | H | O | Cl | H | |
| CH(OCH$_3$)$_2$ | CH$_3$ | H | O | CO$_2$CH$_3$ | H | |
| CH(OCH$_3$)$_2$ | CH$_3$ | H | O | SO$_2$N(CH$_3$)$_2$ | H | |

TABLE 2-continued

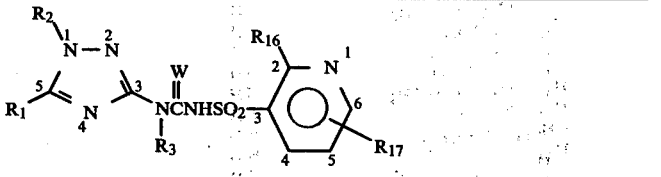

| R1 | R2 | R3 | W | R16 | R17 | m.p. (°C.) |
|---|---|---|---|---|---|---|
| O-CH-O (dioxolane) | CH3 | H | O | Cl | H | |
| O-CH-O (dioxolane) | CH3 | H | O | CO2CH3 | H | |
| O-CH-O (dioxolane) | CH3 | H | O | CO2CH2CH=CH2 | H | |
| O-CH-O (dioxolane) | CH3 | H | O | SO2CH2CH=CH2 | H | |

TABLE 3

| R1 | R2 | R3 | W | R16 | R17 | m.p. (°C.) |
|---|---|---|---|---|---|---|
| H | C2H5 | H | O | CO2CH3 | H | |
| H | n-C3H7 | H | O | Cl | H | |
| CH3 | CH2CH(CH3)2 | H | O | CO2CH3 | H | |
| CH3 | C2H5 | H | O | Cl | H | |
| CH3 | C2H5 | H | O | H | H | |
| CH3 | C2H5 | H | S | Cl | H | |
| CH3 | C2H5 | H | O | CO2CH(CH3)C2H5 | H | |
| CH3 | C2H5 | CH3 | O | CO2CH3 | H | |
| C2H5 | CH3 | H | O | CO2(CH2)3CH3 | H | |
| C2H5 | CH3 | CH3 | O | Cl | H | |
| C2H5 | CH3 | H | S | Cl | H | |
| C2H5 | CH3 | H | O | CO2CH2CH2OCH3 | H | |
| C2H5 | CH3 | H | O | CO2CH2CH(CH3)2 | H | |
| n-C4H9 | CH3 | H | O | CO2CH3 | H | |
| CH(CH3)2 | CH3 | H | O | NO2 | H | |
| n-C3H7 | CH3 | H | O | CF3 | H | |
| CH3 | n-C3H7 | H | O | CO2CH3 | H | |
| CH3 | CH2CH=CH2 | H | O | Cl | H | |
| CH3 | CH2C(CH3)=CH2 | H | O | OCH3 | H | |
| CH2CH=CH2 | CH3 | H | O | C2H5 | H | |
| CH2C(CH3)=CH2 | CH3 | H | O | SO2CH3 | H | |
| CH3 | CH2C≡CCH3 | H | O | SO2CH3 | H | |
| CH2C≡C—CH3 | CH3 | H | O | SO2C2H5 | H | |
| C2H5 | CH3 | H | O | SO2N(CH3)2 | H | |
| C2H5 | CH3 | H | O | SO2N(CH3)OCH3 | H | |
| CH3 | C2H5 | H | O | SCH3 | H | |
| C2H5 | CH3 | H | O | S(CH2)3CH3 | H | |
| C2H5 | CH3 | H | O | F | H | |
| C2H5 | CH3 | H | S | CH3 | H | |
| C2H5 | CH3 | CH3 | O | SO2CH3 | H | |
| C2H5 | C2H5 | H | O | n-C4H9 | H | |
| CH3 | CH2C≡CH | H | O | Cl | H | |
| SCH3 | CH3 | H | O | CH3 | H | |

TABLE 3-continued

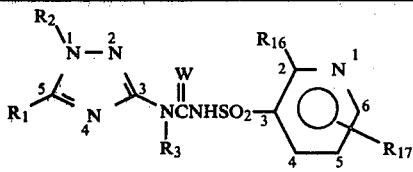

| R₁ | R₂ | R₃ | W | R₁₆ | R₁₇ | m.p. (°C.) |
|---|---|---|---|---|---|---|
| SCH₃ | CH₃ | H | O | H | H | |
| SCH₃ | CH₃ | H | O | Cl | H | |
| SCH₃ | CH₃ | H | O | NO₂ | H | |
| SCH₃ | CH₃ | H | S | Cl | H | |
| SCH₃ | CH₃ | CH₃ | O | Cl | H | |
| SCH₃ | CH₃ | H | O | Cl | 5-F | |
| SCH₃ | CH₃ | H | O | SO₂CH₃ | 4-Br | |
| SCH₃ | C₂H₅ | H | O | SO₂CH₃ | 6-Br | |
| SCH₃ | CH₃ | H | O | SO₂N(CH₃)₂ | 6-Cl | |
| CH₃ | C₂H₅ | H | O | NO₂ | 5-F | |
| C₂H₅ | CH₃ | H | O | CH₃ | 4-Cl | |
| SCH₃ | CH₃ | CH₃ | O | Cl | 6-Cl | |
| SCH₃ | C₂H₅ | H | S | OCH₃ | H | |
| SCH₃ | CH₃ | H | O | CO₂CH₂CH=CH₂ | H | |
| SCH₃ | CH₃ | H | O | CO₂CH(CH₃)₂ | H | |
| SCH₃ | C₂H₅ | H | O | CO₂CH₂CH₂Cl | H | |
| SCH₃ | CH₃ | H | O | CO₂CH₂CH(CH₃)₂ | H | |
| SCH₃ | C₂H₅ | H | O | n-C₄H₉ | H | |
| SCH₃ | CH₃ | H | O | SCH₃ | H | |
| SCH₃ | CH₃ | H | O | S(CH₂)₂CH₃ | H | |
| SCH₃ | CH₃ | H | O | F | H | |
| SC₂H₅ | CH₃ | H | S | CH₃ | H | |
| SC₂H₅ | CH₃ | H | O | SO₂CH₃ | H | |
| S(CH₂)₂CH₃ | CH₃ | H | O | SO₂CH₃ | H | |
| SCH(CH₃)C₂H₅ | CH₃ | H | O | Cl | H | |
| SCH(CH₃)₂ | CH₃ | H | O | SO₂C₂H₅ | H | |
| SCH₂CH=CH₂ | CH₃ | H | O | CO₂C₂H₅ | H | |
| SCH₂C(CH₃)=CH₂ | CH₃ | H | O | SO₂CH₃ | H | |
| SCH₂C≡C—CH₃ | CH₃ | H | O | CO₂CH₃ | H | |
| SCH₂C≡CH | CH₃ | H | O | Cl | H | |
| SCH₂CO₂CH₃ | CH₃ | H | O | CF₃ | H | |
| SCH₂CO₂CH(CH₃)₂ | CH₃ | H | O | NO₂ | H | |
| SCH(CH₃)CO₂CH₃ | CH₃ | H | O | CO₂CH₃ | H | |
| OCH₃ | C₂H₅ | H | S | Cl | H | |
| OCH₃ | C₂H₅ | CH₃ | O | Cl | H | |
| OCH₃ | C₂H₅ | H | O | H | H | |
| OCH₃ | C₂H₅ | H | O | F | H | |
| OCH₃ | C₂H₅ | H | O | H | 4-F | |
| OCH₃ | C₂H₅ | H | O | H | 5-F | |
| OCH₃ | C₂H₅ | H | O | Cl | H | |
| OCH₃ | C₂H₅ | H | O | SO₂CH₃ | H | |
| OCH₃ | C₂H₅ | H | O | CF₃ | H | |
| OCH₃ | C₂H₅ | H | O | NO₂ | H | |
| OC₂H₅ | CH₃ | H | S | CH₃ | H | |
| OC₂H₅ | CH₃ | H | O | OC₂H₅ | H | |
| OC₂H₅ | CH₃ | CH₃ | O | Cl | H | |
| OC₂H₅ | CH₃ | CH₃ | O | SO₂CH₃ | H | |
| OC₂H₅ | CH₃ | H | S | SO₂CH₃ | H | |
| OC₂H₅ | CH₃ | H | O | SO₂N(CH₃)[(CH₂)₂CH₃] | H | |
| OCH₃ | C₂H₅ | H | O | SO₂N(CH₃)₂ | H | |
| OCH₃ | C₂H₅ | H | O | SO₂N(CH₃)OCH₃ | H | |
| OCH₃ | C₂H₅ | H | O | SO₂C₂H₅ | H | |
| OC₂H₅ | CH₃ | H | O | SO₂(CH₂)₃CH₃ | H | |
| OC₂H₅ | CH₃ | H | O | Cl | 6-CH₃ | |
| OCH₃ | C₂H₅ | H | O | NO₂ | 5-Cl | |
| OCH₃ | C₂H₅ | H | O | Cl | 5-CH₃ | |
| OCH₃ | C₂H₅ | H | O | Br | 4-Cl | |
| OCH₃ | C₂H₅ | H | O | OCH₃ | 5-F | |
| OCH₃ | C₂H₅ | H | O | SO₂CH₃ | 4-Br | |
| OCH₃ | C₂H₅ | H | O | SO₂CH₃ | 6-Cl | |
| OC₂H₅ | CH₃ | H | O | SO₂CH₃ | 5-OCH₃ | |
| OCH₃ | C₂H₅ | H | O | SO₂CH₃ | 4-OCH₃ | |
| OCH₃ | C₂H₅ | H | O | SCH₃ | H | |
| OC₂H₅ | CH₃ | H | O | S(CH₂)₃CH₃ | H | |
| OC₂H₅ | CH₃ | H | O | SO₂N(CH₃)C₂H₅ | H | |
| OC₂H₅ | CH₃ | H | O | CF₃ | H | |
| OCH₃ | C₂H₅ | H | O | Br | H | |
| OCH₃ | C₂H₅ | H | O | NO₂ | H | |
| OCH₃ | C₂H₅ | H | O | n-C₃H₇ | H | |
| OC₂H₅ | CH₃ | H | O | OCH₂(CH₂)₂CH₃ | H | |
| OC₂H₅ | CH₃ | H | O | OCH₂CH(CH₃)₂ | H | |
| OC₂H₅ | CH₃ | H | O | OC₂H₅ | H | |

TABLE 3-continued

| R₁ | R₂ | R₃ | W | R₁₆ | R₁₇ | m.p. (°C.) |
|---|---|---|---|---|---|---|
| OCH₃ | CH₃ | H | O | CO₂CH₂CH₂OCH₃ | H | |
| OCH₃ | C₂H₅ | H | O | CO₂(CH₂)₃OCH₃ | H | |
| OCH₃ | C₂H₅ | H | O | CO₂(CH₂)₂OCH₃ | H | |
| OC₂H₅ | C₂H₅ | H | O | CO₂CH₂CH₂Cl | H | |
| OCH₃ | C₂H₅ | CH₃ | O | CO₂C₂H₅ | H | |
| OCH₃ | C₂H₅ | CH₃ | O | CO₂CH₃ | H | |
| OC₂H₅ | C₂H₅ | CH₃ | O | SO₂N(C₂H₅)₂ | H | |
| OCH₂CH=CH₂ | CH₃ | H | O | SO₂CH₃ | H | |
| OCH₂C(CH₃)=CH₂ | CH₃ | H | O | Cl | H | |
| OCH(CH₃)C₂H₅ | CH₃ | H | O | SO₂CH₃ | H | |
| O(CH₂)₂CH₃ | CH₃ | H | O | SO₂CH₃ | H | |
| OCH(CH₃)₂ | CH₃ | H | O | CO₂C₂H₅ | H | |
| O(CH₂)₂CH₃ | CH₃ | H | O | CO₂CH(CH₃)₂ | H | |
| OCH₂CH=CHCH₃ | CH₃ | H | O | Cl | H | |
| OCH₂C≡CCH₃ | CH₃ | H | O | SO₂CH₃ | H | |
| CH₂OCH₃ | CH₃ | H | O | NO₂ | H | |
| CH₂OCH₃ | CH₃ | H | O | SO₂N(CH₃)[CH(CH₃)₂] | H | |
| CH₂OCH₃ | CH₃ | H | O | SO₂N(CH₃)₂ | H | |
| CH₂OCH₃ | CH₃ | H | O | SO₂CH₃ | H | |
| CH₂OCH₃ | CH₃ | H | O | Cl | H | |
| CH₂OCH₃ | CH₃ | H | O | F | H | |
| CH₂OCH₃ | CH₃ | H | O | H | H | |
| CH₂OCH₃ | CH₃ | H | S | Cl | H | |
| CH₂OCH₃ | CH₃ | CH₃ | O | CH₃ | H | |
| CH₂OCH₃ | CH₃ | CH₃ | O | Cl | H | |
| CH₂OCH₃ | CH₃ | H | O | SC₂H₅ | H | |
| CH₂OCH₃ | CH₃ | H | O | OCH₃ | H | |
| CH₂OCH₃ | CH₃ | H | O | CO₂CH₂CH₂Cl | H | |
| CH₂OC₂H₅ | CH₃ | CH₃ | O | CO₂CH(CH₃)₂ | H | |
| CH₂OC₂H₅ | CH₃ | H | O | CO₂CH₂CH=CH₂ | H | |
| CH₂O(CH₂)₃CH₃ | CH₃ | H | O | CO₂CH₃ | H | |
| CH₂CH(CH₃)₂ | CH₃ | H | O | Cl | H | |
| CH₂CH₂OCH₃ | CH₃ | H | O | CO₂C₂H₅ | H | |
| CH₂CH₂OCH(CH₃)₂ | CH₃ | H | O | CO₂CH(CH₃)₂ | H | |
| CH₂CH₂O(CH₂)₂CH₃ | CH₃ | H | O | SO₂CH₃ | H | |
| N(CH₃)₂ | CH₃ | H | O | Cl | H | |
| CF₂CF₃ | CH₃ | H | O | SO₂CH₃ | H | |
| CF₃ | CH₃ | H | O | Cl | H | |
| CF₂CF₃ | CH₃ | H | O | CO₂CH₃ | H | |
| CF₂CF₃ | CH₃ | H | O | NO₂ | H | |
| CF₂CF₃ | CH₃ | H | O | SO₂CH(CH₃)₂ | H | |
| CH₃ | CH₂OCH₃ | H | S | Cl | H | |
| CH₃ | CH₂OCH₃ | H | O | SO₂C₂H₅ | H | |
| CH₃ | CH₂OCH₃ | H | O | CO₂CH₃ | H | |
| CH₃ | CH₂CH₂OCH₃ | H | O | Cl | H | |
| CH₃ | CH₂SCH₃ | H | O | CO₂CH₃ | H | |
| CH₃ | CH₂CH₂SCH₃ | H | O | SO₂C₂H₅ | H | |
| SCH₃ | CH₃ | CH₃ | O | SO₂N(CH₃)₂ | H | |
| SCH₃ | CH₃ | H | O | SO₂(CH₂)₃CH₃ | H | |
| SCH₃ | CH₃ | H | O | S(CH₂)₃CH₃ | H | |
| SCH₃ | CH₃ | H | O | SO₂CH₂CH(CH₃)₂ | H | |
| SCH₃ | CH₃ | H | O | SCH(CH₃)₂ | H | |
| OC₂H₅ | CH₃ | H | O | NO₂ | 4-F | |
| SCH₃ | CH₃ | H | O | NO₂ | 4-OCH₃ | |
| SCH₃ | CH₃ | CH₃ | O | CO₂CH₂CH₂OCH₃ | H | |
| SCH₃ | CH₃ | H | O | O—CH(CH₃)C₂H₅ | H | |
| SCH₃ | CH₃ | CH₃ | O | SO₂(CH₂)CH₃ | H | |
| OC₂H₅ | C₂H₅ | H | O | F | H | |
| CF₃ | C₂H₅ | CH₃ | O | SO₂CH₃ | H | |
| SCH₃ | CH₃ | CH₃ | O | SO₂N(OCH₃)CH₃ | H | |
| OCH₃ | CH₃ | H | O | CH₃ | H | |
| OCH₃ | CH₃ | H | O | CH(CH₃)₂ | H | |
| OCH₃ | CH₃ | H | O | OCH₃ | H | |
| OCH₃ | CH₃ | H | O | O(CH₂)₃CH₃ | H | |
| OCH₃ | CH₃ | H | O | F | H | |
| OCH₃ | CH₃ | H | O | Cl | H | 165–168° |
| OCH₃ | CH₃ | H | O | Br | H | |
| OCH₃ | CH₃ | H | O | CF₃ | H | |
| OCH₃ | CH₃ | H | O | CO₂CH₃ | H | |
| OCH₃ | CH₃ | H | O | CO₂C₂H₅ | H | |
| OCH₃ | CH₃ | H | O | CO₂CH(CH₃)₂ | H | |
| OCH₃ | CH₃ | H | O | CO₂CH₂CH₂CH₂CH₃ | H | |

TABLE 3-continued

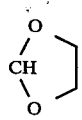

| $R_1$ | $R_2$ | $R_3$ | W | $R_{16}$ | $R_{17}$ | m.p. (°C.) |
|---|---|---|---|---|---|---|
| OCH$_3$ | CH$_3$ | H | O | CO$_2$CH$_2$CH$_2$Cl | H | |
| OCH$_3$ | CH$_3$ | H | O | CO$_2$CH$_2$CH=CH$_2$ | H | |
| OCH$_3$ | CH$_3$ | H | O | SO$_2$N(CH$_3$)$_2$ | H | |
| OCH$_3$ | CH$_3$ | H | O | SO$_2$N(CH$_3$)C$_2$H$_5$ | H | |
| OCH$_3$ | CH$_3$ | H | O | SO$_2$N(C$_2$H$_5$)$_2$ | H | |
| OCH$_3$ | CH$_3$ | H | O | SO$_2$N(OCH$_3$)CH$_3$ | H | |
| OCH$_3$ | CH$_3$ | H | O | SO$_2$CH$_3$ | H | |
| OCH$_3$ | CH$_3$ | H | O | SOCH$_3$ | H | |
| OCH$_3$ | CH$_3$ | H | O | SCH$_3$ | H | |
| OCH$_3$ | CH$_3$ | H | O | SC$_2$H$_5$ | H | |
| OCH$_3$ | CH$_3$ | H | O | SO$_2$C$_2$H$_5$ | H | |
| OCH$_3$ | CH$_3$ | H | O | SO$_2$CH$_2$CH$_2$CH$_3$ | H | |
| OCH$_3$ | CH$_3$ | H | O | SO$_2$CH(CH$_3$)$_2$ | H | |
| OCH$_3$ | CH$_3$ | H | O | SO$_2$CH$_2$CH=CH$_2$ | H | |
| OCH$_3$ | CH$_3$ | H | O | SCH$_2$CH=CH$_2$ | H | |
| OCH$_3$ | CH$_3$ | H | O | SO$_2$CF$_3$ | H | |
| OCH$_3$ | CH$_3$ | H | O | SO$_2$CF$_2$CF$_3$ | H | |
| OC$_2$H$_5$ | CH$_3$ | H | O | Cl | H | |
| OC$_2$H$_5$ | CH$_3$ | H | O | Br | H | |
| OC$_2$H$_5$ | CH$_3$ | H | O | SO$_2$CH$_3$ | H | |
| OC$_2$H$_5$ | CH$_3$ | H | O | CO$_2$CH$_3$ | H | |
| OC$_2$H$_5$ | CH$_3$ | H | O | CO$_2$C$_2$H$_5$ | H | |
| OC$_2$H$_5$ | CH$_3$ | H | O | CO$_2$CH$_2$CH=CH$_2$ | H | |
| OC$_2$H$_5$ | CH$_3$ | H | O | SO$_2$N(CH$_3$)$_2$ | H | |
| OC$_2$H$_5$ | CH$_3$ | H | O | CH$_3$ | H | |
| OC$_2$H$_5$ | CH$_3$ | H | O | CH(CH$_3$)$_2$ | H | |
| OC$_2$H$_5$ | CH$_3$ | H | O | CO$_2$CH(CH$_3$)$_2$ | H | |
| OCH$_3$ | CH$_2$CF$_3$ | H | O | Cl | H | |
| OCH$_3$ | CH$_2$CF$_3$ | H | O | SO$_2$CH$_3$ | H | |
| OCH$_3$ | CH$_2$CF$_3$ | H | O | SO$_2$N(CH$_3$)$_2$ | H | |
| OCH$_3$ | CH$_2$CF$_3$ | H | O | CO$_2$CH$_3$ | H | |
| OCH$_3$ | CH$_2$CF$_3$ | H | O | Br | H | |
| Cl | CH$_3$ | H | O | Cl | H | |
| Cl | CH$_3$ | H | O | Br | H | |
| Cl | CH$_3$ | H | O | CH$_3$ | H | |
| Cl | CH$_3$ | H | O | OCH$_3$ | H | |
| Cl | CH$_3$ | H | O | CF$_3$ | H | |
| Cl | CH$_3$ | H | O | CO$_2$CH$_3$ | H | |
| Cl | CH$_3$ | H | O | CO$_2$CH$_2$CH=CH$_2$ | H | |
| Cl | CH$_3$ | H | O | SO$_2$N(CH$_3$)$_2$ | H | |
| Cl | CH$_3$ | H | O | SO$_2$CH$_3$ | H | |
| NHCH$_3$ | CH$_3$ | H | O | Cl | H | |
| NHCH$_3$ | CH$_3$ | H | O | CO$_2$CH$_3$ | H | |
| NHCH$_3$ | CH$_3$ | H | O | SO$_2$CH$_3$ | H | |
| CH(OCH$_3$)$_2$ | CH$_3$ | H | O | Cl | H | |
| CH(OCH$_3$)$_2$ | CH$_3$ | H | O | CO$_2$CH$_3$ | H | |
| CH(OCH$_3$)$_2$ | CH$_3$ | H | O | SO$_2$N(CH$_3$)$_2$ | H | |
| 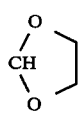 | CH$_3$ | H | O | Cl | H | |
| 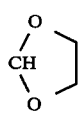 | CH$_3$ | H | O | CO$_2$CH$_3$ | H | |
| 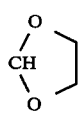 | CH$_3$ | H | O | CO$_2$CH$_2$CH=CH$_2$ | H | |

TABLE 3-continued

Structure: R₂-N¹-N²-N with R₁ at position 5, N⁴, connected to C³(=W)-N(R₃)-C(=NHSO₂)- attached to phenyl ring with R₁₆ at position 2, N¹, and R₁₇ at position 6.

| R₁ | R₂ | R₃ | W | R₁₆ | R₁₇ | m.p. (°C.) |
|---|---|---|---|---|---|---|
| $\begin{array}{c}O\\ \|\\ CH\\ \|\\ O\end{array}$ (dioxolane) | CH₃ | H | O | SO₂CH₂CH=CH₂ | H | |

TABLE 4

Structure with thiophene ring: R₁₈ at position 2, S¹, R₁₇ at position 5.

| R₁ | R₂ | R₃ | W | R₁₇ | R₁₈ | m.p. (°C.) |
|---|---|---|---|---|---|---|
| H | C₂H₅ | H | O | H | CO₂CH₃ | |
| H | n-C₃H₇ | H | O | H | CO₂C₂H₅ | |
| CH₃ | C₂H₅ | H | O | H | Br | |
| CH₃ | C₂H₅ | H | O | H | CO₂CH(CH₃)₂ | |
| CH₃ | CH₂CH(CH₃)₂ | H | O | H | CO₂CH₃ | |
| CH₃ | C₂H₅ | H | O | H | NO₂ | |
| CH₃ | C₂H₅ | H | O | H | H | |
| CH₃ | C₂H₅ | H | S | H | Cl | |
| CH₃ | C₂H₅ | H | O | H | Cl | |
| CH₃ | C₂H₅ | CH₃ | O | H | CO₂CH₂CH=CH₂ | |
| CH₃ | C₂H₅ | H | O | H | CO₂CH₂CH₂Cl | |
| CH₃ | C₂H₅ | CH₃ | O | H | CO₂CH₃ | |
| CH₃ | C₂H₅ | CH₃ | O | H | SO₂CH₃ | |
| C₂H₅ | CH₃ | CH₃ | O | H | SO₂CH₃ | |
| C₂H₅ | CH₃ | CH₃ | O | H | OCH₃ | |
| CH₃ | C₂H₅ | CH₃ | O | H | SO₂N(CH₃)₂ | |
| CH₃ | C₂H₅ | H | S | H | NO₂ | |
| CH₃ | C₂H₅ | H | O | H | SO₂N(CH₃)OCH₃ | |
| C₂H₅ | CH₃ | H | S | H | SO₂CH₃ | |
| C₂H₅ | CH₃ | H | O | 5-F | SO₂CH₃ | |
| C₂H₅ | CH₃ | H | O | 4-F | Br | |
| CH₃ | C₂H₅ | H | O | 5-Cl | Br | |
| CH₃ | C₂H₅ | H | O | 5-CH₃ | Cl | |
| C₂H₅ | C₂H₅ | H | O | H | Br | |
| C₂H₅ | C₂H₅ | H | O | H | CO₂CH₃ | |
| C₂H₅ | C₂H₅ | H | O | H | SO₂CH₃ | |
| C₂H₅ | C₂H₅ | H | O | H | SO₂N(CH₃)C₂H₅ | |
| CH₃ | C₂H₅ | H | O | H | SO₂(CH₂)₂CH₃ | |
| C₂H₅ | CH₃ | H | O | H | SCH₃ | |
| C₂H₅ | C₂H₅ | CH₃ | O | H | SO₂CH₃ | |
| C₂H₅ | C₂H₅ | CH₃ | O | H | CO₂CH₃ | |
| C₂H₅ | C₂H₅ | H | O | H | H | |
| CH₃ | C₂H₅ | H | O | 5-F | H | |
| CH₃ | C₂H₅ | H | O | 5-Cl | H | |
| C₂H₅ | C₂H₅ | H | O | H | SO₂N(CH₃)₂ | |
| C₂H₅ | C₂H₅ | H | S | H | Br | |
| CH₃ | C₂H₅ | H | O | H | F | |
| C₂H₅ | C₂H₅ | H | O | H | F | |
| n-C₃H₇ | CH₃ | H | O | H | CO₂CH₃ | |
| CH(CH₃)₂ | CH₃ | H | O | H | SO₂CH₃ | |
| CH₂CH(CH₃)₂ | CH₃ | H | O | H | CO₂C₂H₅ | |
| CH₃ | n-C₃H₇ | H | O | H | Br | |
| CH₃ | CH₂CH=CH₂ | H | O | H | CO₂CH(CH₃)₂ | |
| CH₃ | CH₂C(CH₃)=CH₂ | H | O | H | CO₂CH₃ | |
| CH₂CH=CH₂ | CH₃ | H | O | H | C₂H₅ | |
| CH₂C(CH₃)=CH₂ | CH₃ | H | O | H | SO₂CH₃ | |
| CH₃ | CH₂C≡CCH₃ | H | O | H | CO₂CH₃ | |
| CH₂C≡CCH₃ | CH₃ | H | O | H | SO₂C₂H₅ | |
| SCH₃ | CH₃ | H | S | H | Br | |
| SCH₃ | CH₃ | CH₃ | O | H | Br | |
| SCH₃ | CH₃ | H | O | 4-Cl | Br | |
| SCH₃ | CH₃ | H | O | 5-OCH₃ | H | |
| SCH₃ | CH₃ | H | O | 5-Cl | Cl | |

TABLE 4-continued

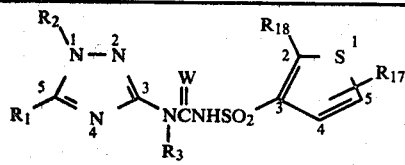

| $R_1$ | $R_2$ | $R_3$ | W | $R_{17}$ | $R_{18}$ | m.p. (°C.) |
|---|---|---|---|---|---|---|
| $SCH_3$ | $CH_3$ | H | O | H | $NO_2$ | |
| $SCH_3$ | $CH_3$ | H | O | H | $SO_2N(CH_3)C_2H_5$ | |
| $SCH_3$ | $CH_3$ | H | O | H | $SO_2N(CH_3)[CH(CH_3)_2]$ | |
| $SCH_3$ | $CH_3$ | H | O | H | F | |
| $SCH_3$ | $CH_3$ | H | O | 5-F | H | |
| $SCH_3$ | $CH_3$ | H | O | 4-Br | H | |
| $SCH_3$ | $CH_3$ | H | O | 5-Br | H | |
| $SCH_3$ | $CH_3$ | $CH_3$ | O | H | $SO_2CH_3$ | |
| $SCH_3$ | $CH_3$ | H | O | H | $CO_2CH_3$ | 200–202° |
| $SCH_3$ | $CH_3$ | $CH_3$ | O | H | $SO_2N(CH_3)_2$ | |
| $SCH_3$ | $CH_3$ | H | O | H | $OC_2H_5$ | |
| $SCH_3$ | $CH_3$ | H | S | H | H | |
| $SCH_3$ | $CH_3$ | H | O | H | $CO_2(CH_2)_3CH_3$ | |
| $SCH_3$ | $CH_3$ | H | O | H | $CO_2CH_2CH_2OCH_3$ | |
| $SCH_3$ | $CH_3$ | H | O | 5-Cl | H | |
| $SCH_3$ | $CH_3$ | H | O | H | $OCH(CH_3)C_2H_5$ | |
| $SCH_3$ | $CH_3$ | H | O | 5-$CH_3$ | $CH_3$ | |
| $SCH_3$ | $CH_3$ | H | O | H | $SCH_3$ | |
| $SCH_3$ | $CH_3$ | H | O | H | $S(CH_2)_3CH_3$ | |
| $SCH_3$ | $C_2H_5$ | H | O | H | $SO_2C_2H_5$ | |
| $SCH_3$ | $CH_3$ | H | O | H | $CO_2CH(CH_3)_2$ | |
| $SCH_3$ | $CH_3$ | H | O | H | $CO_2CH_2CH=CH_2$ | |
| $SCH_3$ | $C_2H_5$ | H | O | H | $CO_2CH_3$ | |
| $SCH_3$ | $C_2H_5$ | H | O | H | Br | |
| $SCH_3$ | $C_2H_5$ | H | O | H | $SO_2CH_3$ | |
| $SCH_3$ | $C_2H_5$ | H | S | H | Cl | |
| $SCH_3$ | $C_2H_5$ | H | O | H | $NO_2$ | |
| $SC_2H_5$ | $CH_3$ | H | O | H | $CO_2CH(CH_3)_2$ | |
| $SC_2H_5$ | $CH_3$ | H | O | H | $CH_3$ | |
| $SC_2H_5$ | $CH_3$ | H | O | H | $CO_2CH_3$ | |
| $SC_2H_5$ | $CH_3$ | H | O | H | $SO_2CH_3$ | |
| $SC_2H_5$ | $CH_3$ | H | O | H | Br | |
| $SC_2H_5$ | $CH_3$ | $CH_3$ | O | H | Cl | |
| $SC_2H_5$ | $CH_3$ | H | S | H | Br | |
| $SCH(CH_3)_2$ | $CH_3$ | H | O | H | $CO_2CH_3$ | |
| $S(CH_2)_3CH_3$ | $CH_3$ | H | O | H | $SO_2CH_3$ | |
| $SCH_2CH=CH_2$ | $CH_3$ | H | O | H | $CO_2CH_3$ | |
| $S(CH_2)_2CH_3$ | $CH_3$ | H | O | H | $CO_2CH_3$ | |
| $SCH_2C(CH_3)=CH_2$ | $CH_3$ | H | O | H | $CO_2C_2H_5$ | |
| $SCH_2C\equiv CCH_3$ | $CH_3$ | H | O | H | $CO_2CH_3$ | |
| $SCH_2CO_2CH_3$ | $CH_3$ | H | O | H | $NO_2$ | |
| $SCH_2CO_2(CH_2)_3CH_3$ | $CH_3$ | H | O | H | $CO_2CH_3$ | |
| $SCH(CH_3)CO_2CH_3$ | $CH_3$ | H | O | H | $CO_2CH_3$ | |
| $OCH_3$ | $CH_3$ | H | O | H | $CO_2CH_3$ | 183–186° |
| $OCH_3$ | $CH_3$ | H | O | H | $SO_2N(CH_3)C_2H_5$ | |
| $OCH_3$ | $CH_3$ | H | O | H | Br | |
| $OCH_3$ | $CH_3$ | H | O | H | Cl | |
| $OCH_3$ | $CH_3$ | H | O | H | $NO_2$ | |
| $OCH_3$ | $CH_3$ | H | S | H | $SO_2CH_3$ | |
| $OCH_3$ | $CH_3$ | $CH_3$ | O | H | $SO_2CH_3$ | |
| $OCH_3$ | $CH_3$ | H | O | H | $SO_2CH_3$ | |
| $OCH_3$ | $CH_3$ | H | O | H | $SO_2(CH_2)_2CH_3$ | |
| $OCH_3$ | $CH_3$ | H | O | H | $OCH_3$ | |
| $OC_2H_5$ | $CH_3$ | H | O | H | $O(CH_2)_3CH_3$ | |
| $OC_2H_5$ | $CH_3$ | H | O | H | $CO_2CH_2CH=CH_2$ | |
| $OCH_3$ | $CH_3$ | H | O | H | $CO_2CH_2CH_2Cl$ | |
| $OCH_3$ | $C_2H_5$ | H | O | H | $CO_2CH(CH_3)_2$ | |
| $OCH_3$ | $C_2H_5$ | H | O | H | $CO_2(CH_2)_2CH_3$ | |
| $OC_2H_5$ | $CH_3$ | H | O | H | $CO_2C_2H_5$ | |
| $OCH_3$ | $C_2H_5$ | $CH_3$ | O | H | $CO_2CH_3$ | |
| $OCH_3$ | $C_2H_5$ | H | S | H | Cl | |
| $OC_2H_5$ | $CH_3$ | H | S | H | Br | |
| $OCH_3$ | $C_2H_5$ | H | O | H | $SO_2CH_3$ | |
| $OCH_3$ | $C_2H_5$ | H | O | H | $SO_2(CH_2)_3CH_3$ | |
| $OCH_3$ | $C_2H_5$ | H | O | H | $SO_2CH_2CH(CH_3)_2$ | |
| $OCH_3$ | $C_2H_5$ | $CH_3$ | O | H | $SO_2CH_3$ | |
| $OCH_3$ | $C_2H_5$ | $CH_3$ | O | 5-Cl | $SO_2CH_3$ | |
| $OCH_3$ | $C_2H_5$ | $CH_3$ | O | 5-Br | $SO_2CH_3$ | |
| $OCH_3$ | $C_2H_5$ | H | O | H | $OC_2H_5$ | |
| $OCH_3$ | $C_2H_5$ | H | O | H | F | |
| $OCH_3$ | $C_2H_5$ | H | O | 5-F | F | |
| $OCH_3$ | $C_2H_5$ | H | O | H | $SC_2H_5$ | |

TABLE 4-continued

Structure:
$$R_2-N_1-N_2, \quad R_1-C_5=N_4-C_3(=W)-N(R_3)-C(=O)NHSO_2-\text{(ring with }R_{17}, R_{18}, S_1\text{)}$$

| $R_1$ | $R_2$ | $R_3$ | W | $R_{17}$ | $R_{18}$ | m.p. (°C.) |
|---|---|---|---|---|---|---|
| OC$_2$H$_5$ | CH$_3$ | H | O | H | SO$_2$N(OCH$_3$)CH$_3$ | |
| OC$_2$H$_5$ | CH$_3$ | H | O | H | SO$_2$N(CH$_3$)[(CH$_2$)$_2$CH$_3$] | |
| OC$_2$H$_5$ | CH$_3$ | H | S | H | H | |
| OC$_2$H$_5$ | CH$_3$ | H | S | H | NO$_2$ | |
| OC$_2$H$_5$ | CH$_3$ | H | O | H | CO$_2$CH(CH$_3$)$_2$ | |
| OC$_2$H$_5$ | CH$_3$ | H | O | H | CO$_2$CH$_2$CH$_2$Cl | |
| OC$_2$H$_5$ | CH$_3$ | H | O | H | CH$_3$ | |
| OC$_2$H$_5$ | CH$_3$ | H | O | H | CH(CH$_3$)$_2$ | |
| OC$_2$H$_5$ | CH$_3$ | H | O | H | CH$_2$CH(CH$_3$)$_2$ | |
| OC$_2$H$_5$ | CH$_3$ | CH$_3$ | O | H | CH$_3$ | |
| OC$_2$H$_5$ | CH$_3$ | CH$_3$ | O | H | SO$_2$CH$_3$ | |
| OC$_2$H$_5$ | CH$_3$ | CH$_3$ | O | H | Cl | |
| OC$_2$H$_5$ | CH$_3$ | H | O | H | C$_2$H$_5$ | |
| OC$_2$H$_5$ | CH$_3$ | H | O | H | NO$_2$ | |
| OC$_2$H$_5$ | CH$_3$ | H | O | 4-Br | Br | |
| OC$_2$H$_5$ | CH$_3$ | H | O | 4-Cl | Cl | |
| OC$_2$H$_5$ | C$_2$H$_5$ | H | O | H | Cl | |
| OC$_2$H$_5$ | C$_2$H$_5$ | H | O | H | CO$_2$CH$_3$ | |
| OC$_2$H$_5$ | C$_2$H$_5$ | H | O | H | SO$_2$CH$_3$ | |
| OC$_2$H$_5$ | C$_2$H$_5$ | H | O | H | SO$_2$N(CH$_3$)$_2$ | |
| OC$_2$H$_5$ | C$_2$H$_5$ | H | O | H | NO$_2$ | |
| OC$_2$H$_5$ | C$_2$H$_5$ | H | O | H | Br | |
| OC$_2$H$_5$ | C$_2$H$_5$ | H | O | H | CO$_2$CH(CH$_3$)$_2$ | |
| OCH$_3$ | C$_2$H$_5$ | H | O | H | SO$_2$C$_2$H$_5$ | |
| OCH$_3$ | C$_2$H$_5$ | H | O | 4-F | F | |
| OC$_2$H$_5$ | CH$_3$ | H | O | H | OCH(CH$_3$)$_2$ | |
| OCH$_2$CH=CH$_2$ | CH$_3$ | H | O | H | SO$_2$CH$_3$ | |
| OCH$_2$C(CH$_3$)=CH$_2$ | CH$_3$ | H | O | H | CO$_2$CH$_3$ | |
| OCH(CH$_3$)C$_2$H$_5$ | CH$_3$ | H | O | H | CO$_2$CH$_3$ | |
| OCH(CH$_3$)$_2$ | CH$_3$ | H | O | H | CO$_2$C$_2$H$_5$ | |
| O(CH$_2$)$_2$CH$_3$ | CH$_3$ | H | O | H | Cl | |
| OCH$_2$C≡CCH$_3$ | CH$_3$ | H | O | H | NO$_2$ | |
| CH$_2$OCH$_3$ | CH$_3$ | H | O | H | Br | |
| CH$_2$OCH$_3$ | CH$_3$ | H | O | H | Cl | |
| CH$_2$OCH$_3$ | CH$_3$ | CH$_3$ | O | H | SO$_2$CH$_3$ | |
| CH$_2$OCH$_3$ | CH$_3$ | CH$_3$ | O | H | CO$_2$CH$_3$ | |
| CH$_2$OCH$_3$ | CH$_3$ | H | O | H | CO$_2$CH$_3$ | |
| CH$_2$OCH$_3$ | CH$_3$ | H | O | H | NO$_2$ | |
| CH$_2$OCH$_3$ | CH$_3$ | H | S | H | Cl | |
| CH$_2$OCH$_3$ | CH$_3$ | H | O | H | H | |
| CH$_2$OCH$_3$ | CH$_3$ | H | O | H | SO$_2$N(CH$_3$)$_2$ | |
| CH$_2$OCH$_3$ | CH$_3$ | CH$_3$ | O | H | SO$_2$N(CH$_3$)C$_2$H$_5$ | |
| CH$_2$OCH$_3$ | C$_2$H$_5$ | H | O | H | SO$_2$C$_2$H$_5$ | |
| CH$_2$OCH$_3$ | C$_2$H$_5$ | H | O | H | CO$_2$CH$_3$ | |
| CH$_2$OC$_2$H$_5$ | CH$_3$ | H | O | H | Br | |
| CH$_2$OCH(CH$_3$)$_2$ | CH$_3$ | H | O | H | CO$_2$CH$_3$ | |
| CH$_2$O(CH$_2$)$_3$CH$_3$ | CH$_3$ | H | O | H | CO$_2$CH$_3$ | |
| CH$_2$CH$_2$OCH$_3$ | CH$_3$ | H | O | H | Cl | |
| CH$_2$CH$_2$OCH(CH$_3$)$_2$ | CH$_3$ | H | O | H | CO$_2$CH$_3$ | |
| N(CH$_3$)$_2$ | CH$_3$ | H | O | H | CO$_2$CH$_3$ | |
| CF$_3$ | CH$_3$ | H | O | H | SO$_2$CH$_3$ | |
| CF$_3$ | CH$_3$ | H | O | H | CO$_2$CH$_3$ | |
| CF$_3$ | C$_2$H$_5$ | H | O | H | CO$_2$CH(CH$_3$)$_2$ | |
| CF$_3$ | C$_2$H$_5$ | H | O | H | SO$_2$CH$_3$ | |
| CF$_3$ | C$_2$H$_5$ | H | O | H | Br | |
| CF$_2$CF$_3$ | CH$_3$ | H | O | H | CO$_2$CH$_3$ | |
| CF$_2$CF$_3$ | CH$_3$ | H | O | H | Cl | |
| CH$_3$ | CH$_2$OCH$_3$ | H | O | H | CO$_2$CH$_3$ | |
| CH$_3$ | CH$_2$SCH$_3$ | H | O | H | Cl | |
| CH$_3$ | CH$_2$CH$_2$OCH$_3$ | H | O | H | CO$_2$CH$_3$ | |
| CH$_3$ | CH$_2$CH$_2$SCH$_3$ | H | O | H | Br | |
| CH$_2$OCH$_3$ | C$_2$H$_5$ | H | O | H | CO$_2$CH$_3$ | |
| CH$_2$OCH$_3$ | CH$_3$ | CH$_3$ | O | H | CO$_2$CH$_3$ | |
| OC$_2$H$_5$ | CH$_3$ | CH$_3$ | O | H | SO$_2$(CH$_2$)$_2$CH$_3$ | |
| OC$_2$H$_5$ | CH$_3$ | H | O | H | SO$_2$CH(CH$_3$)$_2$ | |
| OC$_2$H$_5$ | CH$_3$ | H | O | H | SO$_2$N(C$_2$H$_5$)$_2$ | |
| OCH$_3$ | CH$_2$CF$_3$ | H | O | H | CO$_2$CH$_3$ | 152–155° |
| OCH$_3$ | CH$_3$ | H | O | H | CH$_3$ | |
| OCH$_3$ | CH$_3$ | H | O | H | C$_2$H$_5$ | |
| OCH$_3$ | CH$_3$ | H | O | H | CH(CH$_3$)$_2$ | |
| OCH$_3$ | CH$_3$ | H | O | H | OCH$_2$CH$_2$CH$_3$ | |
| OCH$_3$ | CH$_3$ | H | O | H | F | |

TABLE 4-continued

| $R_1$ | $R_2$ | $R_3$ | W | $R_{17}$ | $R_{18}$ | m.p. (°C.) |
|---|---|---|---|---|---|---|
| OCH$_3$ | CH$_3$ | H | O | H | CO$_2$C$_2$H$_5$ | |
| OCH$_3$ | CH$_3$ | H | O | H | CO$_2$CH$_2$CH$_2$OCH$_3$ | |
| OCH$_3$ | CH$_3$ | H | O | H | CO$_2$CH$_2$CH=CH$_2$ | |
| OCH$_3$ | CH$_3$ | H | O | H | SO$_2$N(CH$_3$)$_2$ | |
| OCH$_3$ | CH$_3$ | H | O | H | SO$_2$N(OCH$_3$)CH$_3$ | |
| OCH$_3$ | CH$_3$ | H | O | H | SO$_2$CH$_2$CH=CH$_2$ | |
| OC$_2$H$_5$ | CH$_3$ | H | O | H | F | |
| OC$_2$H$_5$ | CH$_3$ | H | O | H | Cl | |
| OC$_2$H$_5$ | CH$_3$ | H | O | H | Br | |
| OC$_2$H$_5$ | CH$_3$ | H | O | H | CO$_2$CH$_3$ | 194–197° |
| OC$_2$H$_5$ | CH$_3$ | H | O | H | SO$_2$N(CH$_3$)$_2$ | |
| OC$_2$H$_5$ | CH$_3$ | H | O | H | SO$_2$CH$_3$ | |
| OC$_2$H$_5$ | CH$_3$ | H | O | H | SO$_2$CH$_2$CH=CH$_2$ | |
| OCH$_3$ | CH$_2$CF$_3$ | H | O | H | CH$_3$ | |
| OCH$_3$ | CH$_2$CF$_3$ | H | O | H | OCH$_3$ | |
| OCH$_3$ | CH$_2$CF$_3$ | H | O | H | Cl | |
| OCH$_3$ | CH$_2$CF$_3$ | H | O | H | NO$_2$ | |
| OCH$_3$ | CH$_2$CF$_3$ | H | O | H | CO$_2$CH$_2$CH$_3$ | |
| OCH$_3$ | CH$_2$CF$_3$ | H | O | H | SO$_2$N(CH$_3$)$_2$ | |
| OCH$_3$ | CH$_2$CF$_3$ | H | O | H | SO$_2$CH$_3$ | |
| Cl | CH$_3$ | H | O | H | CH$_3$ | |
| Cl | CH$_3$ | H | O | H | OCH$_3$ | |
| Cl | CH$_3$ | H | O | H | Cl | |
| Cl | CH$_3$ | H | O | H | NO$_2$ | |
| Cl | CH$_3$ | H | O | H | CO$_2$CH$_3$ | |
| Cl | CH$_3$ | H | O | H | SO$_2$N(CH$_3$)$_2$ | |
| Cl | CH$_3$ | H | O | H | SO$_2$CH$_3$ | |
| NHCH$_3$ | CH$_3$ | H | O | H | CH$_3$ | |
| NHCH$_3$ | CH$_3$ | H | O | H | OCH$_3$ | |
| NHCH$_3$ | CH$_3$ | H | O | H | Cl | |
| NHCH$_3$ | CH$_3$ | H | O | H | NO$_2$ | |
| NHCH$_3$ | CH$_3$ | H | O | H | CO$_2$CH$_3$ | |
| NHCH$_2$ | CH$_3$ | H | O | H | SO$_2$N(CH$_3$)$_2$ | |
| NHCH$_3$ | CH$_3$ | H | O | H | SO$_2$CH$_3$ | |
| CH(OCH$_3$)$_2$ | CH$_3$ | H | O | H | CH$_3$ | |
| CH(OCH$_3$)$_2$ | CH$_3$ | H | O | H | OCH$_3$ | |
| CH(OCH$_3$)$_2$ | CH$_3$ | H | O | H | Cl | |
| CH(OCH$_3$)$_2$ | CH$_3$ | H | O | H | NO$_2$ | |
| CH(OCH$_3$)$_2$ | CH$_3$ | H | O | H | CO$_2$CH$_3$ | |
| CH(OCH$_3$)$_2$ | CH$_3$ | H | O | H | SO$_2$N(CH$_3$)$_2$ | |
| CH(OCH$_3$)$_2$ | CH$_3$ | H | O | H | SO$_2$CH$_3$ | |
| 1,3-dioxolan-2-yl | CH$_3$ | H | O | H | CH$_3$ | |
| 1,3-dioxolan-2-yl | CH$_3$ | H | O | H | OCH$_3$ | |
| 1,3-dioxolan-2-yl | CH$_3$ | H | O | H | Cl | |
| 1,3-dioxolan-2-yl | CH$_3$ | H | O | H | NO$_2$ | |
| 1,3-dioxolan-2-yl | CH$_3$ | H | O | H | CO$_2$CH$_3$ | |

TABLE 4-continued

| R₁ | R₂ | R₃ | W | R₁₇ | R₁₈ | m.p. (°C.) |
|---|---|---|---|---|---|---|
| $\begin{array}{c}O\\|\\CH\\|\\O\end{array}$ (dioxolane) | CH₃ | H | O | H | SO₂N(CH₃)₂ | |
| $\begin{array}{c}O\\|\\CH\\|\\O\end{array}$ (dioxolane) | CH₃ | H | O | H | SO₂CH₃ | |

TABLE 5

| R₁ | R₂ | R₃ | W | R₁₇ | R₁₈ | m.p. (°C.) |
|---|---|---|---|---|---|---|
| H | C₂H₅ | H | O | H | CO₂CH₃ | |
| H | n-C₃H₇ | H | O | H | CO₂C₂H₅ | |
| CH₃ | C₂H₅ | H | O | H | Br | |
| CH₃ | C₂H₅ | H | O | H | CO₂CH(CH₃)₂ | |
| CH₃ | CH₂CH(CH₃)₂ | H | O | H | CO₂CH₃ | |
| CH₃ | C₂H₅ | H | O | H | NO₂ | |
| CH₃ | C₂H₅ | H | O | H | H | |
| CH₃ | C₂H₅ | H | S | H | Cl | |
| CH₃ | C₂H₅ | H | O | H | Cl | |
| CH₃ | C₂H₅ | CH₃ | O | H | CO₂CH₂CH=CH₂ | |
| CH₃ | C₂H₅ | H | O | H | CO₂CH₂CH₂Cl | |
| CH₃ | C₂H₅ | CH₃ | O | H | CO₂CH₃ | |
| CH₃ | C₂H₅ | CH₃ | O | H | SO₂CH₃ | |
| C₂H₅ | CH₃ | CH₃ | O | H | SO₂CH₃ | |
| C₂H₅ | CH₃ | CH₃ | O | H | OCH₃ | |
| CH₃ | C₂H₅ | CH₃ | O | H | SO₂N(CH₃)₂ | |
| CH₃ | C₂H₅ | H | S | H | NO₂ | |
| CH₃ | C₂H₅ | H | O | H | SO₂N(CH₃)OCH₃ | |
| C₂H₅ | CH₃ | H | S | H | SO₂CH₃ | |
| C₂H₅ | CH₃ | H | O | 5-F | SO₂CH₃ | |
| C₂H₅ | CH₃ | H | O | 4-F | Br | |
| CH₃ | C₂H₅ | H | O | 5-Cl | Br | |
| CH₃ | C₂H₅ | H | O | 5-CH₃ | Cl | |
| C₂H₅ | C₂H₅ | H | O | H | Br | |
| C₂H₅ | C₂H₅ | H | O | H | CO₂CH₃ | |
| C₂H₅ | C₂H₅ | H | O | H | SO₂CH₃ | |
| C₂H₅ | C₂H₅ | H | O | H | SO₂N(CH₃)C₂H₅ | |
| CH₃ | C₂H₅ | H | O | H | SO₂(CH₂)₂CH₃ | |
| C₂H₅ | CH₃ | H | O | H | SCH₃ | |
| C₂H₅ | C₂H₅ | CH₃ | O | H | SO₂CH₃ | |
| C₂H₅ | C₂H₅ | CH₃ | O | H | CO₂CH₃ | |
| C₂H₅ | C₂H₅ | H | O | H | H | |
| CH₃ | C₂H₅ | H | O | 5-F | H | |
| CH₃ | C₂H₅ | H | O | 5-Cl | H | |
| C₂H₅ | C₂H₅ | H | O | H | SO₂N(CH₃)₂ | |
| C₂H₅ | C₂H₅ | H | S | H | Br | |
| CH₃ | C₂H₅ | H | O | H | F | |
| C₂H₅ | C₂H₅ | H | O | H | F | |
| n-C₃H₇ | CH₃ | H | O | H | CO₂CH₃ | |
| CH(CH₃)₂ | CH₃ | H | O | H | SO₂CH₃ | |
| CH₂CH(CH₃)₂ | CH₃ | H | O | H | CO₂C₂H₅ | |
| CH₃ | n-C₃H₇ | H | O | H | Br | |
| CH₃ | CH₂CH=CH₂ | H | O | H | CO₂CH(CH₃)₂ | |
| CH₃ | CH₂C(CH₃)=CH₂ | H | O | H | CO₂CH₃ | |
| CH₂CH=CH₂ | CH₃ | H | O | H | C₂H₅ | |
| CH₂C(CH₃)=CH₂ | CH₃ | H | O | H | SO₂CH₃ | |

TABLE 5-continued

| $R_1$ | $R_2$ | $R_3$ | W | $R_{17}$ | $R_{18}$ | m.p. (°C.) |
|---|---|---|---|---|---|---|
| $CH_3$ | $CH_2C\equiv CCH_3$ | H | O | H | $CO_2CH_3$ | |
| $CH_2C\equiv CCH_3$ | $CH_3$ | H | O | H | $SO_2C_2H_5$ | |
| $SCH_3$ | $CH_3$ | H | S | H | Br | |
| $SCH_3$ | $CH_3$ | $CH_3$ | O | H | Br | |
| $SCH_3$ | $CH_3$ | H | O | 4-Cl | Br | |
| $SCH_3$ | $CH_3$ | H | O | 5-$OCH_3$ | H | |
| $SCH_3$ | $CH_3$ | H | O | 5-Cl | Cl | |
| $SCH_3$ | $CH_3$ | H | O | H | $NO_2$ | |
| $SCH_3$ | $CH_3$ | H | O | H | $SO_2N(CH_3)C_2H_5$ | |
| $SCH_3$ | $CH_3$ | H | O | H | $SO_2N(CH_3)[CH(CH_3)_2]$ | |
| $SCH_3$ | $CH_3$ | H | O | H | F | |
| $SCH_3$ | $CH_3$ | H | O | 5-F | H | |
| $SCH_3$ | $CH_3$ | H | O | 4-Br | H | |
| $SCH_3$ | $CH_3$ | H | O | 5-Br | H | |
| $SCH_3$ | $CH_3$ | $CH_3$ | O | H | $SO_2CH_3$ | |
| $SCH_3$ | $CH_3$ | $CH_3$ | O | H | $CO_2CH_3$ | |
| $SCH_3$ | $CH_3$ | $CH_3$ | O | H | $SO_2N(CH_3)_2$ | |
| $SCH_3$ | $CH_3$ | H | O | H | $OC_2H_5$ | |
| $SCH_3$ | $CH_3$ | H | S | H | H | |
| $SCH_3$ | $CH_3$ | H | O | H | $CO_2(CH_2)_3CH_3$ | |
| $SCH_3$ | $CH_3$ | H | O | H | $CO_2CH_2CH_2OCH_3$ | |
| $SCH_3$ | $CH_3$ | H | O | 5-Cl | H | |
| $SCH_3$ | $CH_3$ | H | O | H | $OCH(CH_3)C_2H_5$ | |
| $SCH_3$ | $CH_3$ | H | O | 5-$CH_3$ | $CH_3$ | |
| $SCH_3$ | $CH_3$ | H | O | H | $SCH_3$ | |
| $SCH_3$ | $CH_3$ | H | O | H | $S(CH_2)_3CH_3$ | |
| $SCH_3$ | $C_2H_5$ | H | O | H | $SO_2C_2H_5$ | |
| $SCH_3$ | $CH_3$ | H | O | H | $CO_2CH(CH_3)_2$ | |
| $SCH_3$ | $CH_3$ | H | O | H | $CO_2CH_2CH=CH_2$ | |
| $SCH_3$ | $C_2H_5$ | H | O | H | $CO_2CH_3$ | |
| $SCH_3$ | $C_2H_5$ | H | O | H | Br | |
| $SCH_3$ | $C_2H_5$ | H | O | H | $SO_2CH_3$ | |
| $SCH_3$ | $C_2H_5$ | H | S | H | Cl | |
| $SCH_3$ | $C_2H_5$ | H | O | H | $NO_2$ | |
| $SC_2H_5$ | $CH_3$ | H | O | H | $CO_2CH(CH_3)_2$ | |
| $SC_2H_5$ | $CH_3$ | H | O | H | $CH_3$ | |
| $SC_2H_5$ | $CH_3$ | H | O | H | $CO_2CH_3$ | |
| $SC_2H_5$ | $CH_3$ | H | O | H | $SO_2CH_3$ | |
| $SC_2H_5$ | $CH_3$ | H | O | H | Br | |
| $SC_2H_5$ | $CH_3$ | $CH_3$ | O | H | Cl | |
| $SC_2H_5$ | $CH_3$ | H | S | H | Br | |
| $SCH(CH_3)_2$ | $CH_3$ | H | O | H | $CO_2CH_3$ | |
| $S(CH_2)_3CH_3$ | $CH_3$ | H | O | H | $SO_2CH_3$ | |
| $SCH_2CH=CH_2$ | $CH_3$ | H | O | H | $CO_2CH_3$ | |
| $S(CH_2)_2CH_3$ | $CH_3$ | H | O | H | $CO_2CH_3$ | |
| $SCH_2C(CH_3)=CH_2$ | $CH_3$ | H | O | H | $CO_2C_2H_5$ | |
| $SCH_2C\equiv CCH_3$ | $CH_3$ | H | O | H | $CO_2CH_3$ | |
| $SCH_2CO_2CH_3$ | $CH_3$ | H | O | H | $NO_2$ | |
| $SCH_2CO_2(CH_2)_3CH_3$ | $CH_3$ | H | O | H | $CO_2CH_3$ | |
| $SCH(CH_3)CO_2CH_3$ | $CH_3$ | H | O | H | $CO_2CH_3$ | |
| $OCH_3$ | $CH_3$ | H | O | H | $CO_2CH_3$ | |
| $OCH_3$ | $CH_3$ | H | O | H | $SO_2N(CH_3)C_2H_5$ | |
| $OCH_3$ | $CH_3$ | H | O | H | Br | |
| $OCH_3$ | $CH_3$ | H | O | H | Cl | |
| $OCH_3$ | $CH_3$ | H | O | H | $NO_2$ | |
| $OCH_3$ | $CH_3$ | H | S | H | $SO_2CH_3$ | |
| $OCH_3$ | $CH_3$ | $CH_3$ | O | H | $SO_2CH_3$ | |
| $OCH_3$ | $CH_3$ | H | O | H | $SO_2CH_3$ | |
| $OCH_3$ | $CH_3$ | H | O | H | $SO_2(CH_2)_2CH_3$ | |
| $OCH_3$ | $CH_3$ | H | O | H | $OCH_3$ | |
| $OC_2H_5$ | $CH_3$ | H | O | H | $O(CH_2)_3CH_3$ | |
| $OC_2H_5$ | $CH_3$ | H | O | H | $CO_2CH_2CH=CH_2$ | |
| $OCH_3$ | $CH_3$ | H | O | H | $CO_2CH_2CH_2Cl$ | |
| $OCH_3$ | $C_2H_5$ | H | O | H | $CO_2CH(CH_3)_2$ | |
| $OCH_3$ | $C_2H_5$ | H | O | H | $CO_2(CH_2)_2CH_3$ | |
| $OC_2H_5$ | $CH_3$ | H | O | H | $CO_2C_2H_5$ | |
| $OCH_3$ | $C_2H_5$ | $CH_3$ | O | H | $CO_2CH_3$ | |
| $OCH_3$ | $C_2H_5$ | H | S | H | Cl | |
| $OC_2H_5$ | $CH_3$ | H | S | H | Br | |
| $OCH_3$ | $C_2H_5$ | H | O | H | $SO_2CH_3$ | |
| $OCH_3$ | $C_2H_5$ | H | O | H | $SO_2(CH_2)_3CH_3$ | |
| $OCH_3$ | $C_2H_5$ | H | O | H | $SO_2CH_2CH(CH_3)_2$ | |

TABLE 5-continued

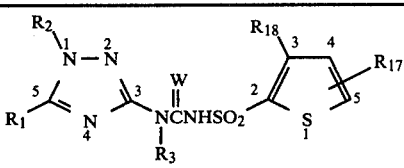

| R₁ | R₂ | R₃ | W | R₁₇ | R₁₈ | m.p. (°C.) |
|---|---|---|---|---|---|---|
| OCH₃ | C₂H₅ | CH₃ | O | H | SO₂CH₃ | |
| OCH₃ | C₂H₅ | CH₃ | O | 5-Cl | SO₂CH₃ | |
| OCH₃ | C₂H₅ | CH₃ | O | 5-Br | SO₂CH₃ | |
| OCH₃ | C₂H₅ | H | O | H | OC₂H₅ | |
| OCH₃ | C₂H₅ | H | O | H | F | |
| OCH₃ | C₂H₅ | H | O | 5-F | F | |
| OCH₃ | C₂H₅ | H | O | H | SC₂H₅ | |
| OC₂H₅ | CH₃ | H | O | H | SO₂N(OCH₃)CH₃ | |
| OC₂H₅ | CH₃ | H | O | H | SO₂N(CH₃)[(CH₂)₂CH₃] | |
| OC₂H₅ | CH₃ | H | S | H | H | |
| OC₂H₅ | CH₃ | H | S | H | NO₂ | |
| OC₂H₅ | CH₃ | H | O | H | CO₂CH(CH₃)₂ | |
| OC₂H₅ | CH₃ | H | O | H | CO₂CH₂CH=CH₂ | |
| OC₂H₅ | CH₃ | H | O | H | CO₂CH₂CH₂Cl | |
| OC₂H₅ | CH₃ | H | O | H | CH₃ | |
| OC₂H₅ | CH₃ | H | O | H | CH(CH₃)₂ | |
| OC₂H₅ | CH₃ | H | O | H | CH₂CH(CH₃)₂ | |
| OC₂H₅ | CH₃ | CH₃ | O | H | CH₃ | |
| OC₂H₅ | CH₃ | CH₃ | O | H | SO₂CH₃ | |
| OC₂H₅ | CH₃ | CH₃ | O | H | Cl | |
| OC₂H₅ | CH₃ | H | O | H | C₂H₅ | |
| OC₂H₅ | CH₃ | H | O | H | NO₂ | |
| OC₂H₅ | CH₃ | H | O | 4-Br | Br | |
| OC₂H₅ | CH₃ | H | O | 4-Cl | Cl | |
| OC₂H₅ | C₂H₅ | H | O | H | Cl | |
| OC₂H₅ | C₂H₅ | H | O | H | CO₂CH₃ | |
| OC₂H₅ | C₂H₅ | H | O | H | SO₂CH₃ | |
| OC₂H₅ | C₂H₅ | H | O | H | SO₂N(CH₃)₂ | |
| OC₂H₅ | C₂H₅ | H | O | H | NO₂ | |
| OC₂H₅ | C₂H₅ | H | O | H | Br | |
| OC₂H₅ | C₂H₅ | H | O | H | CO₂CH(CH₃)₂ | |
| OCH₃ | C₂H₅ | H | O | H | SO₂C₂H₅ | |
| OCH₃ | C₂H₅ | H | O | 4-F | F | |
| OC₂H₅ | CH₃ | H | O | H | OCH(CH₃)₂ | |
| OCH₂CH=CH₂ | CH₃ | H | O | H | SO₂CH₃ | |
| OCH₂C(CH₃)=CH₂ | CH₃ | H | O | H | CO₂CH₃ | |
| OCH(CH₃)C₂H₅ | CH₃ | H | O | H | CO₂CH₃ | |
| OCH(CH₃)₂ | CH₃ | H | O | H | CO₂C₂H₅ | |
| O(CH₂)₂CH₃ | CH₃ | H | O | H | Cl | |
| OCH₂C≡CCH₃ | CH₃ | H | O | H | NO₂ | |
| CH₂OCH₃ | CH₃ | H | O | H | Br | |
| CH₂OCH₃ | CH₃ | H | O | H | Cl | |
| CH₂OCH₃ | CH₃ | CH₃ | O | H | SO₂CH₃ | |
| CH₂OCH₃ | CH₃ | CH₃ | O | H | CO₂CH₃ | |
| CH₂OCH₃ | CH₃ | H | O | H | CO₂CH₃ | |
| CH₂OCH₃ | CH₃ | H | O | H | NO₂ | |
| CH₂OCH₃ | CH₃ | H | S | H | Cl | |
| CH₂OCH₃ | CH₃ | H | O | H | H | |
| CH₂OCH₃ | CH₃ | H | O | H | SO₂N(CH₃)₂ | |
| CH₂OCH₃ | CH₃ | CH₃ | O | H | SO₂N(CH₃)C₂H₅ | |
| CH₂OCH₃ | C₂H₅ | H | O | H | SO₂C₂H₅ | |
| CH₂OCH₃ | C₂H₅ | H | O | H | CO₂CH₃ | |
| CH₂OC₂H₅ | CH₃ | H | O | H | Br | |
| CH₂OCH(CH₃)₂ | CH₃ | H | O | H | CO₂CH₃ | |
| CH₂O(CH₂)₃CH₃ | CH₃ | H | O | H | CO₂CH₃ | |
| CH₂CH₂OCH₃ | CH₃ | H | O | H | Cl | |
| CH₂CH₂OCH(CH₃)₂ | CH₃ | H | O | H | CO₂CH₃ | |
| N(CH₃)₂ | CH₃ | H | O | H | CO₂CH₃ | |
| CF₃ | CH₃ | H | O | H | SO₂CH₃ | |
| CF₃ | CH₃ | H | O | H | CO₂CH₃ | |
| CF₃ | C₂H₅ | H | O | H | CO₂CH(CH₃)₂ | |
| CF₃ | C₂H₅ | H | O | H | SO₂CH₃ | |
| CF₃ | C₂H₅ | H | O | H | Br | |
| CF₂CF₃ | CH₃ | H | O | H | CO₂CH₃ | |
| CF₂CF₃ | CH₃ | H | O | H | Cl | |
| CH₃ | CH₂OCH₃ | H | O | H | CO₂CH₃ | |
| CH₃ | CH₂SCH₃ | H | O | H | Cl | |
| CH₃ | CH₂CH₂OCH₃ | H | O | H | CO₂CH₃ | |
| CH₃ | CH₂CH₂SCH₃ | H | O | H | Br | |
| CH₂OCH₃ | C₂H₅ | H | O | H | CO₂CH₃ | |
| CH₂OCH₃ | CH₃ | CH₃ | O | H | CO₂CH₃ | |
| OC₂H₅ | CH₃ | CH₃ | O | H | SO₂(CH₂)₂CH₃ | |

TABLE 5-continued

| R1 | R2 | R3 | W | R17 | R18 | m.p. (°C.) |
|---|---|---|---|---|---|---|
| OC2H5 | CH3 | H | O | H | SO2CH(CH3)2 | |
| OC2H5 | CH3 | H | O | H | SO2N(C2H5)2 | |
| OCH3 | CH3 | H | O | H | CH3 | |
| OCH3 | CH3 | H | O | H | C2H5 | |
| OCH3 | CH3 | H | O | H | CH(CH3)2 | |
| OCH3 | CH3 | H | O | H | OCH2CH2CH3 | |
| OCH3 | CH3 | H | O | H | F | |
| OCH3 | CH3 | H | O | H | CO2C2H5 | |
| OCH3 | CH3 | H | O | H | CO2CH2CH2OCH3 | |
| OCH3 | CH3 | H | O | H | CO2CH2CH=CH2 | |
| OCH3 | CH3 | H | O | H | SO2N(CH3)2 | |
| OCH3 | CH3 | H | O | H | SO2N(OCH3)CH3 | |
| OCH3 | CH3 | H | O | H | SO2CH2CH=CH2 | |
| OC2H5 | CH3 | H | O | H | F | |
| OC2H5 | CH3 | H | O | H | Cl | |
| OC2H5 | CH3 | H | O | H | Br | |
| OC2H5 | CH3 | H | O | H | CO2CH3 | |
| OC2H5 | CH3 | H | O | H | SO2N(CH3)2 | |
| OC2H5 | CH3 | H | O | H | SO2CH3 | |
| OC2H5 | CH3 | H | O | H | SO2CH2CH=CH2 | |
| OCH3 | CH2CF3 | H | O | H | CH3 | |
| OCH3 | CH2CF3 | H | O | H | OCH3 | |
| OCH3 | CH2CF3 | H | O | H | Cl | |
| OCH3 | CH2CF3 | H | O | H | NO2 | |
| OCH3 | CH2CF3 | H | O | H | CO2CH2CH3 | |
| OCH3 | CH2CF3 | H | O | H | SO2N(CH3)2 | |
| OCH3 | CH2CF3 | H | O | H | SO2CH3 | |
| Cl | CH3 | H | O | H | CH3 | |
| Cl | CH3 | H | O | H | OCH3 | |
| Cl | CH3 | H | O | H | Cl | |
| Cl | CH3 | H | O | H | NO2 | |
| Cl | CH3 | H | O | H | CO2CH3 | |
| Cl | CH3 | H | O | H | SO2N(CH3)2 | |
| Cl | CH3 | H | O | H | SO2CH3 | |
| NHCH3 | CH3 | H | O | H | CH3 | |
| NHCH3 | CH3 | H | O | H | OCH3 | |
| NHCH3 | CH3 | H | O | H | Cl | |
| NHCH3 | CH3 | H | O | H | NO2 | |
| NHCH3 | CH3 | H | O | H | CO2CH3 | |
| NHCH3 | CH3 | H | O | H | SO2N(CH3)2 | |
| NHCH3 | CH3 | H | O | H | SO2CH3 | |
| CH(OCH3)2 | CH3 | H | O | H | CH3 | |
| CH(OCH3)2 | CH3 | H | O | H | OCH3 | |
| CH(OCH3)2 | CH3 | H | O | H | Cl | |
| CH(OCH3)2 | CH3 | H | O | H | NO2 | |
| CH(OCH3)2 | CH3 | H | O | H | CO2CH3 | |
| CH(OCH3)2 | CH3 | H | O | H | SO2N(CH3)2 | |
| CH(OCH3)2 | CH3 | H | O | H | SO2CH3 | |
| CH(OCH2CH2O) | CH3 | H | O | H | CH3 | |
| CH(OCH2CH2O) | CH3 | H | O | H | OCH3 | |
| CH(OCH2CH2O) | CH3 | H | O | H | Cl | |
| CH(OCH2CH2O) | CH3 | H | O | H | NO2 | |

TABLE 5-continued

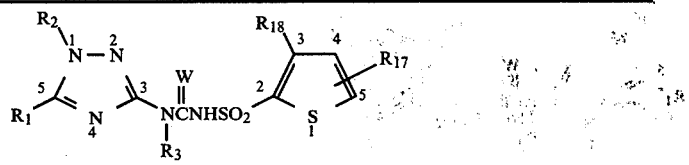

| R₁ | R₂ | R₃ | W | R₁₇ | R₁₈ | m.p. (°C.) |
|---|---|---|---|---|---|---|
| (dioxolane-CH) | CH₃ | H | O | H | CO₂CH₃ | |
| (dioxolane-CH) | CH₃ | H | O | H | SO₂N(CH₃)₂ | |
| (dioxolane-CH) | CH₃ | H | O | H | SO₂CH₃ | |

TABLE 6

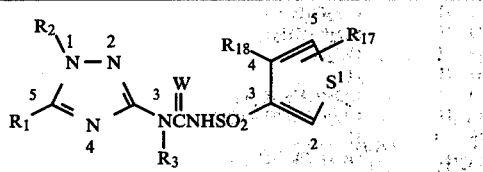

| R₁ | R₂ | R₃ | W | R₁₇ | R₁₈ | m.p. (°C.) |
|---|---|---|---|---|---|---|
| H | C₂H₅ | H | O | H | CO₂CH₃ | |
| H | n-C₃H₇ | H | O | H | CO₂C₂H₅ | |
| CH₃ | C₂H₅ | H | O | H | Br | |
| CH₃ | C₂H₅ | H | O | H | CO₂CH(CH₃)₂ | |
| CH₃ | CH₂CH(CH₃)₂ | H | O | H | CO₂CH₃ | |
| CH₃ | C₂H₅ | H | O | H | NO₂ | |
| CH₃ | C₂H₅ | H | O | H | H | |
| CH₃ | C₂H₅ | H | S | H | Cl | |
| CH₃ | C₂H₅ | H | O | H | Cl | |
| CH₃ | C₂H₅ | CH₃ | O | H | CO₂CH₂CH=CH₂ | |
| CH₃ | C₂H₅ | H | O | H | CO₂CH₂CH₂Cl | |
| CH₃ | C₂H₅ | CH₃ | O | H | CO₂CH₃ | |
| CH₃ | C₂H₅ | CH₃ | O | H | SO₂CH₃ | |
| C₂H₅ | CH₃ | CH₃ | O | H | SO₂CH₃ | |
| C₂H₅ | CH₃ | CH₃ | O | H | OCH₃ | |
| CH₃ | C₂H₅ | CH₃ | O | H | SO₂N(CH₃)₂ | |
| CH₃ | C₂H₅ | H | S | H | NO₂ | |
| CH₃ | C₂H₅ | H | O | H | SO₂N(CH₃)OCH₃ | |
| C₂H₅ | CH₃ | H | S | H | SO₂CH₃ | |
| C₂H₅ | CH₃ | H | O | 5-F | SO₂CH₃ | |
| C₂H₅ | CH₃ | H | O | 2-F | Br | |
| CH₃ | C₂H₅ | H | O | 5-Cl | Br | |
| CH₃ | C₂H₅ | H | O | 5-CH₃ | Cl | |
| C₂H₅ | C₂H₅ | H | O | H | Br | |
| C₂H₅ | C₂H₅ | H | O | H | CO₂CH₃ | |
| C₂H₅ | C₂H₅ | H | O | H | SO₂CH₃ | |
| C₂H₅ | C₂H₅ | H | O | H | SO₂N(CH₃)C₂H₅ | |
| CH₃ | C₂H₅ | H | O | H | SO₂(CH₂)₂CH₃ | |
| C₂H₅ | CH₃ | H | O | H | SCH₃ | |
| C₂H₅ | C₂H₅ | CH₃ | O | H | SO₂CH₃ | |
| C₂H₅ | C₂H₅ | CH₃ | O | H | CO₂CH₃ | |
| C₂H₅ | C₂H₅ | H | O | H | H | |
| CH₃ | C₂H₅ | H | O | 5-F | H | |
| CH₃ | C₂H₅ | H | O | 5-Cl | H | |
| C₂H₅ | C₂H₅ | H | O | H | SO₂N(CH₃)₂ | |
| C₂H₅ | C₂H₅ | H | S | H | Br | |
| CH₃ | C₂H₅ | H | O | H | F | |
| C₂H₅ | C₂H₅ | H | O | H | F | |
| n-C₃H₇ | CH₃ | H | O | H | CO₂CH₃ | |

TABLE 6-continued

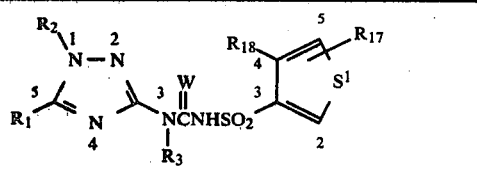

| R₁ | R₂ | R₃ | W | R₁₇ | R₁₈ | m.p. (°C.) |
|---|---|---|---|---|---|---|
| CH(CH₃)₂ | CH₃ | H | O | H | SO₂CH₃ | |
| CH₂CH(CH₃)₂ | CH₃ | H | O | H | CO₂C₂H₅ | |
| CH₃ | n-C₃H₇ | H | O | H | Br | |
| CH₃ | CH₂CH=CH₂ | H | O | H | CO₂CH(CH₃)₂ | |
| CH₃ | CH₂C(CH₃)=CH₂ | H | O | H | CO₂CH₃ | |
| CH₂CH=CH₂ | CH₃ | H | O | H | C₂H₅ | |
| CH₂C(CH₃)=CH₂ | CH₃ | H | O | H | SO₂CH₃ | |
| CH₃ | CH₂C≡CCH₃ | H | O | H | CO₂CH₃ | |
| CH₂C≡CCH₃ | CH₃ | H | O | H | SO₂C₂H₅ | |
| SCH₃ | CH₃ | H | S | H | Br | |
| SCH₃ | CH₃ | CH₃ | O | H | Br | |
| SCH₃ | CH₃ | H | O | 2-Cl | Br | |
| SCH₃ | CH₃ | H | O | 5-OCH₃ | H | |
| SCH₃ | CH₃ | H | O | 5-Cl | Cl | |
| SCH₃ | CH₃ | H | O | H | NO₂ | |
| SCH₃ | CH₃ | H | O | H | SO₂N(CH₃)C₂H₅ | |
| SCH₃ | CH₃ | H | O | H | SO₂N(CH₃)[CH(CH₃)₂] | |
| SCH₃ | CH₃ | H | O | H | F | |
| SCH₃ | CH₃ | H | O | 5-F | H | |
| SCH₃ | CH₃ | H | O | 2-Br | H | |
| SCH₃ | CH₃ | H | O | 5-Br | H | |
| SCH₃ | CH₃ | CH₃ | O | H | SO₂CH₃ | |
| SCH₃ | CH₃ | CH₃ | O | H | CO₂CH₃ | |
| SCH₃ | CH₃ | CH₃ | O | H | SO₂N(CH₃)₂ | |
| SCH₃ | CH₃ | H | O | H | OC₂H₅ | |
| SCH₃ | CH₃ | H | S | H | H | |
| SCH₃ | CH₃ | H | O | H | CO₂(CH₂)₃CH₃ | |
| SCH₃ | CH₃ | H | O | H | CO₂CH₂CH₂OCH₃ | |
| SCH₃ | CH₃ | H | O | 5-Cl | H | |
| SCH₃ | CH₃ | H | O | H | OCH(CH₃)C₂H₅ | |
| SCH₃ | CH₃ | H | O | 5-CH₃ | CH₃ | |
| SCH₃ | CH₃ | H | O | H | SCH₃ | |
| SCH₃ | CH₃ | H | O | H | S(CH₂)₃CH₃ | |
| SCH₃ | C₂H₅ | H | O | H | SO₂C₂H₅ | |
| SCH₂ | CH₃ | H | O | H | CO₂CH(CH₃)₂ | |
| SCH₃ | CH₃ | H | O | H | CO₂CH₂CH=CH₂ | |
| SCH₃ | C₂H₅ | H | O | H | CO₂CH₃ | |
| SCH₃ | C₂H₅ | H | O | H | Br | |
| SCH₃ | C₂H₅ | H | O | H | SO₂CH₃ | |
| SCH₃ | C₂H₅ | H | S | H | Cl | |
| SCH₃ | C₂H₅ | H | O | H | NO₂ | |
| SC₂H₅ | CH₃ | H | O | H | CO₂CH(CH₃)₂ | |
| SC₂H₅ | CH₃ | H | O | H | CH₃ | |
| SC₂H₅ | CH₃ | H | O | H | CO₂CH₃ | |
| SC₂H₅ | CH₃ | H | O | H | SO₂CH₃ | |
| SC₂H₅ | CH₃ | H | O | H | Br | |
| SC₂H₅ | CH₃ | CH₃ | O | H | Cl | |
| SC₂H₅ | CH₃ | H | S | H | Br | |
| SCH(CH₃)₂ | CH₃ | H | O | H | CO₂CH₃ | |
| S(CH₂)₃CH₃ | CH₃ | H | O | H | SO₂CH₃ | |
| SCH₂CH=CH₂ | CH₃ | H | O | H | CO₂CH₃ | |
| S(CH₂)₂CH₃ | CH₃ | H | O | H | CO₂CH₃ | |
| SCH₂C(CH₃)=CH₂ | CH₃ | H | O | H | CO₂C₂H₅ | |
| SCH₂C≡CCH₃ | CH₃ | H | O | H | CO₂CH₃ | |
| SCH₂CO₂CH₃ | CH₃ | H | O | H | NO₂ | |
| SCH₂CO₂(CH₂)₃CH₃ | CH₃ | H | O | H | CO₂CH₃ | |
| SCH(CH₃)CO₂CH₃ | CH₃ | H | O | H | CO₂CH₃ | |
| OCH₃ | CH₃ | H | O | H | CO₂CH₃ | |
| OCH₃ | CH₃ | H | O | H | SO₂N(CH₃)C₂H₅ | |
| OCH₃ | CH₃ | H | O | H | Br | |
| OCH₃ | CH₃ | H | O | H | Cl | |
| OCH₃ | CH₃ | H | O | H | NO₂ | |
| OCH₃ | CH₃ | H | S | H | SO₂CH₃ | |
| OCH₃ | CH₃ | CH₃ | O | H | SO₂CH₃ | |
| OCH₃ | CH₃ | H | O | H | SO₂CH₃ | |
| OCH₃ | CH₃ | H | O | H | SO₂(CH₂)₂CH₃ | |
| OCH₃ | CH₃ | H | O | H | OCH₃ | |
| OC₂H₅ | CH₃ | H | O | H | O(CH₂)₃CH₃ | |
| OC₂H₅ | CH₃ | H | O | H | CO₂CH₂CH=CH₂ | |
| OCH₃ | CH₃ | H | O | H | CO₂CH₂CH₂Cl | |
| OCH₃ | C₂H₅ | H | O | H | CO₂CH(CH₃)₂ | |
| OCH₃ | C₂H₅ | H | O | H | CO₂(CH₂)₂CH₃ | |

TABLE 6-continued

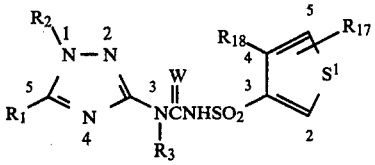

| R₁ | R₂ | R₃ | W | R₁₇ | R₁₈ | m.p. (°C.) |
|---|---|---|---|---|---|---|
| OC₂H₅ | CH₃ | H | O | H | CO₂C₂H₅ | |
| OCH₃ | C₂H₅ | CH₃ | O | H | CO₂CH₃ | |
| OCH₃ | C₂H₅ | H | S | H | Cl | |
| OC₂H₅ | CH₃ | H | S | H | Br | |
| OCH₃ | C₂H₅ | H | O | H | SO₂CH₃ | |
| OCH₃ | C₂H₅ | H | O | H | SO₂(CH₂)₃CH₃ | |
| OCH₃ | C₂H₅ | H | O | H | SO₂CH₂CH(CH₃)₂ | |
| OCH₃ | C₂H₅ | CH₃ | O | H | SO₂CH₃ | |
| OCH₃ | C₂H₅ | CH₃ | O | 5-Cl | SO₂CH₃ | |
| OCH₃ | C₂H₅ | CH₃ | O | 5-Br | SO₂CH₃ | |
| OCH₃ | C₂H₅ | H | O | H | OC₂H₅ | |
| OCH₃ | C₂H₅ | H | O | H | F | |
| OCH₃ | C₂H₅ | H | O | 5-F | F | |
| OCH₃ | C₂H₅ | H | O | H | SC₂H₅ | |
| OC₂H₅ | CH₃ | H | O | H | SO₂N(OCH₃)CH₃ | |
| OC₂H₅ | CH₃ | H | O | H | SO₂N(CH₃)[(CH₂)₂CH₃] | |
| OC₂H₅ | CH₃ | H | S | H | H | |
| OC₂H₅ | CH₃ | H | S | H | NO₂ | |
| OC₂H₅ | CH₃ | H | O | H | CO₂CH(CH₃)₂ | |
| OC₂H₅ | CH₃ | H | O | H | CO₂CH₂CH=CH₂ | |
| OC₂H₅ | CH₃ | H | O | H | CO₂CH₂CH₂Cl | |
| OC₂H₅ | CH₃ | H | O | H | CH₃ | |
| OC₂H₅ | CH₃ | H | O | H | CH(CH₃)₂ | |
| OC₂H₅ | CH₃ | H | O | H | CH₂CH(CH₃)₂ | |
| OC₂H₅ | CH₃ | CH₃ | O | H | CH₃ | |
| OC₂H₅ | CH₃ | CH₃ | O | H | SO₂CH₃ | |
| OC₂H₅ | CH₃ | CH₃ | O | H | Cl | |
| OC₂H₅ | CH₃ | H | O | H | C₂H₅ | |
| OC₂H₅ | CH₃ | H | O | H | NO₂ | |
| OC₂H₅ | CH₃ | H | O | 2-Br | Br | |
| OC₂H₅ | CH₃ | H | O | 2-Cl | Cl | |
| OC₂H₅ | C₂H₅ | H | O | H | Cl | |
| OC₂H₅ | C₂H₅ | H | O | H | CO₂CH₃ | |
| OC₂H₅ | C₂H₅ | H | O | H | SO₂CH₃ | |
| OC₂H₅ | C₂H₅ | H | O | H | SO₂N(CH₃)₂ | |
| OC₂H₅ | C₂H₅ | H | O | H | NO₂ | |
| OC₂H₅ | C₂H₅ | H | O | H | Br | |
| OC₂H₅ | C₂H₅ | H | O | H | CO₂CH(CH₃)₂ | |
| OCH₃ | C₂H₅ | H | O | H | SO₂C₂H₅ | |
| OCH₃ | C₂H₅ | H | O | 2-F | F | |
| OC₂H₅ | CH₃ | H | O | H | OCH(CH₃)₂ | |
| OCH₂CH=CH₂ | CH₃ | H | O | H | SO₂CH₃ | |
| OCH₂C(CH₃)=CH₂ | CH₃ | H | O | H | CO₂CH₃ | |
| OCH(CH₃)C₂H₅ | CH₃ | H | O | H | CO₂CH₃ | |
| OCH(CH₃)₂ | CH₃ | H | O | H | CO₂C₂H₅ | |
| O(CH₂)₂CH₃ | CH₃ | H | O | H | Cl | |
| OCH₂C≡CCH₃ | CH₃ | H | O | H | NO₂ | |
| CH₂OCH₃ | CH₃ | H | O | H | Br | |
| CH₂OCH₃ | CH₃ | H | O | H | Cl | |
| CH₂OCH₃ | CH₃ | CH₃ | O | H | SO₂CH₃ | |
| CH₂OCH₃ | CH₃ | CH₃ | O | H | CO₂CH₃ | |
| CH₂OCH₃ | CH₃ | H | O | H | CO₂CH₃ | |
| CH₂OCH₃ | CH₃ | H | O | H | NO₂ | |
| CH₂OCH₃ | CH₃ | H | S | H | Cl | |
| CH₂OCH₃ | CH₃ | H | O | H | H | |
| CH₂OCH₃ | CH₃ | H | O | H | SO₂N(CH₃)₂ | |
| CH₂OCH₃ | CH₃ | CH₃ | O | H | SO₂N(CH₃)C₂H₅ | |
| CH₂OCH₃ | C₂H₅ | H | O | H | SO₂C₂H₅ | |
| CH₂OCH₃ | C₂H₅ | H | O | H | CO₂CH₃ | |
| CH₂OC₂H₅ | CH₃ | H | O | H | Br | |
| CH₂OCH(CH₃)₂ | CH₃ | H | O | H | CO₂CH₃ | |
| CH₂O(CH₂)₃CH₃ | CH₃ | H | O | H | CO₂CH₃ | |
| CH₂CH₂OCH₃ | CH₃ | H | O | H | Cl | |
| CH₂CH₂OCH(CH₃)₂ | CH₃ | H | O | H | CO₂CH₃ | |
| N(CH₃)₂ | CH₃ | H | O | H | CO₂CH₃ | |
| CF₃ | CH₃ | H | O | H | SO₂CH₃ | |
| CF₃ | CH₃ | H | O | H | CO₂CH₃ | |
| CF₃ | C₂H₅ | H | O | H | CO₂CH(CH₃)₂ | |
| CF₃ | C₂H₅ | H | O | H | SO₂CH₃ | |
| CF₃ | C₂H₅ | H | O | H | Br | |
| CF₂CF₃ | CH₃ | H | O | H | CO₂CH₃ | |
| CF₂CF₃ | CH₃ | H | O | H | Cl | |

TABLE 6-continued

| $R_1$ | $R_2$ | $R_3$ | W | $R_{17}$ | $R_{18}$ | m.p. (°C.) |
|---|---|---|---|---|---|---|
| $CH_3$ | $CH_2OCH_3$ | H | O | H | $CO_2CH_3$ | |
| $CH_3$ | $CH_2SCH_3$ | H | O | H | Cl | |
| $CH_3$ | $CH_2CH_2OCH_3$ | H | O | H | $CO_2CH_3$ | |
| $CH_3$ | $CH_2CH_2SCH_3$ | H | O | H | Br | |
| $CH_2OCH_3$ | $C_2H_5$ | H | O | H | $CO_2CH_3$ | |
| $CH_2OCH_3$ | $CH_3$ | $CH_3$ | O | H | $CO_2CH_3$ | |
| $OC_2H_5$ | $CH_3$ | $CH_3$ | O | H | $SO_2(CH_2)_2CH_3$ | |
| $OC_2H_5$ | $CH_3$ | H | O | H | $SO_2CH(CH_3)_2$ | |
| $OC_2H_5$ | $CH_3$ | H | O | H | $SO_2N(C_2H_5)_2$ | |
| $OCH_3$ | $CH_3$ | H | O | H | $CH_3$ | |
| $OCH_3$ | $CH_3$ | H | O | H | $C_2H_5$ | |
| $OCH_3$ | $CH_3$ | H | O | H | $CH(CH_3)_2$ | |
| $OCH_3$ | $CH_3$ | H | O | H | $OCH_2CH_2CH_3$ | |
| $OCH_3$ | $CH_3$ | H | O | H | F | |
| $OCH_3$ | $CH_3$ | H | O | H | $CO_2C_2H_5$ | |
| $OCH_3$ | $CH_3$ | H | O | H | $CO_2CH_2CH_2OCH_3$ | |
| $OCH_3$ | $CH_3$ | H | O | H | $CO_2CH_2CH=CH_2$ | |
| $OCH_3$ | $CH_3$ | H | O | H | $SO_2N(CH_3)_2$ | |
| $OCH_3$ | $CH_3$ | H | O | H | $SO_2N(OCH_3)CH_3$ | |
| $OCH_3$ | $CH_3$ | H | O | H | $SO_2CH_2CH=CH_2$ | |
| $OC_2H_5$ | $CH_3$ | H | O | H | F | |
| $OC_2H_5$ | $CH_3$ | H | O | H | Cl | |
| $OC_2H_5$ | $CH_3$ | H | O | H | Br | |
| $OC_2H_5$ | $CH_3$ | H | O | H | $CO_2CH_3$ | |
| $OC_2H_5$ | $CH_3$ | H | O | H | $SO_2N(CH_3)_2$ | |
| $OC_2H_5$ | $CH_3$ | H | O | H | $SO_2CH_3$ | |
| $OC_2H_5$ | $CH_3$ | H | O | H | $SO_2CH_2CH=CH_2$ | |
| $OCH_3$ | $CH_2CF_3$ | H | O | H | $CH_3$ | |
| $OCH_3$ | $CH_2CF_3$ | H | O | H | $OCH_3$ | |
| $OCH_3$ | $CH_2CF_3$ | H | O | H | Cl | |
| $OCH_3$ | $CH_2CF_3$ | H | O | H | $NO_2$ | |
| $OCH_3$ | $CH_2CF_3$ | H | O | H | $CO_2CH_2CH_3$ | |
| $OCH_3$ | $CH_2CF_3$ | H | O | H | $SO_2N(CH_3)_2$ | |
| $OCH_3$ | $CH_2CF_3$ | H | O | H | $SO_2CH_3$ | |
| Cl | $CH_3$ | H | O | H | $CH_3$ | |
| Cl | $CH_3$ | H | O | H | $OCH_3$ | |
| Cl | $CH_3$ | H | O | H | Cl | |
| Cl | $CH_3$ | H | O | H | $NO_2$ | |
| Cl | $CH_3$ | H | O | H | $CO_2CH_3$ | |
| Cl | $CH_3$ | H | O | H | $SO_2N(CH_3)_2$ | |
| Cl | $CH_3$ | H | O | H | $SO_2CH_3$ | |
| $NHCH_3$ | $CH_3$ | H | O | H | $CH_3$ | |
| $NHCH_3$ | $CH_3$ | H | O | H | $OCH_3$ | |
| $NHCH_3$ | $CH_3$ | H | O | H | Cl | |
| $NHCH_3$ | $CH_3$ | H | O | H | $NO_2$ | |
| $NHCH_3$ | $CH_3$ | H | O | H | $CO_2CH_3$ | |
| $NHCH_3$ | $CH_3$ | H | O | H | $SO_2N(CH_3)_2$ | |
| $NHCH_3$ | $CH_3$ | H | O | H | $SO_2CH_3$ | |
| $CH(OCH_3)_2$ | $CH_3$ | H | O | H | $CH_3$ | |
| $CH(OCH_3)_2$ | $CH_3$ | H | O | H | $OCH_3$ | |
| $CH(OCH_3)_2$ | $CH_3$ | H | O | H | Cl | |
| $CH(OCH_3)_2$ | $CH_3$ | H | O | H | $NO_2$ | |
| $CH(OCH_3)_2$ | $CH_3$ | H | O | H | $CO_2CH_3$ | |
| $CH(OCH_3)_2$ | $CH_3$ | H | O | H | $SO_2N(CH_3)_2$ | |
| $CH(OCH_3)_2$ | $CH_3$ | H | O | H | $SO_2CH_3$ | |
|  | $CH_3$ | H | O | H | $CH_3$ | |
|  | $CH_3$ | H | O | H | $OCH_3$ | |
|  | $CH_3$ | H | O | H | Cl | |

TABLE 6-continued

| R1 | R2 | R3 | W | R17 | R18 | m.p. (°C.) |
|---|---|---|---|---|---|---|
| 1,3-dioxolan-2-yl | CH3 | H | O | H | NO2 | |
| 1,3-dioxolan-2-yl | CH3 | H | O | H | CO2CH3 | |
| 1,3-dioxolan-2-yl | CH3 | H | O | H | SO2N(CH3)2 | |
| 1,3-dioxolan-2-yl | CH3 | H | O | H | SO2CH3 | |

TABLE 7

| R1 | R2 | R3 | W | R17 | R18 | m.p. (°C.) |
|---|---|---|---|---|---|---|
| H | n-C3H7 | H | O | H | CO2CH3 | |
| CH3 | CH(CH3)2 | H | O | H | CO2CH(CH3)2 | |
| CH3 | CH3 | H | O | H | CO2CH2CH=CH2 | |
| n-C4H9 | CH3 | H | O | H | Cl | |
| CH2CH=CHCH3 | CH3 | H | O | H | Br | |
| CH2C≡CCH3 | CH3 | H | O | H | CH3 | |
| SCH3 | CH3 | H | O | H | CO2CH(CH3)C2H5 | |
| SCH2CH=CH2 | CH3 | H | O | H | Cl | |
| S(CH2)3CH3 | CH3 | H | O | H | Br | |
| SCH(CH3)2 | CH3 | H | O | H | CO2C2H5 | |
| SCH3 | CH3 | CH3 | O | H | CH3 | |
| SCH2C≡CCH3 | CH3 | H | O | H | CO2CH3 | |
| SCH2CO2CH(CH3)2 | CH3 | H | O | H | Cl | |
| SCH(CH3)CO2C2H5 | CH3 | H | O | H | Br | |
| N(CH3)2 | CH3 | H | O | H | CO2CH2CH2CH3 | |
| CF3 | C2H5 | CH3 | O | H | H | |
| CF2CF3 | CH3 | H | S | H | CO2CH2CH2Cl | |
| OC2H5 | CH3 | H | S | H | CH3 | |
| OCH2CH(CH3)2 | CH3 | H | S | H | CO2CH3 | |
| CH2OCH3 | CH3 | CH3 | O | H | CO2CH2CH2OCH3 | |
| CH2OCH(CH3)2 | CH3 | H | O | H | CO2CH(CH3)2 | |
| CH2OCH3 | CH3 | H | S | H | Cl | |
| CH3 | CH2CH2OCH3 | H | O | H | Cl | |
| CH3 | CH2SCH3 | H | O | H | Br | |
| CH3 | CH2OCH3 | H | O | H | CO2CH2CH(CH3)2 | |
| CH3 | CH2CH2SCH3 | H | O | H | CO2CH3 | |
| SCH3 | n-C3H7 | H | S | H | CH3 | |
| CH3 | CH2CH(CH3)2 | H | O | H | Cl | |
| OC2H5 | CH3 | H | O | H | CO2CH3 | |
| OCH3 | CH3 | CH3 | O | H | Cl | |
| OCH3 | C2H5 | H | O | H | CO2CH3 | |
| C2H5 | CH3 | H | S | H | Br | |
| SCH3 | CH3 | H | O | H | CO2CH3 | |
| CH2OCH2CH2CH3 | CH3 | H | O | H | CH3 | |
| SCH3 | CH2C(CH3)=CH2 | H | O | H | Cl | |
| OC2H5 | CH3 | CH3 | S | H | CH3 | |

TABLE 7-continued

| $R_1$ | $R_2$ | $R_3$ | W | $R_{17}$ | $R_{18}$ | m.p. (°C.) |
|---|---|---|---|---|---|---|
| $OC_2H_5$ | $CH_3$ | H | O | H | $CO_2CH(CH_3)_2$ | |
| $CH_2OCH_3$ | $CH_3$ | H | O | H | $CO_2CH_2CH=CH_2$ | |
| $SC_2H_5$ | $CH_3$ | H | O | H | $CO_2C_2H_5$ | |
| $CF_2CF_3$ | $CH_3$ | H | O | H | $CO_2CH_3$ | |
| $CF_3$ | $C_2H_5$ | H | O | H | $CO_2CH_3$ | |
| $CH_3$ | $CH_2CH=CH_2$ | H | O | H | $CO_2CH_3$ | |
| $CH_3$ | $CH_2C\equiv CCH_3$ | H | O | H | $CH_3$ | |
| $SCH_3$ | $CH_3$ | $CH_3$ | O | H | $CO_2CH(CH_3)_2$ | |
| $SCH_3$ | $CH_3$ | H | O | H | H | |
| $SCH_3$ | $CH_3$ | $CH_3$ | O | H | H | |
| $SCH(CH_3)CO_2CH_3$ | $C_2H_5$ | H | O | H | $SO_2CH_3$ | |
| $SCH_3$ | $C_2H_5$ | H | O | H | $CO_2CH_3$ | |
| $CH_2CH_2OCH(CH_3)_2$ | $CH_3$ | H | O | H | Cl | |
| $SCH_3$ | $CH_3$ | H | O | H | H | |
| $OCH_2CH=CH_2$ | $CH_3$ | H | O | H | $CO_2C_2H_5$ | |
| $OCH_3$ | $C_2H_5$ | H | O | H | Br | |
| $CH_2CH_2OCH_3$ | $CH_3$ | H | O | H | $CO_2CH_3$ | |
| $SCH_2CO_2C_2H_5$ | $CH_3$ | H | O | H | $SO_2CH_3$ | |
| $OCH_2C\equiv CH$ | $CH_3$ | H | O | H | $CH_3$ | |
| $OC_2H_5$ | $CH_3$ | $CH_3$ | O | H | $CO_2CH_3$ | |
| $OC_2H_5$ | $CH_3$ | H | O | H | $CO_2CH_2CH=CH_2$ | |
| $OC_2H_5$ | $CH_3$ | H | O | H | $CO_2CH_2CH_2OCH_3$ | |
| $OC_2H_5$ | $CH_3$ | H | O | H | $CO_2CH(CH_3)C_2H_5$ | |
| $OC_2H_5$ | $CH_3$ | H | O | H | Br | |
| $OC_2H_5$ | $CH_3$ | H | O | H | Cl | |
| $OC_2H_5$ | $CH_3$ | H | O | H | H | |
| $OC_2H_5$ | $CH_3$ | H | O | H | $CO_2(CH_2)_3CH_3$ | |
| $SCH_3$ | $CH_3$ | H | O | H | $CO_2CH_2CH=CH_2$ | |
| $SCH_3$ | $CH_3$ | H | O | H | $CO_2C_2H_5$ | |
| $SCH_3$ | $CH_3$ | H | O | H | $CH_3$ | |
| $SCH_3$ | $CH_3$ | H | O | H | $CO_2(CH_2)_2CH_3$ | |
| $SCH_3$ | $CH_3$ | H | O | H | Br | |
| $SCH_3$ | $CH_3$ | H | O | H | Cl | |
| $SCH_3$ | $CH_3$ | $CH_3$ | O | H | Cl | |
| $SCH_3$ | $CH_3$ | $CH_3$ | O | H | Br | |
| $SCH_3$ | $CH_3$ | $CH_3$ | O | H | $CO_2CH_3$ | |
| $SCH_3$ | $C_2H_5$ | H | O | H | $CH_3$ | |
| $SCH_3$ | $C_2H_5$ | H | O | H | $CO_2C_2H_5$ | |
| $SCH_3$ | $C_2H_5$ | H | O | H | Br | |
| $OCH_3$ | $C_2H_5$ | H | O | H | $CO_2(CH_2)_3CH_3$ | |
| $OCH_3$ | $C_2H_5$ | H | O | 4-Br | H | |
| $OCH_3$ | $C_2H_5$ | H | O | 4-Br | $CO_2CH_3$ | |
| $OCH_3$ | $C_2H_5$ | H | O | 5-Cl | $CO_2CH_3$ | |
| $OCH_3$ | $C_2H_5$ | H | O | 4-Cl | $CO_2CH_3$ | |
| $OCH_3$ | $C_2H_5$ | H | O | 4-$CH_3$ | $CO_2CH_3$ | |
| $OCH_3$ | $C_2H_5$ | H | O | H | $CO_2CH_2CH=CH_2$ | |
| $OCH_3$ | $C_2H_5$ | H | O | H | $CO_2CH(CH_3)_2$ | |
| $OCH_3$ | $CH_3$ | H | O | H | H | |
| $OCH_3$ | $CH_3$ | H | O | H | Cl | |
| $OCH_3$ | $CH_3$ | H | O | H | Br | |
| $OCH_3$ | $CH_3$ | H | O | H | $CH_3$ | |
| $OCH_3$ | $CH_3$ | H | O | H | $CO_2CH_3$ | |
| $OCH_3$ | $CH_3$ | H | O | H | $CO_2C_2H_5$ | |
| $OCH_3$ | $CH_3$ | H | O | H | $CO_2CH(CH_3)_2$ | |
| $OCH_3$ | $CH_3$ | H | O | H | $CO_2CH_2CH_2CH_3$ | |
| $OCH_3$ | $CH_3$ | H | O | H | $CO_2(CH_2)_3CH_3$ | |
| $OCH_3$ | $CH_3$ | H | O | H | $CO_2CH_2CH_2OCH_3$ | |
| $OCH_3$ | $CH_3$ | H | O | H | $CO_2CH_2CH_2Cl$ | |
| $OCH_3$ | $CH_3$ | H | O | H | $CO_2CH_2CH=CH_2$ | |
| $OCH_3$ | $CH_2CF_3$ | H | O | H | H | |
| $OCH_3$ | $CH_2CF_3$ | H | O | H | Cl | |
| $OCH_3$ | $CH_2CF_3$ | H | O | H | $CH_3$ | |
| $OCH_3$ | $CH_2CF_3$ | H | O | H | $CO_2CH_3$ | |
| $OCH_3$ | $CH_2CF_3$ | H | O | H | $CO_2CH_2CH=CH_2$ | |
| $OCH_3$ | $CH_2CF_3$ | H | O | H | $CO_2CH_2CH_2Cl$ | |
| Cl | $CH_3$ | H | O | H | Cl | |
| Cl | $CH_3$ | H | O | H | $CH_3$ | |
| Cl | $CH_3$ | H | O | H | $CO_2CH_3$ | |
| Cl | $CH_3$ | H | O | H | $CO_2CH_2CH=CH_2$ | |
| $NHCH_3$ | $CH_3$ | H | O | H | Br | |
| $NHCH_3$ | $CH_3$ | H | O | H | $CO_2C_2H_5$ | |
| $NHCH_3$ | $CH_3$ | H | O | H | $CO_2CH_2CH_2Cl$ | |

TABLE 7-continued

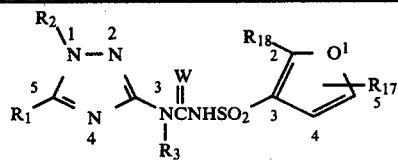

| $R_1$ | $R_2$ | $R_3$ | W | $R_{17}$ | $R_{18}$ | m.p. (°C.) |
|---|---|---|---|---|---|---|
| $CH(OCH_3)_2$ | $CH_3$ | H | O | H | $CO_2CH_3$ | |
| 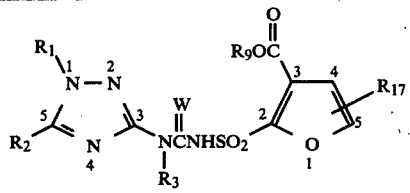 | $CH_3$ | H | O | H | $CO_2CH_3$ | |

TABLE 8

| $R_1$ | $R_2$ | $R_3$ | W | $R_9$ | $R_{17}$ | m.p. (°C.) |
|---|---|---|---|---|---|---|
| H | $n\text{-}C_3H_7$ | H | O | $CH_3$ | H | |
| H | $C_2H_5$ | H | O | $C_2H_5$ | H | |
| $CH_3$ | $CH(CH_3)_2$ | H | O | $CH_3$ | H | |
| $CH_3$ | $CH_3$ | H | S | $CH(CH_3)_2$ | H | |
| $n\text{-}C_4H_9$ | $CH_3$ | H | O | $CH_3$ | H | |
| $CH_2CH=CH_2$ | $CH_3$ | H | O | $CH_3$ | H | |
| $CH_2C(CH_3)=CH_2$ | $CH_3$ | H | O | $CH_3$ | H | |
| $CH_2C\equiv CCH_3$ | $CH_3$ | H | O | $CH_3$ | H | |
| $SCH_2CH=CH_2$ | $CH_3$ | H | O | $C_2H_5$ | H | |
| $SCH_2CH(CH_3)_2$ | $CH_3$ | H | O | $CH_3$ | H | |
| $SCH_2C\equiv CH$ | $CH_3$ | H | O | $CH_3$ | H | |
| $SC_2H_5$ | $CH_3$ | H | O | $CH(CH_3)C_2H_5$ | H | |
| $SCH_3$ | $CH_3$ | $CH_3$ | O | $CH_2CH_2Cl$ | H | |
| $SCH_2CO_2C_2H_5$ | $CH_3$ | H | O | $C_2H_5$ | H | |
| $N(CH_3)_2$ | $CH_3$ | H | O | $CH_3$ | H | |
| $CF_3$ | $C_2H_5$ | H | O | $CH_2CH_2OCH_3$ | H | |
| $CF_2CF_3$ | $CH_3$ | H | O | $n\text{-}C_3H_7$ | H | |
| $OC_2H_5$ | $CH_3$ | $CH_3$ | O | $CH(CH_3)C_2H_5$ | H | |
| $OCH_2CH(CH_3)_2$ | $CH_3$ | H | O | $CH_3$ | H | |
| $OCH(CH_3)_2$ | $CH_3$ | H | O | $C_2H_5$ | H | |
| $CH_2OCH_3$ | $CH_3$ | H | S | $CH_3$ | H | |
| $CH_3$ | $CH_2CH_2OCH_3$ | H | O | $CH_3$ | H | |
| $CH_3$ | $CH_2SCH_3$ | H | O | $CH_3$ | H | |
| $CH_3$ | $CH_2OCH_3$ | H | O | $CH(CH_3)_2$ | H | |
| $CH_3$ | $CH_2CH_2SCH_3$ | H | O | $CH_3$ | H | |
| $SCH_3$ | $n\text{-}C_3H_7$ | H | O | $CH_3$ | H | |
| $CH_3$ | $CH_2CH(CH_3)_2$ | H | O | $CH_3$ | H | |
| $OC_2H_5$ | $CH_3$ | H | O | $CH_3$ | H | |
| $OCH_3$ | $CH_3$ | $CH_3$ | O | $CH_3$ | H | |
| $OCH_3$ | $C_2H_5$ | H | O | $CH_3$ | 5-Cl | |
| $OCH_3$ | $C_2H_5$ | H | O | $CH_3$ | 5-Br | |
| $CH_3$ | $CH_2CH=CH_2$ | H | O | $CH_3$ | H | |
| $CH_3$ | $CH_2CH=CHCH_3$ | H | O | $CH_3$ | H | |
| $CH_3$ | $CH_2C\equiv CCH_3$ | H | O | $CH_3$ | H | |
| $OC_2H_5$ | $CH_3$ | H | O | $CH_3$ | 4-Cl | |
| $OCH_3$ | $C_2H_5$ | H | O | $CH_2CH_2Cl$ | H | |
| $C_2H_5$ | $CH_3$ | H | S | $CH_2CH_2OCH_3$ | H | |
| $SCH_3$ | $CH_3$ | H | O | $CH(CH_3)C_2H_5$ | H | |
| $CF_3$ | $C_2H_5$ | H | O | $CH_2CH=CH_2$ | H | |
| $CH_2CH_2OC_2H_5$ | $CH_3$ | H | O | $CH(CH_3)_2$ | H | |
| $CH_2O-CH_2CH(CH_3)_2$ | $CH_3$ | H | O | $C_2H_5$ | 4-$CH_3$ | |
| $OCH_3$ | $C_2H_5$ | $CH_3$ | O | $n\text{-}C_4H_9$ | H | |
| $SCH_3$ | $CH_3$ | $CH_3$ | O | $n\text{-}C_3H_7$ | H | |
| $CH_2OCH_3$ | $CH_3$ | $CH_3$ | O | $CH_3$ | H | |
| $CH_2OCH_3$ | $CH_3$ | H | O | $C_2H_5$ | H | |
| $CF_2CF_3$ | $C_2H_5$ | H | O | $CH_3$ | H | |
| $OCH_3$ | $C_2H_5$ | H | S | $CH(CH_3)C_2H_5$ | H | |
| $OCH_3$ | $C_2H_5$ | H | S | $CH_3$ | 5-$OCH_3$ | |
| $SCH_3$ | $CH_3$ | H | S | $CH_3$ | H | |
| $S\text{-}n\text{-}C_3H_7$ | $CH_3$ | H | O | $CH_3$ | H | |

TABLE 8-continued

| $R_1$ | $R_2$ | $R_3$ | W | $R_9$ | $R_{17}$ | m.p. (°C.) |
|---|---|---|---|---|---|---|
| $OC_2H_5$ | $C_2H_5$ | H | O | $CH_3$ | H | |
| $OCH_2C\equiv CH$ | $C_2H_5$ | H | O | $CH_3$ | H | |
| $CH_3$ | $C_2H_5$ | H | O | $CH(CH_3)_2$ | H | |
| $SCH_3$ | $CH_3$ | H | O | $n-C_3H_7$ | H | |
| $OCH_2CH=CH_2$ | $CH_3$ | H | O | $CH_3$ | H | |
| $SCH_3$ | $CH_3$ | H | O | $CH_3$ | H | |
| $SCH_3$ | $C_2H_5$ | H | O | $C_2H_5$ | H | |
| $SCH_3$ | $C_2H_5$ | H | O | $CH_3$ | H | |
| $SCH_3$ | $C_2H_5$ | H | O | $C_2H_5$ | H | |
| $SCH_3$ | $CH_3$ | H | O | $CH_2CH=CH_2$ | H | |
| $SCH_3$ | $CH_3$ | H | O | $CH_2(CH_3)_2$ | H | |
| $SCH_3$ | $CH_3$ | $CH_3$ | S | $CH_3$ | H | |
| $SCH_3$ | $CH_3$ | H | S | $C_2H_5$ | H | |
| $OC_2H_5$ | $CH_3$ | H | O | $CH_3$ | 5-F | |
| $OC_2H_5$ | $CH_3$ | H | O | $C_2H_5$ | 5-Cl | |
| $OC_2H_5$ | $CH_3$ | H | O | $CH_3$ | 5-Br | |
| $OC_2H_5$ | $CH_3$ | H | O | $CH(CH_3)_2$ | H | |
| $OC_2H_5$ | $CH_3$ | H | O | $CH_3$ | 4-Br | |
| $OC_2H_5$ | $CH_3$ | H | O | $CH_3$ | $5-CH_3$ | |
| $OC_2H_5$ | $CH_3$ | H | S | $CH_3$ | H | |
| $OC_2H_5$ | $CH_3$ | $CH_3$ | O | $CH_3$ | H | |
| $OC_2H_5$ | $CH_3$ | $CH_3$ | O | $CH(CH_3)_2$ | H | |
| $OC_2H_5$ | $CH_3$ | $CH_3$ | O | $CH_2CH=CH_2$ | H | |
| $OC_2H_5$ | $CH_3$ | H | O | $n-C_4H_9$ | H | |
| $OC_2H_5$ | $CH_3$ | H | O | $CH_2CH(CH_3)_2$ | H | |
| $OC_2H_5$ | $CH_3$ | H | O | $n-C_3H_7$ | H | |
| $OCH_3$ | $C_2H_5$ | H | O | $CH_3$ | H | |
| $OCH_3$ | $C_2H_5$ | H | S | $CH_3$ | H | |
| $OCH_3$ | $C_2H_5$ | H | O | $CH_3$ | 4-F | |
| $OCH_3$ | $C_2H_5$ | H | O | $CH_3$ | 5-F | |
| $OCH_3$ | $C_2H_5$ | $CH_3$ | O | $CH_3$ | H | |
| $OCH_3$ | $C_2H_5$ | $CH_3$ | O | $CH_2CH=CH_2$ | H | |
| $OCH_3$ | $CH_3$ | H | O | $CH_3$ | H | |
| $OCH_3$ | $CH_3$ | H | O | $CH(CH_3)_2$ | H | |
| $OCH_3$ | $CH_3$ | H | O | $C_2H_5$ | H | |
| $OCH_3$ | $CH_3$ | H | O | $CH_2CH_2CH_3$ | H | |
| $OCH_3$ | $CH_3$ | H | O | $CH_2CH=CH_2$ | H | |
| $OCH_3$ | $CH_3$ | H | O | $CH_2CH_2OCH_3$ | H | |
| $OCH_3$ | $CH_3$ | H | O | $CH_2CH_2Cl$ | H | |
| $OC_2H_5$ | $CH_3$ | H | O | $CH_3$ | H | |
| $OCH_3$ | $CH_2CF_3$ | H | O | $CH_3$ | H | |
| $OCH_3$ | $CH_2CF_3$ | H | O | $C_2H_5$ | H | |
| $OCH_3$ | $CH_2CF_3$ | H | O | $CH(CH_3)_2$ | H | |
| $OCH_3$ | $CH_2CF_3$ | H | O | $CH_2CH=CH_2$ | H | |
| $OCH_3$ | $CH_2CF_3$ | H | O | $CH_2CH_2OCH_3$ | H | |
| $OCH_3$ | $CH_2CF_3$ | H | O | $CH_2CH_2Cl$ | H | |
| Cl | $CH_3$ | H | O | $CH_3$ | H | |
| Cl | $CH_3$ | H | O | $C_2H_5$ | H | |
| Cl | $CH_3$ | H | O | $CH_2CH=CH_2$ | H | |
| $NHCH_3$ | $CH_3$ | H | O | $CH_3$ | H | |
| $NHCH_3$ | $CH_3$ | H | O | $CH_2CH_2Cl$ | H | |
| $NHCH_3$ | $CH_3$ | H | O | $CH_2CH_2OCH_3$ | H | |
| $NHCH_3$ | $CH_3$ | H | O | $C_2H_5$ | H | |
| $CH(OCH_3)_2$ | $CH_3$ | H | O | $CH_3$ | H | |
| $CH(OCH_3)_2$ | $CH_3$ | H | O | $C_2H_5$ | H | |
| $CH(OCH_3)_2$ | CH | H | O | $CH(CH_3)_2$ | H | |
| $CH(OCH_3)_2$ | $CH_3$ | H | O | $CH_2CH=CH_2$ | H | |
| $CH(OCH_3)_2$ | $CH_3$ | H | O | $CH_2CH_2Cl$ | H | |
|  | $CH_3$ | H | O | $CH_3$ | H | |
|  | $CH_3$ | H | O | $CH_2CH_2CH_3$ | H | |

TABLE 8-continued

| $R_1$ | $R_2$ | $R_3$ | W | $R_9$ | $R_{17}$ | m.p. (°C.) |
|---|---|---|---|---|---|---|
| dioxolane-CH | $CH_3$ | H | O | $CH_2CH_2OCH_3$ | H | |
| dioxolane-CH | $CH_3$ | H | O | $CH_2CH_2Cl$ | H | |

TABLE 9

| $R_1$ | $R_2$ | $R_3$ | W | $R_9$ | $R_{17}$ | m.p. (°C.) |
|---|---|---|---|---|---|---|
| H | $n\text{-}C_3H_7$ | H | O | $CH_3$ | H | |
| $CH_3$ | $C_2H_5$ | H | O | $C_2H_5$ | H | |
| $CH_3$ | $CH(CH_3)_2$ | H | O | $CH_3$ | H | |
| $CH_3$ | $CH_3$ | H | O | $CH_3$ | H | |
| $n\text{-}C_4H_9$ | $CH_3$ | H | O | $CH_3$ | H | |
| $CH_2CH=CH_2$ | $CH_3$ | H | O | $CH_3$ | H | |
| $CH_2CH(CH_3)=CH_2$ | $CH_3$ | H | O | $CH_3$ | H | |
| $CH_2C\equiv CCH_3$ | $CH_3$ | H | O | $CH_3$ | H | |
| $SCH_2CH=CH_2$ | $CH_3$ | H | O | $CH_3$ | H | |
| $CH(CH_3)C_2H_5$ | $CH_3$ | H | O | $CH_3$ | H | |
| $SCH_2(CH_3)_2$ | $CH_3$ | H | O | $CH_3$ | H | |
| $SCH_2C\equiv CH$ | $CH_3$ | H | O | $CH_3$ | H | |
| $SC_2H_5$ | $CH_3$ | H | O | $CH_3$ | H | |
| $SCH_3$ | $CH_3$ | $CH_3$ | O | $CH_3$ | H | |
| $SCH_2CO_2CH(CH_3)_2$ | $CH_3$ | H | O | $CH_3$ | H | |
| $N(CH_3)_2$ | $CH_3$ | H | O | $CH_3$ | H | |
| $SCH_3$ | $CH_3$ | $CH_3$ | O | $CH_3$ | H | |
| $SCH_3$ | $CH_3$ | H | S | $C_2H_5$ | H | |
| $SCH_3$ | $CH_3$ | H | O | $CH(CH_3)C_2H_5$ | H | |
| $SCH_3$ | $CH_3$ | H | O | $CH_2CH_2OCH_3$ | H | |
| $SCH_3$ | $C_2H_5$ | H | O | $CH(CH_3)_2$ | H | |
| $CF_3$ | $C_2H_5$ | H | O | $CH_2CH=CH_2$ | H | |
| $CF_2CF_3$ | $CH_3$ | H | S | $CH_3$ | H | |
| $OC_2H_5$ | $CH_3$ | H | O | $n\text{-}C_3H_7$ | H | |
| $OCH_2CH(CH_3)_2$ | $CH_3$ | H | O | $CH_3$ | H | |
| $OCH(CH_3)_2$ | $CH_3$ | H | S | $CH_3$ | H | |
| $CH_2OCH_3$ | $CH_3$ | H | O | $CH_2CH_2Cl$ | H | |
| $SCH_2CO_2CH_3$ | $CH_3$ | H | O | $CH_3$ | H | |
| $SCH(CH_3)CO_2C_2H_5$ | $CH_3$ | H | O | $CH_3$ | H | |
| $CH_3$ | $CH_2CH_2OCH_3$ | H | O | $CH_3$ | H | |
| $CH_3$ | $CH_2SCH_3$ | H | O | $CH(CH_3)_2$ | H | |
| $CF_3$ | $CH_2OCH_3$ | H | S | $C_2H_5$ | H | |
| $CH_2OCH(CH_3)_2$ | $CH_3$ | H | O | $CH_3$ | H | |
| $CH_2CH_2OC_2H_5$ | $CH_3$ | H | O | $CH_3$ | H | |
| $SCH_3$ | $n\text{-}C_3H_7$ | $CH_3$ | O | $CH_3$ | H | |
| $OC_2H_5$ | $CH_3$ | $CH_3$ | S | $CH_3$ | H | |
| $OCH_3$ | $CH_3$ | $CH_3$ | O | $CH_3$ | H | |
| $OCH_3$ | $CH_3$ | H | O | $CH_3$ | 5-Cl | |
| $OCH_3$ | $C_2H_5$ | H | O | $CH_3$ | 2-Br | |
| $OCH_3$ | $C_2H_5$ | H | S | $CH_3$ | H | |
| $C_2H_5$ | $CH_3$ | H | O | $CH_3$ | 5-$CH_3$ | |
| $CH_3$ | $CH_2CH=CH_2$ | H | O | $n\text{-}C_3H_7$ | H | |
| $CH_3$ | $CH_2CH(CH_3)_2$ | H | O | $CH(CH_3)_2$ | H | |
| $CH_3$ | $CH_2C\equiv CH_3$ | H | O | $CH_3$ | H | |
| $OC_2H_5$ | $CH_3$ | $CH_3$ | O | $C_2H_5$ | H | |
| $CF_3$ | $C_2H_5$ | H | S | $CH_3$ | H | |

TABLE 9-continued

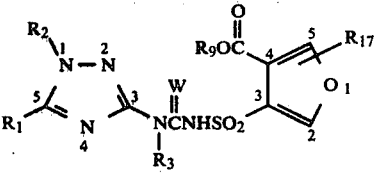

| $R_1$ | $R_2$ | $R_3$ | W | $R_9$ | $R_{17}$ | m.p. (°C.) |
|---|---|---|---|---|---|---|
| $OCH_2CH=CH_2$ | $CH_3$ | H | O | $CH_3$ | H | |
| $OCH_2C\equiv CH$ | $CH_3$ | H | O | $CH_3$ | H | |
| $SCH_3$ | $CH_3$ | H | O | $CH_2CH_2OCH_3$ | H | |
| $SCH_3$ | $CH_3$ | H | O | $CH_2CH_2Cl$ | H | |
| $CF_2CF_3$ | $CH_3$ | $CH_3$ | O | $CH_3$ | H | |
| $OCH_3$ | $C_2H_5$ | $CH_3$ | O | $CH_3$ | H | |
| $OCH_3$ | $C_2H_5$ | H | O | $CH_2CH=CH_2$ | H | |
| $CH_2OCH_3$ | $CH_3$ | H | O | $CH_3$ | H | |
| $SCH_3$ | $CH_3$ | H | O | $CH_3$ | H | |
| $SCH_3$ | $CH_3$ | H | O | $CH_3$ | H | |
| $SCH_3$ | $CH_3$ | H | O | $C_2H_5$ | H | |
| $SCH_3$ | $C_2H_5$ | H | O | $CH_3$ | H | |
| $SCH_3$ | $C_2H_5$ | H | O | $C_2H_5$ | H | |
| $SCH_3$ | $CH_3$ | H | O | $CH_2CH=CH_2$ | H | |
| $SCH_3$ | $CH_3$ | H | O | $CH(CH_3)_2$ | H | |
| $SCH_3$ | $CH_3$ | $CH_3$ | S | $CH_3$ | H | |
| $SCH_3$ | $CH_3$ | H | S | $C_2H_5$ | H | |
| $OC_2H_5$ | $CH_3$ | H | O | $CH_3$ | 5-F | |
| $OC_2H_5$ | $CH_3$ | H | O | $C_2H_5$ | 5-Cl | |
| $OC_2H_5$ | $CH_3$ | H | O | $CH_3$ | 5-Br | |
| $OC_2H_5$ | $CH_3$ | H | O | $CH(CH_3)_2$ | H | |
| $OC_2H_5$ | $CH_3$ | H | O | $CH_3$ | 2-Br | |
| $OC_2H_5$ | $CH_3$ | H | O | $CH_3$ | 5-$CH_3$ | |
| $OC_2H_5$ | $CH_3$ | H | S | $CH_3$ | H | |
| $OC_2H_5$ | $CH_3$ | $CH_3$ | O | $CH_3$ | H | |
| $OC_2H_5$ | $CH_3$ | $CH_3$ | O | $CH(CH_3)_2$ | H | |
| $OC_2H_5$ | $CH_3$ | $CH_3$ | O | $CH_2CH=CH_2$ | H | |
| $OC_2H_5$ | $CH_3$ | H | O | $n-C_4H_9$ | H | |
| $OC_2H_5$ | $CH_3$ | H | O | $CH_2CH(CH_3)_2$ | H | |
| $OC_2H_5$ | $CH_3$ | H | O | $n-C_3H_7$ | H | |
| $OCH_3$ | $C_2H_5$ | H | O | $CH_3$ | H | |
| $OCH_3$ | $C_2H_5$ | H | S | $CH_3$ | H | |
| $OCH_3$ | $C_2H_5$ | H | O | $CH_3$ | 2-F | |
| $OCH_3$ | $C_2H_5$ | H | O | $CH_3$ | 5-F | |
| $OCH_3$ | $C_2H_5$ | $CH_3$ | O | $CH_3$ | H | |
| $OCH_3$ | $C_2H_5$ | $CH_3$ | O | $CH_2CH=CH_2$ | H | |
| $OCH_3$ | $CH_3$ | H | O | $CH_3$ | H | |
| $OCH_3$ | $CH_3$ | H | O | $CH(CH_3)_2$ | H | |
| $OCH_3$ | $CH_3$ | H | O | $C_2H_5$ | H | |
| $OCH_3$ | $CH_3$ | H | O | $CH_2CH_2CH_3$ | H | |
| $OCH_3$ | $CH_3$ | H | O | $CH_2CH=CH_2$ | H | |
| $OCH_3$ | $CH_3$ | H | O | $CH_2CH_2OCH_3$ | H | |
| $OCH_3$ | $CH_3$ | H | O | $CH_2CH_2Cl$ | H | |
| $OCH_3$ | $CH_3$ | H | O | $CH_2CH_2CH_2CH_3$ | H | |
| $OC_2H_5$ | $CH_3$ | H | O | $CH_3$ | H | |
| $OCH_3$ | $CH_2CF_3$ | H | O | $CH_3$ | H | |
| $OCH_3$ | $CH_2CF_3$ | H | O | $C_2H_5$ | H | |
| $OCH_3$ | $CH_2CF_3$ | H | O | $CH(CH_3)_2$ | H | |
| $OCH_3$ | $CH_2CF_3$ | H | O | $CH_2CH=CH_2$ | H | |
| $OCH_3$ | $CH_2CF_3$ | H | O | $CH_2CH_2OCH_3$ | H | |
| $OCH_3$ | $CH_2CF_3$ | H | O | $CH_2CH_2Cl$ | H | |
| Cl | $CH_3$ | H | O | $CH_3$ | H | |
| Cl | $CH_3$ | H | O | $C_2H_5$ | H | |
| Cl | $CH_3$ | H | O | $CH_2CH=CH_2$ | H | |
| $NHCH_3$ | $CH_3$ | H | O | $CH_3$ | H | |
| $NHCH_3$ | $CH_3$ | H | O | $CH_2CH_2Cl$ | H | |
| $NHCH_3$ | $CH_3$ | H | O | $CH_2CH_2OCH_3$ | H | |
| $NHCH_3$ | $CH_3$ | H | O | $C_2H_5$ | H | |
| $CH(OCH_3)_2$ | $CH_3$ | H | O | $CH_3$ | H | |
| $CH(OCH_3)_2$ | $CH_3$ | H | O | $C_2H_5$ | H | |
| $CH(OCH_3)_2$ | CH | H | O | $CH(CH_3)_2$ | H | |
| $CH(OCH_3)_2$ | $CH_3$ | H | O | $CH_2CH=CH_2$ | H | |
| $CH(OCH_3)_2$ | $CH_3$ | H | O | $CH_2CH_2Cl$ | H | |
| 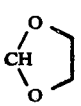 | $CH_3$ | H | O | $CH_3$ | H | |

TABLE 9-continued

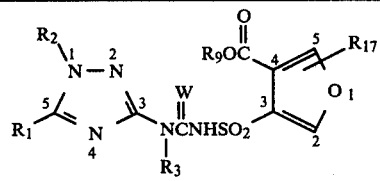

| R$_1$ | R$_2$ | R$_3$ | W | R$_9$ | R$_{17}$ | m.p. (°C.) |
|---|---|---|---|---|---|---|
| (dioxolane-CH) | CH$_3$ | H | O | CH$_2$CH$_2$CH$_3$ | H | |
| (dioxolane-CH) | CH$_3$ | H | O | CH$_2$CH$_2$OCH$_3$ | H | |
| (dioxolane-CH) | CH$_3$ | H | O | CH$_2$CH$_2$Cl | H | |

TABLE 10

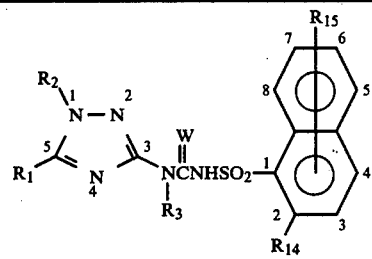

| R$_1$ | R$_2$ | R$_3$ | W | R$_{14}$ | R$_{15}$ | m.p. (°C.) |
|---|---|---|---|---|---|---|
| H | n-C$_3$H$_7$ | H | O | Cl | H | |
| H | C$_2$H$_5$ | H | O | Br | H | |
| CH$_3$ | C$_2$H$_5$ | H | O | F | H | |
| C$_2$H$_5$ | CH$_3$ | H | O | H | H | |
| CH$_3$ | CH(CH$_3$)$_2$ | H | O | Cl | H | |
| CH$_3$ | CH(CH$_3$)C$_2$H$_5$ | H | O | Cl | H | |
| CH$_3$ | n-C$_3$H$_7$ | H | S | Cl | H | |
| n-C$_3$H$_7$ | CH$_3$ | H | O | OCH$_3$ | H | |
| CH(CH$_3$)$_2$ | CH$_3$ | H | O | CH$_3$ | H | |
| CH(CH$_3$)C$_2$H$_5$ | CH$_3$ | H | O | Br | H | |
| n-C$_4$H$_9$ | CH$_3$ | H | O | Cl | H | |
| C$_2$H$_5$ | CH$_3$ | H | O | NO$_2$ | 4-Cl | |
| C$_2$H$_5$ | CH$_3$ | H | O | CH$_3$ | 8-NO$_2$ | |
| CH$_3$ | C$_2$H$_5$ | H | O | Cl | 3-Cl | |
| CH$_3$ | C$_2$H$_5$ | H | O | NO$_2$ | 6-Br | |
| CH$_3$ | C$_2$H$_5$ | CH$_3$ | O | NO$_2$ | H | |
| C$_2$H$_5$ | CH$_3$ | H | S | Cl | H | |
| C$_2$H$_5$ | CH$_3$ | CH$_3$ | O | NO$_2$ | H | |
| C$_2$H$_5$ | CH$_3$ | CH$_3$ | O | Cl | H | |
| CH$_3$ | CH$_3$ | H | O | F | H | |
| C$_2$H$_5$ | C$_2$H$_5$ | H | O | H | H | |
| C$_2$H$_5$ | CH$_3$ | H | O | SO$_2$N(CH$_3$)$_2$ | H | |
| CH$_3$ | C$_2$H$_5$ | H | O | SO$_2$CH$_3$ | H | |
| CH$_3$ | C$_2$H$_5$ | CH$_3$ | O | SO$_2$(CH$_2$)CH$_3$ | H | |
| CH$_3$ | C$_2$H$_5$ | H | O | SO$_2$N(OCH$_3$)CH$_3$ | H | |
| C$_2$H$_5$ | C$_2$H$_5$ | CH$_3$ | O | SO$_2$C$_2$H$_5$ | H | |
| C$_2$H$_5$ | C$_2$H$_5$ | H | O | OSO$_2$CH$_3$ | H | |
| C$_2$H$_5$ | C$_2$H$_5$ | H | O | NO$_2$ | H | |
| C$_2$H$_5$ | C$_2$H$_5$ | H | O | Cl | H | |
| CH$_3$ | C$_2$H$_5$ | H | O | SO$_2$N(CH$_3$)C$_2$H$_5$ | H | |
| CH$_3$ | C$_2$H$_5$ | H | O | H | 7-F | |
| CH$_3$ | C$_2$H$_5$ | H | O | H | 5-OCH$_3$ | |
| CH$_3$ | C$_2$H$_5$ | H | O | NO$_2$ | 8-Cl | |

TABLE 10-continued

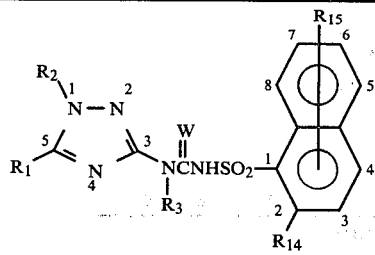

| R₁ | R₂ | R₃ | W | R₁₄ | R₁₅ | m.p. (°C.) |
|---|---|---|---|---|---|---|
| $CH_3$ | $CH_3$ | H | S | $CH_3$ | H | |
| $CH_2CH=CH_2$ | $CH_3$ | H | O | Cl | H | |
| $CH_2C(CH_3)=CH_2$ | $CH_3$ | H | O | Cl | H | |
| $CH_2C\equiv CH$ | $CH_3$ | H | O | $NO_2$ | H | |
| $CH_2C\equiv CCH_3$ | $CH_3$ | H | O | Br | H | |
| $CH_3$ | $CH_2CH=CH_2$ | H | O | $OCH_3$ | H | |
| $CH_3$ | $CH_2C(CH_3)=CH_2$ | H | O | $NO_2$ | H | |
| $CH_3$ | $CH_2C\equiv CCH_3$ | H | O | $SO_2CH_3$ | H | |
| $SCH_3$ | $CH_3$ | $CH_3$ | O | H | H | |
| $SCH_3$ | $CH_3$ | $CH_3$ | O | $NO_2$ | H | |
| $SCH_3$ | $CH_3$ | $CH_3$ | O | Cl | H | |
| $SCH_3$ | $CH_3$ | H | O | H | H | |
| $SCH_3$ | $CH_3$ | H | O | $NO_2$ | H | |
| $SCH_3$ | $CH_3$ | H | O | Cl | H | |
| $SCH_3$ | $CH_3$ | H | O | $OCH_3$ | H | |
| $SCH_3$ | $CH_3$ | H | O | $CH_3$ | H | |
| $SCH_3$ | $CH_3$ | H | O | F | H | |
| $SCH_3$ | $CH_3$ | H | S | H | H | |
| $SCH_3$ | $CH_3$ | H | S | Cl | H | |
| $SCH_3$ | $CH_3$ | H | S | $NO_2$ | H | |
| $SCH_3$ | $C_2H_5$ | H | O | $CH_3$ | H | |
| $SCH_3$ | $C_2H_5$ | $CH_3$ | O | $NO_2$ | H | |
| $SCH_3$ | $C_2H_5$ | $CH_3$ | O | H | H | |
| $SCH_3$ | $C_2H_5$ | H | O | $OSO_2CHCl_2$ | H | |
| $SCH_3$ | $CH_3$ | H | O | $OSO_2CH_2CHFCl$ | H | |
| $SCH_3$ | $CH_3$ | H | O | $OSO_2CH(CH_3)CH_2F$ | H | |
| $SCH_3$ | $CH_3$ | H | O | $OSO_2(CH_2)_3Br$ | H | |
| $SCH_3$ | $CH_3$ | H | O | $OSO_2(CH_2)_2CHCl_2$ | H | |
| $CH_3$ | $C_2H_5$ | H | O | $OSO_2CF_3$ | H | |
| $CH_3$ | $C_2H_5$ | H | O | $OSO_2CF_2CH_2F$ | H | |
| $C_2H_5$ | $C_2H_5$ | H | O | $OSO_2CH_2CF_3$ | H | |
| $SCH_3$ | $C_2H_5$ | H | O | $OSO_2CHF_2$ | H | |
| $CH_3$ | $C_2H_5$ | H | O | $OSO_2CCl_3$ | H | |
| $SC_2H_5$ | $CH_3$ | H | O | $OSO_2CH_3$ | H | |
| $SC_2H_5$ | $C_2H_5$ | H | O | $NO_2$ | 4-Br | |
| $SC_2H_5$ | $CH_3$ | H | S | H | 5-$OCH_3$ | |
| $SCH_3$ | $CH_3$ | $CH_3$ | O | F | 7-F | |
| $S(CH_2)_2CH_3$ | $CH_3$ | H | O | $CH_3$ | H | |
| $SCH(CH_3)_2$ | $CH_3$ | H | O | $SO_2N(CH_3)_2$ | H | |
| $SCH(CH_3)C_2H_5$ | $CH_3$ | H | O | Br | H | |
| $SCH_2CH=CH_2$ | $CH_3$ | H | O | Cl | H | |
| $SCH_2C(CH_3)=CH_2$ | $CH_3$ | H | O | Cl | H | |
| $SCH_2C\equiv CCH_3$ | $CH_3$ | H | O | $NO_2$ | H | |
| $SCH_2CO_2CH_3$ | $CH_3$ | H | O | $SO_2C_2H_5$ | H | |
| $SCH_2CO_2CH_2CH_3$ | $CH_3$ | H | O | Cl | H | |
| $SCH(CH_3)CO_2CH_3$ | $CH_3$ | H | O | Br | H | |
| $SCH(CH_3)CO_2C_2H_5$ | $CH_3$ | H | O | H | H | |
| $CH_2OCH_3$ | $CH_3$ | $CH_3$ | O | H | H | |
| $CH_2OCH_3$ | $CH_3$ | H | S | H | H | |
| $CH_2OCH_3$ | $CH_3$ | H | O | $NO_2$ | H | |
| $CH_2OCH_3$ | $CH_3$ | H | O | Cl | H | |
| $CH_2OCH_3$ | $CH_3$ | H | O | Br | H | |
| $CH_2OCH_3$ | $CH_3$ | H | O | $OCH_3$ | H | |
| $CH_2OCH_3$ | $CH_3$ | H | S | H | 6-Br | |
| $CH_2OCH_3$ | $CH_3$ | H | S | H | 3-Cl | |
| $CH_2OCH_3$ | $C_2H_5$ | H | O | F | H | |
| $CH_2OCH_3$ | $CH_3$ | H | O | $SO_2C_2H_5$ | H | |
| $CH_2OCH_3$ | $CH_3$ | H | O | $SO_2N(CH_3)_2$ | H | |
| $CH_2OCH_3$ | $CH_3$ | H | O | $OSO_2C_2H_5$ | H | |
| $CH_2OC_2H_5$ | $CH_3$ | H | O | $CH_3$ | H | |
| $CH_2OC_2H_5$ | $CH_3$ | H | S | H | H | |
| $CH_2O(CH_2)_3CH_3$ | $CH_3$ | H | O | $NO_2$ | H | |
| $CH_2OCH(CH_3)_2$ | $CH_3$ | H | O | Cl | H | |
| $CH_2CH_2OCH_3$ | $CH_3$ | H | O | H | H | |
| $CH_2CH_2OCH(CH_3)_2$ | $CH_3$ | H | O | $OCH_3$ | H | |
| $OCH_3$ | $C_2H_5$ | H | O | H | H | |
| $OCH_3$ | $CH_3$ | H | S | H | H | |
| $OCH_3$ | $CH_3$ | $CH_3$ | O | H | H | |

TABLE 10-continued

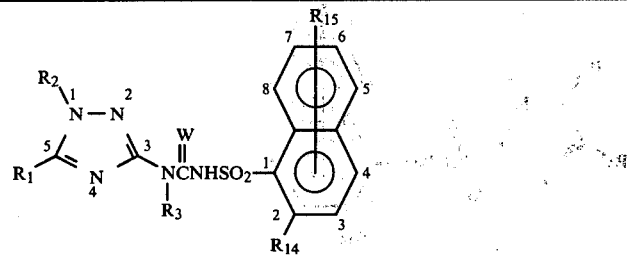

| $R_1$ | $R_2$ | $R_3$ | W | $R_{14}$ | $R_{15}$ | m.p.(°C.) |
|---|---|---|---|---|---|---|
| $OCH_3$ | $CH_3$ | $CH_3$ | O | Cl | H | |
| $OCH_3$ | $C_2H_5$ | H | O | $SO_2N(CH_3)[CH(CH_3)_2]$ | H | |
| $OCH_3$ | $C_2H_5$ | H | O | $SO_2N(CH_3)[(CH_2)_2CH_3]$ | H | |
| $OCH_3$ | $C_2H_5$ | H | O | $SO_2N(CH_3)_2$ | H | |
| $OCH_3$ | $CH_3$ | H | O | $OSO_2(CH_2)_2CHCl_2$ | H | |
| $OCH_3$ | $CH_3$ | H | O | $OSO_2CH(CH_3)CHF_2$ | H | |
| $OCH_3$ | $CH_3$ | H | O | $OSO_2CHFCF_3$ | H | |
| $OC_2H_5$ | $CH_3$ | H | O | Br | H | |
| $OC_2H_5$ | $CH_3$ | H | O | Cl | 4-Cl | |
| $OC_2H_5$ | $CH_3$ | H | O | H | 8-$NO_2$ | |
| $OC_2H_5$ | $CH_3$ | H | S | H | H | |
| $OC_2H_5$ | $CH_3$ | H | S | $NO_2$ | H | |
| $OC_2H_5$ | $CH_3$ | H | O | $SCH_3$ | H | |
| $OC_2H_5$ | $CH_3$ | H | O | $SCH_2CH(CH_3)_2$ | H | |
| $OC_2H_5$ | $CH_3$ | H | O | $S(CH_2)_3CH_3$ | H | |
| $OC_2H_5$ | $CH_3$ | H | O | $S(CH_2)_2CH_3$ | H | |
| $OCH_3$ | $C_2H_5$ | H | O | $SC_2H_5$ | H | |
| $OCH_3$ | $C_2H_5$ | H | O | $SO_2CH_2CH(CH_3)_2$ | H | |
| $OCH_3$ | $C_2H_5$ | H | O | $SO_2CH(CH_3)_2$ | H | |
| $OCH_3$ | $C_2H_5$ | H | O | $SO_2CH_3$ | H | |
| $OCH_3$ | $C_2H_5$ | H | O | $SO_2(CH_2)_2CH_3$ | H | |
| $O(CH_2)_2CH_3$ | $CH_3$ | H | O | $SO_2N(CH_3)_2$ | H | |
| $OCH(CH_3)_2$ | $CH_3$ | H | O | $CH_3$ | H | |
| $OCH(CH_3)C_2H_5$ | $CH_3$ | H | O | $OCH_3$ | H | |
| $OCH_2CH=CH_2$ | $CH_3$ | H | O | H | H | |
| $OCH_2C(CH_3)=CH_2$ | $CH_3$ | H | O | Cl | H | |
| $OCH_2C\equiv CCH_3$ | $CH_3$ | H | O | $NO_2$ | H | |
| $N(CH_3)_2$ | $CH_3$ | H | O | H | H | |
| $N(CH_3)_2$ | $CH_3$ | H | O | Cl | H | |
| $CF_3$ | $CH_3$ | H | O | Cl | H | |
| $CF_3$ | $CH_3$ | H | O | $NO_2$ | H | |
| $CF_3$ | $CH_3$ | H | S | Cl | H | |
| $CF_3$ | $C_2H_5$ | H | O | H | H | |
| $CF_3$ | $C_2H_5$ | H | O | F | H | |
| $CF_3$ | $C_2H_5$ | H | O | $SO_2CH(CH_3)_2$ | H | |
| $CF_3$ | $C_2H_5$ | H | O | $OSO_2C_2H_5$ | H | |
| $CF_3$ | $C_2H_5$ | H | O | $OSO_2CH(CH_3)_2$ | H | |
| $CF_2CF_3$ | $CH_3$ | H | O | $OSO_2CH_3$ | H | |
| $CF_2CF_3$ | $CH_3$ | H | O | $OSO_2CH_2CH_2Cl$ | H | |
| $CF_2CF_3$ | $CH_3$ | H | O | $NO_2$ | H | |
| $CF_2CF_3$ | $C_2H_5$ | H | O | Cl | H | |
| $CH_3$ | $CH_2OCH_3$ | H | O | Br | H | |
| $CH_3$ | $CH_2OCH_3$ | H | O | $NO_2$ | H | |
| $CH_3$ | $CH_2OCH(CH_3)_2$ | H | O | Br | H | |
| $CH_3$ | $CH_2CH_2OCH_3$ | H | O | $NO_2$ | H | |
| $CH_3$ | $CH_2CH_2S(CH_2)_2CH_3$ | H | O | Cl | H | |
| $CH_3$ | $CH_2CH_2SCH_3$ | H | O | H | H | |
| $CH_3$ | $CH_2SCH_3$ | H | O | $CH_3$ | H | |
| $CH_3$ | $CH_2CH_2SCH_3$ | H | O | $OCH_3$ | H | |
| $CH_3$ | $CH_2OC_2H_5$ | H | O | F | H | |
| $OCH_3$ | $C_2H_5$ | H | O | $OSO_2CH_2CH_2OCH_3$ | H | |
| $OC_2H_5$ | $CH_3$ | H | O | $OSO_2(CH_2)_3OCH_3$ | H | |
| $SCH_3$ | $CH_3$ | H | O | $OSO_2(CH_2)_3CH_3$ | H | |
| $SCH_3$ | $CH_3$ | H | S | Br | H | |
| $SCH_3$ | $CH_3$ | H | O | Br | 8-Cl | |
| $SCH_3$ | $CH_3$ | H | O | H | 5-$OCH_3$ | |
| $SCH_3$ | $CH_3$ | H | O | H | 6-Br | |
| $SCH_3$ | $CH_3$ | $CH_3$ | O | $SO_2CH_3$ | H | |
| $SCH_3$ | $CH_3$ | $CH_3$ | O | $SO_2C_2H_5$ | H | |
| $OC_2H_5$ | $CH_3$ | $CH_3$ | O | Cl | H | |
| $OC_2H_5$ | $CH_3$ | $CH_3$ | O | $NO_2$ | H | |
| $SC_2H_5$ | $CH_3$ | H | O | F | H | |
| $C_2H_5$ | $C_2H_5$ | $CH_3$ | O | H | H | |
| $SCH_3$ | $CH_3$ | H | S | Cl | H | |
| $OC_2H_5$ | $CH_3$ | H | O | $OSO_2CH_2Cl$ | H | |
| $OC_2H_5$ | $CH_3$ | H | O | $SO_2CH_3$ | H | |
| $OC_2H_5$ | $CH_3$ | H | O | $SO_2(CH_2)_2CH_3$ | H | |
| $OC_2H_5$ | $CH_3$ | H | O | $SCH_2CH_3$ | H | |

TABLE 10-continued

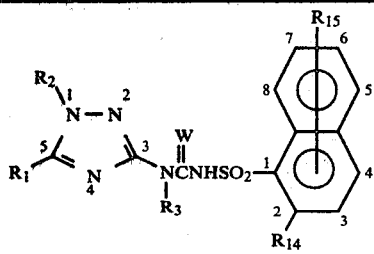

| R₁ | R₂ | R₃ | W | R₁₄ | R₁₅ | m.p. (°C.) |
|---|---|---|---|---|---|---|
| OC₂H₅ | CH₃ | H | O | OSO₂CF₃ | H | |
| OC₂H₅ | CH₃ | H | O | SO₂N(CH₃)[(CH₂)₂CH₃] | H | |
| OC₂H₅ | CH₃ | H | O | CH₃ | H | |
| OC₂H₅ | CH₃ | H | O | OCH₃ | H | |
| OC₂H₅ | CH₃ | H | O | F | H | |
| OC₂H₅ | CH₃ | H | O | Cl | H | |
| OC₂H₅ | CH₃ | H | O | NO₂ | H | |
| OC₂H₅ | CH₃ | H | O | SO₂N(CH₃)₂ | H | |
| OC₂H₅ | CH₃ | H | O | SO₂N(C₂H₅)₂ | H | |
| OC₂H₅ | CH₃ | H | O | SO₂N(OCH₃)CH₃ | H | |
| OC₂H₅ | CH₃ | H | O | OSO₂CH₃ | H | |
| OC₂H₅ | CH₃ | H | O | OSO₂(CH₂)₃CH₃ | H | |
| OC₂H₅ | CH₃ | H | O | SO₂CH₂CH=CH₂ | H | |
| OC₂H₅ | CH₃ | H | O | SO₂CF₃ | H | |
| OC₂H₅ | CH₃ | H | O | SO₂CF₂CF₃ | H | |
| OCH₃ | CH₃ | H | O | H | H | |
| OCH₃ | CH₃ | H | O | CH₃ | H | |
| OCH₃ | CH₃ | H | O | OCH₃ | H | |
| OCH₃ | CH₃ | H | O | F | H | |
| OCH₃ | CH₃ | H | O | Cl | H | |
| OCH₃ | CH₃ | H | O | Br | H | |
| OCH₃ | CH₃ | H | O | NO₂ | H | |
| OCH₃ | CH₃ | H | O | SO₂N(CH₃)₂ | H | |
| OCH₃ | CH₃ | H | O | SO₂N(C₂H₅)₂ | H | |
| OCH₃ | CH₃ | H | O | SO₂N(CH₃)C₂H₅ | H | |
| OCH₃ | CH₃ | H | O | SO₂N(OCH₃)CH₃ | H | |
| OCH₃ | CH₃ | H | O | OSO₂CH₃ | H | |
| OCH₃ | CH₃ | H | O | OSO₂C₂H₅ | H | |
| OCH₃ | CH₃ | H | O | OSO₂CF₃ | H | |
| OCH₃ | CH₃ | H | O | SCH₃ | H | |
| OCH₃ | CH₃ | H | O | SOCH₃ | H | |
| OCH₃ | CH₃ | H | O | SO₂CH₃ | H | |
| OCH₃ | CH₃ | H | O | SC₂H₅ | H | |
| OCH₃ | CH₃ | H | O | SO₂C₂H₅ | H | |
| OCH₃ | CH₃ | H | O | SO₂CH₂CH₂CH₃ | H | |
| OCH₃ | CH₃ | H | O | SO₂CH₂CH=CH₂ | H | |
| OCH₃ | CH₃ | H | O | SO₂CF₃ | H | |
| OCH₃ | CH₃ | H | O | SO₂CH₂CF₃ | H | |
| OCH₃ | CH₃ | H | O | SO₂CH₂CHClCF₃ | H | |
| OCH₃ | CH₂CF₃ | H | O | CH₃ | H | |
| OCH₃ | CH₂CF₃ | H | O | OCH₃ | H | |
| OCH₃ | CH₂CF₃ | H | O | Cl | H | |
| OCH₃ | CH₂CF₃ | H | O | NO₂ | H | |
| OCH₃ | CH₂CF₃ | H | O | SO₂N(CH₃)₂ | H | |
| OCH₃ | CH₂CF₃ | H | O | SO₂(OCH₃)CH₃ | H | |
| OCH₃ | CH₂CF₃ | H | O | OSO₂CH₃ | H | |
| OCH₃ | CH₂CF₃ | H | O | OSO₂CF₃ | H | |
| OCH₃ | CH₂CF₃ | H | O | SO₂CH₃ | H | |
| OCH₃ | CH₂CF₃ | H | O | SO₂CH₂CH₂CH₃ | H | |
| OCH₃ | CH₂CF₃ | H | O | SO₂CH₂CH=CH₂ | H | |
| Cl | CH₃ | H | O | CH₃ | H | |
| Cl | CH₃ | H | O | Cl | H | |
| Cl | CH₃ | H | O | NO₂ | H | |
| Cl | CH₃ | H | O | SO₂N(CH₃)₂ | H | |
| Cl | CH₃ | H | O | OSO₂CH₃ | H | |
| Cl | CH₃ | H | O | SO₂CH₃ | H | |
| NHCH₃ | CH₃ | H | O | OCH₃ | H | |
| NHCH₃ | CH₃ | H | O | Br | H | |
| NHCH₃ | CH₃ | H | O | SO₂N(OCH₃)CH₃ | H | |
| NHCH₃ | CH₃ | H | O | OSO₂CF₃ | H | |
| NHCH₃ | CH₃ | H | O | SO₂CH₂CH₃ | H | |
| NHCH₃ | CH₃ | H | O | SO₂CH₂CH=CH₂ | H | |
| CH(OCH₃)₂ | CH₃ | H | O | CH₃ | H | |
| CH(OCH₃)₂ | CH₃ | H | O | F | H | |
| CH(OCH₃)₂ | CH₃ | H | O | NO₂ | H | |
| CH(OCH₃)₂ | CH₃ | H | O | SO₂N(C₂H₅)₂ | H | |
| CH(OCH₃)₂ | CH₃ | H | O | SO₂CH₃ | H | |

TABLE 10-continued
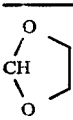
| $R_1$ | $R_2$ | $R_3$ | W | $R_{14}$ | $R_{15}$ | m.p. (°C.) |
|---|---|---|---|---|---|---|
| 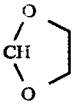 | $CH_3$ | H | O | H | H | |
| 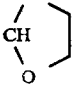 | $CH_{33}$ | H | O | $CH_3$ | H | |
| 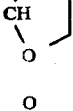 | $CH_3$ | H | O | $OCH_3$ | H | |
| 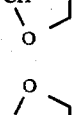 | $CH_3$ | H | O | F | H | |
| 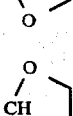 | $CH_3$ | H | O | Cl | H | |
| 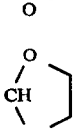 | $CH_3$ | H | O | Br | H | |
| 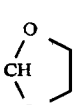 | $CH_3$ | H | O | $NO_2$ | H | |
| 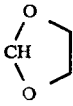 | $CH_3$ | H | O | $SO_2N(CH_3)_2$ | H | |
| 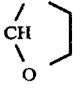 | $CH_3$ | H | O | $SO_2N(OCH_3)CH_3$ | H | |
|  | $CH_3$ | H | O | $OSO_2CH_3$ | H | |
|  | $CH_3$ | H | O | $OSO_2CF_3$ | H | |

TABLE 10-continued

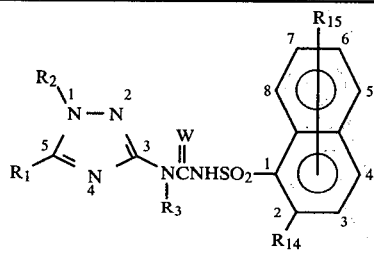

| $R_1$ | $R_2$ | $R_3$ | W | $R_{14}$ | $R_{15}$ | m.p. (°C.) |
|---|---|---|---|---|---|---|
| ⟨O-CH-O⟩ | $CH_3$ | H | O | $SCH_3$ | H | |
| ⟨O-CH-O⟩ | $CH_3$ | H | O | $SO_2C_2H_5$ | H | |
| ⟨O-CH-O⟩ | $CH_3$ | H | O | $SO_2CH_2CH=CH_2$ | H | |
| ⟨O-CH-O⟩ | $CH_3$ | H | O | $SO_2CH_2CH_2CH_3$ | H | |
| ⟨O-CH-O⟩ | $CH_3$ | H | O | $SO_2CH_3$ | H | |

TABLE 11

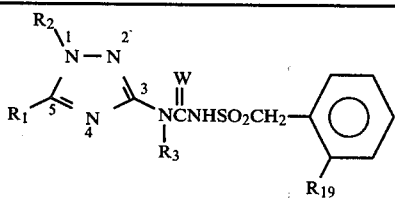

| $R_1$ | $R_2$ | $R_3$ | W | $R_{19}$ | m.p. (°C.) |
|---|---|---|---|---|---|
| $OCH_3$ | $CH_3$ | H | O | Cl | |
| $OCH_3$ | $CH_3$ | H | O | $NO_2$ | |
| $OCH_3$ | $CH_3$ | H | O | $CF_3$ | |
| $OCH_3$ | $CH_3$ | H | O | $CO_2CH_3$ | 164–166° |
| $OCH_3$ | $CH_3$ | H | O | $CO_2C_2H_5$ | |
| $OCH_3$ | $CH_3$ | H | O | $CO_2(CH_2)_2CH_3$ | |
| $OCH_3$ | $CH_3$ | H | O | $CO_2(CH_2)_3CH_3$ | |
| $OCH_3$ | $CH_3$ | H | O | $CO_2(CH_2)_4CH_3$ | |
| $OCH_3$ | $CH_3$ | H | O | $CO_2(CH_2)_5CH_3$ | |
| $OCH_3$ | $CH_3$ | H | O | $CO_2CH(CH_3)_2$ | |
| $OCH_3$ | $CH_3$ | H | O | $CO_2CH_2CH_2OCH_3$ | |
| $OCH_3$ | $CH_3$ | H | O | $CO_2CH_2CH_2OC_2H_5$ | |
| $OCH_3$ | $CH_3$ | H | O | $CO_2(CH_2)_3OC_2H_5$ | |
| $OCH_3$ | $CH_3$ | H | O | $CO_2CH_2CH=CH_2$ | |
| $OCH_3$ | $CH_3$ | H | O | $CO_2CH_2CH=CHCH_3$ | |
| $OCH_3$ | $CH_3$ | H | O | $CO_2(CH_2)_4CH=CH_2$ | |
| $OCH_3$ | $CH_3$ | H | O | $CO_2CH_2C\equiv CH$ | |
| $OCH_3$ | $CH_3$ | H | O | $CO_2CH_2C\equiv CCH_3$ | |
| $OCH_3$ | $CH_3$ | H | O | $CO_2(CH_2)_4C\equiv CH$ | |
| $OCH_3$ | $CH_3$ | H | O | $CO_2CH(CH_3)C_2H_5$ | |
| $OCH_3$ | $CH_3$ | H | O | $CO_2CH_2CH(CH_3)_2$ | |

TABLE 11-continued

[Structure: pyrazole ring with R$_2$ on N1, N1-N2, R$_1$ on C5, N4, C3 connected to N(R$_3$)C(=W)NHSO$_2$CH$_2$-phenyl with R$_{19}$ substituent]

| R$_1$ | R$_2$ | R$_3$ | W | R$_{19}$ | m.p. (°C.) |
|---|---|---|---|---|---|
| OCH$_3$ | CH$_3$ | H | O | CO$_2$CF$_3$ | |
| OCH$_3$ | CH$_3$ | H | O | CO$_2$CH$_2$CH$_2$Cl | |
| OCH$_3$ | CH$_3$ | H | O | CO$_2$CH$_2$CF$_3$ | |
| OCH$_3$ | CH$_3$ | H | O | CO$_2$CH$_2$CCl$_3$ | |
| OCH$_3$ | CH$_3$ | H | O | CO$_2$CH$_2$CH$_2$CF$_3$ | |
| OCH$_3$ | CH$_3$ | H | O | CO$_2$CH$_2$CH$_2$CH$_2$Cl | |
| OCH$_3$ | CH$_3$ | H | O | CO$_2$CClF$_2$ | |
| OCH$_3$ | CH$_3$ | H | O | CO$_2$CF$_2$H | |
| OCH$_3$ | CH$_3$ | H | O | CO$_2$CHFCF$_2$H | |
| OCH$_3$ | CH$_3$ | H | O | CO$_2$CHClCF$_2$H | |
| OCH$_3$ | CH$_3$ | H | O | CO$_2$CH$_2$CHFCF$_2$H | |
| OCH$_3$ | CH$_3$ | H | O | SO$_2$N(OCH$_3$)CH$_3$ | |
| OCH$_3$ | CH$_3$ | H | O | SO$_2$N(CH$_3$)$_2$ | |
| OCH$_3$ | CH$_3$ | H | O | SO$_2$N(C$_2$H$_5$)$_2$ | |
| OCH$_3$ | CH$_3$ | H | O | SO$_2$N(CH$_3$)C$_2$H$_5$ | |
| OCH$_3$ | CH$_3$ | H | O | SO$_2$N(CH$_3$)CH$_2$CH$_2$CH$_3$ | |
| OCH$_3$ | CH$_3$ | H | O | OSO$_2$CH$_3$ | |
| OCH$_3$ | CH$_3$ | H | O | OSO$_2$C$_2$H$_5$ | |
| OCH$_3$ | CH$_3$ | H | O | OSO$_2$(CH$_2$)$_2$CH$_3$ | |
| OCH$_3$ | CH$_3$ | H | O | OSO$_2$(CH$_2$)$_3$CH$_3$ | |
| OCH$_3$ | CH$_3$ | H | O | OSO$_2$CH(CH$_3$)$_2$ | |
| OCH$_3$ | CH$_3$ | H | O | OSO$_2$CH(CH$_3$)C$_2$H$_5$ | |
| OCH$_3$ | CH$_3$ | H | O | OSO$_2$CH$_2$CH$_2$OCH$_3$ | |
| OCH$_3$ | CH$_3$ | H | O | OSO$_2$(CH$_2$)$_3$OCH$_3$ | |
| OCH$_3$ | CH$_3$ | H | O | OSO$_2$CF$_3$ | |
| OCH$_3$ | CH$_3$ | H | O | OSO$_2$CH$_2$CF$_3$ | |
| OCH$_3$ | CH$_3$ | H | O | OSO$_2$CHFCF$_2$H | |
| OCH$_3$ | CH$_3$ | H | O | OSO$_2$CF$_2$CH$_2$CH$_2$CH$_3$ | |
| OCH$_3$ | CH$_3$ | H | O | OSO$_2$CClF$_2$ | |
| OCH$_3$ | CH$_3$ | H | O | OSO$_2$CBr$_2$CH$_3$ | |
| OCH$_3$ | CH$_3$ | H | O | N(CH$_3$)SO$_2$CH$_3$ | |
| OCH$_3$ | CH$_3$ | H | O | N(CH$_3$)SO$_2$C$_2$H$_5$ | |
| OCH$_3$ | CH$_3$ | H | O | N(CH$_3$)SO$_2$C$_3$H$_5$ | |
| OCH$_3$ | CH$_3$ | H | O | N(CH$_3$)SO$_2$CH(CH$_3$)C$_2$H$_5$ | |
| OCH$_3$ | CH$_3$ | H | O | N(CH$_3$)SO$_2$CH$_2$CH$_2$OCH$_3$ | |
| OCH$_3$ | CH$_3$ | H | O | N(CH$_3$)SO$_2$CF$_3$ | |
| OCH$_3$ | CH$_3$ | H | O | SCH$_3$ | |
| OCH$_3$ | CH$_3$ | H | O | SOCH$_3$ | |
| OCH$_3$ | CH$_3$ | H | O | SO$_2$CH$_3$ | |
| OCH$_3$ | CH$_3$ | H | O | SO$_2$C$_2$H$_5$ | |
| OCH$_3$ | CH$_3$ | H | O | SO$_2$CH$_2$CH$_2$CH$_3$ | |
| OCH$_3$ | CH$_3$ | H | O | SO$_2$CH(CH$_3$)$_2$ | |
| OCH$_3$ | CH$_3$ | H | O | SO$_2$CH$_2$CH=CH$_2$ | |
| OCH$_3$ | CH$_3$ | H | O | SO$_2$CH(CH$_3$)C$_2$H$_5$ | |
| OCH$_3$ | CH$_3$ | H | O | SCH$_2$CH$_2$CH$_3$ | |
| OCH$_3$ | CH$_3$ | H | O | SCF$_3$ | |
| OCH$_3$ | CH$_3$ | H | O | SOCF$_3$ | |
| OCH$_3$ | CH$_3$ | H | O | SO$_2$CF$_3$ | |
| OCH$_3$ | CH$_3$ | H | O | OCCl$_3$ | |
| OCH$_3$ | CH$_3$ | H | O | OCF$_3$ | |
| OCH$_3$ | CH$_3$ | H | O | OCF$_2$CF$_3$ | |
| OCH$_3$ | CH$_3$ | H | O | OCF$_2$CF$_2$CH$_3$ | |
| OCH$_3$ | CH$_3$ | H | O | OCClF$_2$ | |
| OCH$_3$ | CH$_3$ | H | O | OCCl$_2$CF$_3$ | |
| OC$_2$H$_5$ | CH$_3$ | H | O | Cl | |
| OC$_2$H$_5$ | CH$_3$ | H | O | NO$_2$ | |
| OC$_2$H$_5$ | CH$_3$ | H | O | CF$_3$ | |
| OC$_2$H$_5$ | CH$_3$ | H | O | CO$_2$CH$_3$ | |
| OC$_2$H$_5$ | CH$_3$ | H | O | CO$_2$C$_2$H$_5$ | |
| OC$_2$H$_5$ | CH$_3$ | H | O | CO$_2$CH$_2$CH$_2$CH$_3$ | |
| OC$_2$H$_5$ | CH$_3$ | H | O | CO$_2$CH(CH$_3$)$_2$ | |
| OC$_2$H$_5$ | CH$_3$ | H | O | CO$_2$CH$_2$CH=CH$_2$ | |
| OC$_2$H$_5$ | CH$_3$ | H | O | CO$_2$CH$_2$C≡CH | |
| OC$_2$H$_5$ | CH$_3$ | H | O | CO$_2$CH$_2$CH$_2$OCH$_3$ | |
| OC$_2$H$_5$ | CH$_3$ | H | O | CO$_2$CH$_2$CH$_2$OC$_2$H$_5$ | |
| OC$_2$H$_5$ | CH$_3$ | H | O | CO$_2$CF$_3$ | |
| OC$_2$H$_5$ | CH$_3$ | H | O | SO$_2$N(OCH$_3$)CH$_3$ | |
| OC$_2$H$_5$ | CH$_3$ | H | O | SO$_2$N(CH$_3$)$_2$ | |
| OC$_2$H$_5$ | CH$_3$ | H | O | SO$_2$N(CH$_3$)C$_2$H$_5$ | |
| OC$_2$H$_5$ | CH$_3$ | H | O | SO$_2$N(C$_2$H$_5$)$_2$ | |
| OC$_2$H$_5$ | CH$_3$ | H | O | OSO$_2$CH$_3$ | |

TABLE 11-continued

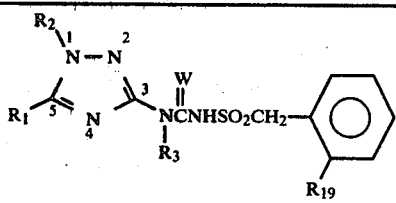

| R1 | R2 | R3 | W | R19 | m.p. (°C.) |
|---|---|---|---|---|---|
| OC2H5 | CH3 | H | O | OSO2C2H5 | |
| OC2H5 | CH3 | H | O | N(CH3)SO2CH3 | |
| OC2H5 | CH3 | H | O | SO2CH3 | |
| OC2H5 | CH3 | H | O | SO2C2H5 | |
| OC2H5 | CH3 | H | O | SO2CH2CH2CH3 | |
| OC2H5 | CH3 | H | O | SO2CHCH=CH2 | |
| OC2H5 | CH3 | H | O | SO2CF3 | |
| OC2H5 | CH3 | H | O | OCF3 | |
| OC2H5 | CH3 | H | O | OCF2CF3 | |
| OC2H5 | C2H5 | H | O | Cl | |
| OC2H5 | C2H5 | H | O | NO2 | |
| OC2H5 | C2H5 | H | O | CF3 | |
| OC2H5 | C2H5 | H | O | CO2CH3 | |
| OC2H5 | C2H5 | H | O | CO2C2H5 | |
| OC2H5 | C2H5 | H | O | CO2CH2CH2CH3 | |
| OC2H5 | C2H5 | H | O | CO2CH(CH3)2 | |
| OC2H5 | C2H5 | H | O | CO2CHCH=CH2 | |
| OC2H5 | C2H5 | H | O | CO2CH2C≡CH | |
| OC2H5 | C2H5 | H | O | CO2CH2CH2OCH3 | |
| OC2H5 | C2H5 | H | O | SO2N(OCH3)CH3 | |
| OC2H5 | C2H5 | H | O | SO2N(CH3)2 | |
| OC2H5 | C2H5 | H | O | OSO2CH3 | |
| OC2H5 | C2H5 | H | O | N(CH3)SO2CH3 | |
| OC2H5 | C2H5 | H | O | SO2CH3 | |
| OC2H5 | C2H5 | H | O | SO2CH2CH3 | |
| OC2H5 | C2H5 | H | O | SO2CH2CH2CH3 | |
| OC2H5 | C2H5 | H | O | OCF3 | |
| OCH2CH2CH3 | CH3 | H | O | Cl | |
| OCH2CH2CH3 | CH3 | H | O | NO2 | |
| OCH2CH2CH3 | CH3 | H | O | CF3 | |
| OCH2CH2CH3 | CH3 | H | O | CO2CH3 | |
| OCH2CH2CH3 | CH3 | H | O | CO2CH2CH=CH2 | |
| OCH2CH2CH3 | CH3 | H | O | SO2N(OCH3)CH3 | |
| OCH2CH2CH3 | CH3 | H | O | SO2N(CH3)2 | |
| OCH2CH2CH3 | CH3 | H | O | OSO2CH3 | |
| OCH2CH2CH3 | CH3 | H | O | N(CH3)SO2CH3 | |
| OCH2CH2CH3 | CH3 | H | O | SO2CH3 | |
| OCH2CH2CH3 | CH3 | H | O | SO2CH2CH2CH3 | |
| OCH2CH2CH3 | CH3 | H | O | OCF3 | |
| O(CH2)3CH3 | CH3 | H | O | Cl | |
| O(CH2)3CH3 | CH3 | H | O | NO2 | |
| O(CH2)3CH3 | CH3 | H | O | CF3 | |
| O(CH2)3CH3 | CH3 | H | O | CO2CH3 | |
| O(CH2)3CH3 | CH3 | H | O | CO2C2H5 | |
| O(CH2)3CH3 | CH3 | H | O | CO2CH(CH3)2 | |
| O(CH2)3CH3 | CH3 | H | O | SO2N(CH3)2 | |
| O(CH2)3CH3 | CH3 | H | O | SO2CH3 | |
| O(CH2)3CH3 | CH3 | H | O | SO2CH2CH2CH3 | |
| O(CH2)3CH3 | CH3 | H | O | OCF3 | |
| OCH3 | C2H5 | H | O | Cl | |
| OCH3 | C2H5 | H | O | NO2 | |
| OCH3 | C2H5 | H | O | CF3 | |
| OCH3 | C2H5 | H | O | CO2CH3 | |
| OCH3 | C2H5 | H | O | CO2C2H5 | |
| OCH3 | C2H5 | H | O | CO2CH(CH3)2 | |
| OCH3 | C2H5 | H | O | CO2CH2CH=CH2 | |
| OCH3 | C2H5 | H | O | CO2CH2CH2OCH3 | |
| OCH3 | C2H5 | H | O | CO2CH2CH2Cl | |
| OCH3 | C2H5 | H | O | SO2N(OCH3)CH3 | |
| OCH3 | C2H5 | H | O | SO2N(CH3)2 | |
| OCH3 | C2H5 | H | O | OSO2CH3 | |
| OCH3 | C2H5 | H | O | N(CH3)SO2CH3 | |
| OCH3 | C2H5 | H | O | SO2CH3 | |
| OCH3 | C2H5 | H | O | SO2CH2CH2CH3 | |
| OCH3 | C2H5 | H | O | OCF3 | |
| OCH3 | CH2CH=CH2 | H | O | Cl | |
| OCH3 | CH2CH=CH2 | H | O | NO2 | |
| OCH3 | CH2CH=CH2 | H | O | CF3 | |
| OCH3 | CH2CH=CH2 | H | O | CO2CH3 | |
| OCH3 | CH2CH=CH2 | H | O | CO2C2H5 | |
| OCH3 | CH2CH=CH2 | H | O | CO2CH(CH3)2 | |

TABLE 11-continued

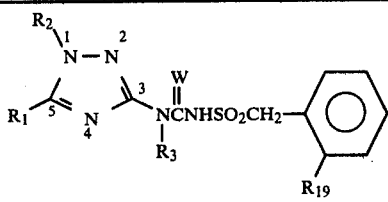

| R₁ | R₂ | R₃ | W | R₁₉ | m.p. (°C.) |
|---|---|---|---|---|---|
| OCH₃ | CH₂CH=CH₂ | H | O | CO₂CH₂CH=CH₂ | |
| OCH₃ | CH₂CH=CH₂ | H | O | CO₂CH₂CH₂OCH₃ | |
| OCH₃ | CH₂CH=CH₂ | H | O | SO₂N(Me)₂ | |
| OCH₃ | CH₂CH=CH₂ | H | O | OSO₂CH₃ | |
| OCH₃ | CH₂CH=CH₂ | H | O | SO₂CH₃ | |
| OCH₃ | CH₂CH=CH₂ | H | O | SO₂CH₂CH₂CH₃ | |
| OCH₃ | CH₂CH=CH₂ | H | O | OCF₃ | |
| OCH₃ | CH₂OCH₃ | H | O | Cl | |
| OCH₃ | CH₂OCH₃ | H | O | NO₂ | |
| OCH₃ | CH₂OCH₃ | H | O | CO₂CH₃ | |
| OCH₃ | CH₂OCH₃ | H | O | CO₂CH₂CH₂CH₃ | |
| OCH₃ | CH₂OCH₃ | H | O | CO₂CH₂CH=CH₂ | |
| OCH₃ | CH₂OCH₃ | H | O | SO₂N(Me)₂ | |
| OCH₃ | CH₂OCH₃ | H | O | SO₂CH₃ | |
| OCH₃ | CH₂OCH₃ | H | O | SO₂CH₂CH₂CH₃ | |
| OCH₃ | CH₂OCH₃ | H | O | OSO₂CH₃ | |
| OCH₃ | CH₂OCH₃ | H | O | OCF₃ | |
| OCH₃ | CH₂SCH₃ | H | O | Cl | |
| OCH₃ | CH₂SCH₃ | H | O | NO₂ | |
| OCH₃ | CH₂SCH₃ | H | O | CO₂CH₃ | |
| OCH₃ | CH₂SCH₃ | H | O | CO₂CH₂CH₃ | |
| OCH₃ | CH₂SCH₃ | H | O | CO₂CH(CH₃)₂ | |
| OCH₃ | CH₂SCH₃ | H | O | CO₂CH₂CH=CH₂ | |
| OCH₃ | CH₂SCH₃ | H | O | SO₂N(CH₃)₂ | |
| OCH₃ | CH₂SCH₃ | H | O | OSO₂CH₃ | |
| OCH₃ | CH₂SCH₃ | H | O | SO₂CH₃ | |
| OCH₃ | CH₂SCH₃ | H | O | SO₂CH₂CH₂CH₃ | |
| OCH₃ | CH₂SCH₃ | H | O | OCF₃ | |
| OCH₃ | CH₂CF₃ | H | O | Cl | |
| OCH₃ | CH₂CF₃ | H | O | NO₂ | |
| OCH₃ | CH₂CF₃ | H | O | CF₃ | |
| OCH₃ | CH₂CF₃ | H | O | CO₂CH₃ | |
| OCH₃ | CH₂CF₃ | H | O | CO₂CH₂CH=CH₂ | |
| OCH₃ | CH₂CF₃ | H | O | OSO₂CH₃ | |
| OCH₃ | CH₂CF₃ | H | O | SO₂CH₃ | |
| OCH₃ | CH₂CF₃ | H | O | SO₂CH₂CH₂CH₃ | |
| OCH₃ | CH₂CF₃ | H | O | SO₂N(CH₃)₂ | |
| OCH₃ | CH₂C≡CH | H | O | CO₂CH₃ | |
| OCH₃ | CH₂CH₂OCH₃ | H | O | CO₂CH₃ | |
| OCH₃ | CH₂CH₂SCH₃ | H | O | CO₂CH₃ | |
| OCH₃ | CH₂CH₂CH₃ | H | O | CO₂CH₃ | |
| CH₃ | CH₃ | H | O | Cl | |
| CH₃ | CH₃ | H | O | NO₂ | |
| CH₃ | CH₃ | H | O | CF₃ | |
| CH₃ | CH₃ | H | O | CO₂CH₃ | |
| CH₃ | CH₃ | H | O | CO₂CH₂CH=CH₂ | |
| CH₃ | CH₃ | H | O | SO₂N(CH₃)₂ | |
| CH₃ | CH₃ | H | O | SO₂CH₃ | |
| C₂H₅ | CH₃ | H | O | CO₂CH₃ | |
| (CH₂)₃CH₃ | CH₃ | H | O | CO₂CH₃ | |
| CH₂CH=CH₂ | CH₃ | H | O | CO₂CH₃ | |
| CH₂C≡CH | CH₃ | H | O | CO₂CH₃ | |
| SCH₃ | CH₃ | H | O | CO₂CH₃ | |
| SCH₂CH₃ | CH₃ | H | O | CO₂CH₃ | |
| SCH₂CH=CH₂ | CH₃ | H | O | CO₂CH₃ | |
| SCH₂CO₂CH₃ | CH₃ | H | O | CO₂CH₃ | |
| CH₂OCH₃ | CH₃ | H | O | CO₂CH₃ | |
| CH₂OCH₂CH₃ | CH₃ | H | O | CO₂CH₃ | |
| CH₂CH₂OCH₃ | CH₃ | H | O | CO₂CH₃ | |
| N(CH₃)₂ | CH₃ | H | O | CO₂CH₃ | |
| CF₃ | CH₃ | H | O | CO₂CH₃ | |
| CF₂CF₃ | CH₃ | H | O | CO₂CH₃ | |
| Cl | CH₃ | H | O | CO₂CH₃ | |
| NH(CH₃) | CH₃ | H | O | CO₂CH₃ | |
| CH(OCH₃)₂ | CH₃ | H | O | CO₂CH₃ | |

TABLE 11-continued

| R₁ | R₂ | R₃ | W | R₁₉ | m.p. (°C.) |
|---|---|---|---|---|---|
| O-CH-O (dioxolane, CH with two O attachments via CH₂CH₂) | CH₃ | H | O | CO₂CH₃ | |
| OCH₃ | CH₃ | CH₃ | O | CO₂CH₃ | |
| OCH₃ | CH₃ | H | S | CO₂CH₃ | |
| OCH₃ | CH₃ | H | S | SO₂N(CH₃)₂ | |
| OCH₃ | CH₃ | CH₃ | O | SO₂N(CH₃)₂ | |

TABLE 12

| R₁ | R₂ | R₃ | W | R₁₉ | m.p. (°C.) |
|---|---|---|---|---|---|
| OCH₃ | CH₃ | H | O | Cl | |
| OCH₃ | CH₃ | H | O | NO₂ | |
| OCH₃ | CH₃ | H | O | CF₃ | |
| OCH₃ | CH₃ | H | O | CO₂CH₃ | |
| OCH₃ | CH₃ | H | O | CO₂C₂H₅ | |
| OCH₃ | CH₃ | H | O | CO₂(CH₂)₂CH₃ | |
| OCH₃ | CH₃ | H | O | CO₂(CH₂)₃CH₃ | |
| OCH₃ | CH₃ | H | O | CO₂(CH₂)₄CH₃ | |
| OCH₃ | CH₃ | H | O | CO₂(CH₂)₅CH₃ | |
| OCH₃ | CH₃ | H | O | CO₂CH(CH₃)₂ | |
| OCH₃ | CH₃ | H | O | CO₂CH₂CH₂OCH₃ | |
| OCH₃ | CH₃ | H | O | CO₂CH₂CH₂OC₂H₅ | |
| OCH₃ | CH₃ | H | O | CO₂(CH₂)₃OC₂H₅ | |
| OCH₃ | CH₃ | H | O | CO₂CH₂CH=CH₂ | |
| OCH₃ | CH₃ | H | O | CO₂CH₂CH=CHCH₃ | |
| OCH₃ | CH₃ | H | O | CO₂(CH₂)₄CH=CH₂ | |
| OCH₃ | CH₃ | H | O | CO₂CH₂C≡CH | |
| OCH₃ | CH₃ | H | O | CO₂CH₂C≡CCH₃ | |
| OCH₃ | CH₃ | H | O | CO₂(CH₂)₄C≡CH | |
| OCH₃ | CH₃ | H | O | CO₂CH(CH₃)C₂H₅ | |
| OCH₃ | CH₃ | H | O | CO₂CH₂CH(CH₃)₂ | |
| OCH₃ | CH₃ | H | O | CO₂CF₃ | |
| OCH₃ | CH₃ | H | O | CO₂CH₂CH₂Cl | |
| OCH₃ | CH₃ | H | O | CO₂CH₂CF₃ | |
| OCH₃ | CH₃ | H | O | CO₂CH₂CCl₃ | |
| OCH₃ | CH₃ | H | O | CO₂CH₂CH₂CF₃ | |
| OCH₃ | CH₃ | H | O | CO₂CH₂CH₂CH₂Cl | |
| OCH₃ | CH₃ | H | O | CO₂CClF₂ | |
| OCH₃ | CH₃ | H | O | CO₂CF₂H | |
| OCH₃ | CH₃ | H | O | CO₂CHFCF₂H | |
| OCH₃ | CH₃ | H | O | CO₂CHClCF₂H | |
| OCH₃ | CH₃ | H | O | CO₂CH₂CHFCF₂H | |
| OCH₃ | CH₃ | H | O | SO₂N(OCH₃)CH₃ | |
| OCH₃ | CH₃ | H | O | SO₂N(CH₃)₂ | |
| OCH₃ | CH₃ | H | O | SO₂N(C₂H₅)₂ | |
| OCH₃ | CH₃ | H | O | SO₂N(CH₃)C₂H₅ | |
| OCH₃ | CH₃ | H | O | SO₂N(CH₃)CH₂CH₂CH₃ | |
| OCH₃ | CH₃ | H | O | OSO₂CH₃ | |
| OCH₃ | CH₃ | H | O | OSO₂C₂H₅ | |
| OCH₃ | CH₃ | H | O | OSO₂(CH₂)₂CH₃ | |
| OCH₃ | CH₃ | H | O | OSO₂(CH₂)₃CH₃ | |
| OCH₃ | CH₃ | H | O | OSO₂CH(CH₃)₂ | |
| OCH₃ | CH₃ | H | O | OSO₂CH(CH₃)C₂H₅ | |
| OCH₃ | CH₃ | H | O | OSO₂CH₂CH₂OCH₃ | |
| OCH₃ | CH₃ | H | O | OSO₂(CH₂)₃OCH₃ | |

TABLE 12-continued

| R₁ | R₂ | R₃ | W | R₁₉ | m.p. (°C.) |
|---|---|---|---|---|---|
| OCH₃ | CH₃ | H | O | OSO₂CF₃ | |
| OCH₃ | CH₃ | H | O | OSO₂CH₂CF₃ | |
| OCH₃ | CH₃ | H | O | OSO₂CHFCF₂H | |
| OCH₃ | CH₃ | H | O | OSO₂CF₂CH₂CH₂CH₃ | |
| OCH₃ | CH₃ | H | O | OSO₂CClF₂ | |
| OCH₃ | CH₃ | H | O | OSO₂CBr₂CH₃ | |
| OCH₃ | CH₃ | H | O | N(CH₃)SO₂CH₃ | |
| OCH₃ | CH₃ | H | O | N(CH₃)SO₂C₂H₅ | |
| OCH₃ | CH₃ | H | O | N(CH₃)SO₂C₃H₅ | |
| OCH₃ | CH₃ | H | O | N(CH₃)SO₂CH(CH₃)C₂H₅ | |
| OCH₃ | CH₃ | H | O | N(CH₃)SO₂CH₂CH₂OCH₃ | |
| OCH₃ | CH₃ | H | O | N(CH₃)SO₂CF₃ | |
| OCH₃ | CH₃ | H | O | SCH₃ | |
| OCH₃ | CH₃ | H | O | SOCH₃ | |
| OCH₃ | CH₃ | H | O | SO₂CH₃ | |
| OCH₃ | CH₃ | H | O | SO₂C₂H₅ | |
| OCH₃ | CH₃ | H | O | SO₂CH₂CH₂CH₃ | |
| OCH₃ | CH₃ | H | O | SO₂CH(CH₃)₂ | |
| OCH₃ | CH₃ | H | O | SO₂CH₂CH=CH₂ | |
| OCH₃ | CH₃ | H | O | SO₂CH(CH₃)C₂H₅ | |
| OCH₃ | CH₃ | H | O | SCH₂CH₂CH₃ | |
| OCH₃ | CH₃ | H | O | SCF₃ | |
| OCH₃ | CH₃ | H | O | SOCF₃ | |
| OCH₃ | CH₃ | H | O | SO₂CF₃ | |
| OCH₃ | CH₃ | H | O | OCCl₃ | |
| OCH₃ | CH₃ | H | O | OCF₃ | |
| OCH₃ | CH₃ | H | O | OCF₂CF₃ | |
| OCH₃ | CH₃ | H | O | OCF₂CF₂CH₃ | |
| OCH₃ | CH₃ | H | O | OCClF₂ | |
| OCH₃ | CH₃ | H | O | OCCl₂CF₃ | |
| OC₂H₅ | CH₃ | H | O | Cl | |
| OC₂H₅ | CH₃ | H | O | NO₂ | |
| OC₂H₅ | CH₃ | H | O | CF₃ | |
| OC₂H₅ | CH₃ | H | O | CO₂CH₃ | |
| OC₂H₅ | CH₃ | H | O | CO₂C₂H₅ | |
| OC₂H₅ | CH₃ | H | O | CO₂CH₂CH₂CH₃ | |
| OC₂H₅ | CH₃ | H | O | CO₂CH(CH₃)₂ | |
| OC₂H₅ | CH₃ | H | O | CO₂CH₂CH=CH₂ | |
| OC₂H₅ | CH₃ | H | O | CO₂CH₂C≡CH | |
| OC₂H₅ | CH₃ | H | O | CO₂CH₂CH₂OCH₃ | |
| OC₂H₅ | CH₃ | H | O | CO₂CH₂CH₂OC₂H₅ | |
| OC₂H₅ | CH₃ | H | O | CO₂CF₃ | |
| OC₂H₅ | CH₃ | H | O | SO₂N(OCH₃)CH₃ | |
| OC₂H₅ | CH₃ | H | O | SO₂N(CH₃)₂ | |
| OC₂H₅ | CH₃ | H | O | SO₂N(CH₃)C₂H₅ | |
| OC₂H₅ | CH₃ | H | O | SO₂N(C₂H₅)₂ | |
| OC₂H₅ | CH₃ | H | O | OSO₂CH₃ | |
| OC₂H₅ | CH₃ | H | O | OSO₂C₂H₅ | |
| OC₂H₅ | CH₃ | H | O | N(CH₃)SO₂CH₃ | |
| OC₂H₅ | CH₃ | H | O | SO₂CH₃ | |
| OC₂H₅ | CH₃ | H | O | SO₂C₂H₅ | |
| OC₂H₅ | CH₃ | H | O | SO₂CH₂CH₂CH₃ | |
| OC₂H₅ | CH₃ | H | O | SO₂CHCH=CH₂ | |
| OC₂H₅ | CH₃ | H | O | SO₂CF₃ | |
| OC₂H₅ | CH₃ | H | O | OCF₃ | |
| OC₂H₅ | CH₃ | H | O | OCF₂CF₃ | |
| OC₂H₅ | C₂H₅ | H | O | Cl | |
| OC₂H₅ | C₂H₅ | H | O | NO₂ | |
| OC₂H₅ | C₂H₅ | H | O | CF₃ | |
| OC₂H₅ | C₂H₅ | H | O | CO₂CH₃ | |
| OC₂H₅ | C₂H₅ | H | O | CO₂C₂H₅ | |
| OC₂H₅ | C₂H₅ | H | O | CO₂CH₂CH₂CH₃ | |
| OC₂H₅ | C₂H₅ | H | O | CO₂CH(CH₃)₂ | |
| OC₂H₅ | C₂H₅ | H | O | CO₂CHCH=CH₂ | |
| OC₂H₅ | C₂H₅ | H | O | CO₂CH₂C≡CH | |
| OC₂H₅ | C₂H₅ | H | O | CO₂CH₂CH₂OCH₃ | |
| OC₂H₅ | C₂H₅ | H | O | SO₂N(OCH₃)CH₃ | |
| OC₂H₅ | C₂H₅ | H | O | SO₂N(CH₃)₂ | |
| OC₂H₅ | C₂H₅ | H | O | OSO₂CH₃ | |
| OC₂H₅ | C₂H₅ | H | O | N(CH₃)SO₂CH₃ | |
| OC₂H₅ | C₂H₅ | H | O | SO₂CH₃ | |

TABLE 12-continued

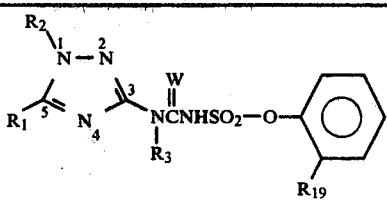

| R₁ | R₂ | R₃ | W | R₁₉ | m.p. (°C.) |
|---|---|---|---|---|---|
| OC₂H₅ | C₂H₅ | H | O | SO₂CH₂CH₃ | |
| OC₂H₅ | C₂H₅ | H | O | SO₂CH₂CH₂CH₃ | |
| OC₂H₅ | C₂H₅ | H | O | OCF₃ | |
| OCH₂CH₂CH₃ | CH₃ | H | O | Cl | |
| OCH₂CH₂CH₃ | CH₃ | H | O | NO₂ | |
| OCH₂CH₂CH₃ | CH₃ | H | O | CF₃ | |
| OCH₂CH₂CH₃ | CH₃ | H | O | CO₂CH₃ | |
| OCH₂CH₂CH₃ | CH₃ | H | O | CO₂CH₂CH=CH₂ | |
| OCH₂CH₂CH₃ | CH₃ | H | O | SO₂N(OCH₃)CH₃ | |
| OCH₂CH₂CH₃ | CH₃ | H | O | SO₂N(CH₃)₂ | |
| OCH₂CH₂CH₃ | CH₃ | H | O | OSO₂CH₃ | |
| OCH₂CH₂CH₃ | CH₃ | H | O | N(CH₃)SO₂CH₃ | |
| OCH₂CH₂CH₃ | CH₃ | H | O | SO₂CH₃ | |
| OCH₂CH₂CH₃ | CH₃ | H | O | SO₂CH₂CH₂CH₃ | |
| OCH₂CH₂CH₃ | CH₃ | H | O | OCF₃ | |
| O(CH₂)₃CH₃ | CH₃ | H | O | Cl | |
| O(CH₂)₃CH₃ | CH₃ | H | O | NO₂ | |
| O(CH₂)₃CH₃ | CH₃ | H | O | CF₃ | |
| O(CH₂)₃CH₃ | CH₃ | H | O | CO₂CH₃ | |
| O(CH₂)₃CH₃ | CH₃ | H | O | CO₂C₂H₅ | |
| O(CH₂)₃CH₃ | CH₃ | H | O | CO₂CH(CH₃)₂ | |
| O(CH₂)₃CH₃ | CH₃ | H | O | SO₂N(CH₃)₂ | |
| O(CH₂)₃CH₃ | CH₃ | H | O | SO₂CH₃ | |
| O(CH₂)₃CH₃ | CH₃ | H | O | SO₂CH₂CH₂CH₃ | |
| O(CH₂)₃CH₃ | CH₃ | H | O | OCF₃ | |
| OCH₃ | C₂H₅ | H | O | Cl | |
| OCH₃ | C₂H₅ | H | O | NO₂ | |
| OCH₃ | C₂H₅ | H | O | CF₃ | |
| OCH₃ | C₂H₅ | H | O | CO₂CH₃ | |
| OCH₃ | C₂H₅ | H | O | CO₂C₂H₅ | |
| OCH₃ | C₂H₅ | H | O | CO₂CH(CH₃)₂ | |
| OCH₃ | C₂H₅ | H | O | CO₂CH₂CH=CH₂ | |
| OCH₃ | C₂H₅ | H | O | CO₂CH₂CH₂OCH₃ | |
| OCH₃ | C₂H₅ | H | O | CO₂CH₂CH₂Cl | |
| OCH₃ | C₂H₅ | H | O | SO₂N(OCH₃)CH₃ | |
| OCH₃ | C₂H₅ | H | O | SO₂N(CH₃)₂ | |
| OCH₃ | C₂H₅ | H | O | OSO₂CH₃ | |
| OCH₃ | C₂H₅ | H | O | N(CH₃)SO₂CH₃ | |
| OCH₃ | C₂H₅ | H | O | SO₂CH₃ | |
| OCH₃ | C₂H₅ | H | O | SO₂CH₂CH₂CH₃ | |
| OCH₃ | C₂H₅ | H | O | OCF₃ | |
| OCH₃ | CH₂CH=CH₂ | H | O | Cl | |
| OCH₃ | CH₂CH=CH₂ | H | O | NO₂ | |
| OCH₃ | CH₂CH=CH₂ | H | O | CF₃ | |
| OCH₃ | CH₂CH=CH₂ | H | O | CO₂CH₃ | |
| OCH₃ | CH₂CH=CH₂ | H | O | CO₂C₂H₅ | |
| OCH₃ | CH₂CH=CH₂ | H | O | CO₂CH(CH₃)₂ | |
| OCH₃ | CH₂CH=CH₂ | H | O | CO₂CH₂CH=CH₂ | |
| OCH₃ | CH₂CH=CH₂ | H | O | CO₂CH₂CH₂OCH₃ | |
| OCH₃ | CH₂CH=CH₂ | H | O | SO₂N(Me)₂ | |
| OCH₃ | CH₂CH=CH₂ | H | O | OSO₂CH₃ | |
| OCH₃ | CH₂CH=CH₂ | H | O | SO₂CH₃ | |
| OCH₃ | CH₂CH=CH₂ | H | O | SO₂CH₂CH₂CH₃ | |
| OCH₃ | CH₂CH=CH₂ | H | O | OCF₃ | |
| OCH₃ | CH₂OCH₃ | H | O | Cl | |
| OCH₃ | CH₂OCH₃ | H | O | NO₂ | |
| OCH₃ | CH₂OCH₃ | H | O | CO₂CH₃ | |
| OCH₃ | CH₂OCH₃ | H | O | CO₂CH₂CH₂CH₃ | |
| OCH₃ | CH₂OCH₃ | H | O | CO₂CH₂CH=CH₂ | |
| OCH₃ | CH₂OCH₃ | H | O | SO₂N(Me)₂ | |
| OCH₃ | CH₂OCH₃ | H | O | SO₂CH₃ | |
| OCH₃ | CH₂OCH₃ | H | O | SO₂CH₂CH₂CH₃ | |
| OCH₃ | CH₂OCH₃ | H | O | OSO₂CH₃ | |
| OCH₃ | CH₂OCH₃ | H | O | OCF₃ | |
| OCH₃ | CH₂SCH₃ | H | O | Cl | |
| OCH₃ | CH₂SCH₃ | H | O | NO₂ | |
| OCH₃ | CH₂SCH₃ | H | O | CO₂CH₃ | |
| OCH₃ | CH₂SCH₃ | H | O | CO₂CH₂CH₃ | |
| OCH₃ | CH₂SCH₃ | H | O | CO₂CH(CH₃)₂ | |
| OCH₃ | CH₂SCH₃ | H | O | CO₂CH₂CH=CH₂ | |
| OCH₃ | CH₂SCH₃ | H | O | SO₂N(CH₃)₂ | |

TABLE 12-continued

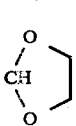

| $R_1$ | $R_2$ | $R_3$ | W | $R_{19}$ | m.p. (°C.) |
|---|---|---|---|---|---|
| OCH$_3$ | CH$_2$SCH$_3$ | H | O | OSO$_2$CH$_3$ | |
| OCH$_3$ | CH$_2$SCH$_3$ | H | O | SO$_2$CH$_3$ | |
| OCH$_3$ | CH$_2$SCH$_3$ | H | O | SO$_2$CH$_2$CH$_2$CH$_3$ | |
| OCH$_3$ | CH$_2$SCH$_3$ | H | O | OCF$_3$ | |
| OCH$_3$ | CH$_2$CF$_3$ | H | O | Cl | |
| OCH$_3$ | CH$_2$CF$_3$ | H | O | NO$_2$ | |
| OCH$_3$ | CH$_2$CF$_3$ | H | O | CF$_3$ | |
| OCH$_3$ | CH$_2$CF$_3$ | H | O | CO$_2$CH$_3$ | |
| OCH$_3$ | CH$_2$CF$_3$ | H | O | CO$_2$CH$_2$CH=CH$_2$ | |
| OCH$_3$ | CH$_2$CF$_3$ | H | O | OSO$_2$CH$_3$ | |
| OCH$_3$ | CH$_2$CF$_3$ | H | O | SO$_2$CH$_3$ | |
| OCH$_3$ | CH$_2$CF$_3$ | H | O | SO$_2$CH$_2$CH$_2$CH$_3$ | |
| OCH$_3$ | CH$_2$CF$_3$ | H | O | SO$_2$N(CH$_3$)$_2$ | |
| OCH$_3$ | CH$_2$C≡CH | H | O | CO$_2$CH$_3$ | |
| OCH$_3$ | CH$_2$CH$_2$OCH$_3$ | H | O | CO$_2$CH$_3$ | |
| OCH$_3$ | CH$_2$CH$_2$SCH$_3$ | H | O | CO$_2$CH$_3$ | |
| OCH$_3$ | CH$_2$CH$_2$CH$_3$ | H | O | CO$_2$CH$_3$ | |
| CH$_3$ | CH$_3$ | H | O | Cl | |
| CH$_3$ | CH$_3$ | H | O | NO$_2$ | |
| CH$_3$ | CH$_3$ | H | O | CF$_3$ | |
| CH$_3$ | CH$_3$ | H | O | CO$_2$CH$_3$ | |
| CH$_3$ | CH$_3$ | H | O | CO$_2$CH$_2$CH=CH$_2$ | |
| CH$_3$ | CH$_3$ | H | O | SO$_2$N(CH$_3$)$_2$ | |
| CH$_3$ | CH$_3$ | H | O | SO$_2$CH$_3$ | |
| C$_2$H$_5$ | CH$_3$ | H | O | CO$_2$CH$_3$ | |
| (CH$_2$)$_3$CH$_3$ | CH$_3$ | H | O | CO$_2$CH$_3$ | |
| CH$_2$CH=CH$_2$ | CH$_3$ | H | O | CO$_2$CH$_3$ | |
| CH$_2$C≡CH | CH$_3$ | H | O | CO$_2$CH$_3$ | |
| SCH$_3$ | CH$_3$ | H | O | CO$_2$CH$_3$ | |
| SCH$_2$CH$_3$ | CH$_3$ | H | O | CO$_2$CH$_3$ | |
| SCH$_2$CH=CH$_2$ | CH$_3$ | H | O | CO$_2$CH$_3$ | |
| SCH$_2$CO$_2$CH$_3$ | CH$_3$ | H | O | CO$_2$CH$_3$ | |
| CH$_2$OCH$_3$ | CH$_3$ | H | O | CO$_2$CH$_3$ | |
| CH$_2$OCH$_2$CH$_3$ | CH$_3$ | H | O | CO$_2$CH$_3$ | |
| CH$_2$CH$_2$OCH$_3$ | CH$_3$ | H | O | CO$_2$CH$_3$ | |
| N(CH$_3$)$_2$ | CH$_3$ | H | O | CO$_2$CH$_3$ | |
| CF$_3$ | CH$_3$ | H | O | CO$_2$CH$_3$ | |
| CF$_2$CF$_3$ | CH$_3$ | H | O | CO$_2$CH$_3$ | |
| Cl | CH$_3$ | H | O | CO$_2$CH$_3$ | |
| NH(CH$_3$) | CH$_3$ | H | O | CO$_2$CH$_3$ | |
| CH(OCH$_3$)$_2$ | CH$_3$ | H | O | CO$_2$CH$_3$ | |
| (dioxolane-CH) | CH$_3$ | H | O | CO$_2$CH$_3$ | |
| OCH$_3$ | CH$_3$ | CH$_3$ | O | CO$_2$CH$_3$ | |
| OCH$_3$ | CH$_3$ | H | S | CO$_2$CH$_3$ | |
| OCH$_3$ | CH$_3$ | H | S | SO$_2$N(CH$_3$)$_2$ | |
| OCH$_3$ | CH$_3$ | CH$_3$ | O | SO$_2$N(CH$_3$)$_2$ | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE 13

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |

TABLE 13-continued

|  | Active Ingredient | Weight Percent* Diluent(s) | Surfactant(s) |
|---|---|---|---|
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp, 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE X

Wettable Powder

2-[[(1-methyl-5-methylthio-1H-1,2,4-triazol-3-yl)aminocarbonyl]aminosulfonyl]benzoic acid, methyl ester—80%
sodium alkylnaphthalenesulfonate—2%
sodium ligninsulfonate—2%
synthetic amorphous silica—3%
kaolinite—13%

The ingredients are blended, hammer-milled until all the solids are essentially under 50 microns, reblended, and packaged.

EXAMPLE XI

Wettable Powder

2-[[(5-ethylthio-1-methyl-1H-1,2,4-triazol-3-yl)aminocarbonyl]aminosulfonyl]benzoic acid, methyl ester—50%
sodium alkylnaphthalenesulfonate—2%
low viscosity methyl cellulose—2%
diatomaceous earth—46%

The ingredients are blended, coarsely hammer-milled and then air-milled to produce particles essentially all below 10 microns in diameter. The product is reblended before packaging.

EXAMPLE XII

Granule

Wettable Powder of Example XI—5%
attapulgite granules (U.S.S. 20–40 mesh; 0.84–0.42 mm)—95%

A slurry of wettable powder containing ≈25% solids is sprayed on the surface of attapulgite granules in a double-cone blender. The granules are dried and packaged.

EXAMPLE XIII

Extruded Pellet

2-[[(5-ethyl-1-methyl-1H-1,2,4-triazol-3-yl)aminocarbonyl]aminosulfonyl]benzoic acid, methyl ester—25%
anhydrous sodium sulfate—10%
crude calcium ligninsulfonate—5%
sodium alkylnaphthalenesulfonate—1%
calcium/magnesium bentonite—59%

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE XIV

Oil Suspension

2-[[(5-methoxy-1-methyl-1H-1,2,4-triazol-3-yl)aminocarbonyl]aminosulfonyl]benzoic acid, methyl ester—25%
polyoxyethylene sorbitol hexaoleate—5%
highly aliphatic hydrocarbon oil—70%

The ingredients are ground together in a sand mill until the solid particles have been reduced to under about 5 microns. The resulting thick suspension may be applied directly, but preferably after being extended with oils or emulsified in water.

EXAMPLE XV

Wettable Powder

N-[(5-methoxy-1-methyl-1H-1,2,4-triazol-3-yl)aminocarbonyl]-2-chlorobenzenesulfonamide—20%
sodium alkylnaphthalenesulfonate—4%
sodium ligninsulfonate—4%
low viscosity methyl cellulose—3%
attapulgite—69%

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE XVI

Low Strength Granule

N-[(5-methoxy-1-methyl-1H-1,2,4-triazol-3-yl)aminocarbonyl]-N',N'-dimethyl-1,2-benzenedisulfonamide —1%
N,N-dimethylformamide—9%
attapulgite granules (U.S.S. 20–40 sieve)—90%

The active ingredient is dissolved in the solvent and the solution is sprayed upon dedusted granules in a double cone blender. After spraying of the solution has been completed, the blender is allowed to run for a short period and then the granules are packaged.

EXAMPLE XVII

Aqueous Suspension

2-[[(5-methylthio-1-methyl-1H-1,2,4-triazol)-3-yl)aminocarbonyl]aminosulfonyl]benzoic acid, methyl ester—40%
polyacrylic acid thickener—0.3%
dodecylphenol polyethylene glcyol ether—0.5%
disodium phosphate—1%
monosodium phosphate—0.5%
polyvinyl alcohol—1.0%
water—56.7%

The ingredients are blended and ground together in a sand mill to produce particles essentially all under 5 microns in size.

EXAMPLE XVIII

Solution

2-[[(5-ethyl-1-methyl-1H-1,2,4-triazol-3-yl)aminocarbonyl]aminosulfonyl]benzoic acid, methyl ester, sodium salt—5%
water—95%

The salt is added directly to the water with stirring to produce the solution, which may then be packaged for use.

EXAMPLE XIX

Low Strength Granule

2-[[(5-ethylthio-1-methyl-1H-1,2,4-triazol-3-yl)aminocarbonyl]aminosulfonyl]benzoic acid, methyl ester—0.1%
attapulgite granules (U.S.S. 20–40 mesh)—99.9%

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE XX

Granule

2-[[(5-methoxy-1-methyl-1H-1,2,4-triazol-3-yl)aminocarbonyl]aminosulfonyl]benzoic acid, methyl ester—80%
wetting agent—1%
crude ligninsulfonate salt (containing 5-20% of the natural sugars)—10%
attapulgite clay—9%

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE XXI

High Strength Concentrate

N-[(5-methoxy-1-methyl-1H-1,2,4-triazol-3-yl)aminocarbonyl]-2-chlorobenzenesulfonamide—99%
silica aerogel—0.5%
synthetic amorphous silica—0.5%

The ingredients are blended and ground in a hammer-mill to produce a material essentially all passing a U.S.S. No. 50 screen (0.3 mm opening). The concentrate may be formulated further if necessary.

EXAMPLE XXII

Wettable Powder

N-[(5-methoxy-1-methyl-1H-1,2,4-triazol-3-yl)aminocarbonyl]-N',N'-dimethyl-1,2-benzenedisulfonamide—90%
dioctyl sodium sulfosuccinate—0.1%
synthetic fine silica—9.9%

The ingredients are blended and ground in a hammer-mill to produce particles essentially all below 100 microns. The material is sifted through a U.S.S. No. 50 screen and then packaged.

EXAMPLE XXIII

Wettable Powder

2-[[(5-methylthio-1-methyl-1H-1,2,4-triazol-3-yl)aminocarbonyl]aminosulfonyl]benzoic acid, methyl ester—40%
sodium ligninsulfonate—20%
montmorillonite clay—40%

The ingredients are thoroughly blended, coarsely hammer-milled and then air-milled to produce particles essentially all below 10 microns in size. The material is reblended and then packaged.

EXAMPLE XXIV

Oil Suspension

2-[[(5-ethylthio-1-methyl-1H-1,2,4-triazol-3-yl)aminocarbonyl]aminosulfonyl]benzoic acid, methyl ester—35% blend of polyalcohol carboxylic esters and oil soluble petroleum sulfonates—6%
xylene—59%

The ingredients are combined and ground together in a sand mill to produce particles essentially all below 5 microns. The product can be used directly, extended with oils, or emulsified in water.

EXAMPLE XXV

Dust

2-[[(5-ethyl-1-methyl-1H-1,2,4-triazol-3-yl)aminocarbonyl]aminosulfonyl]benzoic acid, methyl ester—10%
attapulgite—10%
Pyrophyllite—80%

The active ingredient is blended with attapulgite and then passed through a hammer-mill to produce particles substantially all below 200 microns. The ground concentrate is then blended with powdered pyrophyllite until homogeneous.

Utility

The compounds of the present invention have herbicidal activity. They have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. In addition, some of the compounds are useful for the selective control of weeds in certain crops, including wheat and soybeans.

The rates of application for the compounds of the invention are determined by a number of factors, including their use as selective or general herbicides, the crop species involved, the types of weeds to be controlled, weather conditions, formulations selected, mode of application, amount of foliage present, etc. In general terms, the subject compounds should be applied at levels of around 0.125 to 10 kg/ha, the lower rates being suggested for use on lighter soils and/or those having a low organic matter content, or for situations where only short-term persistence is required.

The compounds of the invention may be used in combination with any other commercial herbicide, examples of which are those of the triazine, triazole, uracil, urea, amide, diphenylether, carbamate and bipyridylium types.

The herbicidal properties of the subject compounds were discovered in a number of greenhouse tests. The test procedures and results follow.

Test A

Seeds of crabgrass (Digitaria sp.), barnyardgrass (Echinochloa crusgalli), wild oats (Avena fatua), cassia (Cassia tora), morningglory (Impomoea sp.), cocklebur (Xanthium sp.), sorghum, corn, soybean, rice, wheat and nutsedge tubers (Cyperus rotundus) were planted in a growth medium and treated pre-emergence with the chemicals dissolved in a non-phytotoxic solvent. At the same time, cotton having five leaves (including cotyledonary ones), bush beans with the third trifoliate leaf expanding, crabgrass, barnyardgrass and wild oats with two leaves, cassia with three leaves (including cotyledonary ones), morningglory and cocklebur with four leaves (including the cotyledonary ones), sorghum and corn with four leaves, soybean with two cotyledonary leaves, rice with three leaves, wheat with one leaf, and nutsedge with three to five leaves were sprayed. Treated plants and controls were maintained in a greenhouse for sixteen days, whereupon all species were compared to controls and visually rated for response to treatment.

The ratings are based on a numerical scale extending from 0=no injury, to 10=complete kill. The accompanying descriptive symbols have the following meanings:
A=growth acceleration;
C=chlorosis or necrosis;
E=emergence inhibition;
G=growth retardation;
H=formative effects;
P=terminal bud injury;
U=unusual pigmentation;
X=axillary stimulation; and
6Y=abscised buds or flowers.

The ratings for the compounds tested by this procedure are presented in Table A. The compounds tested demonstrate good control of nutsedge, especially in pre-emergence application. The results show one compound to be relatively tolerant to soybeans, and a few to be tolerant to wheat.

Table A Structures

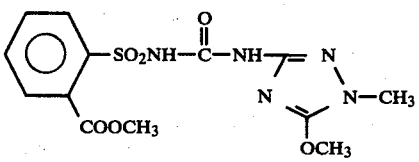

Compound 1

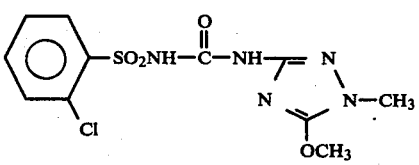

Compound 2

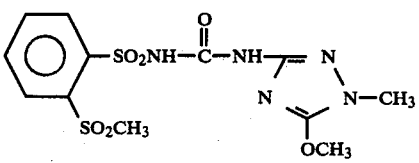

Compound 3

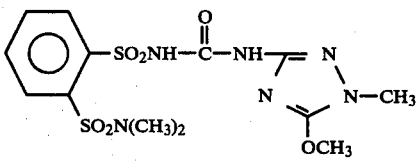

Compound 4

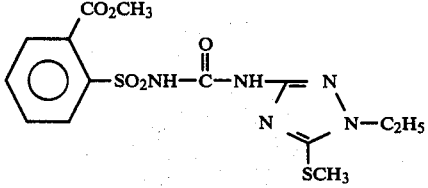

Compound 5

-continued
Table A Structures
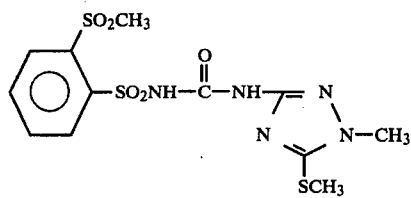 Compound 6
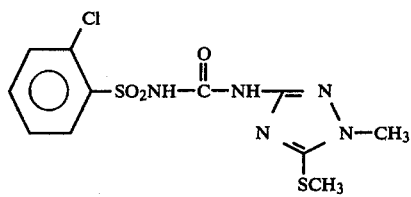 Compound 7
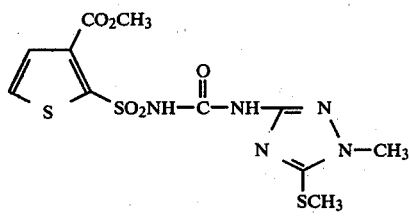 Compound 8
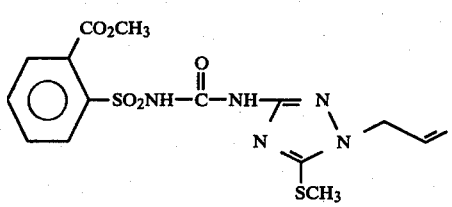 Compound 9
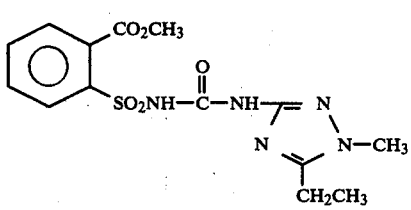 Compound 10
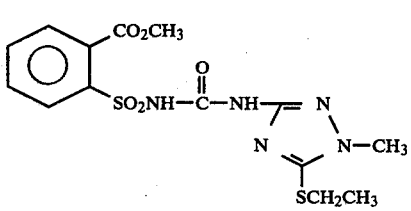 Compound 11
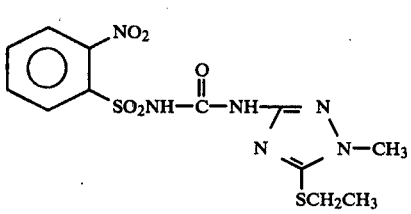 Compound 12
-continued
Table A Structures
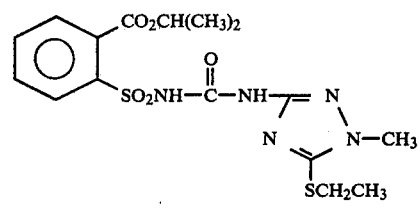 Compound 13
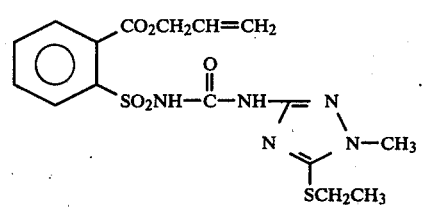 Compound 14
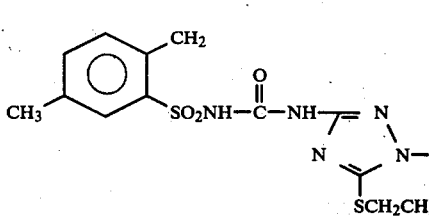 Compound 15
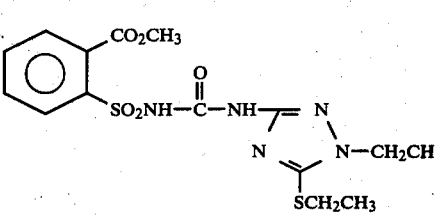 Compound 16
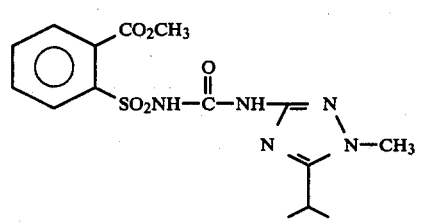 Compound 17
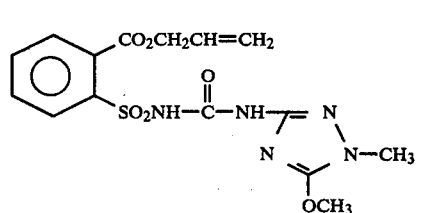 Compound 18
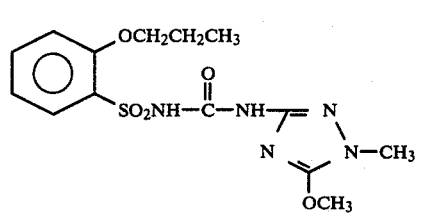 Compound 19

-continued
Table A Structures
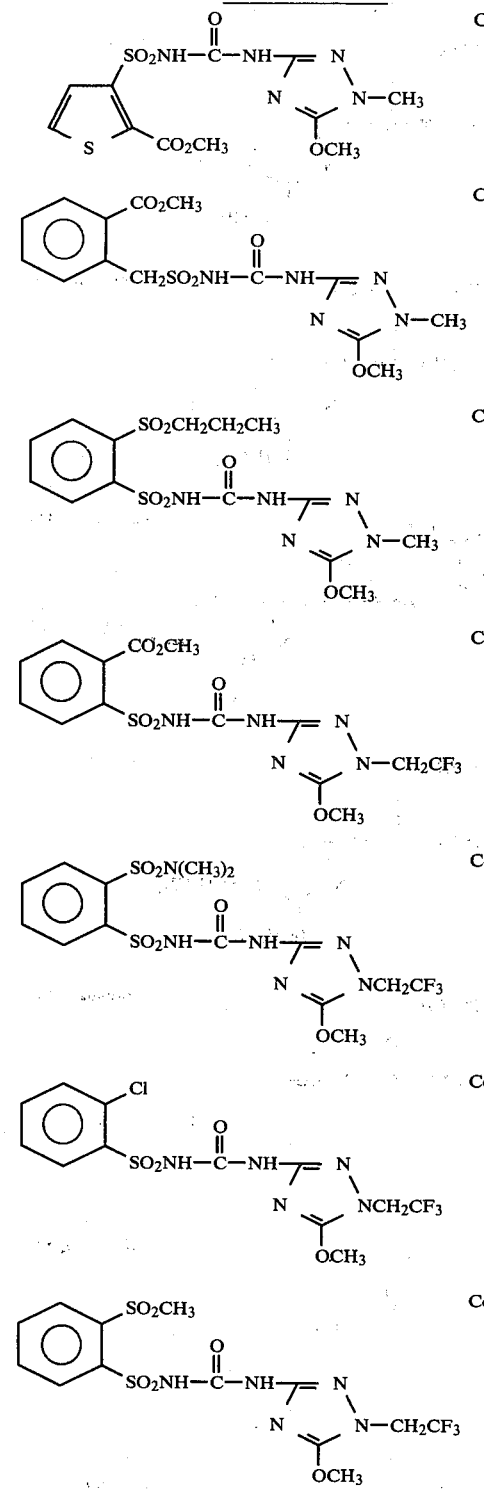
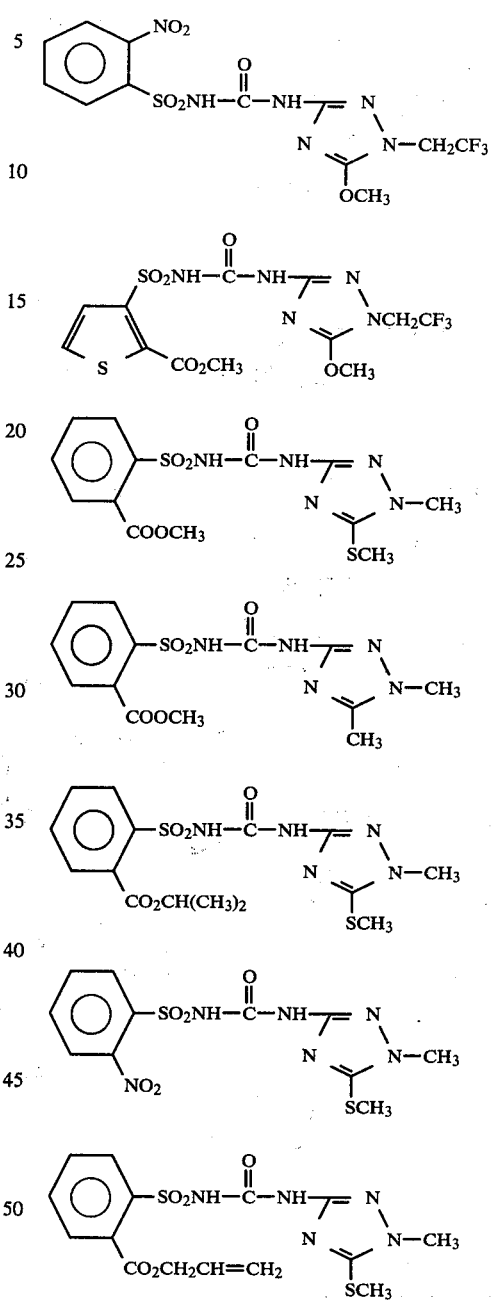
TABLE A
| | Compound 1 | | Compound 2 | | Compound 3 | | Compound 4 | | Cmpd. 5 |
|---|---|---|---|---|---|---|---|---|---|
| Rate kg/ha | 0.4 | .05 | 0.4 | .05 | 0.4 | .05 | 0.4 | .05 | 0.1 |
| POST-EMERGENCE | | | | | | | | | |
| Bush bean | 9C | 5C,9G,6Y | 5C,9G,6Y | 5C,9G,6Y | 5C,9G,6Y | 4C,9G,6Y | 9C | 5C,9G,6Y | 9C |
| Cotton | 5C,9G | 2C,9G | 4C,9G | 4C,8G | 5C,5H | 3C,3G | 6C,9G | 4C,8G | 5C,9G |
| Morningglory | 5C,9G | 9C | 5C,9G | 4C,8H | 4C,9G | 4C,8H | 9C | 5C,9G | 2C,8G |
| Cocklebur | 10C | 9C | 9C | 3G | 2C,8G | 1C,4G | 9C | 9C | 8G |

TABLE A-continued

| | | | | | | | | | |
|---|---|---|---|---|---|---|---|---|---|
| Cassia | 9C | 9C | 5C,9G | 3C,8G | 4C,8H | 2C,5G | 5C,9G | 4C,8H | 3C,5G |
| Nutsedge | 9C | 10C | 4C,9G | 2C,8G | 2C,9G | 2C,5G | 9C | 2C,9G | 9C,9G |
| Crabgrass | 9C | 9C | 5C,9G | 2C,8G | 3C,9G | 2C,3G | 9C | 9C | 3C,8G |
| Barnyardgrass | 9C | 9C | 9C | 9C | 9C | 5C,8H | 9C | 9C | 5C,9H |
| Wild Oats | 9C | 9C | 2C,9G | 2C,8G | 4C,9G | 2C,3G | 9C | 9C | 1C,9G |
| Wheat | 9C | 9C | 2C,9G | 5G | 5C,9G | 2C,8G | 9C | 9C | 9G |
| Corn | 10C | 9C | 5U,9C | 9C | 5U,9C | 2C,9H | 10C | 9C | 3U,9H |
| Soybean | 9C | 9C | 5C,9G | 4C,9G | 5C,9G | 3C,8G | 9C | 9C | 6C,9G |
| Rice | 9C | 9C | 5C,9G | 5C,9G | 6C,9G | 5C,9G | 9C | 9C | 6C,9G |
| Sorghum | 9C | 9C | 4C,9G | 4C,9G | 3C,9G | 4C,8H | 9C | 5C,9G | 7U,9G |
| Sugar beet | 9C | 9C | 9C | 5C,9G | 5C,9G | 2C,5G | 9C | 5C,9G | — |
| PRE-EMERGENCE | | | | | | | | | |
| Morningglory | 9C | 9G | 9G | 2C,8H | 4C,8H | 1C | 9C | 2C,9G | 9G |
| Cocklebur | 9H | 9H | 9H | 8H | 4G | 0 | 9H | 9H | 9H |
| Cassia | 9C | 3C,9G | 2C,9G | 2C,7G | 1C | 1C | 2C,8G | 3C,8G | 2C,8G |
| Nutsedge | 10E | 10E | 5C,9G | 2C,7G | 2C,6G | 0 | 10E | 5C,9G | 10E |
| Crabgrass | 6C,9G | 5C,9G | 3C,7G | 2C,3G | 2G | 0 | 6C,9G | 1C,3G | 2C,4G |
| Barnyardgrass | 10E | 6C,9H | 5C,9H | 3C,8H | 3C,6G | 1C | 10H | 5C,9H | 3C,9G |
| Wild Oats | 6C,9H | 6C,9H | 4C,9G | 2C,7G | 3C,6G | 1C | 6C,9H | 6C,9H | 2C,9G |
| Wheat | 6C,9H | 6C,9H | 9H | 2C,8G | 2C,9G | 2G | 7C,9H | 10H | 2C,9G |
| Corn | 10E | 10H | 10H | 3C,9H | 3C,9H | 2C,3G | 10H | 5C,9H | 1C,9G |
| Soybean | 9H | 3C,8H | 9H | 3C,4H | 2C,3G | 1C | 9H | 4C,6H | 3C,8G |
| Rice | 10E | 10E | 10E | 10E | 5C,8H | 3C | 10E | 10E | 10E |
| Sorghum | 6C,9H | 5C,9H | 6C,9H | 5C,9H | 4C,9H | 3G | 6C,9H | 6C,9H | 3C,9H |
| Sugar beet | 10E | 10E | 6C,9G | 5C,9G | 1C | 0 | 6C,9G | 5C,9G | — |

| | Cmpd. 6 | Cmpd. 7 | Cmpd. 8 | Cmpd. 9 | Cmpd. 10 | Cmpd. 11 | Cmpd. 12 | Cmpd. 13 | Cmpd. 14 |
|---|---|---|---|---|---|---|---|---|---|
| Rate kg/ha | 0.1 | 0.1 | 0.1 | 0.1 | 0.1 | .05 | .05 | .05 | .05 |
| POST-EMERGENCE | | | | | | | | | |
| Bush bean | 2H | 2C,9G,6Y | 4C,9G,6Y | 9C | 9C | 6C,9G,6Y | 0 | 4C,9G,6Y | 3C,8G,6Y |
| Cotton | 0 | 1C | 1C,1H | 5C,8H | 5C,9G | 4C,8G | 0 | 2C,6G | 2C |
| Morningglory | 0 | 1C,4H | 4H | 5C,9H | 3C,9G | 2C | 0 | 2C,5G | 1C |
| Cocklebur | 0 | 2G | 3C,9G | 2C,8G | 8H | 1C | 0 | 2C,8H | 5G |
| Cassia | 0 | 2C | 0 | 5C,8G | 5C,8H | 1C | 0 | 1C | 3G |
| Nutsedge | 0 | 1C,4G | 0 | 2C,7G | 7C,9G | 3C,6G | 0 | 0 | 0 |
| Crabgrass | 0 | 1C,3G | 2C | 9C | 9C | 2C | 0 | 0 | 0 |
| Barnyardgrass | 2H | 5C,9H | 2C,8H | 9C | 10C | 3C,7H | 0 | 0 | 0 |
| Wild Oats | 0 | 0 | 0 | 1C,9G | 9C | 1C | 0 | 0 | 0 |
| Wheat | 0 | 0 | 0 | 9C | 9C | 0 | 0 | 0 | 0 |
| Corn | 4G | 1C,5G | 2C,8H | 9C | 10C | 2C,4H | 0 | 0 | 0 |
| Soybean | 2H | 2C,9G,5X | 1C,3G | 5C,9G | 6C,9G | 4C,9G | 4H | 2C,6H | 2C,6G |
| Rice | 5G | 2C,9G | 6G | 5C,9G | 10C | 4C,9G | 0 | 6G | 2G |
| Sorghum | 5G | 2C,8H | 2C,8H | 5C,9G | 10C | 2C,9G | 0 | 2C | 0 |
| Sugar beet | — | — | — | — | — | — | — | — | — |
| PRE-EMERGENCE | | | | | | | | | |
| Morningglory | 0 | 2C | 0 | 9G | 8H | 3C | 0 | 3C,5G | 1C |
| Cocklebur | 0 | 1C | 4G | 9H | 9H | 9H | — | 7G | — |
| Cassia | 0 | 2C | 3H | 8G | 3C,7G | 2C | 2C | 0 | 0 |
| Nutsedge | 0 | 3G | 0 | 9G | 10E | 1C,4G | 0 | 8G | 0 |
| Crabgrass | 0 | 1C | 0 | 2C,3G | 3C,5G | 1C,2H | 0 | 0 | 0 |
| Barnyardgrass | 0 | 1C | 0 | 5C,9H | 3C,9H | 2C | 0 | 1C | 1C |
| Wild Oats | 0 | 0 | 0 | 2C,8G | 3C,9G | 2C | 0 | 0 | 0 |
| Wheat | 0 | 0 | 0 | 9H | 2C,9G | 2G | 0 | 0 | 0 |
| Corn | 0 | 2C,6G | 1C,7H | 2C,9G | 3C,9G | 3C,7H | 0 | 2C,5G | 2G |
| Soybean | 0 | 2C,3H | 2A | 9H | 3C,7H | 2C,5H | 0 | 1C | 0 |
| Rice | 0 | 6G | 2C,7H | 10E | 10E | 5C,7G | 5G | 2C | 0 |
| Sorghum | 0 | 2C,6G | 2C,6G | 2C,9H | 4C,9H | 3C,9H | 0 | 1C | 0 |
| Sugar beet | — | — | — | — | — | — | — | — | — |

| | Cmpd. 15 | Cmpd. 16 | Cmpd. 17 | Cmpd. 18 | Cmpd. 19 | Cmpd. 20 | Cmpd. 21 | Cmpd. 22 | Cmpd. 23 |
|---|---|---|---|---|---|---|---|---|---|
| Rate kg/ha | .05 | .05 | .05 | 1/20 | 1/20 | 1/20 | 1/20 | 1/20 | 1/20 |
| POST-EMERGENCE | | | | | | | | | |
| Bush bean | 0 | 4C,8G,6Y | 1C | 9C | 5C,9G,6Y | 4C,9G,6Y | 0 | 3C,8G,6Y | 9C |
| Cotton | 0 | 4C,7H | 1C | 4C,8H | 5C,8G | 4C,5H | 2C | 3C,4H | 4C,9G |
| Morningglory | 0 | 2C,6G | 1C | 4C,8H | 4C,7G | 5C,8H | 2C,5G | 3C,8G | 4C,9G |
| Cocklebur | 5H | 2G | 0 | 5C,9G | 9C | 9C | 1C | 2C,6G | 6G |
| Cassia | 0 | 1C | 1C | 4C,7H | 3C,6H | 3C,3G | 1C | 3C | 3C,8G |
| Nutsedge | 0 | 0 | 0 | 2C,8G | 3C,9G | 2C,7G | 0 | 3G | 3C,8G |
| Crabgrass | 0 | 0 | 0 | 2C,5G | 3C,7G | 3C,8G | 0 | 3G | 5C,9G |
| Barnyardgrass | 0 | 5H | 1C | 9C | 9C | 9C | 2H | 9C | 9C |
| Wild Oats | 0 | 0 | 0 | 3C,9G | 0 | 1C | 0 | 3C,9G | 9C |
| Wheat | 0 | 0 | 0 | 3C,9G | 0 | 7G | 0 | 2C,6G | 6U,9G |
| Corn | 0 | 2C | 0 | 3C,9H | 5C,9G | 2C,9G | 1C,3G | 2C,5H | 6U,9G |
| Soybean | 2G | 2C,9G,5X | 1C | 5C,9G | 6C,9G | 1C,2H | 1C | 1C,3H | 4C,9G |
| Rice | 0 | 4C,8G | 0 | 5C,9G | 5C,9G | 5C,9G | 0 | 5C,9G | 3C,9G |
| Sorghum | 0 | 3C,8H | 2C | 3U,9G | 2C,9G | 4C,9G | 2C,5G | 4C,9G | 3U,9G |
| Sugar beet | — | — | — | 9C | 5C,9G | 9C | 2C,5G | 4C,9H | 9C |
| PRE-EMERGENCE | | | | | | | | | |
| Morningglory | 0 | 0 | 0 | 2C,8H | 2C,8H | 4C,8H | 3C,3H | 2C,6H | 9C |
| Cocklebur | 0 | — | 0 | 8H | 10E | 9H | — | 1C | — |
| Cassia | 0 | 0 | 0 | 3C,6G | 9G | 2C,3G | 2C | 0 | 5C,8G |

TABLE A-continued

| | | | | | | | | | |
|---|---|---|---|---|---|---|---|---|---|
| Nutsedge | 0 | 0 | 0 | 10E | 4C,9G | 2C,9G | 0 | 0 | 9G |
| Crabgrass | 0 | 0 | 0 | 2C,3G | 2C | 3C,6G | 3G | 1C,4G | 5G |
| Barnyardgrass | 0 | 3C | 0 | 3C,8H | 3C,8H | 5C,9H | 0 | 2C,6H | 2C,4G |
| Wild Oats | 0 | 0 | 0 | 2C,6G | 5G | 2C,4G | 0 | 4G | 4C,9G |
| Wheat | 0 | 0 | 0 | 2C,8H | 6G | 3C,7G | 0 | 0 | 4C,9H |
| Corn | 0 | 2G | 1C | 5C,9G | 5C,9G | 5C,9H | 0 | 3C,8H | 5C,9H |
| Soybean | 2H | 1C | 0 | 3C,5H | 3C,7G | 0 | 1H | 0 | 8H |
| Rice | 2G | 1C | 0 | 10E | 10E | 10E | 2C | 4C,9H | 10E |
| Sorghum | 0 | 1C | 0 | 5C,8H | 2C,9G | 5C,9H | 3C | 4C,9H | 5C,9H |
| Sugar beet | — | — | — | 5C,9G | 9C | 5C,9G | 9G | 2C,4H | 5C,9G |

| | Cmpd. 23 | Compound 24 | | Compound 25 | | Compound 26 | | Compound 27 | |
|---|---|---|---|---|---|---|---|---|---|
| Rate kg/ha | 2/5 | 1/20 | 2/5 | 2/5 | 1/20 | 2/5 | 1/20 | 2/5 | 1/20 |
| POST-EMERGENCE | | | | | | | | | |
| Bush bean | 9C | 2C,7G,6Y | 5C,9G | 9C | 4C,9G,6Y | 2C | 0 | 5C,9G,6Y | 4C,9G,6Y |
| Cotton | 5C,9G | 3C,7G | 5C,8G | 4C,8G | 4C,4H | 1C | 0 | 4C,8G | 2C,3H |
| Morningglory | 5C,9G | 3C,7G | 4C,9G | 5C,9G | 3C,8G | 2C,5G | 2G | 4C,8G | 2C,9G |
| Cocklebur | 5C,9G | 8G | 2C,9G | 7G | 0 | 1H | 0 | 6G | 5H |
| Cassia | 3C,9G | 3C,5H | 3C,5H | 5C,9G | 3C,8G | 3G | 0 | 4C,8G | 3C,6H |
| Nutsedge | 9C | 4G | 2C,7G | 9C | 3C,8G | 0 | 0 | 4C,9G | 6G |
| Crabgrass | 9C | 3C,7G | 5C,9G | 9C | 4C,9G | 0 | 0 | 9C | 2C,8G |
| Barnyardgrass | 9C | 9C | 9C | 9C | 9C | 0 | 0 | 9C | 9C |
| Wild Oats | 9C | 3C,9G | 9C | 2C,8G | 4G | 0 | 0 | 9C | 2C,5G |
| Wheat | 9C | 5C,9G | 5U,9G | 5U,9G | 3U,9G | 0 | 0 | 3U,9G | 2G |
| Corn | 10C | 2C,8H | 3U,9G | 9C | 3U,9G | 2C,3H | 0 | 9C | 4C,9G |
| Soybean | 5C,9G | 5C,9G | 5C,9G | 5C,9G | 3C,9G | 2C,2H | 0 | 5C,9G | 4C,9H |
| Rice | 5C,9G | 5C,9G | 5C,9G | 5C,9G | 5C,9G | 0 | 0 | 4C,9G | 5C,9G |
| Sorghum | 9C | 3C,9H | 5C,9G | 3U,9G | 5C,9G | 2G | 0 | 4U,9G | 2C,9G |
| Sugar beet | 9C | 5C,8H | 5C,9H | 9C | 9C | 0 | 0 | 4C,9H | 4C,8H |
| PRE-EMERGENCE | | | | | | | | | |
| Morningglory | 9C | 2C,3H | 5C,9G | 5C,9H | 4C,9G | 2C | 0 | 5C,9G | 2C,9H |
| Cocklebur | 9H | 5H | 9H | 9H | 9H | 0 | 0 | 9H | 5H |
| Cassia | 5C,9G | 2C | 5C,8G | 5C,9G | 4C,9G | 0 | 0 | 5C,9G | 3H |
| Nutsedge | 10E | 0 | 2C,8G | 10E | 10E | 0 | 0 | 10E | 2C,9G |
| Crabgrass | 5C,9G | 0 | 3C,5G | 6C,9G | 4G | 0 | 0 | 5C,9G | 1C |
| Barnyardgrass | 5C,9H | 1C | 3C,8H | 5C,9H | 5C,9H | 0 | 0 | 2C,8H | 0 |
| Wild Oats | 5C,9H | 0 | 4C,9H | 3C,9G | 4G | 0 | 0 | 4C,9G | 0 |
| Wheat | 10H | 0 | 4C,9H | 10H | 3C,9H | 0 | 0 | 2C,9G | 0 |
| Corn | 10H | 3C,8H | 5C,9G | 9H | 4C,9H | 0 | 0 | 10E | 3C,8G |
| Soybean | 9H | 1C,1H | 3C,5H | 8H | 3C,3H | 0 | 0 | 2C,8H | 1H,1A |
| Rice | 10E | 2C,8G | 10E | 10E | 10E | 0 | 0 | 10E | 10E |
| Sorghum | 6C,9H | 3C,8H | 5C,9H | 5C,9H | 5C,9H | 0 | 0 | 5C,9H | 2C,9G |
| Sugar beet | 10E | 2C,5G | 5C,9G | 10E | 10E | 0 | 0 | 5C,9G | 2C,7G |

| | | Compound 28 | | Cmpd. 29 | Cmpd. 30 | Cmpd. 31 | Cmpd. 32 | Cmpd. 33 |
|---|---|---|---|---|---|---|---|---|
| Rate kg/ha | | 2/5 | 1/20 | 0.4 | 2 | 2/5 | 2/5 | 2/5 |
| POST-EMERGENCE | | | | | | | | |
| Bush bean | | 3C,8G,6Y | 4C,8G,6Y | 9C | 2S,9G,6Y | 6C,9G,6Y | 9C | 9C |
| Cotton | | 4C,7G | 4C,2H | 6C,9G | 3C,8G | 5C,9G | 4C,4H,8G | 6C,9G |
| Morningglory | | 4C,8G | 4C,8H | 2C,9G | 3C,8G | 10C | 4C,9H | 1C,3G |
| Cocklebur | | 3G | 2G | 9C | 2C | 9C | 5G | 9C |
| Cassia | | 2C,4H | 1C,3G | 4C,9G | 2C | 4C,9G | 2C,4G | 3C |
| Nutsedge | | 2C,9G | 3G | 9C | 1C,7G | 3C,9G | 2C,9G | 1C,9G |
| Crabgrass | | 4C,9G | 2C,7G | 9C | 1C,6G | 2C,5G | 4C,8G | 1H |
| Barnyardgrass | | 9C | 3C,8H | 9C | 2C,6H | 9C | 4C,7H | 2C,9H |
| Wild Oats | | 1C,2G | 0 | 9C | 2C,5G | 3C,9G | 3C | 2C |
| Wheat | | 3U,9G | 3C,9G | 5C,9G | 2C,5G | 1C,9G | 1C | 0 |
| Corn | | 5C,9G | 2C,9G | 10C | 3C | 5C,9G | 8H | 2C,6H |
| Soybean | | 1C,2H | 1C | 4C,9G | 3C,7G | 4C,9G | 4C,9G | 5C,9G |
| Rice | | 5C,9G | 1C,4G | 4C,9G | 2C,9G | 5C,9G | 6C,9G | 6C,9G |
| Sorghum | | 5C,9G | 3C,9G | 10C | 2C,6G | 4U,9G | 2C,9H | 2C,9G |
| Sugar beet | | 9C | 3C,9H | — | — | — | — | — |
| PRE-EMERGENCE | | | | | | | | |
| Morningglory | | 9G | 2C,2H | 9H | 8G | 9H | 9G | 8H |
| Cocklebur | | 9H | 7H | — | 6G | 9H | 9H | 9H |
| Cassia | | 2C,7G | 1C | 2C,9G | 10E | 3C,9G | 2C,8G | 8G |
| Nutsedge | | 5G | 0 | 10E | 10E | 10E | 10E | 10E |
| Crabgrass | | 3G | 1C | 4C,8G | 5G | 3G | 2C,6G | 1C |
| Barnyardgrass | | 2C,6G | 1C | 5C,9H | 2C,8H | 9H | 3C,9H | 2C,9H |
| Wild Oats | | 1C | 0 | 5C,9G | 2C | 2C,9H | 2C,8G | 1C,9G |
| Wheat | | 5C,9H | 0 | 9H | 5G | 2C,9H | 0 | 1C,8G |
| Corn | | 5C,9H | 2C,8G | 10H | 2C,5G | 2C,9G | 9H | 2C,9H |
| Soybean | | 0 | 0 | 9H | 1C | 9H | 9H | 8H |
| Rice | | 5C,9H | 2C,5G | 10E | 9H | 10E | 9H | 9H |
| Sorghum | | 5C,9H | 3C,9H | 10E | 3C,8G | 9H | 1C,5G | 2C,8H |
| Sugar beet | | 5C,9G | 2C,7G | — | — | — | — | — |

Test B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugarbeets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table 8.

TABLE B
PRE-EMERGENCE ON WOODSTOWN SANDY LOAM

|  | Compound 1 | | Compound 2 | |
|---|---|---|---|---|
| Rate kg/ha | 0.03 | 0.12 | 0.03 | 0.12 |
| Crabgrass | 9G,9C | 9G,9C | 7G | 8G |
| Barnyardgrass | 9G,9C | 9G,9C | 6G | 9G |
| Sorghum | 10C | 10C | 9G | 10C |
| Wild Oats | 9G | 9G | 3G | 7G |
| Johnsongrass | 9G | 9G | 7G | 8G |
| Dallisgrass | 9G,9C | 9G,9C | 0 | 7G |
| Giant foxtail | 9G,9C | 9G,9C | 4G | 9G |
| Ky. bluegrass | 9G,9C | 9G,9C | 7G | 8G |
| Cheatgrass | 10C | 10C | 8G | 10C |
| Sugar Beets | 10C | 10C | 9G | 10C |
| Corn | 9G | 10C | 3G | 9G |
| Mustard | 10C | 10C | 9G | 10C |
| Cocklebur | 8G | 9G | 0 | 7G |
| Pigweed | — | — | — | — |
| Nutsedge | 10C | 10C | 9G | 10C |
| Cotton | 8G | 9G | 3G | 7G |
| Morningglory | 8G | 9G | 5G | 7G |
| Cassia | 8G | 9G | 4G | 8G |
| Teaweed | 8G | 9G | 3G | 7G |
| Velvetleaf | 9G | 9G | 8G | 8G |
| Jimsonweed | 9G,9C | 9G,9C | 6G | 8G |
| Soybean | 9G | 9G | 5G,3C | 7G,5C |
| Rice | 10C | 10C | 10C | 10C |
| Wheat | 9G,9C | 9G,9C | 2G | 5G |

|  | Compound 3 | | Compound 4 | |
|---|---|---|---|---|
| Rate kg/ha | 0.03 | 0.12 | 0.03 | 0.12 |
| Crabgrass | 0 | 0 | 6G | 9G |
| Barnyardgrass | 0 | 0 | 6G | 9G |
| Sorghum | 0 | 3G | 10C | 10C |
| Wild Oats | 0 | 2G | 6G | 8G |
| Johnsongrass | 2G | 5G | 7G | 8G |
| Dallisgrass | 0 | 0 | 7G | 8G |
| Giant foxtail | 0 | 0 | 9G | 9G,9C |
| Ky. bluegrass | 0 | 0 | 8G | 9G |
| Cheatgrass | 0 | 5G | 9G | 10C |
| Sugar beets | 5G | 5G | 8G | 9G |
| Corn | 0 | 2G | 2G | 9G,9C |
| Mustard | 8G | 8G | 10C | 10C |
| Cocklebur | 0 | 0 | 8G | 9G |
| Pigweed | — | — | — | — |
| Nutsedge | 0 | 0 | 9G | 9G |

TABLE B-continued
PRE-EMERGENCE ON WOODSTOWN SANDY LOAM

| Cotton | 0 | 0 | 2G | 7G |
|---|---|---|---|---|
| Morningglory | 0 | 2G | 6G | 8G |
| Cassia | 0 | 0 | 0 | 3G |
| Teaweed | 0 | 0 | 0 | 4G |
| Velvetleaf | 0 | 0 | 5G | 8G |
| Jimsonweed | 0 | 0 | 7G | 8G |
| Soybean | 0 | 0 | 2G,2C | 7G,5C |
| Rice | 7G | 9G | 10C | 10C |
| Wheat | 0 | 0 | 8G | 9G |

|  | Compound 5 | | Compound 9 | |
|---|---|---|---|---|
| Rate kg/ha | 0.060 | 0.250 | 0.030 | 0.120 |
| Crabgrass | 0 | 7G | 4G | 5G |
| Barnyardgrass | 4G | 10C | 3G | 7G,3C |
| Sorghum | 10C | 10E | — | — |
| Wild Oats | 0 | 6G,3H | 3G | 6G |
| Johnsongrass | 8G,5H | 10C | 6G,3H | 7G,3H |
| Dallisgrass | 7G | 9G,9C | 7G | 8G |
| Giant foxtail | 2G | 8G,8C | 0 | 4G |
| Ky. bluegrass | 8G | 10E | 7G,5C | 10C |
| Cheatgrass | 7G | 10C | 7G,3C | 7G,7C |
| Sugar beets | 8G,9C | 10C | 8G,7C | 9G,9C |
| Corn | 4G | 10C | 4G | 8G,5H |
| Mustard | 8G,8C | 10C | 7G | 8G |
| Cocklebur | 3G | 7G | 5G | 6G |
| Pigweed | 9G,9C | 10C | 10C | 10C |
| Nutsedge | 8G | 10E | 6G | 8G |
| Cotton | 3G,2C | 8G,5H | 3G,3H | 9G,5H |
| Morningglory | 6G | 9G,3H | 5G | 9G |
| Cassia | 3G | 7G,3H | 6G | 7G,3C |
| Teaweed | 4G,3C | 8G,5H | 3G | 7G,3H |
| Velvetleaf | 6G,5H | 9G,9C | 4G | 7G,5H |
| Jimsonweed | 6G | 9G,9C | 2G | 5G |
| Soybean | 5G,5H | 9G,9C | 5G,3H | 9G,5H |
| Rice | 10C | 10C | 10E | 10E |
| Wheat | 3G | 6G | 2G | 6G |

|  | Compound 10 | | Compound 30 | |
|---|---|---|---|---|
| Rate kg/ha | 0.030 | 0.120 | 0.12 | 0.50 |
| Crabgrass | 0 | 5G | 0 | 0 |
| Barnyardgrass | 0 | 6G | 0 | 0 |
| Sorghum | — | — | 0 | 0 |
| Wild Oats | 0 | 6G | 0 | 0 |
| Johnsongrass | 5G,3H | 8G,3H | 0 | 0 |
| Dallisgrass | 6G,3H | 9G,9C | 0 | 0 |
| Giant foxtail | 0 | 0 | 0 | 0 |
| Ky. bluegrass | 6G,3H | 7G,5H | 0 | 0 |
| Cheatgrass | 7G,5C | 8G,5C | 0 | 0 |
| Sugar beets | 3G | 8G,8C | 0 | 0 |
| Corn | 2G | 9G,9C | 0 | 0 |
| Mustard | 9G,7C | 9G,9C | 0 | 6G |
| Cocklebur | 5G | — | 0 | 6G |
| Pigweed | — | — | 0 | 0 |
| Nutsedge | 8G | 10E | 0 | 4G |
| Cotton | 0 | 4G | 0 | 0 |
| Morningglory | 5G | 7G,3H | 0 | 0 |
| Cassia | 4G | 6G | 0 | 0 |
| Teaweed | 0 | 6G,3H | 0 | 9G,9C |
| Velvetleaf | 0 | 5G,5H | 0 | 0 |
| Jimsonweed | 0 | 6G,3H | 0 | 0 |
| Soybean | 0 | 7G,5H | 0 | 0 |
| Rice | 8G,5H | 10E | 0 | 0 |
| Wheat | 0 | 7G,5H | 0 | 0 |

Test C

The test chemicals, dissolved in a non-phytotoxic solvent, were applied in an overall spray to the foliage and surrounding soil of selected plant species. One day after treatment, plants were observed for rapid burn injury. Approximately fourteen days after treatment, all species were visually compared to untreated controls and rated for response to treatment. The rating system was as described previously for Test A. The data are presented in Table C.

All plant species were seeded in Woodstown sandy loam soil and grown in a greenhouse. The following species were grown in soil contained in plastic pots (25 cm diameter by 13 cm deep): soybeans, cotton, alfalfa, corn, rice, wheat, sorghum, velvetleaf (*Abutilon theophrasti*), sesbania (*Sesbania exaltata*), Cassia (*Cassia tora*), morningglory (*Ipomoea hederacea*), jimsonweed (*Datura stramonium*), cocklebur (*Xanthium pensylvanicum*), crabgrass (*Digitaria* sp.), nutsedge (*Cyperus rotundus*), barnyardgrass (*Echinochloa crusgalli*), giant foxtail (*Setaria faberii*) and wild oats (*Avena fatua*). The following species were grown in soil in a paper cup (12 cm diameter by 13 cm deep): sunflower, sugarbeets, and mustard. All plants were sprayed approximately 14 days after planting.

The compounds tested by this procedure are highly active post-emergence herbicides.

TABLE C

| Over-the-Top Soil/Foliage Treatment | | | | |
|---|---|---|---|---|
| | Compound 1 | | | |
| Rate kg/ha | 0.004 | 0.016 | 0.064 | 0.25 |
| Soybeans | 10C | 10C | 10C | 10C |
| Velvetleaf | 8G | 9G,5C | 9G | 10C |
| Sesbania | 6G | 9G | 10G | 10C |
| Cassia | 5G | 9G | 10G | 10C |
| Cotton | 6G | 9G | 9G | 10C |
| Morningglory | 8G | 9G | 10C | 10C |
| Alfalfa | 7G | 8G | 9G | 10C |
| Jimsonweed | 8G | 9G | 9G | 9G |
| Cocklebur | 8G | 8G | 8G | 10P |
| Corn | 9G | 9G | 10C | 10C |
| Crabgrass | 3G | 9G | 9C | 9C |
| Rice | 8G | 9G | 10C | 10C |
| Nutsedge | 9C | 9C | 10C | 10C |
| Barnyardgrass | 9C | 10C | 10C | 10C |
| Wheat | 4G | 8G | 9G | 9G |
| Giant foxtail | 9G | 10C | 10C | 10C |
| Wild Oats | 8G | 9G | 9G | 9G |
| Sorghum | 9U | 9U | 9G | 10C |
| Sunflower | 9G,3H | 10C | 10C | 10C |
| Rape | 8G | 9G | 9G | 9G |
| Johnsongrass | 10U | 10U | 10C | 10C |
| Sugar beets | 8G | 10C | 10C | 10C |
| Bindweed | 8G | 9G | 9G | 9G |

| | Compound 2 | | |
|---|---|---|---|
| Rate kg/ha | 0.016 | 0.064 | 0.25 |
| Soybeans | 8G | 9G,4C | 10C |
| Velvetleaf | 8G | 9G | 9G |
| Sesbania | 6G | 9G | 10C |
| Cassia | 4G | 7G | 8G |
| Cotton | 6G | 8G | 8G |
| Morningglory | 6G | 7G | 9G |
| Alfalfa | 3G | 6G | 8G |
| Jimsonweed | 3G | 6G | 8G |
| Cocklebur | 4G | 5G | 8G |
| Corn | 9G | 9G | 9G |
| Crabgrass | 0 | 6G | 8G |
| Rice | 9G | 9C | 9C |
| Nutsedge | 4G | 8G | 10C |
| Barnyardgrass | 9G | 10C | 10C |
| Wheat | 0 | 4G | 9G |
| Giant foxtail | 7G | 9G | 9G |
| Wild Oats | 0 | 7G | 9G |
| Sorghum | 7G | 9G | 9U |
| Sunflower | 5G,2H | 10P | 10P |
| Rape | 7G | 8G | 9G |
| Johnsongrass | 8G | 9U | 10U |
| Sugar beets | 9G | 10G | 10C |
| Bindweed | 3G | 7G | 8G |

| | Compound 3 | | |
|---|---|---|---|
| Rate kg/ha | 0.016 | 0.064 | 0.25 |
| Soybeans | 0 | 1G | 7G |
| Velvetleaf | 0 | 2G | 4G |
| Sesbania | 0 | 0 | 5G |
| Cassia | 0 | 0 | 0 |

TABLE C-continued

| Over-the-Top Soil/Foliage Treatment | | | |
|---|---|---|---|
| Cotton | 0 | 0 | 2G |
| Morningglory | 0 | 0 | 3C |
| Alfalfa | 0 | 0 | 3G |
| Jimsonweed | 0 | 2G | 7G |
| Cocklebur | 0 | 3G | 4G |
| Corn | 2G | 2G | 9G |
| Crabgrass | 0 | 0 | 4G |
| Rice | 5G | 8G | 9G |
| Nutsedge | 0 | 0 | 2G |
| Barnyardgrass | 2G | 3G | 6G |
| Wheat | 0 | 3G | 6G |
| Giant foxtail | 0 | 5G | — |
| Wild Oats | 2G | 4G | 9G |
| Sorghum | 6G | 9G | 9G |
| Sunflower | 0 | 2G | 4G |
| Rape | 0 | 1G | 5G |
| Johnsongrass | 0 | 6G | 9U |
| Sugar beets | 0 | 2G | 3G |
| Bindweed | 0 | 0 | 2G |

| | Compound 4 | | | |
|---|---|---|---|---|
| Rate kg/ha | 0.004 | 0.016 | 0.064 | 0.25 |
| Soybeans | 8G | 9G | 9G | 10C |
| Velvetleaf | 4C | 4G | 8G | 9G |
| Sesbania | 3G | 5G | 9G | 9G |
| Cassia | 0 | 0 | 4G | 9G |
| Cotton | 4G | 4G | 6G | 9G |
| Morningglory | 7G | 9G | 9G | 9G |
| Alfalfa | 6G | 6G | 7G | 9C |
| Jimsonweed | 6G | 6G | 9G | 9G |
| Cocklebur | 5G | 5G | 9G | 10P |
| Corn | 0 | 4G,3H | 9G | 9G |
| Crabgrass | 0 | 8G | 9G | 10C |
| Rice | 6G | 8C | 9C | 9C |
| Nutsedge | 3G | 5G | 7G | 10C |
| Barnyardgrass | 8G | 10C | 10C | 10C |
| Wheat | 7G | 8G | 9G | 10C |
| Giant foxtail | 8G | 9G | 9G | 9G |
| Wild Oats | 8G | 9G | 9G | 9G |
| Sorghum | 8G | 8U | 9U | 9U |
| Sunflower | 2G | 4G,3H | 9G | 10C |
| Rape | 6G | 8G | 9G | 9G |
| Johnsongrass | 8G | 9U | 10U | 10U |
| Sugar beets | 6G | 9G | 9G | 9G |
| Bindweed | 4G | 6G | 8G | 8G |

What is claimed is:

1. A compound of the formula:

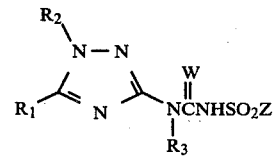

wherein
R$_1$ is H, C$_1$–C$_4$ alkyl, C$_3$–C$_4$ alkenyl, C$_3$–C$_4$ alkynyl, SR$_4$, OR$_5$, CH$_2$OR$_6$, CH$_2$CH$_2$OR$_6$, CF$_3$, CF$_2$CF$_3$, Cl, NHCH$_3$, N(CH$_3$)$_2$, CH(OCH$_3$)$_2$ or

R$_2$ is C$_1$–C$_4$ alkyl, C$_3$–C$_4$ alkenyl, C$_3$–C$_4$ alkynyl, CH$_2$OCH$_3$, CH$_2$CH$_2$OCH$_3$, CH$_2$SCH$_3$, CH$_2$CH$_2$SCH$_3$ or C$_1$–C$_4$ alkyl substituted with 1–3 F atoms;
R$_3$ is H or CH$_3$;

$R_4$ is $C_1$–$C_4$ alkyl, $C_3$–$C_4$ alkenyl, $C_3$–$C_4$ alkynyl, $CH_2CO_2R_6$ or $CH(CH_3)CO_2R_6$;

$R_5$ is $C_1$–$C_4$ alkyl, $C_3$–$C_4$ alkenyl, $C_3$–$C_4$ alkynyl, $CH_2CO_2R_6$, $CH(CH_3)CO_2R_6$ or $CH_2CF_3$;

$R_6$ is $C_1$–$C_4$ alkyl;

W is O or S;

Z is

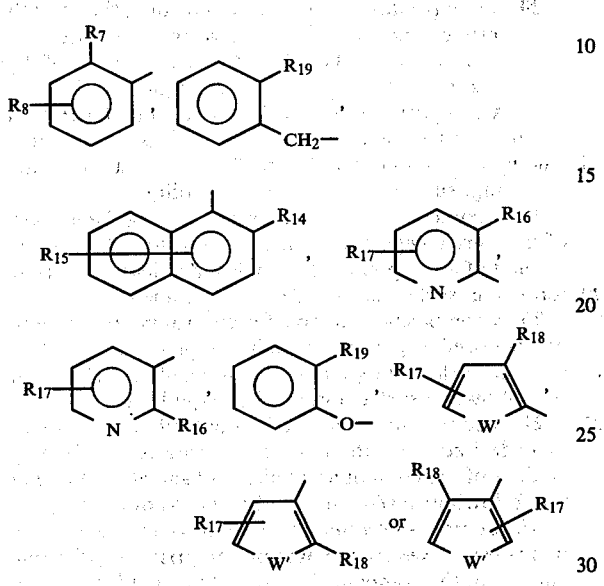

$R_7$ is H, $C_1$–$C_4$ alkyl, $C_1$–$C_4$ alkoxy, F, $C(O)NR_{21}R_{22}$, Cl, Br, $NO_2$, $CF_3$, $CO_2R_9$, $SO_2NR_{10}R_{11}$, $C(O)SR_{10}$, $SO_2N(OCH_3)CH_3$, $QSO_2R_{12}$, $S(O)_nR_{13}$, $CH_2CO_2R_{20}$, $CH(CH_3)CO_2R_{20}$, $CH_2S(O)_nR_{13}$, $CH(CH_3)S(O)_nR_{13}$, $C_{13}$–$C_4$ alkenyloxy, $C_3$–$C_4$ alkynyloxy, $C_1$–$C_2$ alkyl substituted with either $OCH_3$ or $OC_2H_5$, or $C_1$–$C_3$ alkoxy substituted with either (a) 1–5 atoms of Cl, Br or F or (b) $OCH_3$ or $OC_2H_5$;

$R_8$ is H, F, Cl, Br, $CF_3$, $NO_2$, $C_1$–$C_3$ alkyl or $C_1$–$C_3$ alkoxy;

$R_9$ is $C_1$–$C_6$ alkyl, $CH_2CH_2OCH_3$, $CH_2CH_2OCH_2CH_3$, $CH_2CH_2CH_2OCH_2CH_3$, $C_3$–$C_6$ alkenyl, $C_3$–$C_6$ alkynyl or $C_1$–$C_3$ alkyl substituted with 1–3 atoms of Cl or F;

$R_{10}$ and $R_{11}$ are independently $C_1$–$C_3$ alkyl;

$R_{12}$ is $C_1$–$C_4$ alkyl, $CH_2CH_2OCH_3$, $CH_2CH_2CH_2OCH_3$ or $C_1$–$C_4$ alkyl substituted with 1–3 atoms of F, Cl or Br;

$R_{13}$ is $C_1$–$C_4$ alkyl, allyl, $C_1$–$C_3$ alkyl substituted with 1–5 atoms of F, Cl or Br;

n is 0, 1 or 2;

Q is O or $NCH_3$;

$R_{14}$ is H, $CH_3$, $OCH_3$, F, Cl, Br, $NO_2$, $SO_2NR_{10}R_{11}$, $SO_2N(OCH_3)CH_3$, $OSO_2R_{12}$ or $S(O)_nR_{13}$;

$R_{15}$ is H, Cl, Br, $CH_3$, $OCH_3$ or $NO_2$;

$R_{16}$ is H, $C_1$–$C_4$ alkyl, $C_1$–$C_4$ alkoxy, F, Cl, Br, $CF_3$, $CO_2R_{20}$, $SO_2NR_{10}R_{11}$, $SO_2N(OCH_3)CH_3$ or $S(O)_nR_{13}$;

$R_{17}$ is H, F, Cl, Br, $CH_3$ or $OCH_3$;

W' is O or S;

$R_{18}$ is H, $C_1$–$C_4$ alkyl, $C_1$–$C_4$ alkoxy, F, Cl, Br, $NO_2$, $CO_2R_{20}$, $SO_2NR_{10}R_{11}$, $SO_2N(OCH_3)CH_3$ or $S(O)_nR_{13}$;

$R_{19}$ is Cl, $NO_2$, $CF_3$, $CO_2R_9$, $SO_2N(OCH_3)CH_3$, $SO_2NR_{10}R_{11}$, $QSO_2R_{12}$, $S(O)_nR_{13}$ or $C_1$–$C_3$ alkoxy substituted with 1–5 atoms of Cl or F;

$R_{20}$ is $C_1$–$C_4$ alkyl, $CH_2CH_2OCH_3$, $CH_2CH_2Cl$ or $CH_2CH=CH_2$;

$R_{21}$ is $C_1$–$C_3$ alkyl or $C_6H_5$;

$R_{22}$ is $C_1$–$C_3$ alkyl; and $R_{21}$ and $R_{22}$ may be taken together to be

provided that (1) the total number of carbon atoms of $R_{10}$ and $R_{11}$ is less than or equal to 4;

(2) the total number of carbon atoms of $R_1$ and $R_2$ is less than or equal to 6;

(3) when W' is O, then $R_{18}$ is H, Cl, Br, $CH_3$ or $CO_2R_{20}$;

(4) when W' is O and $R_{18}$ is H, Cl, Br or $CH_3$, then Z is

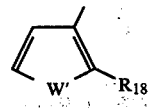

(5) when W is S, then $R_3$ is H;

(6) when $R_7$ is H, then $R_8$ is H; and (7) $R_{14}$ and $R_{15}$ may not both be $NO_2$.

2. Compounds of claim 1 wherein W is O and $R_3$ is H.

3. Compounds of claim 2 where Z is

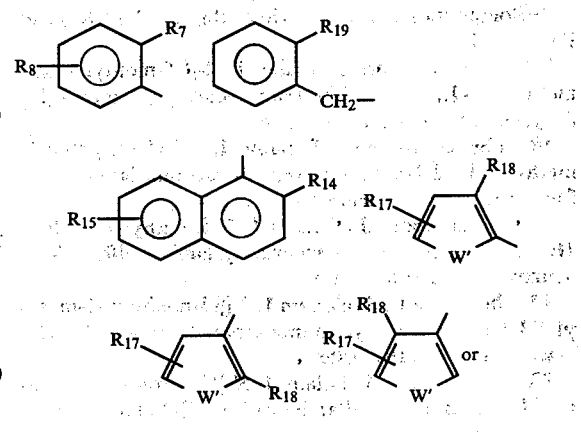

W' is S;

$R_{19}$ is $CO_2CH_3$, $SO_2N(CH_3)_2$ or $SO_2CH_3$; and $R_{15}$ and $R_{17}$ are H.

4. Compounds of claim 3 where Z is

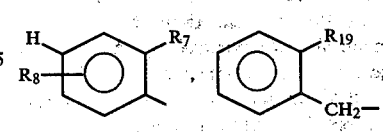

5. Compounds of claim 4 where
$R_1$ is $C_1$-$C_2$ alkyl, $CH_2CF_3$, $SR_4$, $OR_5$, $CH_2OCH_3$, $N(CH_3)_2$ or Cl;
$R_2$ is $C_1$-$C_2$ alkyl, $CH_2CH=CH_2$ or $CH_2C\equiv CH$; and
$R_4$ and $R_5$ are independently $CH_3$ or $C_2H_5$.

6. Compounds of claim 5 where Z is $R_7$ is other than H; and
$R_8$ is H, F, Cl, Br, $CF_3$, $CH_3$ or $OCH_3$.

7. Compounds of claim 6 where
$R_7$ is Cl, $NO_2$, $CO_2R_9$, $SO_2NR_{10}R_{11}$ or $OSO_2R_{12}$;
$R_8$ is H;
$R_9$ is $C_1$-$C_3$ alkyl, $CH_2CH=CH_2$, $CH_2CH_2OCH_3$ or $CH_2CH_2Cl$;
$R_{10}$ and $R_{11}$ are independently $C_1$-$C_2$ alkyl; and
$R_{12}$ and $R_{13}$ are independently $C_1$-$C_3$ alkyl.

8. Compounds of claim 7 where $R_9$, $R_{10}$, $R_{11}$, $R_{12}$ and $R_{13}$ are $CH_3$.

9. The compound of claim 1, 2-[[(5-methylthio-1-methyl-1H-1,2,4-triazol-3-yl)aminocarbonyl]aminosulfonyl]benzoic acid, methyl ester.

10. The compound of claim 1, 2-[[(5-ethylthio-1-methyl-1H-1,2,4-triazol-3-yl)aminocarbonyl]aminosulfonyl]benzoic acid, methyl ester.

11. The compound of claim 1, 2-[[(5-ethyl-1-methyl-1H-1,2,4-triazol-3-yl)aminocarbonyl]aminosulfonyl]benzoic acid, methyl ester.

12. The compound of claim 1, 2-[[(5-methoxy-1-methyl-1H-1,2,4-triazol-3-yl)aminocarbonyl]aminosulfonyl]benzoic acid, methyl ester.

13. The compound of claim 1, N-[(5-methoxy-1-methyl-1H-1,2,4-triazol-3-yl)aminocarbonyl]-2-chlorobenzenesulfonamide.

14. The compound of claim 1, N-[(5-methoxy-1-methyl-1H-1,2,4-triazol-3-yl)aminocarbonyl]-N',N'-dimethyl-1,2-benzenedisulfonamide.

15. A composition suitable for controlling the growth of undesired vegetation which comprises an effective amount of a compound of claim 1 and at least one of the following: surfactant, solid or liquid diluent.

16. A composition suitable for controlling the growth of undesired vegetation which comprises an effective amount of a compound of claim 2 and at least one of the following: surfactant, solid or liquid diluent.

17. A composition suitable for controlling the growth of undesired vegetation which comprises an effective amount of a compound of claim 3 and at least one of the following: surfactant, solid or liquid diluent.

18. A composition suitable for controlling the growth of undesired vegetation which comprises an effective amount of a compound of claim 4 and at least one of the following: surfactant, solid or liquid diluent.

19. A composition suitable for controlling the growth of undesired vegetation which comprises an effective amount of a compound of claim 5 and at least one of the following: surfactant, solid or liquid diluent.

20. A composition suitable for controlling the growth of undesired vegetation which comprises an effective amount of a compound of claim 6 and at least one of the following: surfactant, solid or liquid diluent.

21. A composition suitable for controlling the growth of undesired vegetation which comprises an effective amount of a compound of claim 7 and at least one of the following: surfactant, solid or liquid diluent.

22. A composition suitable for controlling the growth of undesired vegetation which comprises an effective amount of a compound of claim 8 and at least one of the following: surfactant, solid or liquid diluent.

23. A composition suitable for controlling the growth of undesired vegetation which comprises an effective amount of the compound of claim 9 and at least one of the following: surfactant, solid or liquid diluent.

24. A composition suitable for controlling the growth of undesired vegetation which comprises an effective amount of the compound of claim 10 and at least one of the following: surfactant, solid or liquid diluent.

25. A composition suitable for controlling the growth of undesired vegetation which comprises an effective amount of the compound of claim 11 and at least one of the following: surfactant, solid or liquid diluent.

26. A composition suitable for controlling the growth of undesired vegetation which comprises an effective amount of the compound of claim 12 and at least one of the following: surfactant, solid or liquid diluent.

27. A composition suitable for controlling the growth of undesired vegetation which comprises an effective amount of the compound of claim 13 and at least one of the following: surfactant, solid or liquid diluent.

28. A composition suitable for controlling the growth of undesired vegetation which comprises an effective amount of the compound of claim 14 and at least one of the following: surfactant, solid or liquid diluent.

29. A method for controlling the growth of undesired vegetation which comprises applying to the locus to be protected an effective amount of a compound of claim 1.

30. A method for controlling the growth of undesired vegetation which comprises applying to the locus to be protected an effective amount of a compound of claim 2.

31. A method for controlling the growth of undesired vegetation which comprises applying to the locus to be protected an effective amount of a compound of claim 3.

32. A method for controlling the growth of undesired vegetation which comprises applying to the locus to be protected an effective amount of a compound of claim 4.

33. A method for controlling the growth of undesired vegetation which comprises applying to the locus to be protected an effective amount of a compound of claim 5.

34. A method for controlling the growth of undesired vegetation which comprises applying to the locus to be protected an effective amount of a compound of claim 6.

35. A method for controlling the growth of undesired vegetation which comprises applying to the locus to be protected an effective amount of a compound of claim 7.

36. A method for controlling the growth of undesired vegetation which comprises applying to the locus to be protected an effective amount of a compound of claim 8.

37. A method for controlling the growth of undesired vegetation which comprises applying to the locus to be protected an effective amount of the compound of claim 9.

38. A method for controlling the growth of undesired vegetation which comprises applying to the locus to be protected an effective amount of the compound of claim 10.

39. A method for controlling the growth of undesired vegetation which comprises applying to the locus to be protected an effective amount of the compound of claim 11.

40. A method for controlling the growth of undesired vegetation which comprises applying to the locus to be protected an effective amount of the compound of claim 12.

41. A method for controlling the growth of undesired vegetation which comprises applying to the locus to be protected an effective amount of the compound of claim 13.

42. A method for controlling the growth of undesired vegetation which comprises applying to the locus to be protected an effective amount of the compound of claim 14.

* * * * *